United States Patent [19]
Ness et al.

[11] Patent Number: 6,027,890
[45] Date of Patent: *Feb. 22, 2000

[54] METHODS AND COMPOSITIONS FOR ENHANCING SENSITIVITY IN THE ANALYSIS OF BIOLOGICAL-BASED ASSAYS

[75] Inventors: Jeffrey Van Ness, Seattle; John C. Tabone, Bothell; J. Jeffry Howbert, Bellevue; John T. Mulligan, Seattle, all of Wash.

[73] Assignee: Rapigene, Inc., Bothell, Wash.

[ * ] Notice: This patent is subject to a terminal disclaimer.

[21] Appl. No.: 08/898,501

[22] Filed: Jul. 22, 1997

Related U.S. Application Data

[63] Continuation-in-part of application No. 08/787,521, Jan. 22, 1997, abandoned
[60] Provisional application No. 60/010,436, Jan. 23, 1996, and provisional application No. 60/015,402, Mar. 21, 1996.

[51] Int. Cl.$^7$ ..................................................... C12Q 1/68
[52] U.S. Cl. ................................ 435/6; 436/536; 436/518
[58] Field of Search ................................ 435/6; 436/536, 436/518

[56] References Cited

U.S. PATENT DOCUMENTS

| | | | |
|---|---|---|---|
| 4,762,779 | 8/1988 | Snitman | 435/6 |
| 5,118,605 | 6/1992 | Urdea | 435/6 |
| 5,135,870 | 8/1992 | Williams et al. | 436/173 |
| 5,288,644 | 2/1994 | Beavis et al. | 436/94 |
| 5,324,631 | 6/1994 | Helentjaris et al. | 435/6 |
| 5,346,670 | 9/1994 | Renzoni et al. | 422/52 |
| 5,403,708 | 4/1995 | Brennan et al. | 435/6 |

FOREIGN PATENT DOCUMENTS

| | | |
|---|---|---|
| 2062454 A1 | 9/1992 | Canada . |
| 127 154 A2 | 12/1984 | European Pat. Off. . |
| 251 786 A2 | 1/1988 | European Pat. Off. . |
| 300 730 A1 | 1/1989 | European Pat. Off. . |
| 360 940 A2 | 4/1990 | European Pat. Off. . |
| 401 821 A1 | 12/1990 | European Pat. Off. . |

(List continued on next page.)

OTHER PUBLICATIONS

Aebersold et al., "Design, synthesis, and characterization of a protein sequencing reagent yielding amino acid derivatives with enhanced detectability by mass spectrometry," *Protein Science* 1:494–503, 1992.

Amankwa and Kuhr, "Trypsin–Modified Fused–Silica Capillary Microreactor for Peptide Mapping by Capillary Zone Electrophoresis," *Anal. Chem.* 64:1610–1613, 1992.

Baldwin et al., "Synthesis of a Small Molecule Combinatorial Library Encoded with Molecular Tags," *J. Am. Chem. Soc.* 117:5588–5589, 1995. (+ Supplementary Material, 21 pages).

Borchardt and Still, "Synthetic Receptor Binding Elucidated with an Encoded Combinatorial Library," *J. Chem. Soc.* 116:373–374, 1994.

Brown et al., "A single–bead decode strategy using electrospray ionization mass spectrometry and a new photolabile linker: 3–Amino–3-(2–nitrophenyl)propionic acid," *Molecular Diversity* 1:4–12, 1995.

(List continued on next page.)

*Primary Examiner*—Scott W. Houtteman
*Attorney, Agent, or Firm*—Seed and Berry LLP

[57] ABSTRACT

Methods are provided for detecting the binding of a first member to a second member of a ligand pair, comprising the steps of (a) combining a set of first tagged members with a biological sample which may contain one or more second members, under conditions, and for a time sufficient to permit binding of a first member to a second member, wherein said tag is correlative with a particular first member and detectable by non-fluorescent spectrometry, or potentiometry, (b) separating bound first and second members from unbound members, (c) cleaving the tag from the tagged first member, and (d) detecting the tag by non-fluorescent spectrometry, or potentiometry, and therefrom detecting the binding of the first member to the second member.

72 Claims, 19 Drawing Sheets

FOREIGN PATENT DOCUMENTS

| | | |
|---|---|---|
| 502 595 A2 | 9/1992 | European Pat. Off. . |
| 514 927 A1 | 11/1992 | European Pat. Off. . |
| 539 343 A1 | 4/1993 | European Pat. Off. . |
| 639 647 A2 | 2/1995 | European Pat. Off. . |
| 711 362 B1 | 5/1996 | European Pat. Off. . |
| 6-289018 | 10/1994 | Japan . |
| WO 89/12694 | 12/1989 | WIPO . |
| WO 90/13666 | 11/1990 | WIPO . |
| WO 92/02528 | 2/1992 | WIPO . |
| WO 92/02638 | 2/1992 | WIPO . |
| WO 92/10587 | 6/1992 | WIPO . |
| WO 93/20233 | 10/1993 | WIPO . |
| WO 93/20236 | 10/1993 | WIPO . |
| WO 93/21340 | 10/1993 | WIPO . |
| WO 94/08051 | 4/1994 | WIPO . |
| WO 94/16101 | 7/1994 | WIPO . |
| WO 94/21822 | 9/1994 | WIPO . |
| WO 94/28418 | 12/1994 | WIPO . |
| WO 95/04160 | 2/1995 | WIPO . |
| WO 95/06752 | 3/1995 | WIPO . |
| WO 95/11961 | 5/1995 | WIPO . |
| WO 95/14108 | 5/1995 | WIPO . |
| WO 95/25737 | 9/1995 | WIPO . |
| WO 95/28640 | 10/1995 | WIPO . |
| WO 96/00378 | 1/1996 | WIPO . |
| WO 96/22966 | 8/1996 | WIPO . |

OTHER PUBLICATIONS

Ching et al, "Polymers as Surface–Based Tethers with Photolytic Triggers Enabling Laser–Induced Release/Desorption of Covalently Bound Molecules," *Bioconjugate Chemistry* 7(5):525–528, 1996.

Ching et al., "Surface Chemistries Enabled Photoinduced Uncoupling/Desorption of Covalently Tethered Biomolecules," *J. Org. Chem.* 61:3582–3583, 1996.

Church et al., "New Technologies For Genome Sequencing And Analysis," in *DOE Human Genome Program Contractor–Grantee Workshop V*, Sante Fe, New Mexico, Jan. 28–Feb. 1, 1996, available NTIS, CONF–960143, 1996, p. 51.

Church and Kieffer–Higgins, "Multiplex DNA Sequencing," *Science* 240:185–188, 1988.

Cobb and Novotny, "High–Sensitivity Peptide Mapping by Capillary Zone Electrophoresis and Microcol Liquid Chromatography, Using Immobilized Trypsin for Protein Digestion," *Anal. Chem.* 61:2226–2231 1989.

Colombo, Roberto, "Liquid–Phase Synthesis of Naturally Occurring Peptides, II. Syntheses of Three M Cell Degranulating Tetradecapeptide Amides from Wasp Venoms," *Hoppe–Seyler's Physiol. Chem.* 3 1393–1403, 1981.

Covey et al., "The Determination of Protein, Oligonucleotide and Peptide Molecular Weights by Ion–sp Mass Spectrometry," *Rapid Communications In Mass Spectrometry* 2(11):249–256, 1988.

Geysen et al., "Isotope or mass encoding of combinatorial libraries," *Chemistry & Biology* 3(8):679–688, 1996.

Giese et al., "Electrophore Mass Labels For TOF–MS DNA Sequencing," in *Proceedings of the 44th ASMS Conference on Mass Spectrometry and Allied Topics*, Portland, Oregon, May 12–16, 1996, p. 673.

Roger W. Giese, "Electrophoric release tags: ultrasensitive molecular labels providing multiplicity," *Trends in Analytical Chemistry* 2(7):166–168, 1983.

Greenberg and Gilmore, "Cleavage of Oligonucleotides from Solid–Phase Supports Using o–Nitrobenzyl Photochemistry," *J. Org. Chem.* 59:746–753, 1994.

Marc M. Greenberg, "Photochemical Cleavage of Oligonucleotides From Solid Phase Supports," *Tetrahedron Letters* 34(2):251–254, 1993.

Holmes and Jones, "Reagents for Combinatorial Organic Synthesis: Development of a New o–Nitrobenzyl Photolabile Linker for Solid Phase Synthesis," *J. Org. Chem.* 60:2318–2319, 1995. (+ Supplementary Material, 7 pages).

Jacobson et al., "Applications of Mass Spectrometry to DNA Sequencing," *Genetic Analysis Techniques and Applications* 8(8):223–229, 1991.

Jane et al., "High–Performance Liquid Chromatographic Analysis Of Basic Drugs on Silica Columns Using Non–Aqueous Ionic Eluents," *Journal of Chromatography* 323:191–225, 1985.

Kremsky et al., "Immobilization of DNA via oligonucleotides containing an aldehyde or carboxylic acid group at the 5' terminus," *Nucleic Acids Research* 15(7):2891–2909, 1987.

Little et al., "Rapid Sequencing of Oligonucleotides by High–Resolution Mass Spectrometry," *J. Am. Chem. Soc.* 116:4893–4897, 1994.

Lloyd–Williams et al., "Convergent Solid–Phase Peptide Synthesis," *Tetrahedron* 49(48):11065–11133, 1993.

Musch et al., "Expert System For Pharmaceutical Analysis. I. Selection Of The Detection System In High–Performance Liquid Chromatographic Analysis: UV Versus Amperometric Detection," *Journal of Chromatograpy* 348:97–110, 1985.

Nashabeh and El Rassi, "Enzymophoresis of nucleic acids by tandem capillary enzyme reactor–capillary zone electrophoresis," *Journal of Chromatograpy* 596:251–264, 1992.

Nestler et al., "A General Method for Molecular Tagging of Encoded Combinatorial Chemistry Libraries," *J. Org. Chem.* 59:4723–4724, 1994.

Ordoukhanian and Taylor, "Design and Synthesis of a Versatile Photocleavable DNA Building Block. Application to Phototriggered Hybridization," *J. Am. Chem. Soc.* 117:9570–9571, 1995.

V. N. Rajasekharan Pillai, "Photoremovable Protecting Groups in Organic Synthesis," *Synthesis* 1:1–26, 1980.

Rich and Gurwara, "Preparation of a New o–Nitrobenzyl Resin for Solid–Phase Synthesis of tert–Butyloxycarbonyl–Protected Peptide Acids," *J. Am. Chem. Soc.* 97:1575–1579, 1975.

Rock and Chan, "Synthesis and Photolysis Properties of a Photlabile Linker Based on 3'–Methoxybenzoin," *J. Org. Chem.* 61:1526–1529, 1996.

Sanger et al., "DNA sequencing with chain–terminating inhibitors," *Proc. Natl. Acad. Sci. USA* 74(12):5463–5467, 1977.

Senter et al., "Novel Photocleavable Protein Crosslinking Reagents And Their Use In The Preparation Of Antibody–Toxin Conjugates," *Photochemistry and Photobiology* 42(3):231–237, 1985.

Sumer et al., "Factors Determining Relative Sensitivity of Analytes in Positive Mode Atmosphere Pressure Ionization Mass Spectrometry," *Anal. Chem.* 60:1300–1307, 1988.

Simon J. Teague, "Facile Synthesis of a o–Nitrobenzyl Photolabile Linker for Combinatorial Chemistry," *Tetrahedron Letters* 37(32):5751–5754, 1996.

Thiele and Fahrenholz, "Photocleavable Biotinylated Ligands for Affinity Chromatography," *Analytical Biochemistry* 218:330–337, 1994.

Valaskovic et al., "Attomole–Sensitivity Electrospray Source for Large–Molecule Mass Spectrometry," *Anal. Chem.* 67:3802–3805, 1995.

Voivodov et al., "Surface Arrays of Energy Absorbing Polymers Enabling Covalent Attachment of Biomolecules for Subsequent Laser–Induced Uncoupling/Desorption," *Tetrahedron Letters* 37(32):5669–5672, 1996.

Charles Hignite, "Nucleic Acids And Derivatives," in *Biochemical Applications Of Mass Spectrometry, First Supplementary Volume*, Waller et al. (eds.), John Wiley & Sons, New York, 1981, pp. 527–566.

Yoo and Greenberg, "Synthesis of Oligonucleotides Containing 3'–Alkyl Carboxylic Acids Using Universal, Photolabile Solid Phase Synthesis Supports," *J. Org. Chem.* 60:3358–3364, 1995.

Zablocki et al., "Potent in Vitro and in Vivo Inhibitors of Platelet Aggregation Based Upon the Arg–Gly–Asp Sequence of Fibrinogen. (Aminobenzamidino)succinyl (ABAS) Series of Orally Active Fibrinogen Receptor Antagonists," *J. Med. Chem.* 38:2378–2394, 1995.

METHODS AND COMPOSITIONS FOR ENHANCING SENSITIVITY IN THE ANALYSIS OF BIOLOGICAL-BASED ASSAYS

CROSS-REFERENCE TO RELATED APPLICATIONS

This application claims priority according to at least one of 35 U.S.C. §§ 119 and 365 claims priority to, and is a continuation-in-part of, U.S. application Ser. No. 08/787,521, filed Jan. 22, 1997 now abandoned; which claims the benefit of U.S. Provisional Application Ser. No. 60/010,436, filed Jan. 23, 1996 and U.S. Provisional Application Ser. No. 60/015,402 filed Mar. 21, 1996, which application is incorporated by reference in its entirety.

TECHNICAL FIELD

The present invention relates generally to methods and compositions for analyzing nucleic acid molecules, and more specifically, to the use of specialized tags and linkers which may be utilized to enhance sensitivity of the analysis of a wide variety of biological-based assays.

BACKGROUND OF THE INVENTION

Detection and analysis of nucleic acid molecules are among the most important techniques in biology. They are at the heart of molecular biology and play a rapidly expanding role in the rest of biology.

Generally, following essentially all biochemical reactions, analysis entails some form of detection step. Of especial concern is the detection of nucleic acid hybridizations and antibody-antigen binding. Ideally, detection should be sensitive and allow processing of multiple samples. However, current detection techniques are somewhat limited in both these characteristics.

Hybridization of nucleic acid molecules is generally detected by autoradiography or phosphor image analysis when the hybridization probe contains a radioactive label or by densitometer when the hybridization probe contains a label, such as biotin or digoxin, that is recognized by an enzyme-coupled antibody or ligand.

When a radiolabeled probe is used, detection by autoradiography suffers from film limitations, such as reciprocity failure and non-linearity. These film limitations can be overcome by detecting the label by phosphor image analysis. However, radiolabels have safety requirements, increasing resource utilization and necessitating specialized equipment and personnel training. For such reasons, the use of nonradioactive labels has been increasing in popularity. In such systems, nucleotides contain a label, such as biotin or digoxin, which can be detected by an antibody or other molecule that is labeled with an enzyme reactive with a chromogenic substrate. Alternatively, fluorescent labels may be used. These systems do not have the safety concerns as described above, but use components that are often labile and may yield nonspecific reactions, resulting in high background (i.e., low signal-to-noise ratio).

Antibody-antigen binding reactions may be detected by one of several procedures. As for nucleic acid hybridization, a label, radioactive or nonradioactive, is typically conjugated to the antibody. The types of labels are similar: enzyme reacting with a chromogenic substrate, fluorescent, hapten that is detected by a ligand or another antibody, and the like. As in detection of nucleic acid hybridization, similar limitations are inherent in these detection methods.

The present invention provides novel compositions which may be utilized in a wide variety of nucleic acid-based, or protein (e.g., antibody)-based procedures, and further provides other, related advantages.

SUMMARY OF THE INVENTION

Briefly stated, the present invention provides compositions and methods which may be utilized to enhance sensitivity and sample number throughput in a wide variety of based assays. In particular, based upon the inventions described herein, many assays that heretofore have taken a long period of time to complete may now be performed ten to more than a hundred-fold faster. The methods described herein thus represent a dramatic and important improvement over previously available assays.

For example, within one aspect of the invention methods are provided for detecting the binding of a first member to a second member of a ligand pair, comprising the steps of (a) combining a set of first tagged members with a biological sample which may contain one or more second members, under conditions, and for a time sufficient to permit binding of a first member to a second member, wherein said tag is correlative with a particular first member and detectable by non-fluorescent spectrometry, or potentiometry, (b) separating bound first and second members from unbound members, (c) cleaving the tag from the tagged first member, and (d) detecting the tag by non-fluorescent spectrometry, or potentiometry, and therefrom detecting the binding of the first member to the second member.

A wide variety of first and second member pairs may be utilized within the context of the present invention, including for example, nucleic acid molecules (e.g., DNA, RNA, nucleic acid analogues such as PNA, or any combination of these), proteins or polypeptides (e.g., an antibody or antibody fragment (e.g., monoclonal antibody, polyclonal antibody, or a binding partner such as a CDR), oligosaccharides, hormones, organic molecules and other substrates (e.g., xenobiotics such as glucuronidase—drug molecule), or any other ligand pair. Within various embodiments of the invention, the first and second members may be the same type of molecule or of different types. For example, representative first member second member ligand pairs include: nucleic acid molecule/nucleic acid molecule; antibody/nucleic acid molecule; antibody/hormone; antibody/xenobiotic; and antibody/protein.

Preferably, the first member will recognize either a selected second ember specifically (i.e, to the exclusion of other related molecules), or a class of related second member molecules (e.g., a class of related receptors). Preferably the first member will bind to the second member with an affinity of at least about $10^{-5}$/M, and preferably $10^{-6}$/M, $10^{-7}$/M, $10^{-8}$/M, $10^{-9}$/M, or greater than $10^{-12}$/M. The affinity of a first molecule for a second molecule can be readily determined by one of ordinary skill in the art (see Scatchard, *Ann. N.Y. Acad. Sci.* 51:660–672, 1949).

Within other related aspects of the invention, methods are provided for analyzing the pattern of gene expression from a selected biological sample, comprising the steps of (a) exposing nucleic acids from a biological sample, (b) combining the exposed nucleic acids with one or more selected tagged nucleic acid probes, under conditions and for a time sufficient for said probes to hybridize to said nucleic acids, wherein the tag is correlative with a particular nucleic acid probe and detectable by non-fluorescent spectrometry, or potentiometry, (c) separating hybridized probes from unhybridized probes, (d) cleaving the tag from the tagged fragment, and (e) detecting the tag by non-fluorescent spectrometry, or potentiometry, and therefrom determining the patter of gene expression of the biological sample. Within one embodiment, the biological sample may be stimulated with a selected molecule prior to the step of exposing the nucleic acids. Representative examples of "stimulants" include nucleic acid molecules, recombinant gene delivery vehicles, organic molecules, hormones, proteins, inflammatory factors, cytokines, drugs, drug candidates, paracrine and autocrine factors, and the like.

Within the context of the present invention it should be understood that "biological samples" include not only samples obtained from living organisms (e.g., mammals, fish, bacteria, parasites, viruses, fungi and the like) or from the environment (e.g., air, water or solid samples), but biological materials which may be artificially or synthetically produced (e.g., phage libraries, organic molecule libraries, pools of genomic clones and the like). Representative examples of biological samples include biological fluids (e.g., blood, semen, cerebral spinal fluid, urine), biological cells (e.g., stem cells, B or T cells, liver cells, fibroblasts and the like), and biological tissues.

Within various embodiments of the above-described methods, the nucleic acid probes and or molecules of the present invention may be generated by, for example, a ligation, cleavage or extension (e.g., PCR) reaction. Within other related aspects the nucleic acid probes or molecules may be tagged at their 5'-end, and the so-tagged molecules function as oligonucleotide primers or dideoxynucleotide terminators.

Within other embodiments of the invention, 4, 5, 10, 15, 20, 25, 30, 35, 40, 45, 50, 60, 70, 80, 90, 100, 200, 250, 300, 350, 400, 450, or greater than 500 different and unique tagged molecules may be utilized within a given reaction simultaneously, wherein each tag is unique for a selected nucleic acid fragment, probe, or first or second member, and may be separately identifed.

Within further embodiments of the invention, the tag(s) may be detected by fluorometry, mass spectrometry, infrared spectrometry, ultraviolet spectrometry, or, potentiostatic amperometry (e.g., utilizing coulometric or amperometric detectors). Representative examples of suitable spectrometric techniques include time-of-flight mass spectrometry, quadrupole mass spectrometry, magnetic sector mass spectrometry and electric sector mass spectrometry. Specific embodiments of such techniques include ion-trap mass spectrometry, electrospray ionization mass spectrometry, ion-spray mass spectrometry, liquid ionization mass spectrometry, atmospheric pressure ionization mass spectrometry, electron ionization mass spectrometry, fast atom bombard ionization mass spectrometry, MALDI mass spectrometry, photo-ionization time-of-flight mass spectrometry, laser droplet mass spectrometry, MALDI-TOF mass spectrometry, APCI mass spectrometry, nanospray mass spectrometry, nebulised spray ionization mass spectrometry, chemical ionization mass spectrometry, resonance ionization mass spectrometry, secondary ionization mass spectrometry and thermospray mass spectrometry.

Within yet other embodiments of the invention, the bound first and second members, or exposed nucleic acids, may be separated from unbound members or molecules by methods such as gel electrophoresis, capillary electrophoresis, microchannel electrophoresis, HPLC, size exclusion chromatography, filtration, polyacrylamide gel electrophoresis, liquid chromatography, reverse size exclusion chromatography, ion-exchange chromatography, reverse phase liquid chromatography, pulsed-field electrophoresis, field-inversion electrophoresis, dialysis, and fluorescence-activated liquid droplet sorting. Alternatively, either the first or second member, or exposed nucleic acids may be bound to a solid support (e.g., hollow fibers (Amicon Corporation, Danvers, Mass.), beads (Polysciences, Warrington, Pa.), magnetic beads (Robbin Scientific, Mountain View, Calif.), plates, dishes and flasks (Corning Glass Works, Corning, N.Y.), meshes (Becton Dickinson, Mountain View, Calif.), screens and solid fibers (see Edelman et al., U.S. Pat. No. 3,843,324; see also Kuroda etyal., U.S. Pat. No. 4,416,777), membranes (Millipore Corp., Bedford, Mass.), and dipsticks). If the first or second member, or exposed nucleic acids are bound to a solid support, within certain embodiments of the invention the methods disclosed herein may further comprise the step of washing the solid support of unbound material.

Within other embodiments, the tagged first members may be cleaved by a methods such as chemical, oxidation, reduction, acid-labile, base labile, enzymatic, electrochemical, heat and photolabile methods. Within further embodiments, the steps of separating, cleaving and detecting may be performed in a continuous manner (e.g., as a continuous flow), for example, on a single device which may be automated.

These and other aspects of the present invention will become evident upon reference to the following detailed description and attached drawings. In addition, various references are set forth herein which describe in more detail certain procedures or compositions (e.g., plasmids, etc.), and are therefore incorporated by reference in their entirety.

DETAILED DESCRIPTION OF THE INVENTION

Figure 1:
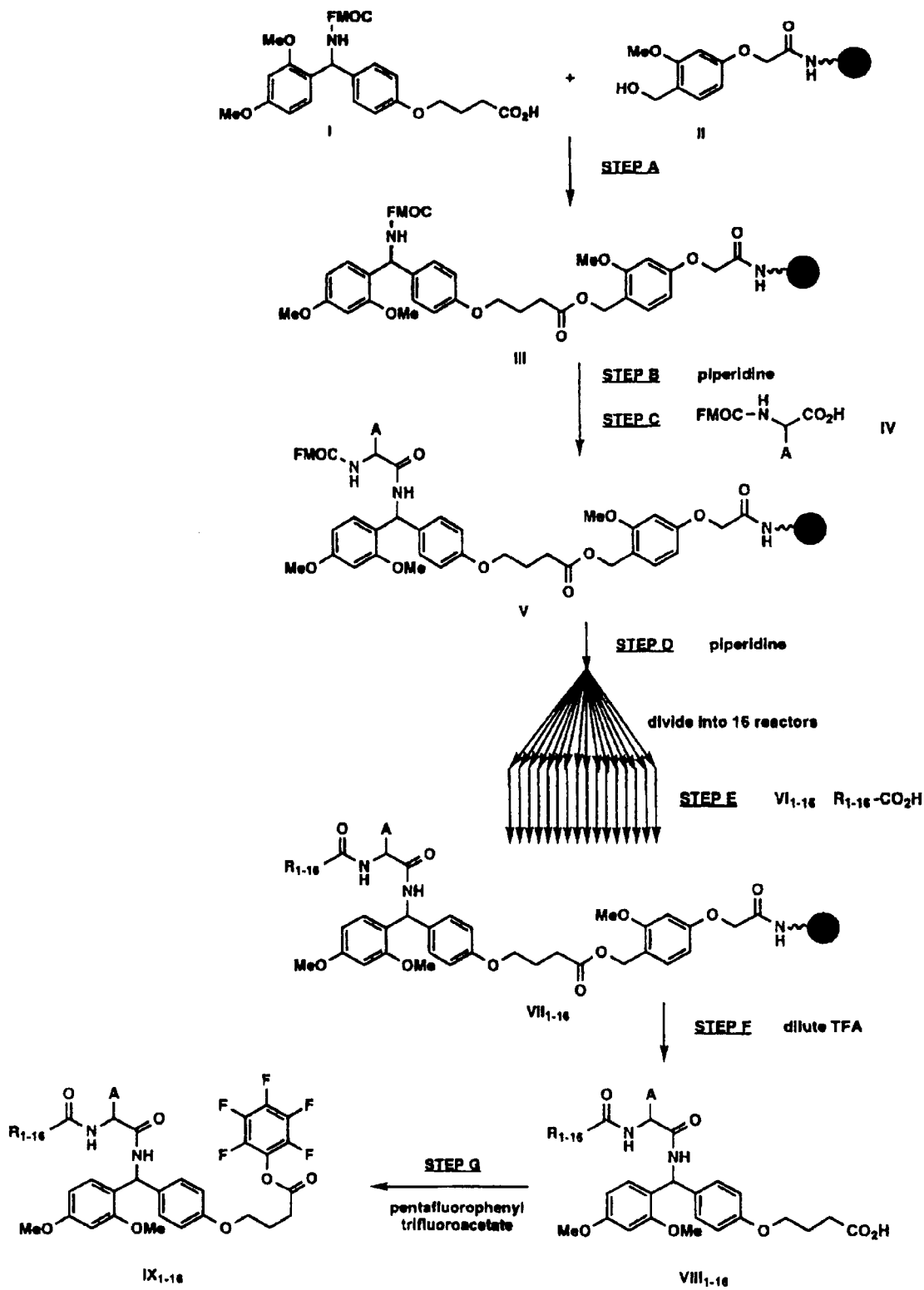
FIG. 1 depicts the flowchart for the synthesis of pentafluorophenyl esters of chemically cleavable mass spectroscopy tags, to liberate tags with carboxyl amide termini.

As noted above, the present invention provides tags and linkers that may be utilized to enhance sensitivity and sample number in a wide variety of biological-based assays. Described in more detail below are representative tags and linkers that may be utilized, a wide variety of methods wherein the tags may be useful, and methods for detecting the tags.

Briefly stated, in one aspect the present invention provides compounds wherein a molecule of interest, or precursor thereto, is linked via a labile bond (or labile bonds) to a tag. Thus, compounds of the invention may be viewed as having the general formula:

T-L-X wherein T is the tag component, L is the linker component that either is, or contains, a labile bond, and X is either the molecule of interest (MOI) component or a functional group component ($L_h$) through which the MOI may be joined to T-L. Compounds of the invention may therefore be represented by the more specific general formulas:

T-L-MOI and T-L-$L_h$

For reasons described in detail below, sets of T-L-MOI compounds may be purposely subjected to conditions that cause the labile bond(s) to break, thus releasing a tag moiety from the remainder of the compound. The tag moiety is then characterized by one or more analytical techniques, to thereby provide direct information about the structure of the tag moiety, and (most importantly) indirect information about the identity of the corresponding MOI.

As a simple illustrative example of a representative compound of the invention wherein L is a direct bond, reference is made to the following structure (i):

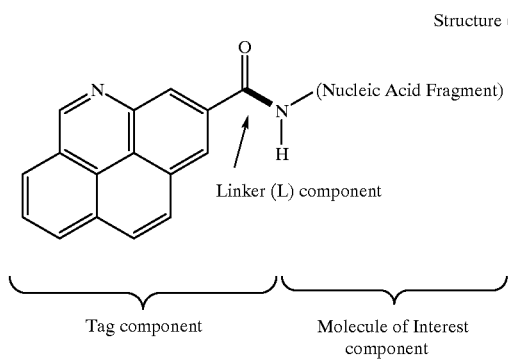

In structure (i), T is a nitrogen-containing polycyclic aromatic moiety bonded to a carbonyl group, X is a MOI (and specifically a nucleic acid fragment terminating in an amine group), and L is the bond which forms an amide group. The amide bond is labile relative to the bonds in T because, as recognized in the art, an amide bond may be chemically cleaved (broken) by acid or base conditions which leave the bonds within the tag component unchanged. Thus, a tag moiety (i.e., the cleavage product that contains T) may be released as shown below:

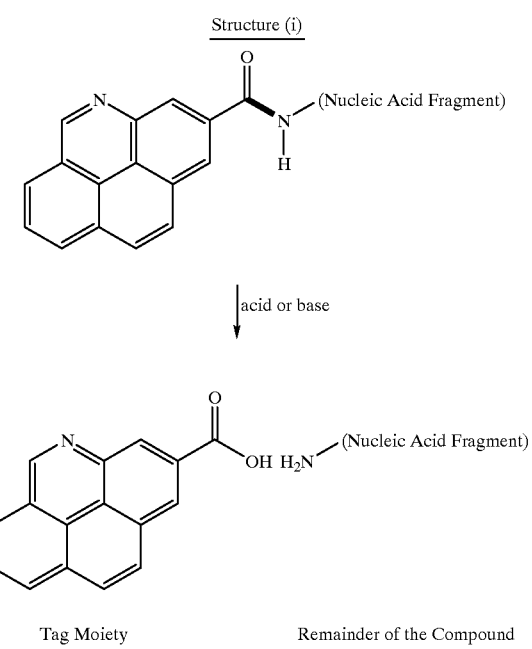

However, the linker L may be more than merely a direct bond, as shown in the following illustrative example, where reference is made to another representative compound of the invention having the structure (ii) shown below:

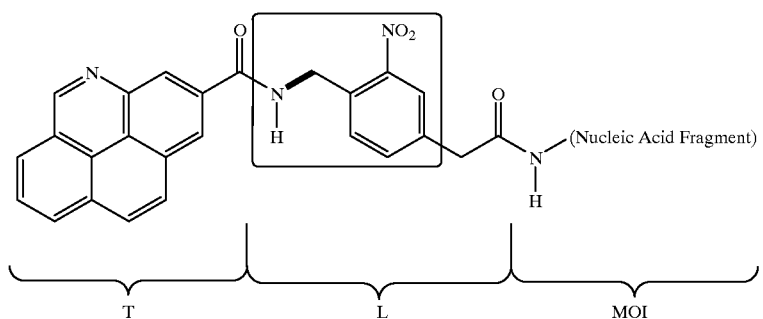

Structure (ii)

It is well-known that compounds having an ortho-nitrobenzylamine moiety (see boxed atoms within structure (ii)) are photolytically unstable, in that exposure of such compounds to actinic radiation of a specified wavelength will cause selective cleavage of the benzylamine bond (see bond denoted with heavy line in structure (ii)). Thus, structure (ii) has the same T and MOI groups as structure (i), however the linker group contains multiple atoms and bonds within which there is a particularly labile bond. Photolysis of structure (ii) thus releases a tag moiety (T-containing moiety) from the remainder of the compound, as shown below.

$T_{vc}\text{-}T_h$

To illustrate this nomenclature, reference may be made to structure (iii), which shows a tag reactant that may be used to prepare the compound of structure (ii). The tag reactant having structure (iii) contains a tag variable component and a tag handle, as shown below:

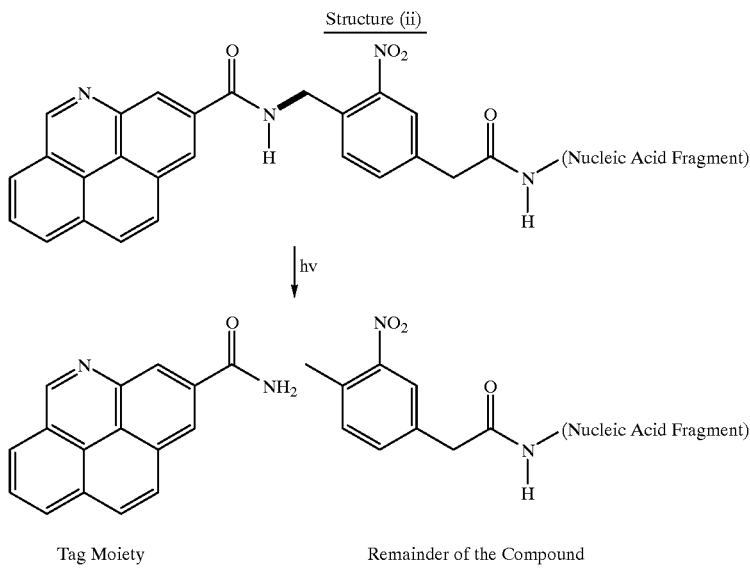

The invention thus provides compounds which, upon exposure to appropriate cleavage conditions, undergo a cleavage reaction so as to release a tag moiety from the remainder of the compound. Compounds of the invention may be described in terms of the tag moiety, the MOI (or precursor thereto, $L_h$), and the labile bond(s) which join the two groups together. Alternatively, the compounds of the invention may be described in terms of the components from which they are formed. Thus, the compounds may be described as the reaction product of a tag reactant, a linker reactant and a MOI reactant, as follows.

The tag reactant consists of a chemical handle ($T_h$) and a variable component ($T_{vc}$), so that the tag reactant is seen to have the general structure:

Structure (iii)

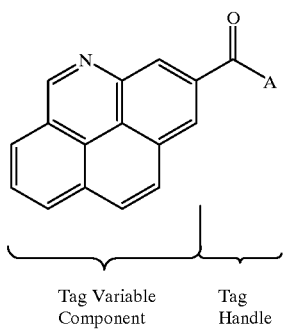

Tag Variable Component | Tag Handle

In structure (iii), the tag handle (—C(=O)—A) simply provides an avenue for reacting the tag reactant with the linker reactant to form a T-L moiety. The group "A" in structure (iii) indicates that the carboxyl group is in a chemically active state, so it is ready for coupling with other handles. "A" may be, for example, a hydroxyl group or pentafluorophenoxy, among many other possibilities. The invention provides for a large number of possible tag handles which may be bonded to a tag variable component, as discussed in detail below. The tag variable component is thus a part of "T" in the formula T-L-X, and will also be part of the tag moiety that forms from the reaction that cleaves L.

As also discussed in detail below, the tag variable component is so-named because, in preparing sets of compounds according to the invention, it is desired that members of a set have unique variable components, so that the individual members may be distinguished from one another by an analytical technique. As one example, the tag variable component of structure (iii) may be one member of the following set, where members of the set may be distinguished by their UV or mass spectra:

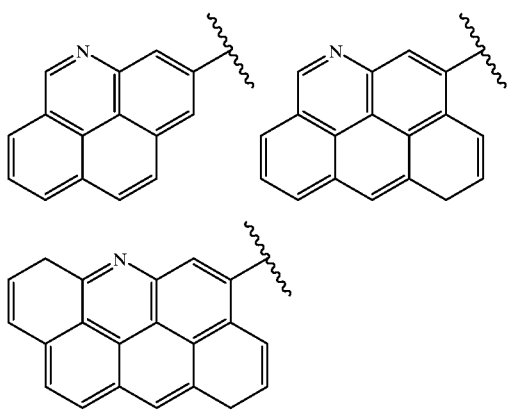

Likewise, the linker reactant may be described in terms of its chemical handles (there are necessarily at least two, each of which may be designated as $L_h$) which flank a linker labile component, where the linker labile component consists of the required labile moiety ($L^2$) and optional labile moieties ($L^1$ and $L^3$), where the optional labile moieties effectively serve to separate $L^2$ from the handles $L_h$, and the required labile moiety serves to provide a labile bond within the linker labile component. Thus, the linker reactant may be seen to have the general formula:

$L_h$-$L^1$-$L^2$-$L^3$-$L_h$

The nomenclature used to describe the linker reactant may be illustrated in view of structure (iv), which again draws from the compound of structure (ii):

Structure (iv)

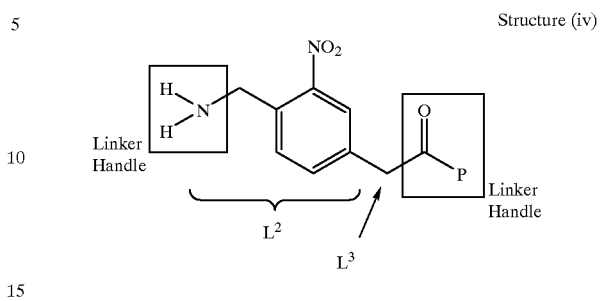

As structure (iv) illustrates, atoms may serve in more than one functional role. Thus, in structure (iv), the benzyl nitrogen functions as a chemical handle in allowing the linker reactant to join to the tag reactant via an amide-forming reaction, and subsequently also serves as a necessary part of the structure of the labile moiety $L^2$ in that the benzylic carbon-nitrogen bond is particularly susceptible to photolytic cleavage. Structure (iv) also illustrates that a linker reactant may have an $L^3$ group (in this case, a methylene group), although not have an $L^1$ group. Likewise, linker reactants may have an $L^1$ group but not an $L^3$ group, or may have $L^1$ and $L^3$ groups, or may have neither of $L^1$ nor $L^3$ groups. In structure (iv), the presence of the group "P" next to the carbonyl group indicates that the carbonyl group is protected from reaction. Given this configuration, the activated carboxyl group of the tag reactant (iii) may cleanly react with the amine group of the linker reactant (iv) to form an amide bond and give a compound of the formula T-L-$L_h$.

The MOI reactant is a suitably reactive form of a molecule of interest. Where the molecule of interest is a nucleic acid fragment, a suitable MOI reactant is a nucleic acid fragment bonded through its 5' hydroxyl group to a phosphodiester group and then to an alkylene chain that terminates in an amino group. This amino group may then react with the carbonyl group of structure (iv), (after, of course, deprotecting the carbonyl group, and preferably after subsequently activating the carbonyl group toward reaction with the amine group) to thereby join the MOI to the linker.

When viewed in a chronological order, the invention is seen to take a tag reactant (having a chemical tag handle and a tag variable component), a linker reactant (having two chemical linker handles, a required labile moiety and 0–2 optional labile moieties) and a MOI reactant (having a molecule of interest component and a chemical molecule of interest handle) to form I-L-MOI. Thus, to form T-L-MOI, either the tag reactant and the linker reactant are first reacted together to provide T-L-$L_h$, and then the MOI reactant is reacted with T-L-$L_h$ so as to provide T-L-MOI, or else (less preferably) the linker reactant and the MOI reactant are reacted together first to provide $L_h$-L-MOI, and then $L_h$-L-MOI is reacted with the tag reactant to provide T-L-MOI. For purposes of convenience, compounds having the formula T-L-MOI will be described in terms of the tag reactant, the linker reactant and the MOI reactant which may be used to form such compounds. Of course, the same compounds of formula T-L-MOI could be prepared by other (typically, more laborious) methods, and still fall within the scope of the inventive T-L-MOI compounds.

In any event, the invention provides that a T-L-MOI compound be subjected to cleavage conditions, such that a tag moiety is released from the remainder of the compound. The tag moiety will comprise at least the tag variable component, and will typically additionally comprise some or all of the atoms from the tag handle, some or all of the atoms from the linker handle that was used to join the tag reactant to the linker reactant, the optional labile moiety $L^1$ if this group was present in T-L-MOI, and will perhaps contain some part of the required labile moiety $L^2$ depending on the precise structure of $L^2$ and the nature of the cleavage chemistry. For convenience, the tag moiety may be referred to as the T-containing moiety because T will typically constitute the major portion (in terms of mass) of the tag moiety.

Given this introduction to one aspect of the present invention, the various components T, L and X will be described in detail. This description begins with the following definitions of certain terms, which will be used hereinafter in describing T, L and X.

As used herein, the term "nucleic acid fragment" means a molecule which is complementary to a selected target nucleic acid molecule (i.e., complementary to all or a portion thereof), and may be derived from nature or synthetically or recombinantly produced, including non-naturally occurring molecules, and may be in double or single stranded form where appropriate; and includes an oligonucleotide (e.g., DNA or RNA), a primer, a probe, a nucleic acid analog (e.g., PNA), an oligonucleotide which is extended in a 5' to 3' direction by a polymerase, a nucleic acid which is cleaved chemically or enzymatically, a nucleic acid that is terminated with a dideoxy terminator or capped at the 3' or 5' end with a compound that prevents polymerization at the 5' or 3' end, and combinations thereof. The complementarity of a nucleic acid fragment to a selected target nucleic acid molecule generally means the exhibition of at least about 70% specific base pairing throughout the length of the fragment. Preferably the nucleic acid fragment exhibits at least about 80% specific base pairing; and most preferably at least about 90%. Assays for determining the percent mismatch (and thus the percent specific base pairing) are well known in the art and are based upon the percent mismatch as a function of the Tm when referenced to the fully base paired control.

As used herein, the term "alkyl," alone or in combination, refers to a saturated, straight-chain or branched-chain hydrocarbon radical containing from 1 to 10, preferably from 1 to 6 and more preferably from 1 to 4, carbon atoms. Examples of such radicals include, but are not limited to, methyl, ethyl, n-propyl, iso-propyl, n-butyl, iso-butyl, sec-butyl, tert-butyl, pentyl, iso-amyl, hexyl, decyl and the like. The term "alkylene" refers to a saturated, straight-chain or branched chain hydrocarbon diradical containing from 1 to 10, preferably from 1 to 6 and more preferably from 1 to 4, carbon atoms. Examples of such diradicals include, but are not limited to, methylene, ethylene (—CH$_2$—CH$_2$—), propylene, and the like.

The term "alkenyl," alone or in combination, refers to a straight-chain or branched-chain hydrocarbon radical having at least one carbon-carbon double bond in a total of from 2 to 10, preferably from 2 to 6 and more preferably from 2 to 4, carbon atoms. Examples of such radicals include, but are not limited to, ethenyl, E- and Z-propenyl, isopropenyl, E- and Z-butenyl, E- and Z-isobutenyl, E- and Z-pentenyl, decenyl and the like. The term "alkenylene" refers to a straight-chain or branched-chain hydrocarbon diradical having at least one carbon-carbon double bond in a total of from 2 to 10, preferably from 2 to 6 and more preferably from 2 to 4, carbon atoms. Examples of such diradicals include, but are not limited to, methylidene (=CH$_2$), ethylidene (—CH=CH—), propylidene (—CH$_2$—CH=CH—) and the like.

The term "alkynyl," alone or in combination, refers to a straight-chain or branched-chain hydrocarbon radical having at least one carbon-carbon triple bond in a total of from 2 to 10, preferably from 2 to 6 and more preferably from 2 to 4, carbon atoms. Examples of such radicals include, but are not limited to, ethynyl (acetylenyl), propynyl (propargyl), butynyl, hexynyl, decynyl and the like. The term "alkynylene", alone or in combination, refers to a straight-chain or branched-chain hydrocarbon diradical having at least one carbon-carbon triple bond in a total of from 2 to 10, preferably from 2 to 6 and more preferably from 2 to 4, carbon atoms. Examples of such radicals include, but are not limited to, ethynylene (—C≡C—), propynylene (—CH$_2$—C≡C—) and the like.

The term "cycloalkyl," alone or in combination, refers to a saturated, cyclic arrangement of carbon atoms which number from 3 to 8 and preferably from 3 to 6, carbon atoms. Examples of such cycloalkyl radicals include, but are not limited to, cyclopropyl, cyclobutyl, cyclopentyl, cyclohexyl and the like. The term "cycloalkylene" refers to a diradical form of a cycloalkyl.

The term "cycloalkenyl," alone or in combination, refers to a cyclic carbocycle containing from 4 to 8, preferably 5 or 6, carbon atoms and one or more double bonds. Examples of such cycloalkenyl radicals include, but are not limited to, cyclopentenyl, cyclohexenyl, cyclopentadienyl and the like. The term "cycloalkenylene" refers to a diradical form of a cycloalkenyl.

The term "aryl" refers to a carbocyclic (consisting entirely of carbon and hydrogen) aromatic group selected from the group consisting of phenyl, naphthyl, indenyl, indanyl, azulenyl, fluorenyl, and anthracenyl; or a heterocyclic aromatic group selected from the group consisting of furyl, thienyl, pyridyl, pyrrolyl, oxazolyly, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl. pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, and phenoxazinyl.

"Aryl" groups, as defined in this application may independently contain one to four substituents which are independently selected from the group consisting of hydrogen, halogen, hydroxyl, amino, nitro, trifluoromethyl, trifluoromethoxy, alkyl, alkenyl, alkynyl, cyano, carboxy, carboalkoxy, 1,2-dioxyethylene, alkoxy, alkenoxy or alkynoxy, alkylamino, alkenylamino, alkynylamino, aliphatic or aromatic acyl, alkoxy-carbonylamino, alkylsulfonylamino, morpholinocarbonylamino, thiomorpholinocarbonylamino, N-alkyl guanidino, aralkylaminosulfonyl; aralkoxyalkyl; N-aralkoxyurea; N-hydroxylurea; N-alkenylurea; N,N-(alkyl, hydroxyl)urea; heterocyclyl; thioaryloxy-substituted aryl; N,N-(aryl, alkyl) hydrazino; Ar'-substituted sulfonylheterocyclyl; aralkyl-substituted heterocyclyl; cycloalkyl and cycloakenyl-substituted heterocyclyl; cycloalkyl-fused aryl; aryloxy-substituted alkyl; heterocyclylamino; aliphatic or aromatic acylaminocarbonyl; aliphatic or aromatic acyl-substituted alkenyl; Ar'-substituted aminocarbonyloxy; Ar', Ar'-disubstituted aryl; aliphatic or aromatic acyl-substituted acyl; cycloalkylcarbonylalkyl; cycloalkyl-substituted amino; aryloxycarbonylalkyl; phosphorodiamidyl acid or ester;

"Ar'" is a carbocyclic or heterocyclic aryl group as defined above having one to three substituents selected from the group consisting of hydrogen, halogen, hydroxyl, amino, nitro, trifluoromethyl, trifluoromethoxy, alkyl, alkenyl, alkynyl, 1,2-dioxymethylene, 1,2-dioxyethylene, alkoxy, alkenoxy, alkynoxy, alkylamino, alkenylamino or alkynylamino, alkylcarbonyloxy, aliphatic or aromatic acyl, alkylcarbonylamino, alkoxycarbonylamino, alkylsulfonylamino, N-alkyl or N,N-dialkyl urea.

The term "alkoxy," alone or in combination, refers to an alkyl ether radical, wherein the term "alkyl" is as defined above. Examples of suitable alkyl ether radicals include, but are not limited to, methoxy, ethoxy, n-propoxy, iso-propoxy, n-butoxy, iso-butoxy, sec-butoxy, tert-butoxy and the like.

The term "alkenoxy," alone or in combination, refers to a radical of formula alkenyl-O—, wherein the term "alkenyl" is as defined above provided that the radical is not an enol ether. Examples of suitable alkenoxy radicals include, but are not limited to, allyloxy, E- and Z-3-methyl-2-propenoxy and the like.

The term "alkynyloxy," alone or in combination, refers to a radical of formula alkynyl-O—, wherein the term "alkynyl" is as defined above provided that the radical is not an ynol ether. Examples of suitable alkynoxy radicals include, but are not limited to, propargyloxy, 2-butynyloxy and the like.

The term "thioalkoxy" refers to a thioether radical of formula alkyl-S-, wherein alkyl is as defined above.

The term "alkylamino," alone or in combination, refers to a mono- or di-alkyl-substituted amino radical (i.e., a radical of formula alkyl-NH— or (alkyl)$_2$-N-), wherein the term "alkyl" is as defined above. Examples of suitable alkylamino radicals include, but are not limited to, methylamino, ethylamino, propylamino, isopropylamino, t-butylamino, N,N-diethylamino and the like.

The term "alkenylamino," alone or in combination, refers to a radical of formula alkenyl-NH- or (alkenyl)$_2$N-, wherein the term "alkenyl" is as defined above, provided that the radical is not an enamine. An example of such alkenylamino radicals is the allylamino radical.

The term "alkynylamino," alone or in combination, refers to a radical of formula alkynyl—NH— or (alkynyl)$_2$N—, wherein the term "alkynyl" is as defined above, provided that the radical is not an ynamine. An example of such alkynylamino radicals is the propargyl amino radical.

The term "amide" refers to either —N(R$^1$)—C(=O)— or —C(=O)—N(R$^1$)— where R$^1$ is defined herein to include hydrogen as well as other groups. The term "substituted amide" refers to the situation where R$^1$ is not hydrogen, while the term "unsubstituted amide" refers to the situation where R$^1$ is hydrogen.

The term "aryloxy," alone or in combination, refers to a radical of formula aryl-O—, wherein aryl is as defined above. Examples of aryloxy radicals include, but are not limited to, phenoxy, naphthoxy, pyridyloxy and the like.

The term "arylamino," alone or in combination, refers to a radical of formula aryl-NH—, wherein aryl is as defined above. Examples of arylamino radicals include, but are not limited to, phenylamino (anilido), naphthylamino, 2-, 3- and 4-pyridylamino and the like.

The term "aryl-fused cycloalkyl," alone or in combination, refers to a cycloalkyl radical which shares two adjacent atoms with an aryl radical, wherein the terms "cycloalkyl" and "aryl" are as defined above An example of an aryl-fused cycloalkyl radical is the benzofused cyclobutyl radical.

The term "alkylcarbonylamino," alone or in combination, refers to a radical of formula alkyl-CONH, wherein the term "alkyl" is as defined above.

The term "alkoxycarbonylamino," alone or in combination, refers to a radical of formula alkyl-OCONH—, wherein the term "alkyl" is as defined above.

The term "alkylsulfonylamino," alone or in combination, refers to a radical of formula alkyl-SO$_2$NH—, wherein the term "alkyl" is as defined above.

The term "arylsulfonylamino," alone or in combination, refers to a radical of formula aryl-SO$_2$NH—, wherein the term "aryl" is as defined above.

The term "N-alkylurea," alone or in combination, refers to a radical of formula alkyl—NH—CO—NH—, wherein the term "alkyl" is as defined above.

The term "N-arylurea," alone or in combination, refers to a radical of formula aryl—NH—CO—NH—, wherein the term "aryl" is as defined above.

The term "halogen" means fluorine, chlorine, bromine and iodine.

The term "hydrocarbon radical" refers to an arrangement of carbon and hydrogen atoms which need only a single hydrogen atom to be an independent stable molecule. Thus, a hydrocarbon radical has one open valence site on a carbon atom, through which the hydrocarbon radical may be bonded to other atom(s). Alkyl, alkenyl, cycloalkyl, etc. are examples of hydrocarbon radicals.

The term "hydrocarbon diradical" refers to an arrangement of carbon and hydrogen atoms which need two hydrogen atoms in order to be an independent stable molecule. Thus, a hydrocarbon radical has two open valence sites on one or two carbon atoms, through which the hydrocarbon radical may be bonded to other atom(s). Alkylene, alkenylene, alkynylene, cycloalkylene, etc. are examples of hydrocarbon diradicals.

The term "hydrocarbyl" refers to any stable arrangement consisting entirely of carbon and hydrogen having a single valence site to which it is bonded to another moiety, and thus includes radicals known as alkyl, alkenyl, alkynyl, cycloalkyl, cycloalkenyl, aryl (without heteroatom incorporation into the aryl ring), arylalkyl, alkylaryl and the like. Hydrocarbon radical is another name for hydrocarbyl.

The term "hydrocarbylene" refers to any stable arrangement consisting entirely of carbon and hydrogen having two valence sites to which it is bonded to other moieties, and thus includes alkylene, alkenylene, alkynylene, cycloalkylene, cycloalkenylene, arylene (without heteroatom incorporation into the arylene ring), arylalkylene, alkylarylene and the like. Hydrocarbon diradical is another name for hydrocarbylene.

The term "hydrocarbyl-O-hydrocarbylene" refers to a hydrocarbyl group bonded to an oxygen atom, where the oxygen atom is likewise bonded to a hydrocarbylene group at one of the two valence sites at which the hydrocarbylene group is bonded to other moieties. The terms "hydrocarbyl-S-hydrocarbylene", "hydrocarbyl-NH-hydrocarbylene" and "hydrocarbyl-amide-hydrocarbylene" have equivalent meanings, where oxygen has been replaced with sulfur, —NH— or an amide group, respectively.

The term N-(hydrocarbyl)hydrocarbylene refers to a hydrocarbylene group wherein one of the two valence sites is bonded to a nitrogen atom, and that nitrogen atom is simultaneously bonded to a hydrogen and a hydrocarbyl group. The term N,N-di(hydrocarbyl)hydrocarbylene refers to a hydrocarbylene group wherein one of the two valence sites is bonded to a nitrogen atom, and that nitrogen atom is simultaneously bonded to two hydrocarbyl groups.

The term "hydrocarbylacyl-hydrocarbylene" refers to a hydrocarbyl group bonded through an acyl (—C(=O)—) group to one of the two valence sites of a hydrocarbylene group.

The terms "heterocyclylhydrocarbyl" and "heterocylyl" refer to a stable, cyclic arrangement of atoms which include carbon atoms and up to four atoms (referred to as heteroatoms) selected from oxygen, nitrogen, phosphorus and sulfur. The cyclic arrangement may be in the form of a monocyclic ring of 3–7 atoms, or a bicyclic ring of 8–11 atoms. The rings may be saturated or unsaturated (including aromatic rings), and may optionally be benzofused. Nitrogen and sulfur atoms in the ring may be in any oxidized form, including the quaternized form of nitrogen. A heterocyclylhydrocarbyl may be attached at any endocyclic carbon or heteroatom which results in the creation of a stable structure. Preferred heterocyclylhydrocarbyls include 5–7 membered monocyclic heterocycles containing one or two nitrogen heteroatoms.

A substituted heterocyclylhydrocarbyl refers to a heterocyclylhydrocarbyl as defined above, wherein at least one ring atom thereof is bonded to an indicated substituent which extends off of the ring.

In referring to hydrocarbyl and hydrocarbylene groups, the term "derivatives of any of the foregoing wherein one or more hydrogens is replaced with an equal number of fluorides" refers to molecules that contain carbon, hydrogen and fluoride atoms, but no other atoms.

The term "activated ester" is an ester that contains a "leaving group" which is readily displaceable by a nucleophile, such as an amine, and alcohol or a thiol nucleophile. Such leaving groups are well known and include, without limitation, N-hydroxysuccinimide, N-hydroxybenzotriazole, halogen (halides), alkoxy including tetrafluorophenolates, thioalkoxy and the like. The term "protected ester" refers to an ester group that is masked or otherwise unreactive. See, e.g., Greene, "Protecting Groups In Organic Solutions."

In view of the above definitions, other chemical terms used throughout this application can be easily understood by those of skill in the art. Terms may be used alone or in any combination thereof. The preferred and more preferred chain lengths of the radicals apply to all such combinations.

Genation of Tagged Nuclic Acid Fragments

As noted above, one aspect of the present invention provides a general scheme for DNA sequencing which allows the use of more than 16 tags in each lane; with continuous detection, the tags can be detected and the sequence read as the size separation is occurring, just as with conventional fluorescence-based sequencing. This scheme is applicable to any of the DNA sequencing techniques based on size separation of tagged molecules. Suitable tags and linkers for use within the present invention, as well as methods for sequencing nucleic acids, are discussed in more detail below.

1. Tags

"Tag", as used herein, generally refers to a chemical moiety which is used to uniquely identify a "molecule of interest", and more specifically refers to the tag variable component as well as whatever may be bonded most closely to it in any of the tag reactant, tag component and tag moiety.

A tag which is useful in the present invention possesses several attributes:

1) It is capable of being distinguished from all other tags. This discrimination from other chemical moieties can be based on the chromatographic behavior of the tag (particularly after the cleavage reaction), its spectroscopic or potentiometric properties, or some combination thereof. Spectroscopic methods by which tags are usefully distinguished include mass spectroscopy (MS), infrared (IR), ultraviolet (UV), and fluorescence, where MS, IR and UV are preferred, and MS most preferred spectroscopic methods. Potentiometric amperometry is a preferred potentiometric method.

2) The tag is capable of being detected when present at $10^{-22}$ to $10^{-6}$ mole.

3) The tag possesses a chemical handle through which it can be attached to the MOI which the tag is intended to uniquely identify. The attachment may be made directly to the MOI, or indirectly through a "linker" group.

4) The tag is chemically stable toward all manipulations to which it is subjected, including attachment and cleavage from the MOI, and any manipulations of the MOI while the tag is attached to it.

5) The tag does not significantly interfere with the manipulations performed on the MOI while the tag is attached to it. For instance, if the tag is attached to an oligonucleotide, the tag must not significantly interfere with any hybridization or enzymatic reactions (e.g., PCR sequencing reactions) performed on the oligonucleotide. Similarly, if the tag is attached to an antibody, it must not significantly interfere with antigen recognition by the antibody.

A tag moiety which is intended to be detected by a certain spectroscopic or potentiometric method should possess properties which enhance the sensitivity and specificity of detection by that method. Typically, the tag moiety will have those properties because they have been designed into the tag variable component, which will typically constitute the major portion of the tag moiety. In the following discussion, the use of the word "tag" typically refers to the tag moiety (i.e., the cleavage product that contains the tag variable component), however can also be considered to refer to the tag variable component itself because that is the portion of the tag moiety which is typically responsible for providing the uniquely detectable properties. In compounds of the formula T-L-X, the "T" portion will contain the tag variable component. Where the tag variable component has been designed to be characterized by, e.g., mass spectrometry, the "T" portion of T-L-X may be referred to as $T^{ms}$. Likewise, the cleavage product from T-L-X that contains T may be referred to as the $T^{ms}$-containing moiety. The following spectroscopic and potentiometric methods may be used to characterize $T^{ms}$-containing moieties.

a. Characteristics of MS Tags

Where a tag is analyzable by mass spectrometry (i.e., is a MS-readable tag, also referred to herein as a MS tag or "$T^{ms}$-containing moiety"), the essential feature of the tag is that it is able to be ionized. It is thus a preferred element in the design of MS-readable tags to incorporate therein a chemical functionality which can carry a positive or negative charge under conditions of ionization in the MS. This feature confers improved efficiency of ion formation and greater overall sensitivity of detection, particularly in electrospray ionization. The chemical functionality that supports an ionized charge may derive from $T^{ms}$ or L or both. Factors that can increase the relative sensitivity of an analyte being detected by mass spectrometry are discussed in, e.g., Sunner, J., et al., *Anal. Chem.* 60:1300–1307 (1988).

A preferred functionality to facilitate the carrying of a negative charge is an organic acid, such as phenolic hydroxyl, carboxylic acid, phosphonate, phosphate, tetrazole, sulfonyl urea, perfluoro alcohol and sulfonic acid.

Preferred functionality to facilitate the carrying of a positive charge under ionization conditions are aliphatic or aromatic amines. Examples of amine functional groups which give enhanced detectability of MS tags include quaternary amines (i.e., amines that have four bonds, each to carbon atoms, see Aebersold, U.S. Pat. No. 5,240,859) and tertiary amines (i.e., amines that have three bonds, each to carbon atoms, which includes C=N—C groups such as are present in pyridine, see Hess et al., *Anal. Biochem.* 224:373, 1995; Bures et al., *Anal. Biochem.* 224:364, 1995). Hindered tertiary amines are particularly preferred. Tertiary and quaternary amines may be alkyl or aryl. A $T^{ms}$-containing moiety must bear at least one ionizable species, but may possess more than one ionizable species. The preferred charge state is a single ionized species per tag. Accordingly, it is preferred that each $T^{ms}$-containing moiety (and each tag variable component) contain only a single hindered amine or organic acid group.

Suitable amine-containing radicals that may form part of the $T^{ms}$-containing moiety include the following:

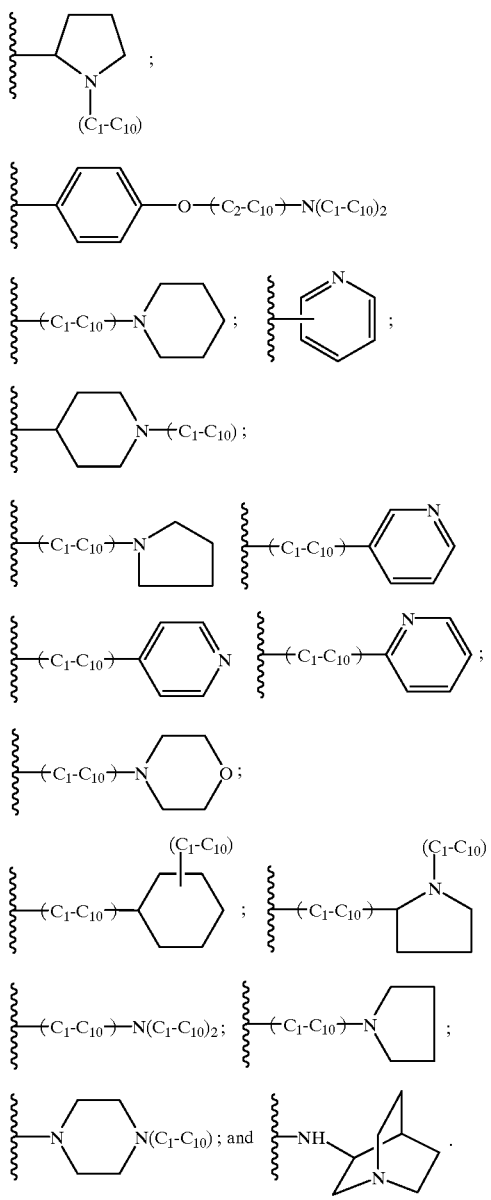

The identification of a tag by mass spectrometry is preferably based upon its molecular mass to charge ratio (m/z). The preferred molecular mass range of MS tags is from about 100 to 2,000 daltons, and preferably the $T^{ms}$-containing moiety has a mass of at least about 250 daltons, more preferably at least about 300 daltons, and still more preferably at least about 350 daltons. It is generally difficult for mass spectrometers to distinguish among moieties having parent ions below about 200–250 daltons (depending on the precise instrument), and thus preferred $T^{ms}$-containing moieties of the invention have masses above that range.

As explained above, the $T^{ms}$-containing moiety may contain atoms other than those present in the tag variable component, and indeed other than present in $T^{ms}$ itself. Accordingly, the mass of $T^{ms}$ itself may be less than about 250 daltons, so long as the $T^{ms}$-containing moiety has a mass of at least about 250 daltons. Thus, the mass of $T^{ms}$ may range from 15 (i.e., a methyl radical) to about 10,000 daltons, and preferably ranges from 100 to about 5,000 daltons, and more preferably ranges from about 200 to about 1,000 daltons.

It is relatively difficult to distinguish tags by mass spectrometry when those tags incorporate atoms that have more than one isotope in significant abundance. Accordingly, preferred T groups which are intended for mass spectroscopic identification ($T^{ms}$ groups), contain carbon, at least one of hydrogen and fluoride, and optional atoms selected from oxygen, nitrogen, sulfur, phosphorus and iodine. While other atoms may be present in the $T^{ms}$, their presence can render analysis of the mass spectral data somewhat more difficult. Preferably, the $T^{ms}$ groups have only carbon, nitrogen and oxygen atoms, in addition to hydrogen and/or fluoride.

Fluoride is an optional yet preferred atom to have in a $T^{ms}$ group. In comparison to hydrogen, fluoride is, of course, much heavier. Thus, the presence of fluoride atoms rather than hydrogen atoms leads to $T^{ms}$ groups of higher mass, thereby allowing the $T^{ms}$ group to reach and exceed a mass of greater than 250 daltons, which is desirable as explained above. In addition, the replacement of hydrogen with fluoride confers greater volatility on the $T^{ms}$-containing moiety, and greater volatility of the analyte enhances sensitivity when mass spectrometry is being used as the detection method.

The molecular formula of $T^{ms}$ falls within the scope of $C_{1-500}N_{0-100}O_{0-100}S_{0-10}P_{0-10}H_\alpha F_\beta I_\delta$ wherein the sum of $\alpha$, $\beta$ and $\delta$ is sufficient to satisfy the otherwise unsatisfied valencies of the C, N, O, S and P atoms. The designation $C_{1-500}N_{0-100}O_{0-100}S_{0-10}P_{0-10}H_\alpha F_\beta I_\delta$ means that $T^{ms}$ contains at least one, and may contain any number from 1 to 500 carbon atoms, in addition to optionally containing as many as 100 nitrogen atoms ("$N_0$-" means that $T^{ms}$ need not contain any nitrogen atoms), and as many as 100 oxygen atoms, and as many as 10 sulfur atoms and as many as 10 phosphorus atoms. The symbols $\alpha$, $\beta$ and $\delta$ represent the number of hydrogen, fluoride and iodide atoms in $T^{ms}$, where any two of these numbers may be zero, and where the sum of these numbers equals the total of the otherwise unsatisfied valencies of the C, N, O, S and P atoms. Preferably, $T^{ms}$ has a molecular formula that falls within the scope of $C_{1-50}N_{0-10}O_{0-10}H_\alpha F_\beta$ where the sum of ax and D equals the number of hydrogen and fluoride atoms, respectively, present in the moiety.

b. Characteristics of IR Tags

There are two primary forms of IR detection of organic chemical groups: Raman scattering IR and absorption IR. Raman scattering IR spectra and absorption IR spectra are complementary spectroscopic methods. In general, Raman excitation depends on bond polarizability changes whereas IR absorption depends on bond dipole moment changes. Weak IR absorption lines become strong Raman lines and vice versa. Wavenumber is the characteristic unit for IR spectra. There are 3 spectral regions for IR tags which have separate applications: near IR at 12500 to 4000 cm$^{-1}$, mid IR at 4000 to 600 cm$^{-1}$, far IR at 600 to 30 cm$^{-1}$. For the uses described herein where a compound is to serve as a tag to identify an MOI, probe or primer, the mid spectral regions would be preferred. For example, the carbonyl stretch (1850 to 1750 cm$^{-1}$) would be measured for carboxylic acids, carboxylic esters and amides, and alkyl and aryl carbonates, carbamates and ketones. N—H bending (1750 to 160 cm$^{-1}$) would be used to identify amines, ammonium ions, and amides. At 1400 to 1250 cm$^{-1}$, R—OH bending is detected as well as the C—N stretch in amides. Aromatic substitution patterns are detected at 900 to 690 cm$^{-1}$ (C—H bending, N—H bending for ArNH$_2$). Saturated C—H, olefins, aromatic rings, double and triple bonds, esters, acetals, ketals, ammonium salts, N—O compounds such as oximes, nitro, N-oxides, and nitrates, azo, hydrazones, quinones, carboxylic acids, amides, and lactams all possess vibrational infrared correlation data (see Pretsch et al., *Spectral Data for Structure Determination of Organic Compounds*, Springer- Verlag, New York, 1989). Preferred compounds would include an aromatic nitrile which exhibits a very strong nitrile stretching vibration at 2230 to 2210 cm$^{-1}$. Other useful types of compounds are aromatic alkynes which have a strong stretching vibration that gives rise to a sharp absorption band between 2140 and 2100 cm$^{-1}$. A third compound type is the aromatic azides which exhibit an intense absorption band in the 2160 to 2120 cm$^{-1}$ region. Thiocyanates are representative of compounds that have a strong absorption at 2275 to 2263 cm$^{-1}$.

c. Characteristics of UV Tags

A compilation of organic chromophore types and their respective UV-visible properties is given in Scott (*Interpretation of the UV Spectra of Natural Products*, Permagon Press, New York, 1962). A chromophore is an atom or group of atoms or electrons that are responsible for the particular light absorption. Empirical rules exist for the $\pi$ to $\pi^*$ maxima in conjugated systems (see Pretsch et al., *Spectral Data for Structure Determination of Organic Compounds*, p. B65 and B70, Springer-Verlag, New York, 1989). Preferred compounds (with conjugated systems) would possess n to $\pi^*$ and $\pi$ to $\pi^*$ transitions. Such compounds are exemplified by Acid Violet 7, Acridine Orange, Acridine Yellow G, Brilliant Blue G, Congo Red, Crystal Violet, Malachite Green oxalate, Metanil Yellow, Methylene Blue, Methyl Orange, Methyl Violet B, Naphtol Green B, Oil Blue N, Oil Red O, 4-phenylazophenol, Safranie O, Solvent Green 3, and Sudan Orange G, all of which are commercially available (Aldrich, Milwaukee, Wis.). Other suitable compounds are listed in, e.g., Jane, I., et al., *J. Chrom.* 323:191–225 (1985).

d. Characteristic of a Fluorescent Tag

Fluorescent probes are identified and quantitated most directly by their absorption and fluorescence emission wavelengths and intensities. Emission spectra (fluorescence and phosphorescence) are much more sensitive and permit more specific measurements than absorption spectra. Other photophysical characteristics such as excited-state lifetime and fluorescence anisotropy are less widely used. The most generally useful intensity parameters are the molar extinction coefficient ($\epsilon$) for absorption and the quantum yield (QY) for fluorescence. The value of $\delta$ is specified at a single wavelength (usually the absorption maximum of the probe), whereas QY is a measure of the total photon emission over the entire fluorescence spectral profile. A narrow optical bandwidth (<20 nm) is usually used for fluorescence excitation (via absorption), whereas the fluorescence detection bandwidth is much more variable, ranging from full spectrum for maximal sensitivity to narrow band (~20 nm) for maximal resolution. Fluorescence intensity per probe molecule is proportional to the product of $\epsilon$ and QY. The range of these parameters among fluorophores of current practical importance is approximately 10,000 to 100,000 cm$^{-1}$M$^{-1}$ for $\epsilon$ and 0.1 to 1.0 for QY. Compounds that can serve as fluorescent tags are as follows: fluorescein, rhodamine, lambda blue 470, lambda green, lambda red 664, lambda red 665, acridine orange, and propidium iodide, which are commercially available from Lambda Fluorescence Co. (Pleasant Gap, Pa.). Fluorescent compounds such as nile red, Texas Red, lissamine™, BODIPY™ s are available from Molecular Probes (Eugene, Oreg.).

e. Characteristics of Potentiometric Tags

The principle of electrochemical detection (ECD) is based on oxidation or reduction of compounds which at certain applied voltages, electrons are either donated or accepted thus producing a current which can be measured. When certain compounds are subjected to a potential difference, the molecules undergo a molecular rearrangement at the working electrodes' surface with the loss (oxidation) or gain (reduction) of electrons, such compounds are said to be electronic and undergo electrochemical reactions. EC detectors apply a voltage at an electrode surface over which the HPLC eluent flows. Electroactive compounds eluting from the column either donate electrons (oxidize) or acquire electrons (reduce) generating a current peak in real time. Importantly the amount of current generated depends on both the concentration of the analyte and the voltage applied, with each compound having a specific voltage at which it begins to oxidize or reduce. The currently most popular electrochemical detector is the amperometric detector in which the potential is kept constant and the current produced from the electrochemical reaction is then measured. This type of spectrometry is currently called "potentiostatic amperometry". Commercial amperometers are available from ESA, Inc., Chelmford, Mass.

When the efficiency of detection is 100%, the specialized detectors are termed "coulometric". Coulometric detectors are sensitive which have a number of practical advantages with regard to selectivity and sensitivity which make these types of detectors useful in an array. In coulometric detectors, for a given concentration of analyte, the signal current is plotted as a function of the applied potential (voltage) to the working electrode. The resultant sigmoidal graph is called the current-voltage curve or hydrodynamic voltammagram (HDV). The HDV allows the best choice of applied potential to the working electrode that permits one to maximize the observed signal. A major advantage of ECD is its inherent sensitivity with current levels of detection in the subfemtomole range.

Numerous chemicals and compounds are electrochemically active including many biochemicals, pharmaceuticals and pesticides. Chromatographically coeluting compounds can be effectively resolved even if their half-wave potentials (the potential at half signal maximum) differ by only 30–60 mV.

Recently developed coulometric sensors provide selectivity, identification and resolution of co-eluting compounds when used as detectors in liquid chromatography based separations. Therefore, these arrayed detectors add another set of separations accomplished in the detector itself. Current instruments possess 16 channels which are in principle limited only by the rate at which data can be acquired. The number of compounds which can be resolved on the EC array is chromatographically limited (i.e., plate count limited). However, if two or more compounds that chromatographically co-elute have a difference in half wave potentials of 30–60 mV, the array is able to distinguish the compounds. The ability of a compound to be electrochemically active relies on the possession of an EC active group (i.e., —OH, —O—, N, —S).

Compounds which have been successfully detected using coulometric detectors include 5-hydroxytryptamine, 3-methoxy-4-hydroxyphenyl-glycol, homogentisic acid, dopamine, metanephrine, 3-hydroxykynureninr, acetominophen, 3-hydroxytryptophol, 5-hydroxyindoleacetic acid, octanesulfonic acid, phenol, o-cresol, pyrogallol, 2-nitrophenol, 4-nitrophenol, 2,4-dinitrophenol, 4,6-dinitrocresol, 3-methyl-2-nitrophenol, 2,4-dichlorophenol, 2,6-dichlorophenol, 2,4,5-trichlorophenol, 4-chloro-3-methylphenol, 5-methylphenol, 4-methyl-2-nitrophenol, 2-hydroxyaniline, 4-hydroxyaniline, 1,2-phenylenediamine, benzocatechin, buturon chlortholuron, diuron, isoproturon, linuron, methobromuron, metoxuron, monolinuron, monuron, methionine, tryptophan, tyrosine, 4-aminobenzoic acid, 4-hydroxybenzoic acid, 4-hydroxycoumaric acid, 7-methoxycoumarin, apigenin baicalein, caffeic acid, catechin, centaurein, chlorogenic acid, daidzein, datiscetin, diosmetin, epicatechin gallate, epigallo catechin, epigallo catechin gallate, eugenol, eupatorin, ferulic acid, fisetin, galangin, gallic acid, gardenin, genistein, gentisic acid, hesperidin, irigenin, kaemferol, leucoyanidin, luteolin, mangostin, morin, myricetin, naringin, narirutin, pelargondin, peonidin, phloretin, pratensein, protocatechuic acid, rhamnetin, quercetin, sakuranetin, scutellarein, scopoletin, syringaldehyde, syringic acid, tangeritin, troxerutin, umbelliferone, vanillic acid, 1,3-dimethyl tetrahydroisoquinoline, 6-hydroxydopamine, r-salsolinol, N-methyl-r-salsolinol, tetrahydroisoquinoline, amitriptyline, apomorphine, capsaicin, chlordiazepoxide, chlorpromazine, daunorubicin, desipramine, doxepin, fluoxetine, flurazepam, imipramine, isoproterenol, methoxamine, morphine, morphine-3-glucuronide, nortriptyline, oxazepam, phenylephrine, trimipramine, ascorbic acid, N-acetyl serotonin, 3,4-dihydroxybenzylamine, 3,4-dihydroxymandelic acid (DOMA), 3,4-dihydroxyphenylacetic acid (DOPAC), 3,4-dihydroxyphenylalanine (L-DOPA), 3,4-dihydroxyphenylglycol (DHPG), 3-hydroxyanthranilic acid, 2-hydroxyphenylacetic acid (2HPAC), 4-hydroxybenzoic acid (4HBAC), 5-hydroxyindole-3-acetic acid (5HIAA), 3-hydroxykynurenine, 3-hydroxymandelic acid, 3-hydroxy-4 -methoxyphenylethylamine, 4-hydroxyphenylacetic acid (4HPAC), 4-hydroxyphenyllactic acid (4HPLA), 5-hydroxytryptophan (5HTP), 5-hydroxytryptophol (5HTOL), 5-hydroxytryptamine (5HT), 5-hydroxytryptamine sulfate, 3-methoxy-4-hydroxyphenylglycol (MHPG), 5-methoxytryptamine, 5-methoxytryptophan, 5-methoxytryptophol, 3-methoxytyramine (3MT), 3-methoxytyrosine (3-OM-DOPA), 5-methylcysteine, 3-methylguanine, bufotenin, dopamine dopamine-3-glucuronide, dopamine-3-sulfate, dopamine-4-sulfate, epinephrine, epinine, folic acid, glutathione (reduced), guanine, guanosine, homogentisic acid (HGA), homovanillic acid (HVA), homovanillyl alcohol (HVOL), homoveratic acid, hva sulfate, hypoxanthine, indole, indole-3-acetic acid, indole-3-lactic acid, kynurenine, melatonin, metanephrine, N-methyltryptamine, N-methyltyramine, N,N-dimethyltryptamine, N,N-dimethyltyramine, norepinephrine, normetanephrine, octopamine, pyridoxal, pyridoxal phosphate, pyridoxamine, synephrine, tryptophol, tryptamine, tyramine, uric acid, vanillylmandelic acid (vma), xanthine and xanthosine. Other suitable compounds are set forth in, e.g., Jane, I., et al. *J. Chrom.* 323:191–225 (1985) and Musch, G., et al., *J. Chrom.* 348:97–110 (1985). These compounds can be incorporated into compounds of formula T-L-X by methods known in the art. For example, compounds having a carboxylic acid group may be reacted with amine, hydroxyl, etc. to form amide, ester and other linkages between T and L.

In addition to the above properties, and regardless of the intended detection method, it is preferred that the tag have a modular chemical structure. This aids in the construction of large numbers of structurally related tags using the techniques of combinatorial chemistry. For example, the $T^{ms}$ group desirably has several properties. It desirably contains a functional group which supports a single ionized charge state when the $T^{ms}$-containing moiety is subjected to mass spectrometry (more simply referred to as a "mass spec sensitivity enhancer" group, or MSSE). Also, it desirably can serve as one member in a family of $T^{ms}$-containing moieties, where members of the family each have a different mass/charge ratio, however have approximately the same sensitivity in the mass spectrometer. Thus, the members of the family desirably have the same MSSE. In order to allow the creation of families of compounds, it has been found convenient to generate tag reactants via a modular synthesis scheme, so that the tag components themselves may be viewed as comprising modules.

In a preferred modular approach to the structure of the $T^{ms}$ group, $T^{ms}$ has the formula $$T^2\text{-}(J\text{-}T^3\text{-})_n\text{-}$$

wherein $T^2$ is an organic moiety formed from carbon and one or more of hydrogen, fluoride, iodide, oxygen, nitrogen, sulfur and phosphorus, having a mass range of 15 to 500 daltons; $T^3$ is an organic moiety formed from carbon and one or more of hydrogen, fluoride, iodide, oxygen, nitrogen, sulfur and phosphorus, having a mass range of 50 to 1000 daltons; J is a direct bond or a functional group such as amide, ester, amine, sulfide, ether, thioester, disulfide, thioether, urea, thiourea, carbamate, thiocarbamate, Schiff base, reduced Schiff base, imine, oxime, hydrazone, phosphate, phosphonate, phosphoramide, phosphonamide, sulfonate, sulfonamide or carbon-carbon bond; and n is an integer ranging from 1 to 50, such that when n is greater than 1, each $T^3$ and J is independently selected.

The modular structure $T^2\text{-}(J\text{-}T^3)_n\text{-}$ provides a convenient entry to families of T-L-X compounds, where each member of the family has a different T group. For instance, when T is $T^{ms}$, and each family member desirably has the same MSSE, one of the $T^3$ groups can provide that MSSE structure. In order to provide variability between members of a family in terms of the mass of $T^{ms}$, the $T^2$ group may be varied among family members. For instance, one family member may have $T^2$=methyl, while another has $T^2$=ethyl, and another has $T^2$=propyl, etc.

Figure 12:
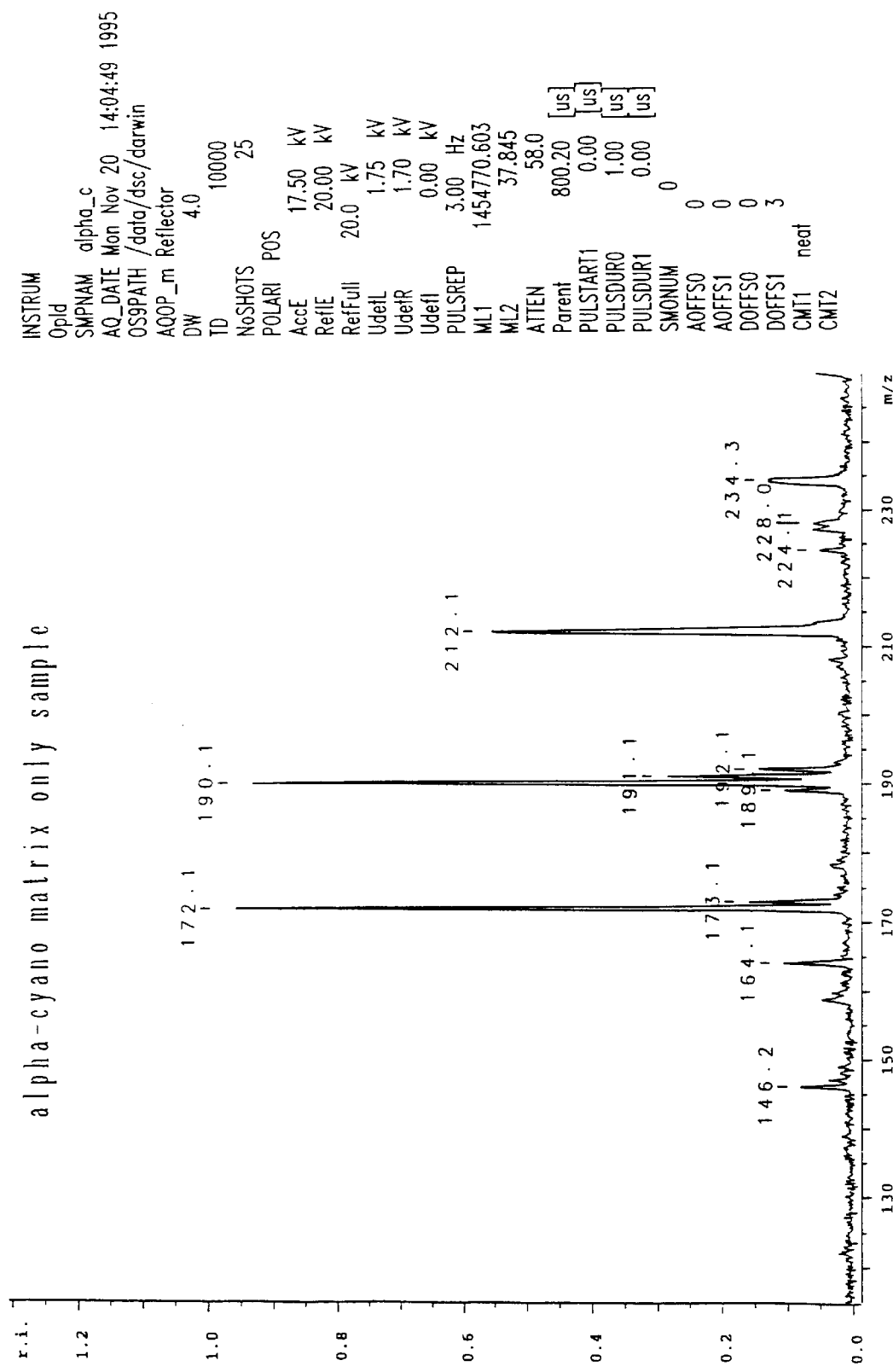
FIG. 12 shows the mass spectrogram of the alpha-cyano matrix alone.
Figure 13:
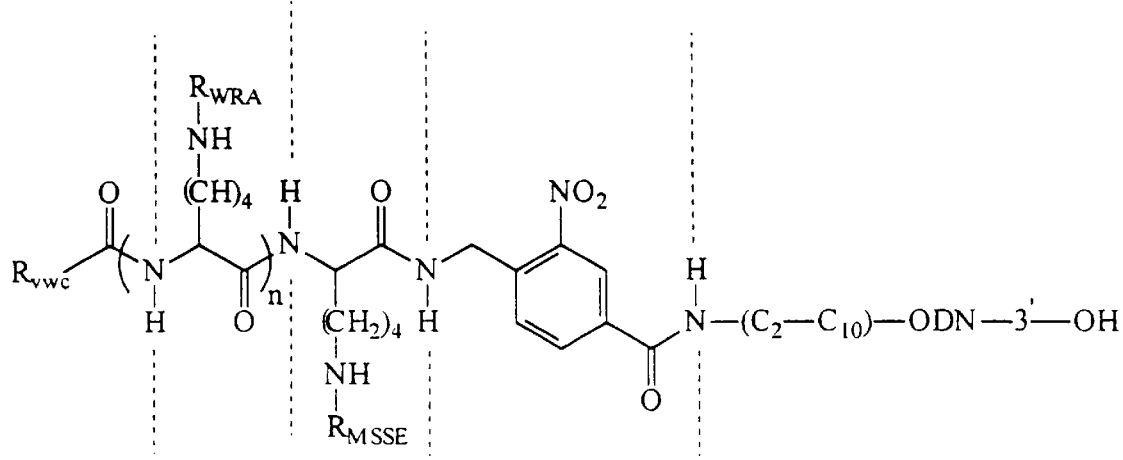
FIG. 13 depicts a modularly-constructed tagged nucleic acid fragment.

In order to provide "gross" or large jumps in mass, a $T^3$ group may be designed which adds significant (e.g., one or several hundreds) of mass units to T-L-X. Such a $T^3$ group may be referred to as a molecular weight range adjuster group("WRA"). A WRA is quite useful if one is working with a single set of $T^2$ groups, which will have masses extending over a limited range. A single set of $T^2$ groups may be used to create $T^{ms}$ groups having a wide range of mass simply by incorporating one or more WRA $T^3$ groups into the $T^{ms}$. Thus, using a simple example, if a set of $T^2$ groups affords a mass range of 250–340 daltons for the $T^{ms}$, the addition of a single WRA, having, as an exemplary number 100 dalton, as a $T^3$ group provides access to the mass range of 350–440 daltons while using the same set of $T^2$ groups. Similarly, the addition of two 100 dalton MWA groups (each as a $T^3$ group) provides access to the mass range of 450–540 daltons, where this incremental addition of WRA groups can be continued to provide access to a very large mass range for the $T^{ms}$ group. Preferred compounds of the formula $T^2\text{-}(J\text{-}T^3\text{-})_n\text{-}$L-X have the formula $R_{VWC}\text{-}(R_{WRA})_w\text{-}R_{MSSE}\text{-}$L-X where VWC is a "$T^2$" group, and each of the WRA and MSSE groups are "$T^3$" groups. This structure is illustrated in FIG. 12, and represents one modular approach to the preparation of $T^{ms}$.

In the formula $T^2\text{-}(J\text{-}T^3\text{-})_n\text{-}$, $T^2$ and $T^3$ are preferably selected from hydrocarbyl, hydrocarbyl-O-hydrocarbylene, hydrocarbyl-S-hydrocarbylene, hydrocarbyl-NH-hydrocarbylene, hydrocarbyl-amide-hydrocarbylene, N-(hydrocarbyl)hydrocarbylene, N,N-di(hydrocarbyl) hydrocarbylene, hydrocarbylacylhydrocarbylene, heterocyclylhydrocarbyl wherein the heteroatom(s) are selected from oxygen, nitrogen, sulfur and phosphorus, substituted heterocyclylhydrocarbyl wherein the heteroatom(s) are selected from oxygen, nitrogen, sulfur and phosphorus and the substituents are selected from hydrocarbyl, hydrocarbyl-O-hydrocarbylene, hydrocarbyl-NH-hydrocarbylene, hydrocarbyl-S-hydrocarbylene, N-(hydrocarbyl) hydrocarbylene, N,N-di(hydrocarbyl)hydrocarbylene and hydrocarbylacyl-hydrocarbylene. In addition, $T^2$ and/or $T^3$ may be a derivative of any of the previously listed potential $T^2/T^3$ groups, such that one or more hydrogens are replaced fluorides.

Also regarding the formula $T^2$-(J-$T^3$-)$_n$-, a preferred $T^3$ has the formula -G($R^2$)—, wherein G is $C_{1-6}$ alkylene chain having a single $R^2$ substituent. Thus, if G is ethylene (—$CH_2$—$CH_2$—) either one of the two ethylene carbons may have a $R^2$ substituent, and $R^2$ is selected from alkyl, alkenyl, alkynyl, cycloalkyl, aryl-fused cycloalkyl, cycloalkenyl, aryl, aralkyl, aryl-substituted alkenyl or alkynyl, cycloalkyl-substituted alkyl, cycloalkenyl-substituted cycloalkyl, biaryl, alkoxy, alkenoxy, alkynoxy, aralkoxy, aryl-substituted alkenoxy or alkynoxy, alkylamino, alkenylamino or alkynylamino, aryl-substituted alkylamino, aryl-substituted alkenylamino or alkynylamino, aryloxy, arylamino, N-alkylurea-substituted alkyl, N-arylurea-substituted alkyl, alkylcarbonylamino-substituted alkyl, aminocarbonyl-substituted alkyl, heterocyclyl, heterocyclyl-substituted alkyl, heterocyclyl-substituted amino, carboxyalkyl substituted aralkyl, oxocarbocyclyl-fused aryl and heterocyclylalkyl; cycloalkenyl, aryl-substituted alkyl and, aralkyl, hydroxy-substituted alkyl, alkoxy-substituted alkyl, aralkoxy-substituted alkyl, alkoxy-substituted alkyl, aralkoxy-substituted alkyl, amino-substituted alkyl, (aryl-substituted alkyloxycarbonylamino)-substituted alkyl, thiol-substituted alkyl, alkylsulfonyl-substituted alkyl, (hydroxy-substituted alkylthio)-substituted alkyl, thioalkoxy-substituted alkyl, hydrocarbylacylamino-substituted alkyl, heterocyclylacylamino-substituted alkyl, hydrocarbyl-substituted-heterocyclylacylamino-substituted alkyl, alkylsulfonylamino-substituted alkyl, arylsulfonylamino-substituted alkyl, morpholino-alkyl, thiomorpholino-alkyl, morpholino carbonyl-substituted alkyl, thiomorpholinocarbonyl-substituted alkyl, [N-(alkyl, alkenyl or alkynyl)- or N,N-[dialkyl, dialkenyl, dialkynyl or (alkyl, alkenyl)-amino]carbonyl-substituted alkyl, heterocyclylaminocarbonyl, heterocylylalkyleneaminocarbonyl, heterocyclylaminocarbonyl-substituted alkyl, heterocylylalkyleneaminocarbonyl-substituted alkyl, N,N-[dialkyl]alkyleneaminocarbonyl, N,N-[dialkyl] alkyleneaminocarbonyl-substituted alkyl, alkyl-substituted heterocyclylcarbonyl, alkyl-substituted heterocyclylcarbonyl-alkyl, carboxyl-substituted alkyl, dialkylamino-substituted acylaminoalkyl and amino acid side chains selected from arginine, asparagine, glutamine, S-methyl cysteine, methionine and corresponding sulfoxide and sulfone derivatives thereof, glycine, leucine, isoleucine, allo-isoleucine, tert-leucine, norleucine, phenylalanine, tyrosine, tryptophan, proline, alanine, ornithine, histidine, glutamine, valine, threonine, serine, aspartic acid, beta-cyanoalanine, and allothreonine; alynyl and heterocyclylcarbonyl, aminocarbonyl, amido, mono- or dialkylaminocarbonyl, mono- or diarylaminocarbonyl, alkylarylaminocarbonyl, diarylaminocarbonyl, mono- or diacylaminocarbonyl, aromatic or aliphatic acyl, alkyl optionally substituted by substituents selected from amino, carboxy, hydroxy, mercapto, mono- or dialkylamino, mono- or diarylamino, alkylarylamino, diarylamino, mono- or diacylamino, alkoxy, alkenoxy, aryloxy, thioalkoxy, thioalkenoxy, thioalkynoxy, thioaryloxy and heterocyclyl.

A preferred compound of the formula $T^2$-(J-$T^3$-)$_n$-L-X has the structure:

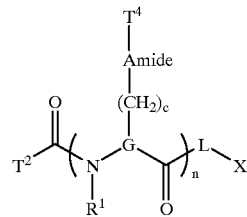

wherein G is $(CH_2)_{1-6}$ such that a hydrogen on one and only one of the $CH_2$ groups represented by a single "G" is replaced with-$(CH_2)_c$-Amide-$T^4$; $T^2$ and $T^4$ are organic moieties of the formula $C_{1-25}N_{0-9}O_{0-9}H_\alpha F_\beta$ such that the sum of $\alpha$ and $\beta$ is sufficient to satisfy the otherwise unsatisfied valencies of the C, N, and O atoms; amide is

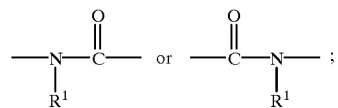

$R^1$ is hydrogen or $C_{1-10}$ alkyl; c is an integer ranging from 0 to 4; and n is an integer ranging from 1 to 50 such that when n is greater than 1, G, c, Amide, $R^1$ and $T^4$ are independently selected.

In a further preferred embodiment, a compound of the formula $T^2$-(J-$T^3$-)$_n$-L-X has the structure:

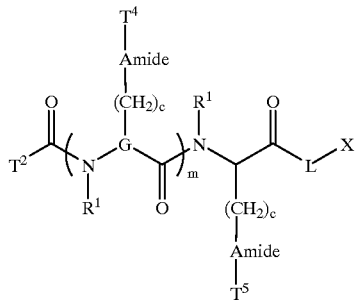

wherein $T^5$ is an organic moiety of the formula $C_{i-25}N_{0-9}O_{0-9}H_\alpha F_\beta$ such that the sum of $\alpha$ and $\beta$ is sufficient to satisfy the otherwise unsatisfied valencies of the C, N, and O atoms; and $T^5$ includes a tertiary or quaternary amine or an organic acid; m is an integer ranging from 0–49, and $T^2$, $T^4$, $R^1$, L and X have been previously defined.

Another preferred compound having the formula $T^2$-(J-$T^3$-)$_n$-L-X has the particular structure:

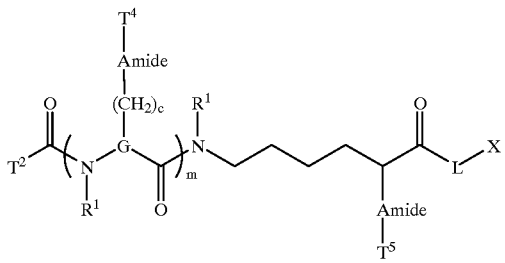

wherein $T^5$ is an organic moiety of the formula $C_{1-25}N_{0-9}O_{0-9}H_\alpha F_\beta$ such that the sum of $\alpha$ and $\beta$ is sufficient to satisfy the otherwise unsatisfied valencies of the C, N, and O atoms; and $T^5$ includes a tertiary or quaternary amine or an organic acid; m is an integer ranging from 0–49, and $T^2$, $T^4$, c, $R^1$, "Amide", L and X have been previously defined.

In the above structures that have a $T^5$ group, -Amide-$T^5$ is preferably one of the following, which are conveniently made by reacting organic acids with free amino groups extending from "G":

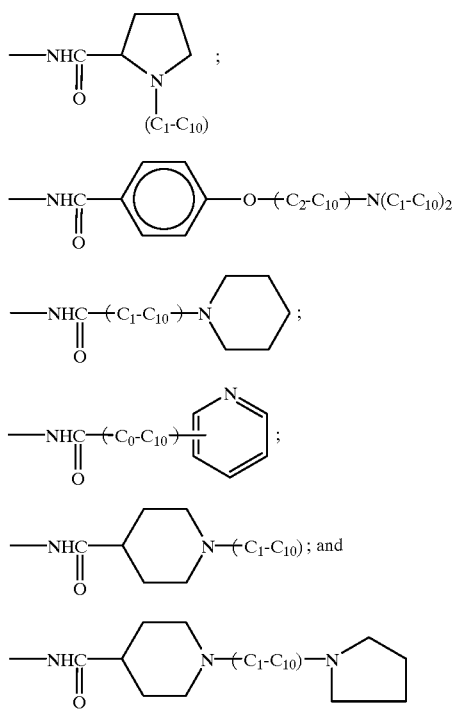

Where the above compounds have a $T^5$ group, and the "G" group has a free carboxyl group (or reactive equivalent thereof), then the following are preferred -Amide-$T^5$ group, which may conveniently be prepared by reacting the appropriate organic amine with a free carboxyl group extending from a "G" group:

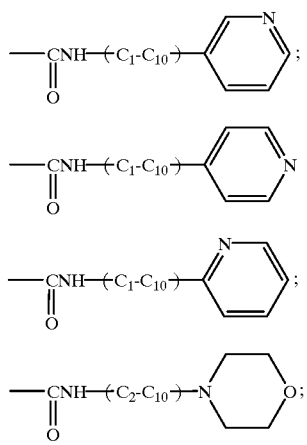

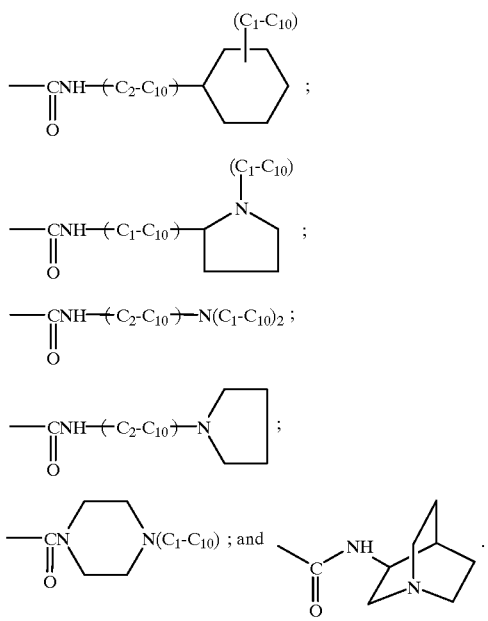

In three preferred embodiments of the invention, T-L-MOI has the structure:

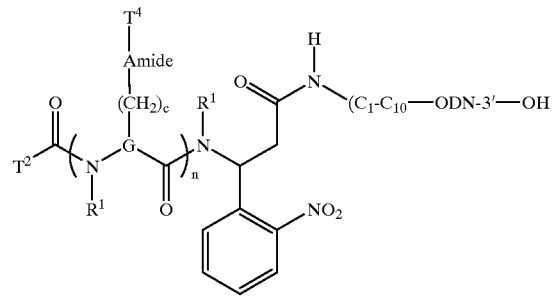

or the structure:

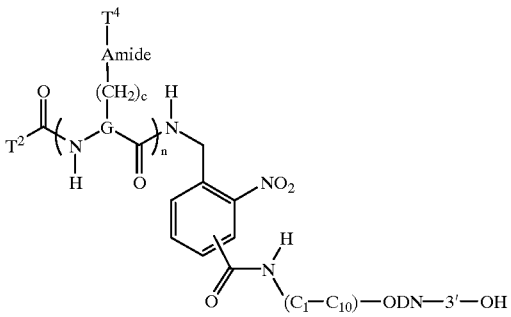

or the structure:

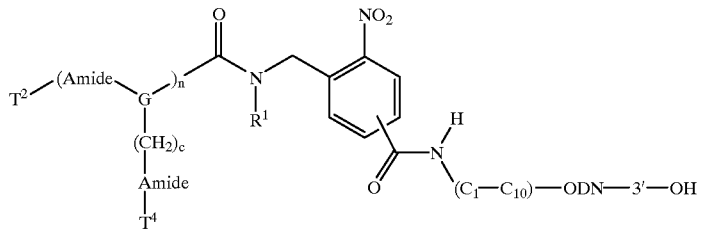

wherein $T^2$ and $T^4$ are organic moieties of the formula $C_{1-25}N_{0-9}O_{0-9}S_{0-3}P_{0-3}H_\alpha F_\beta I_\delta$ such that the sum of $\alpha$, $\beta$ and $\delta$ is sufficient to satisfy the otherwise unsatisfied valencies of the C, N, O, S and P atoms; G is $(CH_2)_{1-6}$ wherein one and only one hydrogen on the $CH_2$ groups represented by each G is replaced with —$(CH_2)_c$-Amide-$T^4$; Amide is

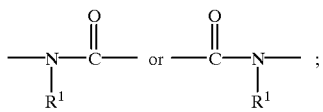

$R^1$ is hydrogen or $C_{1-10}$ alkyl; c is an integer ranging from 0 to 4; "$C_2$–$C_{10}$" represents a hydrocarbylene group having from 2 to 10 carbon atoms, "ODN-3'-OH" represents a nucleic acid fragment having a terminal 3' hydroxyl group (i.e., a nucleic acid fragment joined to $(C_1$–$C_{10})$ at other than the 3' end of the nucleic acid fragment); and n is an integer ranging from 1 to 50 such that when n is greater than 1, then G, c, Amide, $R^1$ and $T^4$ are independently selected. Preferably there are not three heteroatoms bonded to a single carbon atom.

In structures as set forth above that contain a $T^2$-C(=O)—N($R^1$)— group, this group may be formed by reacting an amine of the formula HN($R^1$)— with an organic acid selected from the following, which are exemplary only and do not constitute an exhaustive list of potential organic acids: Formic acid, Acetic acid, Propiolic acid, Propionic acid, Fluoroacetic acid, 2-Butynoic acid, Cyclopropanecarboxylic acid, Butyric acid, Methoxyacetic acid, Difluoroacetic acid, 4-Pentynoic acid, Cyclobutanecarboxylic acid, 3,3-Dimethylacrylic acid, Valeric acid, N,N-Dimethylglycine, N-Formyl-Gly-OH, Ethoxyacetic acid, (Methylthio)acetic acid, Pyrrole-2-carboxylic acid, 3-Furoic acid, Isoxazole-5-carboxylic acid, trans-3-Hexenoic acid, Trifluoroacetic acid, Hexanoic acid, Ac-Gly-OH, 2-Hydroxy-2-methylbutyric acid, Benzoic acid, Nicotinic acid, 2-Pyrazinecarboxylic acid, 1-Methyl-2-pyrrolecarboxylic acid, 2-Cyclopentene-1-acetic acid, Cyclopentylacetic acid, (S)-(–)-2-Pyrrolidone-5-carboxylic acid, N-Methyl-1-proline, Heptanoic acid, Ac-b-Ala-OH, 2-Ethyl-2-hydroxybutyric acid, 2-(2-Methoxyethoxy)acetic acid, p-Toluic acid, 6-Methylnicotinic acid, 5-Methyl-2-pyrazinecarboxylic acid, 2,5-Dimethylpyrrole-3-carboxylic acid, 4-Fluorobenzoic acid, 3,5-Dimethylisoxazole-4-carboxylic acid, 3-Cyclopentylpropionic acid, Octanoic acid, N,N-Dimethylsuccinamic acid, Phenylpropiolic acid, Cinnamic acid, 4-Ethylbenzoic acid, p-Anisic acid, 1,2,5-Trimethylpyrrole-3-carboxylic acid, 3-Fluoro-4-methylbenzoic acid, Ac-DL-Propargylglycine, 3-(Trifluoromethyl)butyric acid, 1-Piperidinepropionic acid, N-Acetylproline, 3,5-Difluorobenzoic acid, Ac-L-Val-OH, Indole-2-carboxylic acid, 2-Benzofurancarboxylic acid, Benzotriazole-5-carboxylic acid, 4-n-Propylbenzoic acid, 3-Dimethylaminobenzoic acid, 4-Ethoxybenzoic acid, 4-(Methylthio)benzoic acid, N-(2-Furoyl)glycine, 2-(Methylthio)nicotinic acid, 3-Fluoro-4-methoxybenzoic acid, Tfa-Gly-OH, 2-Napthoic acid, Quinaldic acid, Ac-L-Ile-OH, 3-Methylindene-2-carboxylic acid, 2-Quinoxalinecarboxylic acid, 1-Methylindole-2-carboxylic acid, 2,3,6-Trifluorobenzoic acid, N-Formyl-L-Met-OH, 2-[2-(2-Methoxyethoxy)ethoxy]acetic acid, 4-n-Butylbenzoic acid, N-Benzoylglycine, 5-Fluoroindole-2-carboxylic acid, 4-n-Propoxybenzoic acid, 4-Acetyl-3,5-dimethyl-2-pyrrolecarboxylic acid, 3,5-Dimethoxybenzoic acid, 2,6-Dimethoxynicotinic acid, Cyclohexanepentanoic acid, 2-Naphthylacetic acid, 4-(1H-Pyrrol-1-yl)benzoic acid, Indole-3-propionic acid, m-Trifluoromethylbenzoic acid, 5-Methoxyindole-2-carboxylic acid, 4-Pentylbenzoic acid, Bz-b-Ala-OH, 4-Diethylaminobenzoic acid, 4-n-Butoxybenzoic acid, 3-Methyl-5-CF3-isoxazole-4-carboxylic acid, (3,4-Dimethoxyphenyl)acetic acid, 4-Biphenylcarboxylic acid, Pivaloyl-Pro-OH, Octanoyl-Gly-OH, (2-Naphthoxy)acetic acid, Indole-3-butyric acid, 4-(Trifluoromethyl)phenylacetic acid, 5-Methoxyindole-3-acetic acid, 4-(Trifluoromethoxy)benzoic acid, Ac-L-Phe-OH, 4-Pentyloxybenzoic acid, Z-Gly-OH, 4-Carboxy-N-(fur-2-ylmethyl)pyrrolidin-2-one, 3,4-Diethoxybenzoic acid, 2,4-Dimethyl-5-$CO_2$Et-pyrrole-3-carboxylic acid, N-(2-Fluorophenyl)succinamic acid, 3,4,5-Trimethoxybenzoic acid, N-Phenylanthranilic acid, 3-Phenoxybenzoic acid, Nonanoyl-Gly-OH, 2-Phenoxypyridine-3-carboxylic acid, 2,5-Dimethyl-1-phenylpyrrole-3-carboxylic acid, trans-4-(Trifluoromethyl)cinnamic acid, (5-Methyl-2-phenyloxazol-4-yl)acetic acid, 4-(2-Cyclohexenyloxy)benzoic acid, 5-Methoxy-2-methylindole-3-acetic acid, trans-4-Cotininecarboxylic acid, Bz-5-Aminovaleric acid, 4-Hexyloxybenzoic acid, N-(3-Methoxyphenyl)succinamic acid, Z-Sar-OH, 4-(3,4-Dimethoxyphenyl)butyric acid, Ac-o-Fluoro-DL-Phe-OH, N-(4-Fluorophenyl)glutaramic acid, 4'-Ethyl-4-biphenylcarboxylic acid, 1,2,3,4-Tetrahydroacridinecarboxylic acid, 3-Phenoxyphenylacetic acid, N-(2,4-Difluorophenyl)succinamic acid, N-Decanoyl-Gly-OH, (+)-6-Methoxy-a-methyl-2-naphthaleneacetic acid, 3-(Trifluoromethoxy)cinnamic acid, N-Formyl-DL-Trp-OH, (R)-(+)-a-Methoxy-a-(trifluoromethyl)phenylacetic acid, Bz-DL-Leu-OH, 4-(Trifluoromethoxy)phenoxyacetic acid, 4-Heptyloxybenzoic acid, 2,3,4-Trimethoxycinnamic acid, 2,6-Dimethoxybenzoyl-Gly-OH, 3-(3,4,5-Trimethoxyphenyl)propionic acid, 2,3,4,5,6-Pentafluorophenoxyacetic acid, N-(2,4-Difluorophenyl)glutaramic acid, N-Undecanoyl-Gly-OH, 2-(4-Fluorobenzoyl)benzoic acid, 5-Trifluoromethoxyindole-2-carboxylic acid, N-(2,4-Difluorophenyl)diglycolamic acid, Ac-L-Trp-OH, Tfa-L-Phenylglycine-OH, 3-Iodobenzoic acid, 3-(4-n-Pentylbenzoyl)propionic acid, 2-Phenyl-4-quinolinecarboxylic acid, 4-Octyloxybenzoic acid, Bz-L-Met-OH, 3,4,5-Triethoxybenzoic acid, N-Lauroyl-Gly-OH, 3,5-Bis(trifluoromethyl)benzoic acid, Ac-5-Methyl-DL-Trp-OH, 2-Iodophenylacetic acid, 3-Iodo-4-methylbenzoic acid, 3-(4-n-Hexylbenzoyl)propionic acid, N—Hexanoyl-L-Phe-OH, 4-Nonyloxybenzoic acid, 4'-(Trifluoromethyl)-2-biphenylcarboxylic acid, Bz-L-Phe-OH, N-Tridecanoyl- Gly-OH, 3,5-Bis(trifluoromethyl)phenylacetic acid, 3-(4-n-Heptylbenzoyl)propionic acid, N-Hepytanoyl-L-Phe-OH, 4-Decyloxybenzoic acid, N-(α,α,α-trifluoro-m-tolyl) anthranilic acid, Niflumic acid, 4-(2-Hydroxyhexafluoroisopropyl)benzoic acid, N-Myristoyl-Gly-OH, 3-(4-n-Octylbenzoyl)propionic acid, N-Octanoyl-L-Phe-OH, 4-Undecyloxybenzoic acid, 3-(3,4,5-Trimethoxyphenyl)propionyl-Gly-OH, 8-Iodonaphthoic acid, N-Pentadecanoyl-Gly-OH, 4-Dodecyloxybenzoic acid, N-Palmitoyl-Gly-OH, and N-Stearoyl-Gly-OH. These organic acids are available from one or more of Advanced ChemTech, Louisville, Ky.; Bachem Bioscience Inc., Torrance, Calif.; Calbiochem-Novabiochem Corp., San Diego, Calif.; Farchan Laboratories Inc., Gainesville Fla.; Lancaster Synthesis, Windham N.H.; and MayBridge Chemical Company (c/o Ryan Scientific), Columbia, S.C. The catalogs from these companies use the abreviations which are used above to identify the acids.

f. Combinatorial Chemistry as a Means for Preparing Tags

Combinatorial chemistry is a type of synthetic strategy which leads to the production of large chemical libraries (see, for example, PCT Application Publication No. WO 94/08051). These combinatorial libraries can be used as tags for the identification of molecules of interest (MOIs). Combinatorial chemistry may be defined as the systematic and repetitive, covalent connection of a set of different "building blocks" of varying structures to each other to yield a large array of diverse molecular entities. Building blocks can take many forms, both naturally occurring and synthetic, such as nucleophiles, electrophiles, dienes, alkylating or acylating agents, diamines, nucleotides, amino acids, sugars, lipids, organic monomers, synthons, and combinations of the above. Chemical reactions used to connect the building blocks may involve alkylation, acylation, oxidation, reduction, hydrolysis, substitution, elimination, addition, cyclization, condensation, and the like. This process can produce libraries of compounds which are oligomeric, non-oligomeric, or combinations thereof. If oligomeric, the compounds can be branched, unbranched, or cyclic. Examples of oligomeric structures which can be prepared by combinatorial methods include oligopeptides, oligonucleotides, oligosaccharides, polylipids, polyesters, polyamides, polyurethanes, polyureas, polyethers, poly(phosphorus derivatives), e.g., phosphates, phosphonates, phosphoramides, phosphonamides, phosphites, phosphinamides, etc., and poly(sulfur derivatives), e.g., sulfones, sulfonates, sulfites, sulfonamides, sulfenamides, etc.

One common type of oligomeric combinatorial library is the peptide combinatorial library. Recent innovations in peptide chemistry and molecular biology have enabled libraries consisting of tens to hundreds of millions of different peptide sequences to be prepared and used. Such libraries can be divided into three broad categories. One category of libraries involves the chemical synthesis of soluble non-support-bound peptide libraries (e.g., Houghten et al., Nature 354:84, 1991). A second category involves the chemical synthesis of support-bound peptide libraries, presented on solid supports such as plastic pins, resin beads, or cotton (Geysen et al., Mol. Immunol. 23:709, 1986; Lam et al., Nature 354:82, 1991; Eichler and Houghten, Biochemistry 32:11035, 1993). In these first two categories, the building blocks are typically L-amino acids, D-amino acids, unnatural amino acids, or some mixture or combination thereof. A third category uses molecular biology approaches to prepare peptides or proteins on the surface of filamentous phage particles or plasmids (Scott and Craig, Curr. Opinion Biotech. 5:40, 1994). Soluble, nonsupport-bound peptide libraries appear to be suitable for a number of applications, including use as tags. The available repertoire of chemical diversities in peptide libraries can be expanded by steps such as permethylation (Ostresh et al., Proc. Natl. Acad. Sci., USA 91:11138, 1994).

Numerous variants of peptide combinatorial libraries are possible in which the peptide backbone is modified, and/or the amide bonds have been replaced by mimetic groups. Amide mimetic groups which may be used include ureas, urethanes, and carbonylmethylene groups. Restructuring the backbone such that sidechains emanate from the amide nitrogens of each amino acid, rather than the alpha-carbons, gives libraries of compounds known as peptoids (Simon et al., Proc. Natl. Acad. Sci., USA 89:9367, 1992).

Another common type of oligomeric combinatorial library is the oligonucleotide combinatorial library, where the building blocks are some form of naturally occurring or unnatural nucleotide or polysaccharide derivatives, including where various organic and inorganic groups may substitute for the phosphate linkage, and nitrogen or sulfur may substitute for oxygen in an ether linkage (Schneider et al., Biochem. 34:9599, 1995; Freier et al., J. Med. Chem. 38:344, 1995; Frank, J. Biotechnology 41:259, 1995; Schneider et al., Published PCT WO 942052; Ecker et al., Nucleic Acids Res. 21:1853, 1993).

More recently, the combinatorial production of collections of non-oligomeric, small molecule compounds has been described (DeWitt et al., Proc. Natl. Acad. Sci., USA 90:690, 1993; Bunin et al., Proc. Natl. Acad. Sci., USA 91:4708, 1994). Structures suitable for elaboration into small-molecule libraries encompass a wide variety of organic molecules, for example heterocyclics, aromatics, alicyclics, aliphatics, steroids, antibiotics, enzyme inhibitors, ligands, hormones, drugs, alkaloids, opioids, terpenes, porphyrins, toxins, catalysts, as well as combinations thereof g. Specific Methods for Combinatorial Synthesis of Tags Two methods for the preparation and use of a diverse set of amine-containing MS tags are outlined below. In both methods, solid phase synthesis is employed to enable simultaneous parallel synthesis of a large number of tagged linkers, using the techniques of combinatorial chemistry. In the first method, the eventual cleavage of the tag from the oligonucleotide results in liberation of a carboxyl amide. In the second method, cleavage of the tag produces a carboxylic acid. The chemical components and linking elements used in these methods are abbreviated as follows:

R=resin
FMOC=fluorenylmethoxycarbonyl protecting group
All=allyl protecting group
$CO_2H$=carboxylic acid group
$CONH_2$=carboxylic amide group
$NH_2$=amino group
OH=hydroxyl group
CONH=amide linkage
COO=ester linkage
$NH_2$—Rink-$CO_2H$=4-[(α-amino)-2,4-dimethoxybenzyl]-phenoxybutyric acid (Rink linker)
OH-1MeO—$CO_2H$=(4-hydroxymethyl)phenoxybutyric acid
OH-2MeO—$CO_2H$=(4-hydroxymethyl-3-methoxy) phenoxyacetic acid
$NH_2$-A-COOH=amino acid with aliphatic or aromatic amine functionality in side chain
X1 . . . Xn-COOH=set of n diverse carboxylic acids with unique molecular weights
oligo1 . . . oligo(n)=set of n oligonucleotides
HBTU=O-benzotriazol-1-yl-N,N,N',N'-tetramethyluronium hexafluorophosphate The sequence of steps in Method 1 is as follows:

```
OH-2MeO-CONH-R
    ↓ FMOC-NH-Rink-CO₂H; couple (e.g, HBTU)
FMOC-NH-Rink-COO-2MeO-CONH-R
    ↓ piperidine (remove FMOC)
NH₂-Rink-COO-2MeO-CONH-R
    ↓ FMOC-NH-A-COOH; couple (e.g, HBTU)
FMOC-NH-A-CONH-Rink-COO-2MeO-CONH-R
    ↓ piperidine (remove FMOC)
NH₂-A-CONH-Rink-COO-2MeO-CONH-R
    ↓ divide into n aliquots
    ↓↓↓↓↓ couple to n different acids X1 . . . Xn-COOH
X1 . . .Xn-CONH-A-CONH-Rink-COO-2Me-CONH-R
    ↓↓↓↓↓ Cleave tagged linkers from resin with 1% TFA
X1 . . . Xn-CONH-A-CONH-Rink-CO₂H
    ↓↓↓↓↓ couple to n oligos (oligo 1 . . . oligo(n))
          (e.g., via Pfp esters)
X1 . . . Xn-CONH-A-CONH-Rink-CONH-oligo1 . . . oligo(n)
    ↓ pool tagged oligos
    ↓ perform sequencing reaction
    ↓ separate different length fragments from
      sequencing reaction (e.g., via HPLC or CB)
    ↓ cleave tags from linkers with 25%–100% TFA
X1 . . . Xn-CONH-A-CONH
    ↓
    analyze by mass spectrometry
```

The sequence of steps in Method 2 is as follows:

```
OH-1MeO-CO₂-All
    ↓ FMOC-NH-A-CO₂H; couple (e.g., HBTU)
FMOC-NH-A-COO-1MeO-CO₂-All
    ↓ Palladium (remove Allyl)
FMOC-NH-A-COO-1MeO-CO₂H
    ↓ OH-2MeO-CONH-R; couple (e.g., HBTU)
FMOC-NH-A-COO-1MeO-COO-2MeO-CONH-R
    ↓ piperidine (remove FMOC)
NH₂-A-COO-1MeO-COO-2MeO-CONH-R
    ↓ divide into n aliquots
    ↓↓↓↓↓ couple to n different acids X1 . . . Xn-CO₂H
X1 . . . Xn-CONH-A-COO-1MeO-COO-2MeO-CONH-R
    ↓↓↓↓↓ cleave tagged linkers from resin with 1% TFA
X1 . . . Xn-CONH-A-COO-1MeO-CO₂H
    ↓↓↓↓↓ couple to n oligos (oligo1 . . . oligo(n))
          (e.g., via Pfp esters)
X1 . . . Xn-CONH-A-COO-1MeO-CONH-oligo1 . . . oligo(n)
    ↓ pool tagged oligos
    ↓ perform sequencing reaction
    ↓ separate different length fragments from
      sequencing reaction (e.g., via HPLC or CE)
    ↓ cleave tags from linkers with 25–100% TFA
X1 . . . Xn-CONH-A-CO₂H
    ↓
    analyze by mass spectrometry
```

2. Linkers

A "linker" component (or L), as used herein, means either a direct covalent bond or an organic chemical group which is used to connect a "tag" (or T) to a "molecule of interest" (or MOI) through covalent chemical bonds. In addition, the direct bond itself, or one or more bonds within the linker component is cleavable under conditions which allows T to be released (in other words, cleaved) from the remainder of the T-L-X compound (including the MOI component). The tag variable component which is present within T should be stable to the cleavage conditions. Preferably, the cleavage can be accomplished rapidly; within a few minutes and preferably within about 15 seconds or less.

In general, a linker is used to connect each of a large set of tags to each of a similarly large set of MOIs. Typically, a single tag-linker combination is attached to each MOI (to give various T-L-MOI), but in some cases, more than one tag-linker combination may be attached to each individual MOI (to give various (T-L)n-MOI). In another embodiment of the present invention, two or more tags are bonded to a single linker through multiple, independent sites on the linker, and this multiple tag-linker combination is then bonded to an individual MOI (to give various (T)n-L-MOI).

After various manipulations of the set of tagged MOIs, special chemical and/or physical conditions are used to cleave one or more covalent bonds in the linker, resulting in the liberation of the tags from the MOIs. The cleavable bond(s) may or may not be some of the same bonds that were formed when the tag, linker, and MOI were connected together. The design of the linker will, in large part, determine the conditions under which cleavage may be accomplished. Accordingly, linkers may be identified by the cleavage conditions they are particularly susceptible too. When a linker is photolabile (i.e., prone to cleavage by exposure to actinic radiation), the linker may be given the designation $L_{hv}$. Likewise, the designations $L^{acid}$, $L^{base}$, $L^{[O]}$, $L^{[R]}$, $L^{enz}$, $L^{elc}$, $L^{\Delta}$ and $L^{ss}$ may be used to refer to linkers that are particularly susceptible to cleavage by acid, base, chemical oxidation, chemical reduction, the catalytic activity of an enzyme (more simply "enzyme"), electrochemical oxidation or reduction, elevated temperature ("thermal") and thiol exchange, respectively.

Certain types of linker are labile to a single type of cleavage condition, whereas others are labile to several types of cleavage conditions. In addition, in linkers which are capable of bonding multiple tags (to give (T)n-L-MOI type structures), each of the tag-bonding sites may be labile to different cleavage conditions. For example, in a linker having two tags bonded to it, one of the tags may be labile only to base, and the other labile only to photolysis.

A linker which is useful in the present invention possesses several attributes:

1) The linker possesses a chemical handle ($L_h$) through which it can be attached to an MOI.

2) The linker possesses a second, separate chemical handle ($L_h$) through which the tag is attached to the linker. If multiple tags are attached to a single linker ((T)n-L-MOI type structures), then a separate handle exists for each tag.

3) The linker is stable toward all manipulations to which it is subjected, with the exception of the conditions which allow cleavage such that a T-containing moiety is released from the remainder of the compound, including the MOI. Thus, the linker is stable during attachment of the tag to the linker, attachment of the linker to the MOI, and any manipulations of the MOI while the tag and linker (T-L) are attached to it.

4) The linker does not significantly interfere with the manipulations performed on the MOI while the T-L is attached to it. For instance, if the T-L is attached to an oligonucleotide, the T-L must not significantly interfere with any hybridization or enzymatic reactions (e.g., PCR) performed on the oligonucleotide. Similarly, if the T-L is attached to an antibody, it must not significantly interfere with antigen recognition by the antibody.

5) Cleavage of the tag from the remainder of the compound occurs in a highly controlled manner, using physical or chemical processes that do not adversely affect the detectability of the tag.

For any given linker, it is preferred that the linker be attachable to a wide variety of MOIs, and that a wide variety of tags be attachable to the linker. Such flexibility is advantageous because it allows a library of T-L conjugates, once prepared, to be used with several different sets of MOIs.

As explained above, a preferred linker has the formula

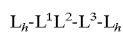

wherein each $L_h$ is a reactive handle that can be used to link the linker to a tag reactant and a molecule of interest reactant. $L^2$ is an essential part of the linker, because $L^2$ imparts lability to the linker. $L^1$ and $L^3$ are optional groups which effectively serve to separate $L^2$ from the handles $L_h$.

$L^1$ (which, by definition, is nearer to T than is $L^3$), serves to separate T from the required labile moiety $L^2$. This separation may be useful when the cleavage reaction generates particularly reactive species (e.g., free radicals) which may cause random changes in the structure of the T-containing moiety. As the cleavage site is further separated from the T-containing moiety, there is a reduced likelihood that reactive species formed at the cleavage site will disrupt the structure of the T-containing moiety. Also, as the atoms in $L^1$ will typically be present in the T-containing moiety, these $L^1$ atoms may impart a desirable quality to the T-containing moiety. For example, where the T-containing moiety is a $T^{ms}$-containing moiety, and a hindered amine is desirably present as part of the structure of the $T^{ms}$-containing moiety (to serve, e.g., as a MSSE), the hindered amine may be present in $L^1$ labile moiety.

In other instances, $L^1$ and/or $L^3$ may be present in a linker component merely because the commercial supplier of a linker chooses to sell the linker in a form having such a $L^1$ and/or $L^3$ group. In such an instance, there is no harm in using linkers having $L^1$ and/or $L^3$ groups, (so long as these group do not inhibit the cleavage reaction) even though they may not contribute any particular performance advantage to the compounds that incorporate them. Thus, the present invention allows for $L^1$ and/or $L^3$ groups to be present in the linker component.

$L^1$ and/or $L^3$ groups may be a direct bond (in which case the group is effectively not present), a hydrocarbylene group (e.g., alkylene, arylene, cycloalkylene, etc.), —O-hydrocarbylene (e.g., —O—$CH_2$—, O—$CH_2$CH($CH_3$)—, etc.) or hydrocarbylene-(O-hydrocarbylene)$_w$- wherein w is an integer ranging from 1 to about 10 (e.g., —$CH_2$—O—Ar—, —$CH_2$—(O—$CH_2CH_2$)$_4$—, etc.).

With the advent of solid phase synthesis, a great body of literature has developed regarding linkers that are labile to specific reaction conditions. In typical solid phase synthesis, a solid support is bonded through a labile linker to a reactive site, and a molecule to be synthesized is generated at the reactive site. When the molecule has been completely synthesized, the solid support-linker-molecule construct is subjected to cleavage conditions which releases the molecule from the solid support. The labile linkers which have been developed for use in this context (or which may be used in this context) may also be readily used as the linker reactant in the present invention.

Lloyd-Williams, P., et al., "Convergent Solid-Phase Peptide Synthesis", Tetrahedron Report No. 347, 49(48): 11065–11133 (1993) provides an extensive discussion of linkers which are labile to actinic radiation (i.e., photolysis), as well as acid, base and other cleavage conditions. Additional sources of information about labile linkers are well known in the art.

As described above, different linker designs will confer cleavability ("lability") under different specific physical or chemical conditions. Examples of conditions which serve to cleave various designs of linker include acid, base, oxidation, reduction, fluoride, thiol exchange, photolysis, and enzymatic conditions.

Examples of cleavable linkers that satisfy the general criteria for linkers listed above will be well known to those in the art and include those found in the catalog available from Pierce (Rockford, Ill.). Examples include:

ethylene glycobis(succinimidylsuccinate) (EGS), an amine reactive cross-linking reagent which is cleavable by hydroxylamine (1 M at 37° C. for 3–6 hours);

disuccinimidyl tartarate (DST) and sulfo-DST, which are amine reactive cross-linking reagents, cleavable by 0.015 M sodium periodate;

bis[2-(succinimidyloxycarbonyloxy)ethyl]sulfone (BSOCOES) and sulfo-BSOCOES, which are amine reactive cross-linking reagents, cleavable by base (pH 11.6);

1,4-di-[3'-(2'-pyridyldithio(propionamido)]butane (DPDPB), a pyridyldithiol crosslinker which is cleavable by thiol exchange or reduction;

N-[4-(p-azidosalicylamido)-butyl]-3'-(2'-pyridyldithio) propionamide (APDP), a pyridyldithiol crosslinker which is cleavable by thiol exchange or reduction;

bis-[beta-4-(azidosalicylamido)ethyl]-disulfide, a photoreactive crosslinker which is cleavable by thiol exchange or reduction;

N-succinimidyl-(4-azidophenyl)-1,3'dithiopropionate (SADP), a photoreactive crosslinker which is cleavable by thiol exchange or reduction;

sulfosuccinimidyl-2-(7-azido-4-methylcoumarin-3-acetamide)ethyl-1,3'-dithiopropionate (SAED), a photoreactive crosslinker which is cleavable by thiol exchange or reduction;

sulfosuccinimidyl-2-(m-azido-o-nitrobenzamido)-ethyl-1,3'dithiopropionate (SAND), a photoreactive crosslinker which is cleavable by thiol exchange or reduction.

Other examples of cleavable linkers and the cleavage conditions that can be used to release tags are as follows. A silyl linking group can be cleaved by fluoride or under acidic conditions. A 3-, 4-, 5-, or 6-substituted-2-nitrobenzyloxy or 2-, 3-, 5-, or 6-substituted-4-nitrobenzyloxy linking group can be cleaved by a photon source (photolysis). A 3-, 4-, 5-, or 6-substituted-2-alkoxyphenoxy or 2-, 3-, 5-, or 6-substituted-4-alkoxyphenoxy linking group can be cleaved by $Ce(NH_4)_2(NO_3)_6$ (oxidation). A $NCO_2$ (urethane) linker can be cleaved by hydroxide (base), acid, or $LiAlH_4$ (reduction). A 3-pentenyl, 2-butenyl, or 1-butenyl linking group can be cleaved by $O_3$, $O_sO_4/IO_4^-$, or $KMnO_4$ (oxidation). A 2-[3-, 4-, or 5-substituted-furyl]oxy linking group can be cleaved by $O_2$, $Br_2$, MeOH, or acid.

Conditions for the cleavage of other labile linking groups include: t-alkyloxy linking groups can be cleaved by acid; methyl(dialkyl)methoxy or 4-substituted-2-alkyl-1,3-dioxlane-2-yl linking groups can be cleaved by $H_3O$; 2-silylethoxy linking groups can be cleaved by fluoride or acid; 2-(X)-ethoxy (where X=keto, ester amide, cyano, $NO_2$, sulfide, sulfoxide, sulfone) linking groups can be cleaved under alkaline conditions; 2-, 3-, 4-, 5-, or 6-substituted-benzyloxy linking groups can be cleaved by acid or under reductive conditions; 2-butenyloxy linking groups can be cleaved by $(Ph_3P)_3RhCl(H)$, 3-, 4-, 5-, or 6-substituted-2-bromophenoxy linking groups can be cleaved by Li, Mg, or BuLi; methylthiomethoxy linking groups can be cleaved by $Hg^{2+}$; 2-(X)-ethyloxy (where X=a halogen) linking groups can be cleaved by Zn or Mg; 2-hydroxyethyloxy linking groups can be cleaved by oxidation (e.g., with $Pb(OAc)_4$).

Preferred linkers are those that are cleaved by acid or photolysis. Several of the acid-labile linkers that have been developed for solid phase peptide synthesis are useful for linking tags to MOIs. Some of these linkers are described in a recent review by Lloyd-Williams et al. (*Tetrahedron* 49:11065–11133, 1993). One useful type of linker is based upon p-alkoxybenzyl alcohols, of which two, 4-ydroxymethylphenoxyacetic acid and 4-(4-hydroxymethyl-3-methoxyphenoxy)butyric acid, are commercially available from Advanced ChemTech (Louisville, Ky.). Both linkers can be attached to a tag via an ester linkage to the benzylalcohol, and to an amine-containing MOI via an amide linkage to the carboxylic acid. Tags linked by these molecules are released from the MOI with varying concentrations of trifluoroacetic acid. The cleavage of these linkers results in the liberation of a carboxylic acid on the tag. Acid cleavage of tags attached through related linkers, such as 2,4-dimethoxy-4'-(carboxymethyloxy)-benzhydrylamine (available from Advanced ChemTech in FMOC-protected form), results in liberation of a carboxylic amide on the released tag.

The photolabile linkers useful for this application have also been for the most part developed for solid phase peptide synthesis (see Lloyd-Williams review). These linkers are usually based on 2-nitrobenzylesters or 2-nitrobenzylamides. Two examples of photolabile linkers that have recently been reported in the literature are 4-(4-(1-Fmoc-amino)ethyl)-2-methoxy-5-nitrophenoxy)butanoic acid (Holmes and Jones, *J. Org. Chem.* 60:2318–2319, 1995) and 3-(Fmoc-amino)-3-(2-nitrophenyl)propionic acid (Brown et al., *Molecular Diversity* 1:4–12, 1995). Both linkers can be attached via the carboxylic acid to an amine on the MOI. The attachment of the tag to the linker is made by forming an amide between a carboxylic acid on the tag and the amine on the linker. Cleavage of photolabile linkers is usually performed with UV light of 350 nm wavelength at intensities and times known to those in the art. Cleavage of the linkers results in liberation of a primary amide on the tag. Examples of photocleavable linkers include nitrophenyl glycine esters, exo- and endo-2-benzonorborneyl chlorides and methane sulfonates, and 3-amino-3(2-nitrophenyl) propionic acid. Examples of enzymatic cleavage include esterases which will cleave ester bonds, nucleases which will cleave phosphodiester bonds, proteases which cleave peptide bonds, etc.

A preferred linker component has an ortho-nitrobenzyl structure as shown below:

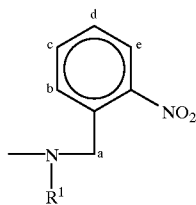

wherein one carbon atom at positions a, b, c, d or e is substituted with -L³-X, and L¹ (which is preferably a direct bond) is present to the left of N(R¹) in the above structure. Such a linker component is susceptible to selective photo-induced cleavage of the bond between the carbon labeled "a" and N(R¹). The identity of R¹ is not typically critical to the cleavage reaction, however R¹ is preferably selected from hydrogen and hydrocarbyl. The present invention provides that in the above structure, —N(R¹)— could be replaced with —O—. Also in the above structure, one or more of positions b, c, d or e may optionally be substituted with alkyl, alkoxy, fluoride, chloride, hydroxyl, carboxylate or amide, where these substituents are independently selected at each occurrence.

A further preferred linker component with a chemical handle $L_h$ has the following structure:

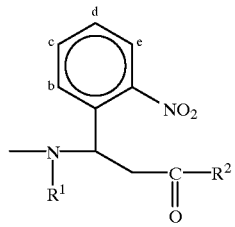

wherein one or more of positions b, c, d or e is substituted with hydrogen, alkyl, alkoxy, fluoride, chloride, hydroxyl, carboxylate or amide, R¹ is hydrogen or hydrocarbyl, and R² is —OH or a group that either protects or activates a carboxylic acid for coupling with another moiety. Fluorocarbon and hydrofluorocarbon groups are preferred groups that activate a carboxylic acid toward coupling with another moiety.

3. Molecule of Interest (MOI)

Examples of MOIs include nucleic acids or nucleic acid analogues (e.g., PNA), fragments of nucleic acids (i.e., nucleic acid fragments), synthetic nucleic acids or fragments, oligonucleotides (e.g., DNA or RNA), proteins, peptides, antibodies or antibody fragments, receptors, receptor ligands, members of a ligand pair, cytokines, hormones, oligosaccharides, synthetic organic molecules, drugs, and combinations thereof.

Preferred MOIs include nucleic acid fragments. Preferred nucleic acid fragments are primer sequences that are complementary to sequences present in vectors, where the vectors are used for base sequencing. Preferably a nucleic acid fragment is attached directly or indirectly to a tag at other than the 3' end of the fragment; and most preferably at the 5' end of the fragment. Nucleic acid fragments may be purchased or prepared based upon genetic databases (e.g., Dib et al., Nature 380:152–154, 1996 and CEPH Genotype Database, http://www.cephb.fr) and commercial vendors (e.g., Promega, Madison, Wis.).

As used herein, MOI includes derivatives of an MOI that contain functionality useful in joining the MOI to a T-L-$L_h$ compound. For example, a nucleic acid fragment that has a phosphodiester at the 5' end, where the phosphodiester is also bonded to an alkyleneamine, is an MOI. Such an MOI is described in, e.g., U.S. Pat. No. 4,762,779 which is incorporated herein by reference. A nucleic acid fragment with an internal modification is also an MOI. An exemplary internal modification of a nucleic acid fragment is where the base (e.g., adenine, guanine, cytosine, thymidine, uracil) has been modified to add a reactive functional group. Such internally modified nucleic acid fragments are commercially available from, e.g., Glen Research, Herndon, Va. Another exemplary internal modification of a nucleic acid fragment is where an abasic phosphoramidate is used to synthesize a modified phosphodiester which is interposed between a sugar and phosphate group of a nucleic acid fragment. The abasic phosphoramidate contains a reactive group which allows a nucleic acid fragment that contains this phosphoramidate-derived moiety to be joined to another moiety, e.g., a T-L-$L_h$ compound. Such abasic phosphoramidates are commercially available from, e.g., Clonetech Laboratories, Inc., Palo Alto, Calif.

4. Chemical Handles ($L_h$)

A chemical handle is a stable yet reactive atomic arrangement present as part of a first molecule, where the handle can undergo chemical reaction with a complementary chemical handle present as part of a second molecule, so as to form a covalent bond between the two molecules. For example, the chemical handle may be a hydroxyl group, and the complementary chemical handle may be a carboxylic acid group (or an activated derivative thereof, e.g., a hydrofluoroaryl ester), whereupon reaction between these two handles forms a covalent bond (specifically, an ester group) that joins the two molecules together.

Chemical handles may be used in a large number of covalent bond-forming reactions that are suitable for attaching tags to linkers, and linkers to MOIs. Such reactions include alkylation (e.g., to form ethers, thioethers), acylation (e.g., to form esters, amides, carbamates, ureas, thioureas), phosphorylation (e.g., to form phosphates, phosphonates, phosphoramides, phosphonamides), sulfonylation (e.g., to form sulfonates, sulfonamides), condensation (e.g., to form imines, oximes, hydrazones), silylation, disulfide formation, and generation of reactive intermediates, such as nitrenes or carbenes, by photolysis. In general, handles and bond-forming reactions which are suitable for attaching tags to linkers are also suitable for attaching linkers to MOIs, and vice-versa. In some cases, the MOI may undergo prior modification or derivitization to provide the handle needed for attaching the linker.

One type of bond especially useful for attaching linkers to MOIs is the disulfide bond. Its formation requires the presence of a thiol group ("handle") on the linker, and another thiol group on the MOI. Mild oxidizing conditions then suffice to bond the two thiols together as a disulfide. Disulfide formation can also be induced by using an excess of an appropriate disulfide exchange reagent, e.g., pyridyl disulfides. Because disulfide formation is readily reversible, the disulfide may also be used as the cleavable bond for liberating the tag, if desired. This is typically accomplished under similarly mild conditions, using an excess of an appropriate thiol exchange reagent, e.g., dithiothreitol.

Of particular interest for linking tags (or tags with linkers) to oligonucleotides is the formation of amide bonds. Primary aliphatic amine handles can be readily introduced onto synthetic oligonucleotides with phosphoramidites such as 6-monomethoxytritylhexylcyanoethyl-N,N-diisopropyl phosphoramidite (available from Glenn Research, Sterling, Va.). The amines found on natural nucleotides such as adenosine and guanosine are virtually unreactive when compared to the introduced primary amine. This difference in reactivity forms the basis of the ability to selectively form amides and related bonding groups (e.g., ureas, thioureas, sulfonamides) with the introduced primary amine, and not the nucleotide amines.

As listed in the Molecular Probes catalog (Eugene, Oreg.), a partial enumeration of amine-reactive functional groups includes activated carboxylic esters, isocyanates, isothiocyanates, sulfonyl halides, and dichlorotriazenes. Active esters are excellent reagents for amine modification since the amide products formed are very stable. Also, these reagents have good reactivity with aliphatic amines and low reactivity with the nucleotide amines of oligonucleotides. Examples of active esters include N-hydroxysuccinimide esters, pentafluorophenyl esters, tetrafluorophenyl esters, and p-nitrophenyl esters. Active esters are useful because they can be made from virtually any molecule that contains a carboxylic acid. Methods to make active esters are listed in Bodansky (*Principles of Peptide Chemistry* (2d ed.), Springer Verlag, London, 1993).

5. Linker Attachment

Typically, a single type of linker is used to connect a particular set or family of tags to a particular set or family of MOIs. In a preferred embodiment of the invention, a single, uniform procedure may be followed to create all the various T-L-MOI structures. This is especially advantageous when the set of T-L-MOI structures is large, because it allows the set to be prepared using the methods of combinatorial chemistry or other parallel processing technology. In a similar manner, the use of a single type of linker allows a single, uniform procedure to be employed for cleaving all the various T-L-MOI structures. Again, this is advantageous for a large set of T-L-MOI structures, because the set may be processed in a parallel, repetitive, and/or automated manner.

There are, however, other embodiment of the present invention, wherein two or more types of linker are used to connect different subsets of tags to corresponding subsets of MOIs. In this case, selective cleavage conditions may be used to cleave each of the linkers independently, without cleaving the linkers present on other subsets of MOIs.

A large number of covalent bond-forming reactions are suitable for attaching tags to linkers, and linkers to MOIs. Such reactions include alkylation (e.g., to form ethers, thioethers), acylation (e.g., to form esters, amides, carbamates, ureas, thioureas), phosphorylation (e.g., to form phosphates, phosphonates, phosphoramides, phosphonamides), sulfonylation (e.g., to form sulfonates, sulfonamides), condensation (e.g., to form imines, oximes, hydrazones), silylation, disulfide formation, and generation of reactive intermediates, such as nitrenes or carbenes, by photolysis. In general, handles and bond-forming reactions which are suitable for attaching tags to linkers are also suitable for attaching linkers to MOIs, and vice-versa. In some cases, the MOI may undergo prior modification or derivitization to provide the handle needed for attaching the linker.

One type of bond especially useful for attaching linkers to MOIs is the disulfide bond. Its formation requires the presence of a thiol group ("handle") on the linker, and another thiol group on the MOI. Mild oxidizing conditions then suffice to bond the two thiols together as a disulfide. Disulfide formation can also be induced by using an excess of an appropriate disulfide exchange reagent, e.g., pyridyl disulfides. Because disulfide formation is readily reversible, the disulfide may also be used as the cleavable bond for liberating the tag, if desired. This is typically accomplished under similarly mild conditions, using an excess of an appropriate thiol exchange reagent, e.g., dithiothreitol.

Of particular interest for linking tags to oligonucleotides is the formation of amide bonds. Primary aliphatic amine handles can be readily introduced onto synthetic oligonucleotides with phosphoramidites such as 6-monomethoxytritylhexylcyanoethyl-N,N-diisopropyl phosphoramidite (available from Glenn Research, Sterling, Va.). The amines found on natural nucleotides such as adenosine and guanosine are virtually unreactive when compared to the introduced primary amine. This difference in reactivity forms the basis of the ability to selectively form amides and related bonding groups (e.g., ureas, thioureas, sulfonamides) with the introduced primary amine, and not the nucleotide amines.

As listed in the Molecular Probes catalog (Eugene, Oreg.), a partial enumeration of amine-reactive functional groups includes activated carboxylic esters, isocyanates, isothiocyanates, sulfonyl halides, and dichlorotriazenes. Active esters are excellent reagents for amine modification since the amide products formed are very stable. Also, these reagents have good reactivity with aliphatic amines and low reactivity with the nucleotide amines of oligonucleotides. Examples of active esters include N-hydroxysuccinimide esters, pentafluorophenyl esters, tetrafluorophenyl esters, and p-nitrophenyl esters. Active esters are useful because they can be made from virtually any molecule that contains a carboxylic acid. Methods to make active esters are listed in Bodansky (*Principles of Peptide Chemistry* (2d ed.), Springer Verlag, London, 1993).

Numerous commercial cross-linking reagents exist which can serve as linkers (e.g., see Pierce Cross-linkers, Pierce Chemical Co., Rockford, Ill.). Among these are homobifunctional amine-reactive cross-linking reagents which are exemplified by homobifunctional imidoesters and N-hydroxysuccinimidyl (NHS) esters. There also exist heterobifunctional cross-linking reagents possess two or more different reactive groups that allows for sequential reactions. Imidoesters react rapidly with amines at alkaline pH. NHS-esters give stable products when reacted with primary or secondary amines. Maleimides, alkyl and aryl halides, alpha-haloacyls and pyridyl disulfides are thiol reactive. Malcimides are specific for thiol (sulfhydryl) groups in the pH range of 6.5 to 7.5, and at alkaline pH can become amine reactive. The thioether linkage is stable under physiological conditions. Alpha-haloacetyl cross-linking reagents contain the iodoacetyl group and are reactive towards sulfhiydryls. Imidazoles can react with the iodoacetyl moiety, but the reaction is very slow. Pyridyl disulfides react with thiol groups to form a disulfide bond. Carbodiimides couple carboxyls to primary amines of hydrazides which give rises to the formation of an acyl-hydrazine bond. The arylazides are photoaffinity reagents which are chemically inert until exposed to UV or visible light. When such compounds are photolyzed at 250–460 nm, a reactive aryl nitrene is formed. The reactive aryl nitrene is relatively non-specific. Glyoxals are reactive towards guanidinyl portion of arginine.

In one typical embodiment of the present invention, a tag is first bonded to a linker, then the combination of tag and linker is bonded to a MOI, to create the structure T-L-MOI. Alternatively, the same structure is formed by first bonding a linker to a MOI, and then bonding the combination of linker and MOI to a tag. An example is where the MOI is a DNA primer or oligonucleotide. In that case, the tag is typically first bonded to a linker, then the T-L is bonded to a DNA primer or oligonucleotide, which is then used, for example, in a sequencing reaction.

One useful form in which a tag could be reversibly attached to an MOI (e.g., an oligonucleotide or DNA sequencing primer) is through a chemically labile linker. One preferred design for the linker allows the linker to be cleaved when exposed to a volatile organic acid, for example, trifluoroacetic acid (TFA). TFA in particular is compatible with most methods of MS ionization, including electrospray.

The invention compositions for mutation analysis. A composition useful for mutation analysis comprises a pair of compounds of the formula:

$T^{ms}$-L-MOI wherein $T^{ms}$ is an organic group detectable by mass spectrometry, comprising carbon, at least one of hydrogen and fluoride, and optional atoms selected from oxygen, nitrogen, sulfur, phosphorus and iodine. In the formula, L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid. In the formula, MOI is a nucleic acid fragment wherein L is conjugated to MOI at other than the 3' end of the MOI. The composition comprises pairs of compounds where the members of a pair have non-identical $T^{ms}$ groups, and have identical sequences except at one base position where the bases are non-identical. In another embodiment of the inventive composition, the member of the pairs of compounds have non-identical $T^{ms}$ groups, and have identical sequences except at one base position where the bases are non-identical. These compositions are then added to a support-bound nucleic acid sequence, which is identical to the sequence of one of the members of each pair. Thus, the invention provides for a composition comprising a plurality of compound pairs as described above, and further comprising an equal plurality of nucleic acids immobilized on a solid support, wherein each member of the plurality of nucleic acids has a base sequence that is exactly complementary to one member of each of the pairs.

The invention also provides a kit for mutation analysis comprising a plurality of containers. Each container comprises a pair of compounds of the formula:

$T^{ms}$-L-MOI wherein $T^{ms}$ is an organic group detectable by mass spectrometry, comprising carbon, at least one of hydrogen and fluoride, and optional atoms selected from oxygen, nitrogen, sulfur, phosphorus and iodine. In the formula, L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid. In the formula, MOI is a nucleic acid fragment wherein L is conjugated to MOI at other than the 3' end of the MOI. In the kit, the compounds of each pair have non-identical $T^{ms}$ groups, and have identical sequences except at one or two base position where the bases are non-identical. In a preferred kit, the plurality is at least 3, and more preferably is at least 5.

Assays

As noted above, the present invention a wide variety of assays wherein the tags and detection methodology provided herein can be utilized in order to greatly increase the sensitivity and throughput of the assay. Within one aspect, such methods can be utilized to detect the binding of a first member to a second member of a ligand pair, comprising the steps of (a) combining a set of first tagged members with a biological sample which may contain one or more second members, under conditions, and for a time sufficient to permit binding of a first member to a second member, wherein said tag is correlative with a particular first member and detectable by non-fluorescent spectrometry, or potentiometry, (b) separating bound first and second members from unbound members, (c) cleaving the tag from the tagged first member, and (d) detecting the tag by non-fluorescent spectrometry, or potentiometry, and therefrom detecting the binding of the first member to the second member.

A wide variety of first and second member pairs may be utilized within the context of the present invention, including for example, nucleic acid molecules (e.g., DNA, RNA, nucleic acid analogues such as PNA, or any combination of these), proteins or polypeptides (e.g., an antibodies or antibody fragments (e.g., monoclonal antibodies, polyclonal antibodies, or binding partners such as a CDR), oligosaccharides, hormones, organic molecules and other substrates (e.g., xenobiotics such as glucuronidase—drug molecule), or any other ligand of a ligand pair. Within various embodiments of the invention, the first and second members may be the same type of molecule or of different types. For example, representative first member second member ligand pairs include: nucleic acid molecule/nucleic acid molecule; antibody/nucleic acid molecule; antibody/hormone; antibody/xenobiotic; and antibody/protein.

In order to further an understanding of assays which can be accomplished given the disclosure provided herein, a brief discussion is provided below of certain particularly preferred assays.

6. Nucleic Acid Assays a. Introduction

As noted above, the present invention also provides a wide variety of methods wherein the above-described cleavable tags and/or linkers may be utilized in place of traditional labels (e.g., radioactive, fluorescent, or enzymatic), in order enhance the specificity, sensitivity, or number of samples that may be simultaneously analyzed, within a given method. Representative examples of such methods which may be enhanced include, for example, standard nucleic acid hybridization reactions (see Sambrook et al., supra), diagnostic reactions such as Cycling Probe Technology (CPT) (see U.S. Pat. Nos. 4,876,187 and 5,011,769) or Oligonucleotide-Ligation Assay (OLA) (Burket et al., *Science* 196:180, 1987). These as well as other techniques are discussed in more detail below.

b. Hybridization Techniques

The successful cloning and sequencing of a gene allows investigation of its structure and expression by making it possible to detect the gene or its mRNA in a large pool of unrelated DNA or RNA molecules. The amount of mRNA encoding a specific protein in a tissue is an important parameter for the activity of a gene and may be significantly related to the activity of function systems. Its regulation is dependent upon the interaction between sequences within the gene (cis-acting elements) and sequence-specific DNA binding proteins (trans-acting factors), which are activated tissue-specifically or by hormones and second messenger systems.

Several techniques are available for analysis of a particular gene, its regulatory sequences, its specific mRNA and the regulation of its expression; these include Southern or Northern blot analysis, ribonuclease (RNase) protection assay and in situ hybridization.

Variations in the nucleotide composition of a certain gene may be of great pathophysiological relevance. When localized in the non-coding regions (5', 3'-flanking regions and intron), they can affect the regulation of gene expression, causing abnormal activation or inhibition. When localized in the coding regions of the gene (exons), they may result in alteration of the protein function or dysfunctional proteins.

Thus, a certain sequence within a gene can correlate to a specific disease and can be useful as a marker of the disease. One primary goal of research in the medical field is, therefore, to detect those genetic variations as diagnostic tools, and to gain important information for the understanding of pathophysiological phenomena.

The basic method for the analysis of a population regarding the variations within a certain gene is DNA analysis using the Southern blot technique. Briefly, prepared genomic DNA is digested with a restriction enzyme (RE), resulting in a large number of DNA fragments of different lengths, determined by the presence of the specific recognition site of the RE on the genome. Alleles of a certain gene with mutations inside this restriction site will be cleaved into fragments of different number and length. This is called restriction fragment length polymorphism (RFLP) and can be an important diagnostic marker with many applications.

The fragment to be analyzed has to be separated from the pool of DNA fragments and distinguished from other DNA species using a specific probe. Thus, DNA is subjected to electrophoretic fractionation using an agarose gel, followed by transfer and fixation to a nylon or nitrocellulose membrane. The fixed, single-stranded DNA is hybridized to a tagged DNA which is complementary to the DNA to be detected. After removing non-specific hybridizations, the DNA fragment of interest can be visualized by MALD1-MS as described in more detail below.

The presence and quantification of a specific gene transcript and its regulation by physiological parameters can be analysed by means of Northern blot analysis and RNase protection assay.

The principle basis of these methods is hybridization of a pool of total cellular RNA to a specific probe. In the Northern blot technique, total RNA of a tissue is electrophoretically fractionated using an agarose gel, transferred and immobilized to a labeled antisense RNA (cRNA), complementary to the RNA to be detected. This cRNA probe is then tagged as described herein. By applying stringent washing conditions, non-specifically bound molecules are eliminated. Specifically bound molecules, which can subsequently be detected by MALD1-MS. In addition, specificity can be controlled by comparing the size of the detected mRNA with the predicted length of the mRNA of interest.

More rapid, but less specific, is the dot blot method, which is performed as the Northern blot technique except that the RNA is directly dotted onto the membrane without preceding fractionation. The RNA is immobilized nonspecifically in the dot blot.

The most specific method for detection of an mRNA species is the RNase protection assay. Briefly, total RNA from a tissue or cell culture is hybridized to a tagged specific cRNA of complete homology. Specificity is accomplished by subsequent RNase digestion. Non-hybridized, single-stranded RNA and non-specifically hybridized fragments with even small mismatches will be recognized and cleaved, while double-stranded RNA of complete homology is not accessible to the enzyme and will be protected. After removing RNase by proteinase K digestion and phenol extraction, the specific protected fragment can be separated from degradation products, usually on a denaturing polyacrylamide gel, and the predicted size can be checked by HPLC. All the assays described above can be quantified by non-fluorescent spectrometry or potentiometry.

The precise location of a given mRNA in a specific population of cells within a tissue can be determined by in situ hybridization. This method is analogous with the immunocytochemical technique and can in fact be used simultaneously with immunocytochemistry on the same section to discover, for example, whether a certain protein is really synthesized locally or actually taken up from other sources. Apart from the possibility of identifying the cell type expressing a specific mRNA, in situ hybridization can be even more sensitive than analysis of a total tissue RNA preparation using the techniques described above. This is the case when the mRNA is expressed in high concentrations in a very discrete region or cell type within the tissue and would be diluted by homogenization of the whole tissue. The analysis of gene expression by in situ hybridization is therefore of particular importance for heterogeneous tissues like the brain. For in situ hybridization, the tissues have to be frozen or perfusion-fixed and sectioned according to histochemical protocol. The hybridization protocol for tissue sections and the labeled probes used are similar to the other hybridization methods described above. A semiquantitative analysis is possible.

c. cDNAs as Representative Populations of mRNAs and use as Probes

Most mRNAs are transcribed from single copy sequences. Another property of cDNAs is that they represent a longer region of the genome because of the introns present in the chromosomal version of most genes. The representation varies from one gene to another but can be very significant as many genes cover more than 100 kb in genomic DNA, represented in a single cDNA. One possible use of molecular hybridization is the use of probes from one species to find clones made from another species. Sequence divergence between the mRNAs of mouse and man permits specific cross-reassociation of long sequences, but except for the most highly conserved regions, prevents cross-hybridization of PCR primers.

Differential screening in complex biological samples such as developing nervous system using cDNA probes prepared from single cells is now possible due to the development of PCR-based and cRNA-based amplification techniques. Several groups reported previously the generation of cDNA libraries from small amounts of poly (A)+ RNA (1 ng or less) prepared from 10–50 cells (Belyav et al., Nuc. Acids Res. 17:2919, 1989). Although the libraries were sufficiently representative of mRNA complexity, the average cDNA insert size of these libraries was quite small (<2 kb).

More recently, methodologies have been combined to generate both PCR-based (Lambolez et al., Neuron 9:247, 1992) and cRNA-based (Van Gelder et al., Proc. Natl. Acad. Sci. USA 87:1663, 1990) probes from single cells. After electrical recordings, the cytoplasmic contents of a single cell were aspirated with patch-clamp microelectrodes for in situ cDNA synthesis and amplification. PCR was used to amplify cDNA of selective glutamate receptor mRNAs from single Purkinje cells and GFAP mRNA from single glia in organotypic cerebellar culture (Lambolez et al., Neuron 9:247, 1992). In the case of cRNA amplification, transcription promoter sequences were designed into primers for cDNA synthesis and complex antisense cRNAs were generated by in vitro transcription with bacteriophage RNA polymerases.

Thus, within one embodiment of the invention, tagged cRNAs can be utilized as tagged probes to screen cDNA libraries randomly or in "expression profiling" experiments to screen Southern blots containing cDNA fragments of interest (receptors, growth factors, ion channels etc.). It appears that the lack of linearity of amplification, often encountered with PCR-based approaches, is minimized with cRNA-based methods.

d. Oligonucleotide-Ligation Assay

Oligonucleotide-ligation assay is an extension of PCR-based screening that uses an ELISA-based assay (OLA, Nickerson et al., Proc. Natl. Acad. Sci. USA 87:8923, 1990) to detect the PCR products that contain the target sequence. Thus, both gel electrophoresis and colony hybridization are eliminated. Briefly, the OLA employs two adjacent oligonucleotides: a "reporter" probe (tagged at the 5' end) and a 5'-phosphorylated/3'-biotinylated "anchor" probe. The two oligonucleotides, which are complementary to sequences internal to the PCR primers, are annealed to target DNA and, if there is perfect complementarity, the two probes are ligated by T4 DNA ligase. Capture of the biotinylated anchor probe on immobilized streptavidin and analysis for the covalently linked reporter probe test for the presence or absence of the target sequences among the PCR products.

e. Application of Hybridization Techniques i. Forensics

The identification of individuals at the level of DNA sequence variation offers a number of practical advantages over such conventional criteria as fingerprints, blood type, or physical characteristics. In contrast to most phenotypic markers, DNA analysis readily permits the deduction of relatedness between individuals such as is required in paternity testing. Genetic analysis has proven highly useful in bone marrow transplantation, where it is necessary to distinguish between closely related donor and recipient cells. Two types of probes are now in use for DNA fingerprinting by DNA blots. Polymorphic minisatellite DNA probes identify multiple DNA sequences, each present in variable forms in different individuals, thus generating patterns that are complex and highly variable between individuals. VNTR probes identify single sequences in the genome, but these sequences may be present in up to 30 different forms in the human population as distinguished by the size of the identified fragments. The probability that unrelated individuals will have identical hybridization patterns for multiple VNTR or minisatellite probes is very low. Much less tissue than that required for DNA blots, even single hairs, provides sufficient DNA for a PCR-based analysis of genetic markers. Also, partially degraded tissue may be used for analysis since only small DNA fragments are needed. Forensic DNA analyses will eventually be carried out with polymorphic DNA sequences that can be studied by simple automatable assays such as OLA. For example, the analysis of 22 separate gene sequences, each one present in two different forms in the population, could generate 1010 different outcomes, permitting the unique identification of human individuals.

ii. Tumor diagnostics

The detection of viral or cellular oncogenes is another important field of application of nucleic acid diagnostics. Viral oncogenes (v-oncogenes) are transmitted by retroviruses while their cellular counterparts (c-oncogenes) are already present in normal cells. The cellular oncogenes can, however, be activated by specific modifications such s point mutations (as in the c-K-ras oncogene in bladder carcinoma and in colorectal tumors), promoter induction, gene amplification (as in the N-myc oncogene in the case of neuroblastoma) or the rearrangement of chromosomes (as in the translocation of the c-abl oncogene from chromosome 9 to chromosome 22 in the case of chronic myeloid leukemia). Each of the activation processes leads, in conjunction with additional degenerative processes, to an increased and uncontrolled cell growth. The so-called "recessive oncogenes" which must be inactivated for the formation of a tumor (as in the retinoblastoma (Rb gene and the osteosarcoma can also be detected with the help of DNA probes. Using probes against immunoglobulin genes and against T-cell receptor genes, the detection of B-cell lymphomas and lymphoblastic leukemia is possible.

iii. Transplantation analyses

The rejection reaction of transplanted tissue is decisively controlled by a specific class of histocompatibility antigens (HLA). They are expressed on the surface of antigen-presenting blood cells, e.g., macrophages. The complex between the HLA and the foreign antigen is recognized by T-helper cells through corresponding T-cell receptors on the cell surface. The interaction between HLA, antigen and T-cell receptor triggers a complex defense reaction which leads to a cascade-like immune response on the body.

The recognition of different foreign antigens is mediated by variable, antigen-specific regions of the T-cell receptor—analogous to the antibody reaction. In a graft rejection, the T-cells expressing a specific T-cell receptor which fits to the foreign antigen, could therefore be eliminated from the T-cell pool. Such analyses are possible by the identification of antigen-specific variable DNA sequences which are amplified by PCR and hence selectively increased. The specific amplification reaction permits the single cell-specific identification of a specific T-cell receptor.

Similar analyses are presently performed for the identification of auto-immune disease like juvenile diabetes, arteriosclerosis, multiple sclerosis, rheumatoid arthritis, or encephalomyelitis.

iv. Genome Diagnostics

Four percent of all newborns are born with genetic defects; of the 3,500 hereditary diseases described which are caused by the modification of only a single gene, the primary molecular defects are only known for about 400 of them.

Hereditary diseases have long since been diagnosed by phenotypic analyses (anamneses, e.g., deficiency of blood: thalassemias), chromosome analyses (karyotype, e.g., mongolism: trisomy 21) or gene product analyses (modified proteins, e.g., phenylketonuria: deficiency of the phenylalanine hydroxylase enzyme resulting in enhanced levels of phenylpyruvic acid). The additional use of nucleic acid detection methods considerably increases the range of genome diagnostics.

In the case of certain genetic diseases, the modification of just one of the two alleles is sufficient for disease (dominantly transmitted monogenic defects); in many cases, both alleles must be modified (recessively transmitted monogenic defects). In a third type of genetic defect, the outbreak of the disease is not only determined by the gene modification but also by factors such as eating habits (in the case of diabetes or arteriosclerosis) or the lifestyle (in the case of cancer). Very frequently, these diseases occur in advanced age. Diseases such as schizophrenia, manic depression or epilepsy should also be mentioned in this context; it is under investigation if the outbreak of the disease in these cases is dependent upon environmental factors as well as on the modification of several genes in different chromosome locations.

Using direct and indirect DNA analysis, the diagnosis of a series of genetic diseases has become possible: sickle-cell anemia, thalassemias, a1-antitrypsin deficiency, Lesch-Nyhan syndrome, cystic fibrosis/mucoviscidosis, Duchenne/Becker muscular dystrophy, Alzheimer's disease, X-chromosome-dependent mental deficiency, Huntington's chorea v. Infectious Disease The application of recombinant DNA methods for diagnosis of infectious diseases has been most extensively explored for viral infections where current methods are cumbersome and results are delayed. In situ hybridization of tissues or cultured cells has made diagnosis of acute and chronic herpes infection possible. Fresh and fomalin-fixed tissues have been reported to be suitable for detection of papillomavirus in invasive cervical carcinoma and in the detection of HIV, while cultured cells have been used for the detection of cytomegalovirus and Epstein-Barr virus. The application of recombinant DNA methods to the diagnosis of microbial diseases has the potential to replace current microbial growth methods if cost-effectiveness, speed, and precision requirements can be met. Clinical situations where recombinant DNA procedures have begun to be applied include the identification of penicillin-resistant Neisseria gonorrhoeae by the presence of a transposon, the fastidiously growing chlamydia, microbes in foods; and simple means of following the spread of an infection through a population. The worldwide epidemiological challenge of diseases involving such parasites as leishmania and plasmodia is already being met by recombinant methods.

7. Protein-Based Assays a. Introduction

As noted above, a wide variety of protein based assays may likewise be enhanced by the tags described herein (see, e.g., *Antibodies: A Laboratory Manual*, Harlow and Lane (eds.), Cold Spring Harbor Laboratory Press, 1988. Representative examples include antigen—antibody assays such as: countercurrent immuno-electrophoresis (CIEP), enzyme-linked immuno-sorbent assays (ELISA), inhibition or competition assays, and sandwich assays, simultaneous immunoassays and immunofiltration assays. A wide variety of other assays however may likewise be enhance, including for example, ligand—receptor assays and the like.

b. Immunoassays

Since the development of RIAs for insulin and thyroxin, methods involving radioisotopically labeled antigens have been widely applied in the measurement of haptenic molecules such as hormones and drugs. The methods are based on the competition between a labeled antigen and an unlabeled antigen for a limited amount of antibody. These methods might also be described as "limited reagent" methods because of the limited amount of antibody used in the assay.

Although labeled antibodies have been used in immunofluorescence methods since 1941, they were not more widely applied in quantitative methods until the introduction of radioisotope-labeled antibodies in IRMA. IRMAs, as well as other solid-phase-based double-antibody or "sandwich" assays (ELISA, IFMA, immunofluoresence staining assays), are characterized by an excess of antibodies over antigens; they could thus be called "excess reagent" methods. In principle, using excess reagents shortens the incubation time and potentially increases sensitivity. The solid phase facilitates separation, and the signal is directly proportional to the amount of antigen—as opposed to the inverse relationship in competitive assays.

The use of avidin-biotin technology has become increasingly important in numerous areas of biochemistry, molecular biology, and medicine, including detection of proteins by nonradioactive immunoassays, cytochemical staining, cell separation, and isolation of nucleic acids and detection of specific DNA/RNA sequences by hybridization. The technique derives its usefulness from the extremely high affinity of the avidin-biotin interaction (association constant 1015M-1) and the ability to biotinylate a wide range of target biomolecules such as antibodies, nucleic acids, and lipids. The first step in the isolation of a target molecule is its biotinylation or the biotinylation of a biomolecule which ultimately binds to the target molecule (e.g., an antibody or hybridization probe that forms a target complex). The biotinylated molecule or the target complex is then separated from other molecules in a heterogeneous mixture by using affinity media based on the avidin-biotin interactions.

Thus, within one embodiment of the invention any of the standard immunoassays may be accomplished utilized tagged reagents, rather than the typical isotopically labeled reagents. Such methods result in greatly increased sensitivity, as well as the capability of analyzing many samples simultaneously.

8. Gene Expression Analysis

One of the inventions disclosed herein is a high throughput method for measuring the expression of numerous genes (1–2000) in a single measurement. The method also has the ability to be done in parallel with greater than one hundred samples per process. The method is applicable to drug screening, developmental biology, molecular medicine studies and the like. Thus, within one aspect of the invention methods are provided for analyzing the pattern of gene expression from a selected biological sample, comprising the steps of (a) exposing nucleic acids from a biological sample, (b) combining the exposed nucleic acids with one or more selected tagged nucleic acid probes, under conditions and for a time sufficient for said probes to hybridize to said nucleic acids, wherein the tag is correlative with a particular nucleic acid probe and detectable by non-fluorescent spectrometry, or potentiometry, (c) separating hybridized probes from unhybridized probes, (d) cleaving the tag from the tagged fragment, and (e) detecting the tag by non-fluorescent spectrometry, or potentiometry, and therefrom determining the patter of gene expression of the biological sample.

Within a particularly preferred embodiment of the invention, assays or methods are provided which are described as follows: RNA from a target source is bound to a solid support through a specific hybridization step (i.e., capture of poly(A) mRNA by a tethered oligo(dT) capture probe). The solid support is then washed and cDNA is synthesized on the solid support using standard methods (i.e., reverse transcriptase). The RNA strand is then removed via hydrolysis. The result is the generation of a DNA population which is covalently immobilized to the solid support which reflects the diversity, abundance, and complexity of the RNA from which the cDNA was synthesized. The solid support then interrogated (hybridized) with 1 to several thousand probes which are complementary to a gene sequence of interest. Each probe type is labelled with a cleavable mass spectrometry tag or other type of cleavable tag. After the interrogation step, excess or unhybridized probe is washed away, the solid support is placed (for example) in the well of a microtiter plate and the mass spectrometry tag is cleaved from the solid support. The solid support is removed from the well of sample container, and the contents of the well are measured with a mass spectrometer. The appearance of specific mass spectrometer tags indicate the presence of RNA in the sample and evidence that a specific gene is expressed in a given biological sample. The method can also be quantifiable.

The compositions and methods for the rapid measurement of gene expression using cleavable tags can be described in detail as follows. Briefly, tissue (liver, muscle, etc.), primary or transformed cell lines, isolated or purified cell types or any other source of biological material in which determining genetic expression is useful can be used as a source of RNA. In the preferred method, the biological source material is lysed in the presence of a chaotrope in order to suppress nucleases and proteases and support stringent hybridization of target nucleic acid to the solid support. Tissues, cells and biological sources can be effectively lysed in 1 to 6 molar chaotropic salts (guanidine hydrochloride, guanidine thiocyanate, sodium perchlorate, etc.). After the source biological sample is lysed, the solution is mixed with a solid support to effect capture of target nucleic acid present in the lysate. In one permutation of the method, RNA is captured using a tethered oligo(dT) capture probe. Solid supports can include nylon beads, polystyrene microbeads, glass beads and glass surfaces or any other type of solid support to which oligonucleotides can be covalently attached. The solid supports are preferentially coated with an amine-polymer such as polyethylene(imine), acrylamide, amine-dendrimers, etc. The amines on the polymers are used to covalently immobilize oligonucleotides. Oligonucleotides are preferentially synthesized with a 5'-amine (generally a hexylamine which is includes a six carbon spacer-arm and a distal amine). Oligonucleotides can be 15 to 50 nucleotides in length. Oligonucleotides are activated with homo-bifunctional or hetero-bifunctional cross-linking reagents such as cyanuric chloride. The activated oligonucleotides are purified from excess cross-linking reagent (i.e., cyanuric chloride) by exclusion chromatography. The activated oligonucleotide are then mixed with the solid supports to effect covalent attachment. After covalent attachment of the oligonucleotides, the unreacted amines of the solid support are capped (i.e., with succinic anhydride) to eliminate the positive charge of the solid support.

The solid supports can be used in parallel and are preferentially configured in a 96-well or 384-well format. The solid supports can be attached to pegs, stems, or rods in a 96-well or 384-well configuration, the solid supports either being detachable or alternatively integral to the particular configuration. The particular configuration of the sold supports is not of critical importance to the functioning of the assay, but rather, affects the ability of the assay to be adapted to automation.

The solid supports are mixed with the lysate for 15 minutes to several hours to effect capture of the target nucleic acid onto the solid support. In general, the "capture" of the target nucleic acid is through complementary base pairing of target RNA and the capture probe immobilized on the solid support. One permutation utilizes the 3' poly(A) stretch found on most eucaryotic messengers RNAs to hybridize to a tethered oligo(dT) on the solid support. Another permutation is to utilize a specific oligonucleotide or long probes (greater than 50 bases) to capture an RNA containing a defined sequence. Another possibility is to employ degenerate primers (oligonucleotides) that would effect the capture of numerous related sequences in the target RNA population. Hybridization times are guided by the sequence complexity of the RNA population and the type of capture probe employed. Hybridization temperatures are dictated by the type of chaotrope employed and the final concentration of chaotrope (see Van Ness and Chen, *Nuc. Acids Res.* for general guidelines). The lysate is preferentially agitated with the solid support continually to effect diffusion of the target RNA. Once the step of capturing the target nucleic acid is accomplished, the lysate is washed from the solid support and all chaotrope or hybridization solution is removed. The solid support is preferentially washed with solutions containing ionic or non-ionic detergents, buffers and salts. The next step is the synthesis of DNA complementary to the captured RNA. In this step, the tethered capture oligonucleotide serves as the extension primer for reverse transcriptase. The reaction is generally performed at 25 to 37° C. and preferably agitated during the polymerization reaction. After the cDNA is synthesized, it becomes covalently attached to the solid support since the capture oligonucleotide serves as the extension primer. The RNA is then hydrolysed from the cDNA/RNA duplex. The step can be effected by the use of heat which denatures the duplex or the use of base (i.e., 0.1 N NaOH) to chemically hydrolyse the RNA. The key result at this step is to make the cDNA available for subsequent hybridization with defined probes. The solid support or set of solid supports are then further washed to remove RNA or RNA fragments. At this point the solid support contains a approximate representative population of cDNA molecules that represents the RNA population in terms of sequence abundance, complexity, and diversity.

The next step is to hybridize selected probes to the solid support to identify the presence or absence and the relative abundance specific cDNA sequences. Probes are preferentially oligonucleotides in length of 15 to 50 nucleotides. The sequence of the probes is dictated by the end-user of the assay. For example, if the end-user intended to study gene expression in an inflammatory response in a tissue, probes would be selected to be complementary to numerous cytokine mRNAs, RNAs that encode enzymes that modulate lipids, RNAs that encode factors that regulate cells involved in an inflammatory response, etc. Once a set of defined sequences are defined for study, each sequence is made into an oligonucleotide probe and each probe is assigned a specific cleavable tag. The tag(s) is then attached to the respective oligonucleotide(s). The oligonucleotide(s) are then hybridized to the cDNA on the solid support under appropriate hybridization conditions. After completion of the hybridization step, the solid support is washed to remove any unhybridized probe. The solid support or array of supports are then place in solutions which effect the cleavage of the mass spectrometer tags. The mass spectrometer tags are then subjected to measurement by a mass spectrometer, the mass each tag present is identified, and the presence (and abundance) or absence of an expressed mRNA is determined.

9. Detection of Micro-Organisms, Specific Gene Expression or Specific Sequences in Nucleic Acid The use of DNA probes with cleavable tags can be used to detect the presence or absence of micro-organisms in any type of sample or specimen. Typically, the sample will be subjected to a lysis step using ionic detergents or choatropes, the nucleic acid is then specifically or non-specifically immobilized on a solid support, and then probed with tagged DNA probes. Unhybridized probe is removed is a washing step, the tags are cleaved form their respective probes, and the measured.

Detectable nucleic acid can include mRNA, genomic DNA, plasmid DNA or RNA, rRNA viral DNA or RNA. To effect detection of the target nucleic acid, the target requires some type of immobilization since the assays described herein are not homogeneous. Two types of immobilization are possible, non-specific or specific. In the former case nucleic acids are immobilized on solid support or substrate which possesses some affinity for nucleic acid. The nucleic acids can be purified or not purified prior to non-specific immobilization. Solid supports can include nylon membranes, membranes composed of nitrocellulose, etc. The solid supports are then probed with tagged oligonucleotides of pre-determined sequence to identify the target nucleic acid of interest. Unhybridized probe is removed is a washing step, the tags are cleaved form their respective probes, and then measured.

Another method which results in higher specificity for the analysis of a population regarding the presence of a certain gene or DNA sequence utilizes the Southern blot technique. Prepared DNA is digested with a restriction enzyme (RE), resulting in a large number of DNA fragments of different lengths, determined by the presence of the specific recognition site of the restriction enzyme on the genome. Alleles of a certain gene with mutations inside this restriction site will be cleaved into fragments of different number and length. The resulting restriction fragment length polymorphism (RFLP) can be an important diagnostic of a microorganism if the fragment can be specifically identified.

The fragment to be analyzed should be separated from the pool of DNA fragments and distinguished from other DNA species using specific probes. Thus, DNA is subjected to electrophoretic fractionation using some type of gel or chromatography, followed by transfer and fixation to a nylon or nitrocellulose membrane. The fixed, single-stranded DNA is hybridized to a tagged oligonucleotide, complementary to the DNA to be detected. After removing non-specific hybridizations, the DNA fragment of interest is identified by cleaving the tag(s) from the hybridized probe. With the technology described here, over one hundred probes can be used simultaneously.

The presence and quantification of a specific gene transcripts can be analysed by means of Northern blot analysis and RNase protection assay. The principle basis of these methods is hybridization of the pool of total cellular RNA to a specific tagged probe or set of specific tagged probes. In the Northern blot technique, total RNA of a tissue is electrophoretically fractionated using an agarose gel, transferred and immobilized to a solid support (nylon, nitrocellulose, etc.). The RNA is hybridized to a tagged oligonucleotide, complementary to the RNA to be detected. After removing non-specific hybridizations, the RNA fragment of interest is identified by cleaving the tag(s) from the hybridized probe. By applying stringent washing conditions, non-specifically bound molecules are eliminated due to their weaker hybridization in comparison with specifically bound molecules. More rapid, but less specific, is the dot blot method, which is performed as the Northern blot technique except that the RNA is directly dotted onto the membrane without preceding fractionation.

A specific method for detection of an mRNA species is the RNase protection assay. Total RNA from a tissue or cell culture is hybridized to a ribonucleotide or deoxyribonucleotide tagged probe, Specificity is accomplished by subsequent RNase digestion. Non-hybridized, single-stranded RNA and non-specifically hybridized fragments with even small mismatches will be recognized and cleaved, while double-stranded RNA or DNA/RNA duplexes of complete homology is not accessible to the enzyme and will be protected. The specific protected fragment can be separated from degradation products, the tag(s) cleaved from the respective probe and subsequently measured.

The precise location of a given mRNA (or any nucleic acid sequence) in a specific population of cells within a tissue can be determined by in situ hybridization. In situ hybridization can be even more sensitive than analysis of a total tissue RNA preparation using the techniques described above. This is the case when the mRNA is expressed in high concentrations in a very discrete region or cell type within the tissue and would be diluted by homogenization of the whole tissue. For in situ hybridization, the tissues have to be frozen or perfusion-fixed and sectioned according to histochemical protocol. The hybridization protocol for tissue sections and the labeled probes used are similar to the other hybridization methods described above. A quantitative analysis is possible.

10. Mutation Detection Techniques

The detection of diseases is increasingly important in prevention and treatments. While multifactorial diseases are difficult to devise genetic tests for, more than 200 known human disorders are caused by a defect in a single gene, often a change of a single amino acid residue (Olsen, *Biotechnology: An industry comes of age*, National Academic Press, 1986). Many of these mutations result in an altered amino acid that causes a disease state.

Sensitive mutation detection techniques offer extraordinary possibilities for mutation screening. For example, analyses may be performed even before the implantation of a fertilized egg (Holding and Monk, *Lancet* 3:532, 1989). Increasingly efficient genetic tests may also enable screening for oncogenic mutations in cells exfoliated from the respiratory tract or the bladder in connection with health checkups (Sidransky et al., *Science* 252:706, 1991). Also, when an unknown gene causes a genetic disease, methods to monitor DNA sequence variants are useful to study the inheritance of disease through genetic linkage analysis. However, detecting and diagnosing mutations in individual genes poses technological and economic challenges. Several different approaches have been pursued, but none are both efficient and inexpensive enough for truly widescale application.

Mutations involving a single nucleotide can be identified in a sample by physical, chemical, or enzymatic means. Generally, methods for mutation detection may be divided into scanning techniques, which are suitable to identify previously unknown mutations, and techniques designed to detect, distinguish, or quantitate known sequence variants.

Several scanning techniques for mutation detection have been developed in heteroduplexes of mismatched complementary DNA strands, derived from wild-type and mutant sequences, exhibit an abnormal behavior especially when denatured. This phenomenon is exploited in denaturing and temperature gradient gel electrophoresis (DGGE and TGGE, respectively) methods. Duplexes mismatched in even a single nucleotide position can partially denature, resulting in retarded migration, when electrophoresed in an increasingly denaturing gradient gel (Myers et al., *Nature* 313:495, 1985; Abrams et al., *Genomics* 7:463, 1990; Henco et al., *Nucl. Acids Res.* 18:6733, 1990). Although mutations may be detected, no information is obtained regarding the precise location of a mutation. Mutant forms must be further isolated and subjected to DNA sequence analysis.

Alternatively, a heteroduplex of an RNA probe and a target strand may be cleaved by RNase A at a position where the two strands are not properly paired. The site of cleavage can then be determined by electrophoresis of the denatured probe. However, some mutations may escape detection because not all mismatches are efficiently cleaved by RNase A.

Mismatched bases in a duplex are also susceptible to chemical modification. Such modification can render the strands susceptible to cleavage at the site of the mismatch or cause a polymerase to stop in a subsequent extension reaction. The chemical cleavage technique allows identification of a mutation in target sequences of up to 2 kb and it provides information on the approximate location of mismatched nucleotide(s) (Cotton et al., *PNAS USA* 85:4397, 1988; Ganguly et al., *Nucl. Acids Res.* 18:3933, 1991). However, this technique is labor intensive and may not identify the precise location of the mutation.

An alternative strategy for detecting a mutation in a DNA strand is by substituting (during synthesis) one of the normal nucleotides with a modified nucleotide, altering the molecular weight or other physical parameter of the product. A strand with an increased or decreased number of this modified nucleotide relative to the wild-type sequence exhibits altered electrophoretic mobility (Naylor et al., *Lancet* 337:635, 1991). This technique detects the presence of a mutation, but does not provide the location.

Two other strategies visualize mutations in a DNA segment by altered gel migration. In the single-strand conformation polymorphism technique (SSCP), mutations cause denatured strands to adopt different secondary structures, thereby influencing mobility during native gel electrophoresis. Heteroduplex DNA molecules, containing internal mismatches, can also be separated from correctly matched molecules by electrophoresis (Orita, *Genomics* 5:874, 1989; Keen, *Trends Genet.* 7:5, 1991). As with the techniques discussed above, the presence of a mutation may be determined but not the location. As well, many of these techniques do not distinguish between a single and multiple mutations.

All of the above-mentioned techniques indicate the presence of a mutation in a limited segment of DNA and some of them allow approximate localization within the segment. However, sequence analysis is still required to unravel the effect of the mutation on the coding potential of the segment. Sequence analysis is very powerful, allowing for example screening for the same mutation in other individuals of an affected family, monitoring disease progression in the case of malignant disease or for detecting residual malignant cells in the bone marrow before autologous transplantation. Despite these advantages, the procedure is unlikely to be adopted as a routine diagnostic method because of the high expense involved.

A large number of other techniques have been developed to analyze known sequence variants. Automation and economy are very important considerations for these types of analyses that may be applied, for screening individuals and the general population. None of the techniques discussed below combine economy, automation with the required specificity.

Mutations may be identified via their destabilizing effects on the hybridization of short oligonucleotide probes to a target sequence (see Wetmur, *Crit. Rev. Biochem. Mol. Biol.*, 26:227, 1991). Generally, this technique, allele-specific oligonucleotide hybridization involves amplification of target sequences and subsequent hybridization with short oligonucleotide probes. An amplified product can thus be scanned for many possible sequence variants by determining its hybridization pattern to an array of immobilized oligonucleotide probes.

However, establishing conditions that distinguish a number of other strategies for nucleotide sequence distinction all depend on enzymes to identify sequence differences (Saiki, *PNAS USA* 86:6230, 1989; Zhang, *Nucl. Acids Res.* 19:3929, 1991).

For example, restriction enzymes recognize sequences of about 4–8 nucleotides. Based on an average G+C content, approximately half of the nucleotide positions in a DNA segment can be monitored with a panel of 100 restriction enzymes. As an alternative, artificial restriction enzyme recognition sequences may be created around a variable position by using partially mismatched PCR primers. With this technique, either the mutant or the wild-type sequence alone may be recognized and cleaved by a restriction enzyme after amplification (Chen et al., *Anal. Biochem.* 195:51, 1991; Levi et al., *Cancer Res.* 51:3497, 1991).

Another method exploits the property that an oligonucleotide primer that is mismatched to a target sequence at the 3' penultimate position exhibits a reduced capacity to serve as a primer in PCR. 1However, some 3' mismatches, notably G-T, are less inhibitory than others limiting its usefulness. In attempts to improve this technique, additional mismatches are incorporated into the primer at the third position from the 3' end. This results in two mismatched positions in the three 3' nucleotides of the primer hybridizing with one allelic variant, and one mismatch in the third position in from the 3' end when the primer hybridizes to the other allelic variant (Newton et al., *Nucl. Acids Res.* 17:2503, 1989). It is necessary to define amplification conditions that significantly favor amplification of a 1 bp mismatch.

DNA polymerases have also been used to distinguish allelic sequence variants by determining which nucleotide is added to an oligonucleotide primer immediately upstream of a variable position in the target strand.

A ligation assay has been developed. In this method, two oligonucleotide probes hybridizing in immediate juxtaposition on a target strand are joined by a DNA ligase. Ligation is inhibited if there is a mismatch where the two oligonucleotide probes abut.

a. Assays for Mutation Detection

Mutations are a single-base pair change in genomic DNA. Within the context of this invention, most such changes are readily detected by hybridization with oligonucleotides that are complementary to the sequence in question. In the system described here, two oligonucleotides are employed to detect a mutation. One oligonucleotide possesses the wild-type sequence and the other oligonucleotide possesses the mutant sequence. When the two oligonucleotides are used as probes on a wild-type target genomic sequence, the wild-type oligonucleotide will form a perfectly based paired structure and the mutant oligonucleotide sequence will form a duplex with a single base pair mismatch.

As discussed above, a 6 to 7° C. difference in the $T_m$ of a wild type versus mismatched duplex permits the ready identification or discrimination of the two types of duplexes. To effect this discrimination, hybridization is performed at the $T_m$ of the mismatched duplex in the respective hybotropic solution. The extent of hybridization is then measured for the set of oligonucleotide probes. When the ratio of the extent of hybridization of the wild-type probe to the mismatched probe is measured, a value to 10/1 to greater than 20/1 is obtained. These types of results permit the development of robust assays for mutation detection.

For exemplary purposes, one assay format for mutation detection utilizes target nucleic acid (e.g., genomic DNA) and oligonucleotide probes that span the area of interest. The oligonucleotide probes are greater or equal to 24 nt in length (with a maximum of about 36 nt) and labeled with a fluorochrome at the 3' or 5' end of the oligonucleotide probe. The target nucleic acid is obtained via the lysis of tissue culture cells, tissues, organisms, etc., in the respective hybridization solution. The lysed solution is then heated to a temperature which denatures the target nucleic acid (15–25° C. above the $T_m$ of the target nucleic acid duplex). The oligonucleotide probes are added at the denaturation temperature, and hybridization is conducted at the $T_m$ of the mismatched duplex for 0.5 to 24 hours. The genomic DNA is then collected and by passage through a GF/C (GF/B, and the like) glass fiber filter. The filter is then washed with the respective hybridization solution to remove any non-hybridized oligonucleotide probes (RNA, short oligos and nucleic acid does not bind to glass fiber filters under these conditions). The hybridization oligo probe can then be thermally eluted from the target DNA and measured (by fluorescence for example). For assays requiring very high levels of sensitivity, the probes are concentrated and measured.

Other highly sensitive hybridization protocols may be used. The methods of the present invention enable one to readily assay for a nucleic acid containing a mutation suspected of being present in cells, samples, etc., i.e., a target nucleic acid. The "target nucleic acid" contains the nucleotide sequence of deoxyribonucleic acid (DNA) or ribonucleic acid (RNA) whose presence is of interest, and whose presence or absence is to be detected for in the hybridization assay. The hybridization methods of the present invention may also be applied to a complex biological mixture of nucleic acid (RNA and/or DNA). Such a complex biological mixture includes a wide range of eucaryotic and procaryotic cells, including protoplasts; and/or other biological materials which harbor polynucleotide nucleic acid. The method is thus applicable to tissue culture cells, animal cells, animal tissue, blood cells (e.g., reticulocytes, lymphocytes), plant cells, bacteria, yeasts, viruses, mycoplasmas, protozoa, fungi and the like. By detecting a specific hybridization between nucleic acid probes of a known source, the specific presence of a target nucleic acid can be established.

A typical hybridization assay protocol for detecting a target nucleic acid in a complex population of nucleic acids is described as follows: Target nucleic acids are separated by size on a gel matrix (electrophoresis), cloned and isolated, sub-divided into pools, or left as a complex population. The target nucleic acids are transferred, spotted, or immobilized onto a solid support such as a nylon membrane or nitrocellulose membrane. (This "immobilization" is also referred to as "arraying"). The immobilized nucleic acids are then subjected to a heating step or UV radiation, which irreversibly immobilizes the nucleic acid. The membranes are then immersed in "blocking agents" which include Dendhart's reagent (Dendhart, *Biochem. Biophys. Res. Comm.* 23:641, 1966), heparin (Singh and Jones, *Nucleic Acids Res.* 12:5627, 1984), and non-fat dried milk (Jones et al., *Gene Anal. Tech.* 1:3, 1984). Blocking agents are generally included in both the prehybridization step and hybridization steps when nitrocellulose is used. The target nucleic acids are then probed with tagged oligonucleotide probes under conditions described above in hybotrope-based solutions. Unbound enzyme is then washed away and the membrane is immersed in a substrate solution. Signal is then detected by MALD1-MS essentially as described below.

b. Sequencing by hybridization

DNA sequence analysis is conventionally performed by hybridizing a primer to target DNA and performing chain extensions using a polymerase. Specific stops are controlled by the inclusion of a dideoxynucleotide. The specificity of priming in this type of analysis can be increased by including a hybotrope in the annealing buffer and/or incorporating an abasic residue in the primer and annealing at a discriminating temperature.

Other sequence analysis methods involve hybridization of the target with an assortment of random, short oligonucleotides. The sequence is constructed by overlap hybridization analysis. In this technique, precise hybridization is essential. Use of hybotropes or abasic residues and annealing at a discriminating temperature is beneficial for this technique to reduce or eliminate mismatched hybridization. The goal is to develop automated hybridization methods in order to probe large arrays of oligonucleotide probes or large arrays of nucleic acid samples. Application of such technologies include gene mapping, clone characterization, medical genetics and gene discovery, DNA sequence analysis by hybridization, and finally, sequencing verification.

Many parameters must be controlled in order to automate or multiplex oligonucleotide probes. The stability of the respective probes must be similar, the degree of mismatch with the target nucleic acid, the temperature, ionic strength, the A+T content of the probe (or target), as well as other parameters when the probe is short (i.e., 6 to 50 nucleotides) should be similar. Usually, the conditions of the experiment and the sequence of the probe are adjusted until the formation of the perfectly based paired probe is thermodynamically favored over the any duplex which contains a mismatch. Very large scale applications of probes such as sequencing by hybridization (SBH), or testing highly polymorphic loci such as the cystic fibrosis trans-membrane protein locus require a more stringent level of control of multiplexed probes.

11. Arrays

Nucleic acid hybridization to arrayed DNA samples has long been employed for a wide variety of applications in basic biological research, and are currently beginning to be used in medical diagnostics, forensics and agriculture. As described in more detail below, nucleic acid molecules or proteins may be attached to a solid support to form an array, and tested with tagged molecules of the present invention.

For example, within one embodiment of the invention, arrayed DNA samples can be utilized in the identification of individual clones. Briefly, known DNA molecules are tagged to make a tagged probe, and tested by hybridization against an array of unknown clones. Clones which show specific hybridization to the probe may then be isolated. Such assays may be accomplished using unordered arrays of clones (Sambrook et al., "Molecular Cloning: A Laboratory Manual" Cold Spring Harbor, N.Y., 1989). Alternatively, membranes carrying regularly spaced arrays of clones of known individual identity (although typically of unknown sequence) may also be purchased (e.g., Research Genetics, BAC clone arrays, Huntsville, Ala.).

Within another embodiment, arrays may be utilized to measure the transcription levels of a large number of genes simultaneously (see generally, Gess et al., *Mammalian Genome* 3: 609–619, 1992). Briefly, pools of cDNA may be tagged an utilized as probes on large arrays of cDNA clones to identify the genes expressed abundantly in specific tissues. Microarrays from individual cDNA clones may also be utilized to quantitatively measure the relative expression of each gene in the array in two different RNA samples (Schena et al., *Science* 270: 467–470, 1995. More specifically, robots may be utilized to produce microarrays of PCR products from individual clones: each element in the array corresponds to a single cDNA clone. Probes for the arrays are prepared by labeling first strand cDNA from each tissue sample with a tag. To compare gene expression in two tissue samples, cDNA from each is labelled with a different tag. The two samples are pooled and hybridized to the array together. After hybridization of the probes to the array, tags may be cleaved and analyzed as described within the present application for each tag hybridized to each sample in the array. For a given gene, the ratio of hybridization to each labeled complex cDNA sample is a measure of the relative gene expression in the two tissue samples. The use of internal controls and of two (and potentially up to four) distinct tags is crucial for this application.

Many of the other applications described below are variations on this basic experiment using different sources of arrayed DNA and different sources of probe DNA, but each application is limited by the use of conventional detection methods to fewer than 4–6 distinguishable probes in the hybridization mix.

Another application of hybridization to DNA arrays which has been demonstrated in principle and has the potential for very wide application is sequencing by hybridization (SBH). The concept of sequencing by hybridization (SBH) makes use of an array of all possible n-nucleotide oligomers (n-mers) to identify n-mers present in an unknown DNA sequence. Computational approaches can then be used to assemble the complete sequence (see generally, Drmanac et al., *Science* 260: 1649–1652, 1993). Applications of SBH include physical mapping (ordering) of overlapping DNA clones, sequence checking, DNA fingerprinting comparisons of normal and disease-causing genes, and the identification of DNA fragments with particular sequence motifs in complementary DNA and genomic libraries.

DNA arrays also have wide application in the detection of genetic variations and polymorphisms. Single base pair changes, deletions and insertions, mutations and polymorphisms can be detected by immobilizing known sequence variants and probing with labeled PCR products from patients or pathogens (see, e.g., Guo, et al., *Nucleic Acids Res.* 22: 5456–5465, 1994). Likewise, arrays of oligonucleotides may be utilized to measure genetic variation, including the detection of drug resistant and drug sensitive variants of HIV (see, e.g., Lipshutz et al., *Biotechniques* 19: 442–447, 1995).

DNA arrays can be produced using at least two different techniques: synthesis in situ and deposition of samples produced separately (spotting). One of the most prominent techniques for production of the DNA samples in situ is the light-directed synthesis of oligonucleotides described in Pease et al, *P.N.A.S. USA* 91: 5022–6, 1994. Briefly, arrays of defined DNA sequences are produced by the use of photolabile blocking groups to direct oligonucleotide synthesis in an array using modem photolithographic methods. Masks are prepared such each array element that needs a particular base in the next synthesis step is and exposed to light. A single nucleotide residue is added to each chain that was exposed by the mask, the synthesis cycle finished, the next cycle initiated by the use of another mask and another oligonucleotide residue. Sequential application of this protocol can be used to quickly build up very large arrays of oligonucleotides. One version of robotic deposition is described in Schena et al. (1995) in connection with the use of arrays for transcription analysis.

Within one embodiment of the invention, second members are arrayed on a solid support such as silica, quartz or glass. The array may then be treated to block non-specific hybridization, followed by incubation of first member labeled probes on the solid support. Within certain preferred embodiments the array is then washed with a solution (at a defined stringency) in order to remove non-specifically hybridizing nucleic acids, rinsed with a solution which includes a matrix material appropriate for spectrometry or potentiometry (e.g., for matrix-assisted laser desorption and ionization mass spectrometry), dried to form an appropriate matrix, and exposed to light in order to cleave tags from the nucleic acid probes. The cleaved tags may then be analyzed by spectrometric or potentiometric techniques (e.g., MALDI-MS).

Within certain embodiments, cleavage and laser desorption occur in a single step. In other variations, laser desorption and ionization is performed without a matrix. In some experiments, reference-tagged oligonucleotides or other tagged compounds are added to the matrix solution to control for variations in the efficiency of photo-cleavage, laser desorption and MS detection efficiency. By measuring the ratio of abundance between a test tag and a series of reference tags, quantitative information is extracted from the MALDI-MS data.

Within other embodiments the array is composed of oligonucleotides of less than 50 bp in length. This can be utilized to detect polymorphisms (e.g., single base-pair changes), for genetic mapping, or to detect the presence or absence of a particular DNA in a sample, for analyzing or sorting clones, paternity testing, foresics, an genetic mapping. Arrays may likewise be composed of proteins.

Separation of Nucleic Acid Fragments

A sample that requires analysis is often a mixture of many components in a complex matrix. For samples containing unknown compounds, the components must be separated from each other so that each individual component can be identified by other analytical methods. The separation properties of the components in a mixture are constant under constant conditions, and therefore once determined they can be used to identify and quantify each of the components. Such procedures are typical in chromatographic and electrophoretic analytical separations.

12. High-Performance Liquid Chromatography (HPLC)

High-Performance liquid chromatography (HPLC) is a chromatographic separations technique to separate compounds that are dissolved in solution. HPLC instruments consist of a reservoir of mobile phase, a pump, an injector, a separation column, and a detector. Compounds are separated by injecting an aliquot of the sample mixture onto the column. The different components in the mixture pass through the column at different rates due to differences in their partitioning behavior between the mobile liquid phase and the stationary phase.

Recently, IP-RO-HPLC on non-porous PS/DVB particles with chemically bonded alkyl chains have been shown to be rapid alternatives to capillary electrophoresis in the analysis of both single and double-strand nucleic acids providing similair degrees of resolution (Huber et al, 1993, Anal. Biochem., 212, p351; Huber et al., 1993, Nuc. Acids Res., 21, p1061; Huber et al., 1993, Biotechniques, 16, p898). In contrast to ion-excahnge chromoatrography, which does not always retain double-strand DNA as a function of strand length (Since AT base pairs intereact with the positively charged stationary phase, more strongly than GC basepairs), IP-RP-HPLC enables a strictly size-dependent separation.

A method has been developed using 100 mM triethylammonium acetate as ion-pairing reagent, phosphodiester oligonucleotides could be successfully separated on alkylated non-porous 2.3 $\mu$M poly(styrene-divinylbenzene) particles by means of high performance liquid chromatography (Oefner et al., 1994, Anal. Biochem., 223, p39). The technique described allowed the separation of PCR products differing only 4 to 8 base pairs in length within a size range of 50 to 200 nucleotides.

13. Electrophoresis

Electrophoresis is a separations technique that is based on the mobility of ions (or DNA as is the case described herein) in an electric field. Negatively charged DNA charged migrate towards a positive electrode and positively-charged ions migrate toward a negative electrode. For safety reasons one electrode is usually at ground and the other is biased positively or negatively. Charged species have different migration rates depending on their total charge, size, and shape, and can therefore be separated. An electrode apparatus consists of a high-voltage power supply, electrodes, buffer, and a support for the buffer such as a polyacrylamide gel, or a capillary tube. Open capillary tubes are used for many types of samples and the other gel supports are usually used for biological samples such as protein mixtures or DNA fragments.

14. Capillary Electrophoresis (CE)

Capillary electrophoresis (CE) in its various manifestations (free solution, isotachophoresis, isoelectric focusing, polyacrylamide gel, micellar electrokinetic "chromatography") is developing as a method for rapid high resolution separations of very small sample volumes of complex mixtures. In combination with the inherent sensitivity and selectivity of MS, CE-MS is a potential powerful technique for bioanalysis. In the novel application disclosed herein, the interfacing of these two methods will lead to superior DNA sequencing methods that eclipse the current rate methods of sequencing by several orders of magnitude.

The correspondence between CE and electrospray ionization (ESI) flow rates and the fact that both are facilitated by (and primarily used for) ionic species in solution provide the basis for an extremely attractive combination. The combination of both capillary zone electrophoresis (CZE) and capillary isotachophoresis with quadrapole mass spectrometers based upon ESI have been described (Olivares et al., *Anal. Chem.* 59:1230, 1987; Smith et al., *Anal. Chem.*

60:436, 1988; Loo et al., *Anal. Chem.* 179:404, 1989; Edmonds et al., *J. Chroma.* 474:21, 1989; Loo et al., *J. Microcolumn Sep.* 1:223, 1989; Lee et al., *J. Chromatog.* 458:313, 1988; Smith et al., *J. Chromatog.* 480:211, 1989; Grese et al., *J. Am. Chem. Soc.* 111:2835, 1989). Small peptides are easily amenable to CZE analysis with good (femtomole) sensitivity.

The most powerful separation method for DNA fragments is polyacrylamide gel electrophoresis (PAGE), generally in a slab gel format. However, the major limitation of the current technology is the relatively long time required to perform the gel electrophoresis of DNA fragments produced in the sequencing reactions. An increase magnitude (10-fold) can be achieved with the use of capillary electrophoresis which utilize ultrathin gels. In free solution to a first approximation all DNA migrate with the same mobility as the addition of a base results in the compensation of mass and charge. In polyacrylamide gels, DNA fragments sieve and migrate as a function of length and this approach has now been applied to CE. Remarkable plate number per meter has now been achieved with cross-linked polyacrylamide ($10^{+7}$ plates per meter, Cohen et al., *Proc. Natl. Acad Sci., USA* 85:9660, 1988). Such CE columns as described can be employed for DNA sequencing. The method of CE is in principle 25 times faster than slab gel electrophoresis in a standard sequencer. For example, about 300 bases can be read per hour. The separation speed is limited in slab gel electrophoresis by the magnitude of the electric field which can be applied to the gel without excessive heat production. Therefore, the greater speed of CE is achieved through the use of higher field strengths (300 V/cm in CE versus 10 V/cm in slab gel electrophoresis). The capillary format reduces the amperage and thus power and the resultant heat generation.

Smith and others (Smith et al., *Nuc. Acids. Res* 18:4417, 1990) have suggested employing multiple capillaries in parallel to increase throughput. Likewise, Mathies and Huang (Mathies and Huang, *Nature* 359:167, 1992) have introduced capillary electrophoresis in which separations are performed on a parallel array of capillaries and demonstrated high through-put sequencing (Huang et al., *Anal. Chem.* 64:967, 1992, Huang et al., *Anal. Chem.* 64:2149, 1992). The major disadvantage of capillary electrophoresis is the limited amount of sample that can be loaded onto the capillary. By concentrating a large amount of sample at the beginning of the capillary, prior to separation, loadability is increased, and detection levels can be lowered several orders of magnitude. The most popular method of preconcentration in CE is sample stacking. Sample stacking has recently been reviewed (Chien and Burgi, *Anal. Chem.* 64:489A, 1992). Sample stacking depends of the matrix difference, (pH, ionic strength) between the sample buffer and the capillary buffer, so that the electric field across the sample zone is more than in the capillary region. In sample stacking, a large volume of sample in a low concentration buffer is introduced for preconcentration at the head of the capillary column. The capillary is filled with a buffer of the same composition, but at higher concentration. When the sample ions reach the capillary buffer and the lower electric field, they stack into a concentrated zone. Sample stacking has increased detectabilities 1–3 orders of magnitude.

Another method of preconcentration is to apply isotachophoresis (ITP) prior to the free zone CE separation of analytes. ITP is an electrophoretic technique which allows microliter volumes of sample to be loaded on to the capillary, in contrast to the low nL injection volumes typically associated with CE. The technique relies on inserting the sample between two buffers (leading and trailing electrolytes) of higher and lower mobility respectively, than the analyte. The technique is inherently a concentration technique, where the analytes concentrate into pure zones migrating with the same speed. The technique is currently less popular than the stacking methods described above because of the need for several choices of leading and trailing electrolytes, and the ability to separate only cationic or anionic species during a separation process.

The heart of the DNA sequencing process is the remarkably selective electrophoretic separation of DNA or oligonucleotide fragments. It is remarkable because each fragment is resolved and differs by only nucleotide. Separations of up to 1000 fragments (1000 bp) have been obtained. A further advantage of sequencing with cleavable tags is as follows. There is no requirement to use a slab gel format when DNA fragments are separated by polyacrylamide gel electrophoresis when cleavable tags are employed. Since numerous samples are combined (4 to 2000) there is no need to run samples in parallel as is the case with current dye-primer or dye-terminator methods (i.e., ABI373 sequencer). Since there is no reason to run parallel lanes, there is no reason to use a slab gel. Therefore, one can employ a tube gel format for the electrophoretic separation method. Grossman (Grossman et al., *Genet. Anal. Tech. Appl.* 9:9, 1992) have shown that considerable advantage is gained when a tube gel format is used in place of a slab gel format. This is due to the greater ability to dissipate Joule heat in a tube format compared to a slab gel which results in faster run times (by 50%), and much higher resolution of high molecular weight DNA fragments (greater than 1000 nt). Long reads are critical in genomic sequencing. Therefore, the use of cleavable tags in sequencing has the additional advantage of allowing the user to employ the most efficient and sensitive DNA separation method which also possesses the highest resolution.

15. Microfabricated Devices

Capillary electrophoresis (CE) is a powerful method for DNA sequencing, forensic analysis, PCR product analysis and restriction fragment sizing. CE is far faster than traditional slab PAGE since with capillary gels a far higher potential field can be applied. However, CE has the drawback of allowing only one sample to be processed per gel. The method combines the faster separations times of CE with the ability to analyze multiple samples in parallel. The underlying concept behind the use of microfabricated devices is the ability to increase the information density in electrophoresis by miniaturizing the lane dimension to about 100 micrometers. The electronics industry routinely uses microfabrication to make circuits with features of less than one micron in size. The current density of capillary arrays is limited the outside diameter of the capillary tube. Microfabrication of channels produces a higher density of arrays. Microfabrication also permits physical assemblies not possible with glass fibers and links the channels directly to other devices on a chip. Few devices have been constructed on microchips for separation technologies. A gas chromatograph (Terry et al., *IEEE Trans. Electron Device*, ED-26: 1880, 1979) and a liquid chromatograph (Manz et al., *Sens. Actuators* B1:249, 1990) have been fabricated on silicon chips, but these devices have not been widely used. Several groups have reported separating fluorescent dyes and amino acids on microfabricated devices (Manz et al., *J. Chromatography* 593:253, 1992, Effenhauser et al., *Anal. Chem.* 65:2637, 1993). Recently Woolley and Mathies (Woolley and Mathies, *Proc. Natl. Acad Sci.* 91:11348, 1994) have shown that photolithography and chemical etching can be used to make large numbers of separation channels on glass substrates. The channels are filled with hydroxyethyl cellulose (HEC) separation matrices. It was shown that DNA restriction fragments could be separated in as little as two minutes.

Cleavage of Tags

As described above, different linker designs will confer cleavability ("lability") under different specific physical or chemical conditions. Examples of conditions which serve to cleave various designs of linker include acid, base, oxidation, reduction, fluoride, thiol exchange, photolysis, and enzymatic conditions.

Examples of cleavable linkers that satisfy the general criteria for linkers listed above will be well known to those in the art and include those found in the catalog available from Pierce (Rockford, Ill.). Examples include:

ethylene glycobis(succinimidylsuccinate) (EGS), an amine reactive cross-linking reagent which is cleavable by hydroxylamine (1 M at 37° C. for 3–6 hours);

disuccinimidyl tartarate (DST) and sulfo-DST, which are amine reactive cross-linking reagents, cleavable by 0.015 M sodium periodate;

bis[2-(succinimidyloxycarbonyloxy)ethyl]sulfone (BSOCOES) and sulfo-BSOCOES, which are amine reactive cross-linking reagents, cleavable by base (pH 11.6);

1,4-di-[3'-(2'-pyridyldithio(propionamido)]butane (DPDPB), a pyridyldithiol crosslinker which is cleavable by thiol exchange or reduction;

N-[4-(p-azidosalicylamido)-butyl]-3'-(2'-pyridydithio) propionamide (APDP), a pyridyldithiol crosslinker which is cleavable by thiol exchange or reduction;

bis-[beta-4-(azidosalicylamido)ethyl]-disulfide, a photoreactive crosslinker which is cleavable by thiol exchange or reduction;

N-succinimidyl-(4-azidophenyl)-1,3'dithiopropionate (SADP), a photoreactive crosslinker which is cleavable by thiol exchange or reduction;

sulfosuccinimidyl-2-(7-azido-4-methylcoumarin-3-acetamide)ethyl-1,3'-dithiopropionate (SAED), a photoreactive crosslinker which is cleavable by thiol exchange or reduction;

sulfosuccinimidyl-2-(m-azido-o-nitrobenzamido)-ethyl-1,3'dithiopropionate (SAND), a photoreactive crosslinker which is cleavable by thiol exchange or reduction.

Other examples of cleavable linkers and the cleavage conditions that can be used to release tags are as follows. A silyl linking group can be cleaved by fluoride or under acidic conditions. A 3-, 4-, 5-, or 6-substituted-2-nitrobenzyloxy or 2-, 3-, 5-, or 6-substituted-4-nitrobenzyloxy linking group can be cleaved by a photon source (photolysis). A 3-, 4-, 5-, or 6-substituted-2-alkoxyphenoxy or 2-, 3-, 5-, or 6-substituted-4-alkoxyphenoxy linking group can be cleaved by $Ce(NH_4)_2(NO_3)_6$ (oxidation). A $NCO_2$ (urethane) linker can be cleaved by hydroxide (base), acid, or $LiAlH_4$ (reduction). A 3-pentenyl, 2-butenyl, or 1-butenyl linking group can be cleaved by $O_3$ $OSO_4/IO_4^-$, or $KMnO_4$ (oxidation). A 2-[3-, 4-, or 5-substituted-furyl]oxy linking group can be cleaved by $O_2$, $Br_2$, MeOH, or acid.

Conditions for the cleavage of other labile linking groups include: t-alkyloxy linking groups can be cleaved by acid; methyl(dialkyl)methoxy or 4-substituted-2-alkyl-1,3-dioxlane-2-yl linking groups can be cleaved by $H_3O^+$; 2-silylethoxy linking groups can be cleaved by fluoride or acid; 2-(X)-ethoxy (where X=keto, ester amide, cyano, $NO_2$, sulfide, sulfoxide, sulfone) linking groups can be cleaved under alkaline conditions; 2-, 3-, 4-, 5-, or 6-substituted-benzyloxy linking groups can be cleaved by acid or under reductive conditions; 2-butenyloxy linking groups can be cleaved by $(Ph_3P)_3RhCl(H)$, 3-, 4-, 5-, or 6-substituted-2-bromophenoxy linking groups can be cleaved by Li, Mg, or BuLi; methylthiomethoxy linking groups can be cleaved by $Hg^{2+}$; 2-(X)-ethyloxy (where X=a halogen) linking groups can be cleaved by Zn or Mg; 2-hydroxyethyloxy linking groups can be cleaved by oxidation (e.g., with $Pb(OAc)_4$).

Preferred linkers are those that are cleaved by acid or photolysis. Several of the acid-labile linkers that have been developed for solid phase peptide synthesis are useful for linking tags to MOIs. Some of these linkers are described in a recent review by Lloyd-Williams etal. (*Tetrahedron* 49:11065–11133, 1993). One useful type of linker is based upon p-alkoxybenzyl alcohols, of which two, 4-hydroxymethylphenoxyacetic acid and 4-(4-hydroxymethyl-3-methoxyphenoxy)butyric acid, are commercially available from Advanced ChemTech (Louisville, Ky.). Both linkers can be attached to a tag via an ester linkage to the benzylalcohol, and to an amine-containing MOI via an amide linkage to the carboxylic acid. Tags linked by these molecules are released from the MOI with varying concentrations of trifluoroacetic acid. The cleavage of these linkers results in the liberation of a carboxylic acid on the tag. Acid cleavage of tags attached through related linkers, such as 2,4-dimethoxy-4'-(carboxymethyloxy)-benzhydrylamine (available from Advanced ChemTech in FMOC-protected form), results in liberation of a carboxylic amide on the released tag.

The photolabile linkers useful for this application have also been for the most part developed for solid phase peptide synthesis (see Lloyd-Williams review). These linkers are usually based on 2-nitrobenzylesters or 2-nitrobenzylamides. Two examples of photolabile linkers that have recently been reported in the literature are 4-(4-(1-Fmoc-amino)ethyl)-2-methoxy-5-nitrophenoxy)butanoic acid (Holmes and Jones, *J. Org. Chem.* 60:2318–2319, 1995) and 3-(Fmoc-amino)-3-(2-nitrophenyl)propionic acid (Brown et al., *Molecular Diversity* 1:4–12, 1995). Both linkers can be attached via the carboxylic acid to an amine on the MOI. The attachment of the tag to the linker is made by forming an amide between a carboxylic acid on the tag and the amine on the linker. Cleavage of photolabile linkers is usually performed with UV light of 350 nm wavelength at intensities and times known to those in the art. Examples of commercial sources of instruments for photochemical cleavage are Aura Industries Inc. (Staten Island, N.Y.) and Agrenetics (Wilmington, Mass.). Cleavage of the linkers results in liberation of a primary amide on the tag. Examples of photocleavable linkers include nitrophenyl glycine esters, exo- and endo-2-benzonorborneyl chlorides and methane sulfonates, and 3-amino-3(2-nitrophenyl) propionic acid. Examples of enzymatic cleavage include esterases which will cleave ester bonds, nucleases which will cleave phosphodiester bonds, proteases which cleave peptide bonds, etc.

Detection of Tags

Detection methods typically rely on the absorption and emission in some type of spectral field. When atoms or molecules absorb light, the incoming energy excites a quantized structure to a higher energy level. The type of excitation depends on the wavelength of the light. Electrons are promoted to higher orbitals by ultraviolet or visible light, molecular vibrations are excited by infrared light, and rotations are excited by microwaves. An absorption spectrum is the absorption of light as a function of wavelength. The spectrum of an atom or molecule depends on its energy level structure. Absorption spectra are useful for identification of compounds. Specific absorption spectroscopic methods include atomic absorption spectroscopy (AA), infrared spectroscopy (IR), and UV-vis spectroscopy (uv-vis).

Atoms or molecules that are excited to high energy levels can decay to lower levels by emitting radiation. This light emission is called fluorescence if the transition is between states of the same spin, and phosphorescence if the transition occurs between states of different spin. The emission intensity of an analyte is linearly proportional to concentration (at low concentrations), and is useful for quantifying the emitting species. Specific emission spectroscopic methods include atomic emission spectroscopy (AES), atomic fluorescence spectroscopy (AFS), molecular laser-induced fluorescence (LIF), and X-ray fluorescence (XRF).

When electromagnetic radiation passes through matter, most of the radiation continues in its original direction but a small fraction is scattered in other directions. Light that is scattered at the same wavelength as the incoming light is called Rayleigh scattering. Light that is scattered in transparent solids due to vibrations (phonons) is called Brillouin scattering. Brillouin scattering is typically shifted by 0.1 to 1 wave number from the incident light. Light that is scattered due to vibrations in molecules or optical phonons in opaque solids is called Raman scattering. Raman scattered light is shifted by as much as 4000 wavenumbers from the incident light. Specific scattering spectroscopic methods include Raman spectroscopy.

IR spectroscopy is the measurement of the wavelength and intensity of the absorption of mid-infrared light by a sample. Mid-infrared light (2.5–50 $\mu$m, 4000–200 cm$^{-1}$) is energetic enough to excite molecular vibrations to higher energy levels. The wavelength of IR absorption bands are characteristic of specific types of chemical bonds and IR spectroscopy is generally most useful for identification of organic and organometallic molecules.

Near-infrared absorption spectroscopy (NIR) is the measurement of the wavelength and intensity of the absorption of near-infrared light by a sample. Near-infrared light spans the 800 nm–2.5 $\mu$m (12,500–4000 cm$^{-1}$) range and is energetic enough to excite overtones and combinations of molecular vibrations to higher energy levels. NIR spectroscopy is typically used for quantitative measurement of organic functional groups, especially O—H, N—H, and C=O. The components and design of NIR instrumentation are similar to uv-vis absorption spectrometers. The light source is usually a tungsten lamp and the detector is usually a PbS solid-state detector. Sample holders can be glass or quartz and typical solvents are $CCl_4$ and $CS_2$. The convenient instrumentation of NIR spectroscopy makes it suitable for on-line monitoring and process control.

Ultraviolet and Visible Absorption Spectroscopy (uv-vis) spectroscopy is the measurement of the wavelength and intensity of absorption of near-ultraviolet and visible light by a sample. Absorption in the vacuum UV occurs at 100–200 rm; (10$^5$–50,000 cm$^{-1}$) quartz UV at 200–350 nm; (50,000–28,570 cm$^{-1}$) and visible at 350–800 nm; (28,570–12,500 cm$^{-1}$) and is described by the Beer-Lambert-Bouguet law. Ultraviolet and visible light are energetic enough to promote outer electrons to higher energy levels. UV-vis spectroscopy can be usually applied to molecules and inorganic ions or complexes in solution. The uv-vis spectra are limited by the broad features of the spectra. The light source is usually a hydrogen or deuterium lamp for uv measurements and a tungsten lamp for visible measurements. The wavelengths of these continuous light sources are selected with a wavelength separator such as a prism or grating monochromator. Spectra are obtained by scanning the wavelength separator and quantitative measurements can be made from a spectrum or at a single wavelength.

Mass spectrometers use the difference in the mass-to-charge ratio (m/z) of ionized atoms or molecules to separate them from each other. Mass spectrometry is therefore useful for quantitation of atoms or molecules and also for determining chemical and structural information about molecules. Molecules have distinctive fragmentation patterns that provide structural information to identify compounds. The general operations of a mass spectrometer are as follows. Gas-phase ions are created, the ions are separated in space or time based on their mass-to-charge ratio, and the quantity of ions of each mass-to-charge ratio is measured. The ion separation power of a mass spectrometer is described by the resolution, which is defined as R=m/delta m, where m is the ion mass and delta m is the difference in mass between two resolvable peaks in a mass spectrum. For example, a mass spectrometer with a resolution of 1000 can resolve an ion with a m/z of 100.0 from an ion with a m/z of 100.1.

In general, a mass spectrometer (MS) consists of an ion source, a mass-selective analyzer, and an ion detector. The magnetic-sector, quadrupole, and time-of-flight designs also require extraction and acceleration ion optics to transfer ions from the source region into the mass analyzer. The details of several mass analyzer designs (for magnetic-sector MS, quadrupole MS or time-of-flight MS) are discussed below. Single Focusing analyzers for magnetic-sector MS utilize a particle beam path of 180, 90, or 60 degrees. The various forces influencing the particle separate ions with different mass-to-charge ratios. With double-focusing analyzers, an electrostatic analyzer is added in this type of instrument to separate particles with difference in kinetic energies.

A quadrupole mass filter for quadrupole MS consists of four metal rods arranged in parallel. The applied voltages affect the trajectory of ions traveling down the flight path centered between the four rods. For given DC and AC voltages, only ions of a certain mass-to-charge ratio pass through the quadrupole filter and all other ions are thrown out of their original path, A mass spectrum is obtained by monitoring the ions passing through the quadrupole filter as the voltages on the rods are varied.

A time-of-flight mass spectrometer uses the differences in transit time through a "drift region" to separate ions of different masses. It operates in a pulsed mode so ions must be produced in pulses and/or extracted in pulses. A pulsed electric field accelerates all ions into a field-free drift region with a kinetic energy of qV, where q is the ion charge and V is the applied voltage. Since the ion kinetic energy is 0.5 mV$^2$, lighter ions have a higher velocity than heavier ions and reach the detector at the end of the drift region sooner. The output of an ion detector is displayed on an oscilloscope as a function of time to produce the mass spectrum.

The ion formation process is the starting point for mass spectrometric analyses. Chemical ionization is a method that employs a reagent ion to react with the analyte molecules (tags) to form ions by either a proton or hydride transfer. The reagent ions are produced by introducing a large excess of methane (relative to the tag) into an electron impact (EI) ion source. Electron collisions produce $CH_4^+0$ and $CH_3^+$ which further react with methane to form $CH_5^+$ and $C_2H_5^+$. Another method to ionize tags is by plasma and glow discharge. Plasma is a hot, partially-ionized gas that effectively excites and ionizes atoms. A glow discharge is a low-pressure plasma maintained between two electrodes. Electron impact ionization employs an electron beam, usually generated from a tungsten filament, to ionize gas-phase atoms or molecules. An electron from the beam knocks an electron off analyte atoms or molecules to create ions. Electrospray ionization utilizes a very fine needle and a series of skimmers. A sample solution is sprayed into the source chamber to form droplets. The droplets carry charge when the exit the capillary and as the solvent vaporizes the droplets disappear leaving highly charged analyte molecules. ESI is particularly useful for large biological molecules that are difficult to vaporize or ionize. Fast-atom bombardment (FAB) utilizes a high-energy beam of neutral atoms, typically Xe or Ar, that strikes a solid sample causing desorption and ionization. It is used for large biological molecules that are difficult to get into the gas phase. FAB causes little fragmentation and usually gives a large molecular ion peak, making it useful for molecular weight determination. The atomic beam is produced by accelerating ions from an ion source though a charge-exchange cell. The ions pick up an electron in collisions with neutral atoms to form a beam of high energy atoms. Laser ionization (LIMS) is a method in which a laser pulse ablates material from the surface of a sample and creates a microplasma that ionizes some of the sample constituents. Matrix-assisted laser desorption ionization (MALDI) is a LIMS method of vaporizing and ionizing large biological molecules such as proteins or DNA fragments. The biological molecules are dispersed in a solid matrix such as nicotinic acid. A UV laser pulse ablates the matrix which carries some of the large molecules into the gas phase in an ionized form so they can be extracted into a mass spectrometer. Plasma-desorption ionization (PD) utilizes the decay of $^{252}Cf$ which produces two fission fragments that travel in opposite directions. One fragment strikes the sample knocking out 1–10 analyte ions. The other fragment strikes a detector and triggers the start of data acquisition. This ionization method is especially useful for large biological molecules. Resonance ionization (RIMS) is a method in which one or more laser beams are tuned in resonance to transitions of a gas-phase atom or molecule to promote it in a stepwise fashion above its ionization potential to create an ion. Secondary ionization (SIMS) utilizes an ion beam; such as $^3He^+$, $^{16}O^+$, or $^{40}Ar^+$; is focused onto the surface of a sample and sputters material into the gas phase. Spark source is a method which ionizes analytes in solid samples by pulsing an electric current across two electrodes.

A tag may become charged prior to, during or after cleavage from the molecule to which it is attached. Ionization methods based on ion "desorption", the direct formation or emission of ions from solid or liquid surfaces have allowed increasing application to nonvolatile and thermally labile compounds. These methods eliminate the need for neutral molecule volatilization prior to ionization and generally minimize thermal degradation of the molecular species. These methods include field desorption (Becky, *Principles of Field Ionization and Field Desorption Mass Spectrometry*, Pergamon, Oxford, 1977), plasma desorption (Sundqvist and Macfarlane, *Mass Spectrom. Rev.* 4:421, 1985), laser desorption (Karas and Hillenkamp, *Anal. Chem.* 60:2299, 1988; Karas et al., *Angew. Chem.* 101:805, 1989), fast particle bombardment (e.g., fast atom bombardment, FAB, and secondary ion mass spectrometry, SIMS, Barber et al., *Anal. Chem.* 54:645A, 1982), and thermospray (TS) ionization (Vestal, *Mass Spectrom. Rev.* 2:447, 1983). Thermospray is broadly applied for the on-line combination with liquid chromatography. The continuous flow FAB methods (Caprioli et al., *Anal. Chem.* 58:2949, 1986) have also shown significant potential. A more complete listing of ionization/mass spectrometry combinations is ion-trap mass spectrometry, electrospray ionization mass spectrometry, ion-spray mass spectrometry, liquid ionization mass spectrometry, atmospheric pressure ionization mass spectrometry, electron ionization mass spectrometry, metastable atom bombardment ionization mass spectrometry, fast atom bombard ionization mass spectrometry, MALDI mass spectrometry, photo-ionization time-of-flight mass spectrometry, laser droplet mass spectrometry, MALDI-TOF mass spectrometry, APCI mass spectrometry, nanospray mass spectrometry, nebulised spray ionization mass spectrometry, chemical ionization mass spectrometry, resonance ionization mass spectrometry, secondary ionization mass spectrometry, thermospray mass spectrometry.

The ionization methods amenable to nonvolatile biological compounds have overlapping ranges of applicability. Ionization efficiencies are highly dependent on matrix composition and compound type. Currently available results indicate that the upper molecular mass for TS is about 8000 daltons (Jones and Krolik, *Rapid Comm. Mass Spectrom.* 1:67, 1987). Since TS is practiced mainly with quadrapole mass spectrometers, sensitivity typically suffers disporportionately at higher mass-to-charge ratios (m/z). Time-of-flight (TOF) mass spectrometers are commercially available and possess the advantage that the m/z range is limited only by detector efficiency. Recently, two additional ionization methods have been introduced. These two methods are now referred to as matrix-assisted laser desorption (MALDI, Karas and Hillenkamp, *Anal. Chem.* 60:2299, 1988; Karas et al., *Angew. Chem.* 101:805, 1989) and electrospray ionization (ESI). Both methodologies have very high ionization efficiency (i.e., very high [molecular ions produced]/[molecules consumed]). Sensitivity, which defines the ultimate potential of the technique, is dependent on sample size, quantity of ions, flow rate, detection efficiency and actual ionization efficiency.

Electrospray-MS is based on an idea first proposed in the 1960s (Dole et al., *J. Chem. Phys.* 49:2240, 1968). Electrospray ionization (ESI) is one means to produce charged molecules for analysis by mass spectroscopy. Briefly, electrospray ionization produces highly charged droplets by nebulizing liquids in a strong electrostatic field. The highly charged droplets, generally formed in a dry bath gas at atmospheric pressure, shrink by evaporation of neutral solvent until the charge repulsion overcomes the cohesive forces, leading to a "Coulombic explosion". The exact mechanism of ionization is controversial and several groups have put forth hypotheses (Blades et al., *Anal. Chem.* 63:2109–14, 1991; Kebarle et al., *Anal. Chem.* 65:A972–86, 1993; Fenn, *J. Am. Soc. Mass. Spectrom.* 4:524–35, 1993). Regardless of the ultimate process of ion formation, ESI produces charged molecules from solution under mild conditions.

The ability to obtain useful mass spectral data on small amounts of an organic molecule relies on the efficient production of ions. The efficiency of ionization for ESI is related to the extent of positive charge associated with the molecule. Improving ionization experimentally has usually involved using acidic conditions. Another method to improve ionization has been to use quaternary amines when possible (see Aebersold et al., *Protein Science* 1:494–503, 1992; Smith et al., *Anal. Chem.* 60:436–41, 1988).

Electrospray ionization is described in more detail as follows. Electrospray ion production requires two steps: dispersal of highly charged droplets at near atmospheric pressure, followed by conditions to induce evaporation. A solution of analyte molecules is passed through a needle that is kept at high electric potential. At the end of the needle, the solution disperses into a mist of small highly charged droplets containing the analyte molecules. The small droplets evaporate quickly and by a process of field desorption or residual evaporation, protonated protein molecules are released into the gas phase. An electrospray is generally produced by application of a high electric field to a small flow of liquid (generally 1–10 uL/min) from a capillary tube. A potential difference of 3–6 kV is typically applied between the capillary and counter electrode located 0.2–2 cm away (where ions, charged clusters, and even charged droplets, depending on the extent of desolvation, may be sampled by the MS through a small orifice). The electric field results in charge accumulation on the liquid surface at the capillary terminus; thus the liquid flow rate, resistivity, and surface tension are important factors in droplet production. The high electric field results in disruption of the liquid surface and formation of highly charged liquid droplets. Positively or negatively charged droplets can be produced depending upon the capillary bias. The negative ion mode requires the presence of an electron scavenger such as oxygen to inhibit electrical discharge.

A wide range of liquids can be sprayed electrostatically into a vacuum, or with the aid of a nebulizing agent. The use of only electric fields for nebulization leads to some practical restrictions on the range of liquid conductivity and dielectric constant. Solution conductivity of less than $10^{-5}$ ohms is required at room temperature for a stable electrospray at useful liquid flow rates corresponding to an aqueous electrolyte solution of $<10^{-4}$ M. In the mode found most useful for ESI-MS, an appropriate liquid flow rate results in dispersion of the liquid as a fine mist. A short distance from the capillary the droplet diameter is often quite uniform and on the order of 1 μm. Of particular importance is that the total electrospray ion current increases only slightly for higher liquid flow rates. There is evidence that heating is useful for manipulating the electrospray. For example, slight heating allows aqueous solutions to be readily electrosprayed, presumably due to the decreased viscosity and surface tension. Both thermally-assisted and gas-nebulization-assisted electrosprays allow higher liquid flow rates to be used, but decrease the extent of droplet charging. The formation of molecular ions requires conditions effecting evaporation of the initial droplet population. This can be accomplished at higher pressures by a flow of dry gas at moderate temperatures (<60° C.), by heating during transport through the interface, and (particularly in the case of ion trapping methods) by energetic collisions at relatively low pressure.

Although the detailed processes underlying ESI remain uncertain, the very small droplets produced by ESI appear to allow almost any species carrying a net charge in solution to be transferred to the gas phase after evaporation of residual solvent. Mass spectrometric detection then requires that ions have a tractable m/z range (<4000 daltons for quadrupole instruments) after desolvation, as well as to be produced and transmitted with sufficient efficiency. The wide range of solutes already found to be amenable to ESI-MS, and the lack of substantial dependence of ionization efficiency upon molecular weight, suggest a highly non-discriminating and broadly applicable ionization process.

The electrospray ion "source" functions at near atmospheric pressure. The electrospray "source" is typically a metal or glass capillary incorporating a method for electrically biasing the liquid solution relative to a counter electrode. Solutions, typically water-methanol mixtures containing the analyte and often other additives such as acetic acid, flow to the capillary terminus. An ESI source has been described (Smith et al., Anal. Chem. 62:885, 1990) which can accommodate essentially any solvent system. Typical flow rates for ESI are 1–10 uL/min. The principal requirement of an ESI-MS interface is to sample and transport ions from the high pressure region into the MS as efficiently as possible.

The efficiency of ESI can be very high, providing the basis for extremely sensitive measurements, which is useful for the invention described herein. Current instrumental performance can provide a total ion current at the detector of about $2 \times 10^{-12}$ A or about $10^7$ counts/s for singly charged species. On the basis of the instrumental performance, concentrations of as low as $10^{-10}$ M or about $10^{-18}$ mol/s of a singly charged species will give detectable ion current (about 10 counts/s) if the analyte is completely ionized. For example, low attomole detection limits have been obtained for quaternary ammonium ions using an ESI interface with capillary zone electrophoresis (Smith et al., Anal. Chem. 59:1230, 1988). For a compound of molecular weight of 1000, the average number of charges is 1, the approximate number of charge states is 1, peak width (m/z) is 1 and the maximum intensity (ion/s) is $1 \times 10^{12}$.

Remarkably little sample is actually consumed in obtaining an ESI mass spectrum (Smith et al., Anal. Chem. 60:1948, 1988). Substantial gains might be also obtained by the use of array detectors with sector instruments, allowing simultaneous detection of portions of the spectrum. Since currently only about $10^{-5}$ of all ions formed by ESI are detected, attention to the factors limiting instrument performance may provide a basis for improved sensitivity. It will be evident to those in the art that the present invention contemplates and accommodates for improvements in ionization and detection methodologies.

An interface is preferably placed between the separation instrumentation (e.g., gel)and the detector (e.g., mass spectrometer). The interface preferably has the following properties: (1) the ability to collect the DNA fragments at discreet time intervals, (2) concentrate the DNA fragments, (3) remove the DNA fragments from the electrophoresis buffers and milieu, (4) cleave the tag from the DNA fragment, (5) separate the tag from the DNA fragment, (6) dispose of the DNA fragment, (7) place the tag in a volatile solution, (8) volatilize and ionize the tag, and (9) place or transport the tag to an electrospray device that introduces the tag into mass spectrometer.

The interface also has the capability of "collecting" DNA fragments as they elute from the bottom of a gel. The gel may be composed of a slab gel, a tubular gel, a capillary, etc. The DNA fragments can be collected by several methods. The first method is that of use of an electric field wherein DNA fragments are collected onto or near an electrode. A second method is that wherein the DNA fragments are collected by flowing a stream of liquid past the bottom of a gel. Aspects of both methods can be combined wherein DNA collected into a flowing stream which can be later concentrated by use of an electric field. The end result is that DNA fragments are removed from the milieu under which the separation method was performed. That is, DNA fragments can be "dragged" from one solution type to another by use of an electric field.

Once the DNA fragments are in the appropriate solution (compatible with electrospray and mass spectrometry) the tag can be cleaved from the DNA fragment. The DNA fragment (or remnants thereof) can then be separated from the tag by the application of an electric field (preferably, the tag is of opposite charge of that of the DNA tag). The tag is then introduced into the electrospray device by the use of an electric field or a flowing liquid.

Fluorescent tags can be identified and quantitated most directly by their absorption and fluorescence emission wavelengths and intensities.

While a conventional spectrofluorometer is extremely flexible, providing continuous ranges of excitation and emission wavelengths ($I_{EX}$, $I_{S1}$, $I_{S2}$)l more specialized instruments such as flow cytometers and laser-scanning microscopes require probes that are excitable at a single fixed wavelength. In contemporary instruments, this is usually the 488-nm line of the argon laser.

Fluorescence intensity per probe molecule is proportional to the product of e and QY. The range of these parameters among fluorophores of current practical importance is approximately 10,000 to 100,000 $cm^{-1}M^{-1}$ for ε and 0.1 to 1.0 for QY. When absorption is driven toward saturation by high-intensity illumination, the irreversible destruction of the excited fluorophore (photobleaching) becomes the factor limiting fluorescence detectability. The practical impact of photobleaching depends on the fluorescent detection technique in question.

It will be evident to one in the art that a device (an interface) may be interposed between the separation and detection steps to permit the continuous operation of size separation and tag detection (in real time). This unites the separation methodology and instrumentation with the detection methodology and instrumentation forming a single device. For example, an interface is interposed between a separation technique and detection by mass spectrometry or potentiostatic amperometry.

The function of the interface is primarily the release of the (e.g., mass spectrometry) tag from analyte. There are several representative implementations of the interface. The design of the interface is dependent on the choice of cleavable linkers. In the case of light or photo-cleavable linkers, an energy or photon source is required. In the case of an acid-labile linker, a base-labile linker, or a disulfide linker, reagent addition is required within the interface. In the case of heat-labile linkers, an energy heat source is required. Enzyme addition is required for an enzyme-sensitive linker such as a specific protease and a peptide linker, a nuclease and a DNA or RNA linker, a glycosylase, HRP or phosphatase and a linker which is unstable after cleavage (e.g., similiar to chemiluminescent substrates). Other characteristics of the interface include minimal band broadening, separation of DNA from tags before injection into a mass spectrometer. Separation techniques include those based on electrophoretic methods and techniques, affinity techniques, size retention (dialysis), filtration and the like.

It is also possible to concentrate the tags (or nucleic acid-linker-tag construct), capture electrophoretically, and then release into alternate reagent stream which is compatible with the particular type of ionization method selected. The interface may also be capable of capturing the tags (or nucleic acid-linker-tag construct) on microbeads, shooting the bead(s) into chamber and then preforming laser desorption/vaporization. Also it is possible to extract in flow into alternate buffer (e.g., from capillary electrophoresis buffer into hydrophobic buffer across a permeable membrane). It may also be desirable in some uses to deliver tags into the mass spectrometer intermittently which would comprise a further function of the interface. Another function of the interface is to deliver tags from multiple columns into a mass spectrometer, with a rotating time slot for each column. Also, it is possible to deliver tags from a single column into multiple MS detectors, separated by time, collect each set of tags for a few milliseconds, and then deliver to a mass spectrometer.

The following is a list of representative vendors for separation and detection technologies which may be used in the present invention. Hoefer Scientific Instruments (San Francisco, Calif.) manufactures electrophoresis equipment (Two Step™, Poker Face™ II) for sequencing applications. Pharmacia Biotech (Piscataway, N.J.) manufactures electrophoresis equipment for DNA separations and sequencing (PhastSystem for PCR-SSCP analysis, MacroPhor System for DNA sequencing). Perkin Elmer/Applied Biosystems Division (ABI, Foster City, Calif.) manufactures semi-automated sequencers based on fluorescent-dyes (ABI373 and ABI377). Analytical Spectral Devices (Boulder, Colo.) manufactures UV spectrometers. Hitachi Instruments (Tokyo, Japan) manufactures Atomic Absorption spectrometers, Fluorescence spectrometers, LC and GC Mass Spectrometers, NMR spectrometers, and UV-VIS Spectrometers. PerSeptive Biosystems (Framingham, Mass.) produces Mass Spectrometers (Voyager™ Elite). Bruker Instruments Inc. (Manning Park, Mass.) manufactures FTIR Spectrometers (Vector 22), FT-Raman Spectrometers, Time of Flight Mass Spectrometers (Reflex II™), Ion Trap Mass Spectrometer (Esquire™) and a Maldi Mass Spectrometer. Analytical Technology Inc. (ATI, Boston, Mass.) makes Capillary Gel Electrophoresis units, UV detectors, and Diode Array Detectors. Teledyne Electronic Technologies (Mountain View, Calif.) manufactures an Ion Trap Mass Spectrometer (3DQ Discovery™ and the 3DQ Apogee™). Perkin Elmer/Applied Biosystems Division (Foster City, Calif.) manufactures a Sciex Mass Spectrometer (triple quadrupole LC/MS/MS, the API 100/300) which is compatible with clectrospray. Hewlett-Packard (Santa Clara, Calif.) produces Mass Selective Detectors (HP 5972A), MALDI-TOF Mass Spectrometers (HP G2025A), Diode Array Detectors, CE units, HPLC units (HP1090) as well as UV Spectrometers. Finnigan Corporation (San Jose, Calif.) manufactures mass spectrometers (magnetic sector (MAT 95 S™), quadrapole spectrometers (MAT 95 SQ™) and four other related mass spectrometers). Rainin (Emeryville, Calif.) manufactures HPLC instruments.

The methods and compositions described herein permit the use of cleaved tags to serve as maps to particular sample type and nucleotide identity. At the beginning of each sequencing method, a particular (selected) primer is assigned a particular unique tag. The tags map to either a sample type, a dideoxy terminator type (in the case of a Sanger sequencing reaction) or preferably both. Specifically, the tag maps to a primer type which in turn maps to a vector type which in turn maps to a sample identity. The tag may also may map to a dideoxy terminator type (ddTTP, ddCTP, ddGTP, ddATP) by reference into which dideoxynucleotide reaction the tagged primer is placed. The sequencing reaction is then performed and the resulting fragments are sequentially separated by size in time.

The tags are cleaved from the fragments in a temporal frame and measured and recorded in a temporal frame. The sequence is constructed by comparing the tag map to the temporal frame. That is, all tag identities are recorded in time after the sizing step and related become related to one another in a temporal frame. The sizing step separates the nucleic acid fragments by a one nucleotide increment and hence the related tag identities are separated by a one nucleotide increment. By foreknowledge of the dideoxy-terminator or nucleotide map and sample type, the sequence is readily deduced in a linear fashion.

Figure 14:
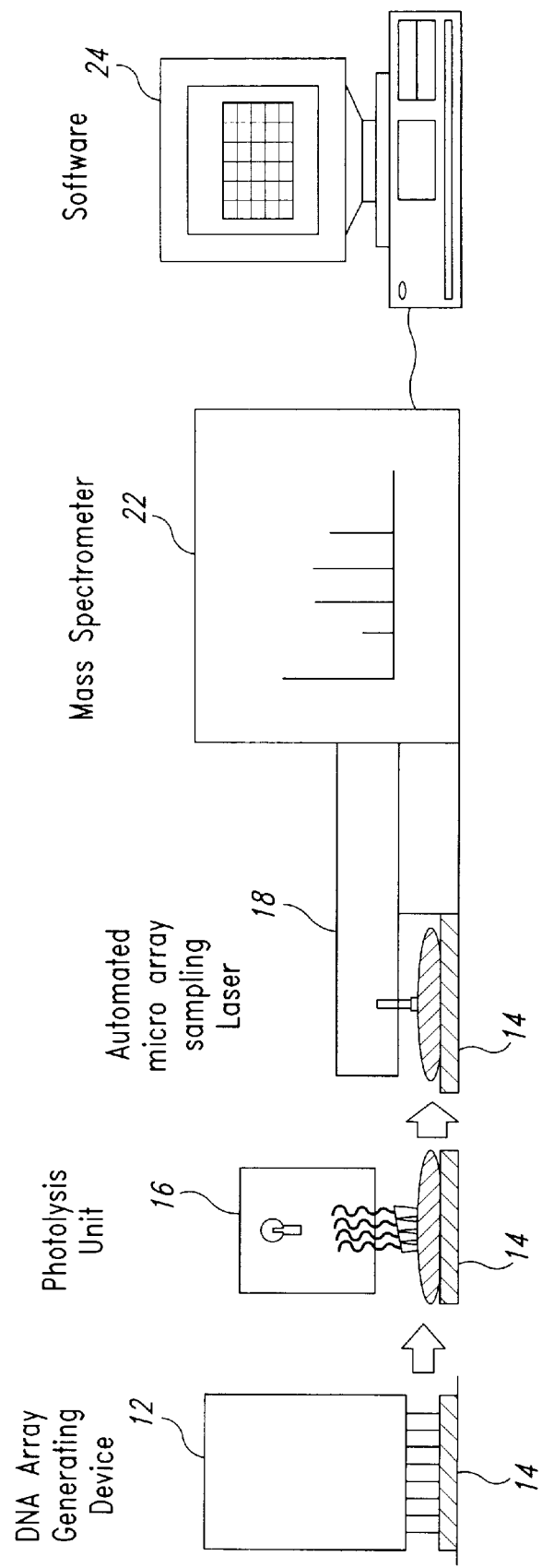
FIG. 14 is a schematic representation of an array interrogation system using Matrix Assisted Laser Desorption Ionization (MALDI) mass spectroscopy in accordance with an embodiment of the present invention.

In an embodiment of the present invention, an array interrogation system is provided that includes a DNA array generating device, a cleaving device, a desorpting device, a detecting device and a data processor and analyzer that analyzes data from the detecting devise to correlate a tag with a nucleic acid fragment from a sample. As best seen in FIG. 14, the array interrogation system 10 includes a DNA array generating device 12 that provides an arrayed DNA chip 14 with selected samples of nucleic acid fragments and cleavable mass spectrometer tags (CMST) attached to the nucleic acid fragments. The arrayed DNA chip 14 is passed through or past a photolytic cleavage device 16 that cleaves the CMSTs from the nucleic acid fragments while still on the DNA chip 14.

After CMSTs are cleaved, the DNA chip 14 is positioned in an automated micro-array sampling laser device 18, such as a Matrix Assisted Laser Desorption Ionization (MALDI) instrument. The MALDI instrument 18 is adapted to irradiate the CMSTs and cause desorption of the CMSTs. The CMSTs, after desorption, are then transferred to a detection device 22, such as a mass spectrometer, wherein the CMSTs are detected based upon the difference in molecular weight between each of the tags used to label the nucleic acid fragment.

Data from the detection device 22 is provided to the data processor and analyzer 24, which includes a software program that maps the signature of a given tag to a specific sample ID. The software is able to display the DNA sequence determined and load the sequence information into respective data bases.

In an alternate embodiment (not shown), the MALDI instrument 18 includes an additional light source that is capable of irradiating the entire DNA chip at an a wavelength in the range of 250 to 360 nm with adjustable intensity, so as to cause the photolytic cleaving of the CMSTs. Accordingly, the cleaving device 16 is incorporated as a component of the MALDI instrument 18. After cleaving the CMSTs, the MALDI instrument 18 volitized the CMSTs, which are transferred to the detecting device 14 as discussed above.

In another embodiment (not shown), the DNA chip 14 is moved from the DNA array generating device 12 directly to the MALDI instrument 18. The MALDI instrument 18 includes a laser that emits at a wavelength in the range of approximately 250 to 360 nm, inclusive. The laser causes the simultaneous photolytic cleavage of the tag from the nucleic acid fragment along with simultaneous desorption of the CMST. The CMSTs are then transferred to the mass spectrometer or other detection device 22 as discussed above. Accordingly, this alternate embodiment provides photocleavage by the MALDI instrument, so a separate cleavage device is not needed.

Tagged Molecules in Array-Based Assays

Arrays with covalently attached oligonucleotides have been made used to perform DNA sequence analysis by hybridization (Southern et al., *Genomics* 13: 1008, 1992; Drmanac et al., *Science* 260: 1649, 1993), determine expression profiles, screen for mutations and the like. In general, detection for these assays uses fluorescent or radioactive labels. Fluorescent labels can be identified and quantitated most directly by their absorption and fluorescence emission wavelengths and intensity. A microscope/camera setup using a fluorescent light source is a convenient means for detecting fluorescent label. Radioactive labels may be visualized by standard autoradiography, phosphor image analysis or CCD detector. For such labels the number of different reactions that can be detected at a single time is limited. For example, the use of four fluorescent molecules, such as commonly employed in DNA sequence analysis, limits anaylsis to four samples at a time. Essentially, because of this limitation, each reaction must be individually assessed when using these detector methods.

A more advantageous method of detection allows pooling of the sample reactions on at least one array and simultaneous detection of the products. By using a tag, such as the ones described herein, having a different molecular weight or other physical attribute in each reaction, the entire set of reaction products can be harvested together and analyzed.

As noted above, the methods described herein are applicable for a variety of purposes. For example, the arrays of oligonucleotides may be used to control for quality of making arrays, for quantitation or qualitative analysis of nucleic acid molecules, for detecting mutations, for determining expression profiles, for toxicology testing, and the like.

16. Probe quantitation or typing

In this embodiment, oligonucleotides are immobilized per element in an array where each oligonucleotide in the element is a different or related sequence. Preferably, each element possesses a known or related set of sequences. The hybridization of a labeled probe to such an array permits the characterization of a probe and the identification and quantification of the sequences contained in a probe population.

A generalized assay format that may be used in the particular applications discussed below is a sandwich assay format. In this format, a plurality of oligonucleotides of known sequence are immobilized on a solid substrate. The immobilized oligonucleotide is used to capture a nucleic acid (e.g., RNA, rRNA, a PCR product, fragmented DNA) and then a signal probe is hybridized to a different portion of the captured target nucleic acid.

Another generalized assay format is a secondary detection system. In this format, the arrays are used to identify and quantify labeled nucleic acids that have been used in a primary binding assay. For example, if an assay results in a labeled nucleic acid, the identity of that nucleic acid can be determined by hybridization to an array. These assay formats are particularly useful when combined with cleavable mass spectometry tags.

17. Mutation detection

Mutations involving a single nucleotide can be identified in a sample by scanning techniques, which are suitable to identify previously unknown mutations, or by techniques designed to detect, distinguish, or quantitate known sequence variants. Several scanning techniques for mutation detection have been developed based on the observation that heteroduplexes of mismatched complementary DNA strands, derived from wild type and mutant sequences, exhibit an abnormal migratory behavior.

The methods described herein may be used for mutation screening. One strategy for detecting a mutation in a DNA strand is by hybridization of the test sequence to target sequences that are wild-type or mutant sequences. A mismatched sequence has a destabilizing effect on the hybridization of short oligonucleotide probes to a target sequence (see Wetmur, *Crit. Rev. Biochem. Mol. Biol.*, 26:227, 1991). The test nucleic acid source can be genomic DNA, RNA, cDNA, or amplification of any of these nucleic acids. Preferably, amplification of test sequences is first performed, followed by hybridization with short oligonucleotide probes immobilized on an array. An amplified product can be scanned for many possible sequence variants by determining its hybridization pattern to an array of immobilized oligonucleotide probes.

A label, such as described herein, is generally incorporated into the final amplification product by using a labeled nucleotide or by using a labeled primer. The amplification product is denatured and hybridized to the array. Unbound product is washed off and label bound to the array is detected by one of the methods herein. For example, when cleavable mass spectrometry tags are used, multiple products can be simultaneously detected.

18. Expression profiles/differential display

Mammals, such as human beings, have about 100,000 different genes in their genome, of which only a small fraction, perhaps 15%, are expressed in any individual cell. Differential display techniques permit the identification of genes specific for individual cell types. Briefly, in differential display, the 3' terminal portions of mRNAs are amplified and identified on the basis of size. Using a primer designed to bind to the 5' boundary of a poly(A) tail for reverse transcription, followed by amplification of the cDNA using upstream arbitrary sequence primers, mRNA subpopulations are obtained.

As disclosed herein, a high throughput method for measuring the expression of numerous genes (e.g., 1–2000) is provided. Within one embodiment of the invention, methods are provided for analyzing the pattern of gene expression from a selected biological sample, comprising the steps of (a) amplifying cDNA from a biological sample using one or more tagged primers, wherein the tag is correlative with a particular nucleic acid probe and detectable by non-fluorescent spectrometry or potentiometry, (b) hybridizing amplified fragments to an array of oligonucleotides as described herein, (c) washing away non-hybridized material, and (d) detecting the tag by non-fluorescent spectrometry or potentiometry, and therefrom determining the pattern of gene expression of the biological sample. Tag-based differential display, especially using cleavable mass spectometry tags, on solid substrates allows characterization of differentially expressed genes.

19. Single nucleotide extension assay

The primer extension technique may be used for the detection of single nucleotide changes in a nucleic acid template (Sokolov, *Nucleic Acids Res.*, 18:3671, 1989). The technique is generally applicable to detection of any single base mutation (Kuppuswamy et al., *Proc. Natl, Acad. Sci. USA*, 88:1143–1147, 1991). Briefly, this method first hybridizes a primer to a sequence adjacent to a known single nucleotide polymorphism. The primed DNA is then subjected to conditions in which a DNA polymerase adds a labeled dNTP, typically a ddNTP, if the next base in the template is complementary to the labeled nucleotide in the reaction mixture. In a modification, cDNA is first amplified for a sequence of interest containing a single-base difference between two alleles. Each amplified product is then analyzed for the presence, absence, or relative amounts of each allele by annealing a primer that is 1 base 5' to the polymorphism and extending by one labeled base (generally a dideoxynucleotide). Only when the correct base is available in the reaction will a base to incorporated at the 3'-end of the primer. Extension products are then analyzed by hybridization to an array of oligonucleotides such that a non-extended product will not hybridize.

Briefly, in the present invention, each dideoxynucleotide is labeled with a unique tag. Of the four reaction mixtures, only one will add a dideoxy-terminator on to the primer sequence. If the mutation is present, it will be detected through the unique tag on the dideoxynucleotide after hybridization to the array. Multiple mutations can be simultaneously determined by tagging the DNA primer with a unique tag as well. Thus, the DNA fragments are reacted in four separate reactions each including a different tagged dideoxyterminator, wherein the tag is correlative with a particular dideoxynucleotide and detectable by non-fluorescent spectrometry, or potentiometry. The DNA fragments are hybridized to an array and non-hybridized material is washed away. The tags are cleaved from the hybridized fragments and detected by the respective detection technology (e.g., mass spectrometry, infrared spectrometry, potentiostatic amperometry or UV/visible spectrophotometry). The tags detected can be correlated to the particular DNA fragment under investigation as well as the identity of the mutant nucleotide.

20. Oligonucleotide ligation assay

The oligonucleotide ligation assay (OLA). (Landegen et al., *Science* 241:487, 1988) is used for the identification of known sequences in very large and complex genomes. The principle of OLA is based on the ability of ligase to covalently join two diagnostic oligonucleotides as they hybridize adjacent to one another on a given DNA target. If the sequences at the probe junctions are not perfectly based-paired, the probes will not be joined by the ligase. When tags are used, they are attached to the probe, which is ligated to the amplified product. After completion of OLA, fragments are hybridized to an array of complementary sequences, the tags cleaved and detected by mass spectrometry.

Within one embodiment of the invention methods are provided for determining the identity of a nucleic acid molecule, or for detecting a selecting nucleic acid molecule, in, for example a biological sample, utilizing the technique of oligonucleotide ligation assay. Briefly, such methods generally comprise the steps of performing amplification on the target DNA followed by hybridization with the 5' tagged reporter DNA probe and a 5' phosphorylated probe. The sample is incubated with T4 DNA ligase. The DNA strands with ligated probes are captured on the array by hybridization to an array, wherein non-ligated products do not hybridize. The tags are cleaved from the separated fragments, and then the tags are detected by the respective detection technology (e.g., mass spectrometry, infrared spectrophotometry, potentiostatic amperometry or UV/visible spectrophotometry.

21. Other assays

The methods described herein may also be used to genotype or identification of viruses or microbes. For example, F+ RNA coliphages may be useful candidates as indicators for enteric virus contamination. Genotyping by nucleic acid amplification and hybridization methods are reliable, rapid, simple, and inexpensive alternatives to serotyping (Kafatos et. al., *Nucleic Acids Res.* 7:1541, 1979). Amplification techniques and nucleic aid hybridization techniques have been successfully used to classify a variety of microorganisms including *E. coli* (Feng, *Mol. Cell Probes* 7:151, 1993), rotavirus (Sethabutr et. al., *J. Med Virol.* 37:192, 1992), hepatitis C virus (Stuyver et. al., *J. Gen Virol:* 74:1093, 1993), and herpes simplex virus (Matsumoto et. al., *J. Virol. Methods* 40:119, 1992).

Genetic alterations have been described in a variety of experimental mammalian and human neoplasms and represent the morphological basis for the sequence of morphological alterations observed in carcinogenesis (Vogelstein et al., *NEJM* 319:525, 1988). In recent years with the advent of molecular biology techniques, allelic losses on certain chromosomes or mutation of tumor suppressor genes as well as mutations in several oncogenes (e.g., c-myc, c-jun, and the ras family) have been the most studied entities. Previous work (Finkelstein et al., *Arch Surg.* 128:526, 1993) has identified a correlation between specific types of point mutations in the K-ras oncogene and the stage at diagnosis in colorectal carcinoma. The results suggested that mutational analysis could provide important information of tumor aggressiveness, including the pattern and spread of metastasis. The prognostic value of TP53 and K-ras-2 mutational analysis in stage III carconoma of the colon has more recently been demonstrated (Pricolo et al., *Am. J. Surg.* 171:41, 1996). It is therefore apparent that genotyping of tumors and pre-cancerous cells, and specific mutation detection will become increasingly important in the treatment of cancers in humans.

The tagged biomolecules as disclosed herein may be used to interrogate (untagged) arrays of biomolecules. Preferred arrays of biomolcules contain a solid substrate comprising a surface, where the surface is at least partially covered with a layer of poly(ethylenimine) (PEI). The PEI layer comprises a plurality of discrete first regions abutted and surrounded by a contiguous second region. The first regions are defined by the presence of a biomolecule and PEI, while the second region is defined by the presence of PEI and the substantial absence of the biomolecule. Preferably, the substrate is a glass plate or a silicon wafer. However, the substrate may be, for example, quartz, gold, nylon-6,6, nylon or polystyrene, as well as composites thereof, as described above.

The PEI coating preferably contains PEI having a molecular weight ranging from 100 to 100,000. The PEI coating may be directly bonded to the substrate using, for example, silylated PEI. Alternatively, a reaction product of a bifunctional coupling agent may be disposed between the substrate surface and the PEI coating, where the reaction product is covalently bonded to both the surface and the PEI coating, and secures the PEI coating to the surface. The bifunctional coupling agent contains a first and a second reactive functional group, where the first reactive functional group is, for example, a tri(O—$C_1$–$C_5$alkyl)silane, and the second reactive functional group is, for example, an epoxide, isocyanate, isothiocyanate and anhydride group. Preferred bifunctional coupling agents include 2-(3,4-epoxycyclohexyl)ethyltrimethoxysilane; 3,4-epoxybutyltrimethoxysilane; 3-isocyanatopropyltriethoxysilane, 3-(triethoxysilyl)-2-methylpropylsuccinic anhydride and 3-(2,3-epoxypropoxy)propyltrimethoxysilane.

The array of the invention contains first, biomolecule-containing regions, where each region has an area within the range of about 1,000 square microns to about 100,000 square microns. In a preferred embodiment, the first regions have areas that range from about 5,000 square microns to about 25,000 square microns.

The first regions are preferably substantially circular, where the circles have an average diameter of about 10 microns to 200 microns. Whether circular or not, the boundaries of the first regions are preferably separated from one another (by the second region) by an average distance of at least about 25 microns, however by not more than about 1 cm (and preferably by no more than about 1,000 microns). In a preferred array, the boundaries of neighboring first regions are separated by an average distance of about 25 microns to 100 microns, where that distance is preferably constant throughout the array, and the first regions are preferably positioned in a repeating geometric pattern as shown in the Figures attached hereto. In a preferred repeating geometric pattern, all neighboring first regions are separated by approximately the same distance (about 25 microns to about 100 microns).

In preferred arrays, there are from 10 to 50 first regions on the substrate. In another embodiment, there are 50 to 400 first regions on a substrate. In yet another preferred embodiment, there are 400 to 800 first regions on the substrate.

The biomolecule located in the first regions is preferably a nucleic acid polymer. A preferred nucleic acid polymer is an oligonucleotide having from about 15 to about 50 nucleotides. The biomolecule may be amplification reaction products having from about 50 to about 1,000 nucleotides.

In each first region, the biomolecule is preferably present at an average concentration ranging from $10^5$ to $10^9$ biomolecules per 2,000 square microns of a first region. More preferably, the average concentration of biomolecule ranges from $10^7$ to $10^9$ biomolecules per 2,000 square microns. In the second region, the biomolecule is preferably present at an average concentration of less than $10^3$ biomolecules per 2,000 square microns of said second region, and more preferably at an average concentration of less than $10^2$ biomolecules per 2,000 square microns. Most preferably, the second regions does not contain any biomolecule.

The chemistry used to adhere the layer of PEI to the substrate depends, in substantial part, upon the chemical identity of the substrate. The prior art provides numerous examples of suitable chemistries that may adhere PEI to a solid support. For example, when the substrate is nylon-6,6, the PEI coating may be applied by the methods disclosed in Van Ness, J. et al. *Nucleic Acids Res.* 19:3345–3350, 1991 and PCT International Publication WO 94/00600, both of which are incorporated herein by reference. When the solid support is glass or silicon, suitable methods of applying a layer of PEI are found in, e.g., Wasserman, B. P. *Biotechnology and Bioengineering XXII*:271–287, 1980; and D'Souza, S. F. *Biotechnology Letters* 8:643–648, 1986.

Preferably, the PEI coating is covalently attached to the solid substrate. When the solid substrate is glass or silicon, the PEI coating may be covalently bound to the substrate using silylating chemistry. For example, PEI having reactive siloxy endgroups is commercially available from Gelest, Inc. (Tullytown, Pa.,). Such reactive PEI may be contacted with a glass slide or silicon wafer, and after gentle agitation, the PEI will adhere to the substrate. Alternatively, a bifunctional silylating reagent may be employed. According to this process, the glass or silicon substrate is treated with the bifunctional silylating reagent to provide the substrate with a reactive surface. PEI is then contacted with the reactive surface, and covalently binds to the surface through the bifunctional reagent.

The biomolecules being placed into the array format are originally present in a so-called "arraying solution". In order to place biomolecule in discrete regions on the PEI-coated substrate, the arraying solution preferably contains a thickening agent at a concentration of about 35 vol % to about 80 vol % based on the total volume of the composition, a biomolecule which is preferably an oligonucleotide at a concentration ranging from 0.001 µg/mL to 10 µg/mL, and water.

The concentration of the thickening agent is 35% V/V to 80% V/V for liquid thickening agents such as glycerol. The preferred concentration of thickening agent in the composition depends, to some extent, on the temperature at which the arraying is performed. The lower the arraying temperature, the lower the concentration of thickening agent that needs to be used. The combination of temperature and liquid thickening agent concentration control permits arrays to be made on most types of solid supports (e.g, glass, wafers, nylon 6/6, nylon membranes, etc.).

The presence of a thickening agent has the additional benefit of allowing the concurrent presence of low concentrations of various other materials to be present in combination with the biomolecule. For example 0.001% V/V to 1% V/V of detergents may be present in the arraying solution. This is useful because PCR buffer contains a small amount of Tween-20 or NP-40, and it is frequently desirable to array sample nucleic acids directly from a PCR vial without prior purification of the amplicons. The use of a thickening agent permits the presence of salts (for example NaCl, KCl, or $MgCl_2$), buffers (for example Tris), and/or chelating reagents (for example EDTA) to also be present in the arraying solution. The use of a thickening agent also has the additional benefit of permitting the use of cross-linking reagents and/or organic solvents to be present in the arraying solution. As commercially obtained, cross-linking reagents are commonly dissolved in organic solvent such as DMSO, DMF, NMP, methanol, ethanol and the like. Commonly used organic solvents can be used in arraying solutions of the invention at levels of 0.05% to 20% (V/V) when thickening agents are used.

In general, the thickening agents impart increased viscosity to the arraying solution. When a proper viscosity is achieved in the arraying solution, the first drop is the substantially the same size as, for example, the 100th drop deposited. When an improper viscosity is used in the arraying solution, the first drops deposited are significantly larger than latter drops which are deposited. The desired viscosity is between those of pure water and pure glycerin.

The biomolecule in the array may be a nucleic acid polymer or analog thereof, such as PNA, phosphorothioates and methylphosphonates. Nucleic acid refers to both ribonucleic acid and deoxyribonucleic acid. The biomolecule may comprise unnatural and/or synthetic bases. The biomolecule may be single or double stranded nucleic acid polymer.

A preferred biomolecule is an nucleic acid polymer, which includes oligonucleotides (up to about 100 nucleotide bases) and polynucleotides (over about 100 bases). A preferred nucleic acid polymer is formed from 15 to 50 nucleotide bases. Another preferred nucleic acid polymer has 50 to 1,000 nucleotide bases. The nucleic acid polymer may be a PCR product, PCR primer, or nucleic acid duplex, to list a few examples. However, essentially any nucleic acid type can be covalently attached to a PEI-coated surface when the nucleic acid contains a primary amine, as disclosed below. The typical concentration of nucleic acid polymer in the arraying solution is 0.001–10 µg/mL, preferably 0.01–1 µg/mL, and more preferably 0.05–0.5 µg/mL.

Preferred nucleic acid polymers are "amine-modified" in that they have been modified to contain a primary amine at the 5'-end of the nucleic acid polymer, preferably with one or more methylene (—$CH_2$—) groups disposed between the primary amine and the nucleic acid portion of the nucleic acid polymer. Six is a preferred number of methylene groups. Amine-modified nucleic acid polymers are preferred because they can be covalently coupled to a solid support through the 5'-amine group. PCR products can be arrayed using 5'-hexylamine modified PCR primers. Nucleic acid duplexes can be arrayed after the introduction of amines by nick translation using aminoallyl-dUTP (Sigma, St. Louis, Mo.). Amines can be introduced into nucleic acids by polymerases such as terminal transferase with amino allyl-dUTP or by ligation of short amine-containing nucleic acid polymers onto nucleic acids by ligases.

Preferably, the nucleic acid polymer is activated prior to be contacted with the PEI coating. This can be conveniently accomplished by combining amine-functionalized nucleic acid polymer with a multi-functional amine-reactive chemical such as trichlorotriazine. When the nucleic acid polymer contains a 5'-amine group, that 5'-amine can be reacted with trichlorotriazine, also known as cyanuric chloride (Van Ness et al., *Nucleic Acids Res.* 19(2):3345–3350, 1991)

Preferably, an excess of cyanuric chloride is added to the nucleic acid polymer solution, where a 10- to 1000-fold molar excess of cyanuric chloride over the number of amines in the nucleic acid polymer in the arraying solution is preferred. In this way, the majority of amine-terminated nucleic acid polymers have reacted with one molecule of trichlorotriazine, so that the nucleic acid polymer becomes terminated with dichlorotriazine.

Preferably, the arraying solution is buffered using a common buffer such as sodium phosphate, sodium borate, sodium carbonate, or Tris HCl. A preferred pH range for the arraying solution is 7 to 9. with a preferred buffer being freshly prepared sodium borate at pH 8.3 to pH 8.5. To prepare a typical arraying solution, hexylamine-modified nucleic acid polymer is placed in 0.2 M sodium borate, pH 8.3, at 0.1 $\mu$g/mL, to a total volume of 50 $\mu$l. Ten $\mu$l of a 15 mg/mL solution of cyanuric chloride is then added, and the reaction is allowed to proceed for 1 hour at 25 C with constant agitation. Glycerol (Gibco Brl®, Grand Island, N.Y.) is added to a final concentration of 56%.

The biomolecular arraying solutions may be applied to the PEI coating by any of the number of techniques currently used in microfabrication. For example, the solutions may be placed into an ink jet print head, and ejected from such a head onto the coating.

A preferred approach to delivering biomolecular solution onto the PEI coating employs a modified spring probe. Spring probes are available from several vendors including Everett Charles (Pomona, Calif.), Interconnect Devices Inc. (Kansas City, Kans.) and Test Connections Inc., (Upland, Calif.). In order for the commercially available spring probes as described above to satisfactorily function as liquid deposition devices according to the present invention, approximately $\frac{1}{1000}$th to $\frac{5}{1000}$th of an inch of metal material must be removed from the tip of the probe. The process must result in a flat surface which is perpendicular to the longitudinal axis of the spring probe. The removal of approximately $\frac{1}{1000}$th to $\frac{5}{1000}$th of an inch of material from the bottom of the tip is preferred and can be accomplished easily with a very fine grained wet stone. Specific spring probes which are commercially available and may be modified to provide a planar tip as described above include the XP54 probe manufactured by Ostby Barton (a division of Everett Charles (Pomona, Calif.)); the SPA 25P probe manufactured by Everett Charles (Pomona, Calif.) and 43-P fluted spring probe from Test Connections Inc., (Upland, Calif.).

The arraying solutions as described above may be used directly in an arraying process. That is, the activated nucleic acid polymers need not be purified away from unreacted cyanuric chloride prior to the printing step. Typically the reaction which attaches the activated nucleic acid to the solid support is allowed to proceed for 1 to 20 hours at 20 to 50 C. Preferably, the reaction time is 1 hour at 25 C.

The arrays as described herein are particularly useful in conducting hybridization assays, for example, using CMST labeled probes. However, in order to perform such assays, the amines on the solid support must be capped prior to conducting the hybridization step. This may be accomplished by reacting the solid support with 0.1–2.0 M succinic anhydride. The preferred reaction conditions are 1.0 M succinic anhydride in 70% m-pyrol and 0.1 M sodium borate. The reaction typically is allowed to occur for 15 minutes to 4 hours with a preferred reaction time of 30 minutes at 25 C. Residual succinic anhydride is removed with a 3x water wash.

The solid support is then incubated with a solution containing 0.1–5 M glycine in 0.1–10.0 M sodium borate at pH 7–9. This step "caps" any dichloro-triazine which may be covalently bound to the PEI surface by conversion into monochlorotriazine. The preferred conditions are 0.2 M glycine in 0.1 M sodium borate at pH 8.3. The solid support may then be washed with detergent-containing solutions to remove unbound materials, for example, trace NMP. Preferably, the solid support is heated to 95 C in 0.01 M NaCl, 0.05 M EDTA and 01 M Tris pH 8.0 for 5 minutes. This heating step removes non-covalently attached nucleic acid polymers, such as PCR products. In the case where double strand nucleic acid are arrayed, this step also has the effect of converting the double strand to single strand form (denaturation).

The arrays are may be interrogated by probes (e.g., oligonucleotides, nucleic acid fragments, PCR products, etc.) which may be tagged with, for example CMST tags as described herein, radioisotopes, fluorophores or biotin. The methods for biotinylating nucleic acids are well known in the art and are adequately described by Pierce (Avidin-Biotin Chemistry: A Handbook, Pierce Chemical Company, 1992, Rockford Ill.). Probes are generally used at 0.1 ng/mL to 10/$\mu$g/mL in standard hybridization solutions that include GuSCN, GuHCl, formamide, etc. (see Van Ness and Chen, *Nucleic Acids Res.*, 19:5143–5151, 1991).

To detect the hybridization event (i.e., the presence of the biotin), the solid support is incubated with streptavidin/horseradish peroxidase conjugate. Such enzyme conjugates are commercially available from, for example, Vector Laboratories (Burlingham, Calif.). The streptavidin binds with high affinity to the biotin molecule bringing the horseradish peroxidase into proximity to the hybridized probe. Unbound streptavidin/horseradish peroxidase conjugate is washed away in a simple washing step. The presence of horseradish peroxidase enzyme is then detected using a precipitating substrate in the presence of peroxide and the appropriate buffers.

A blue enzyme product deposited on a reflective surface such as a wafer has a many-fold lower level of detection (LLD) compared to that expected for a colorimetric substrate. Furthermore, the LLD is vastly different for different colored enzyme products. For example, the LLD for 4-methoxynapthol (which produces a precipitated blue product) per 50 $\mu$M diameter spot is approximately 1000 molecules, whereas a red precipitated substrate gives an LLD about 1000-fold higher at 1,000,000 molecules per 50 $\mu$M diameter spot. The LLD is determined by interrogating the surface with a microscope (such as the Axiotech microscope commercially available from Zeiss) equipped with a visible light source and a CCD camera (Princeton Instruments, Princeton, N.J.). An image of approximately 10,000 $\mu$M×10,000 $\mu$M can be scanned at one time.

In order to use the blue colorimetric detection scheme, the surface must be very clean after the enzymatic reaction and the wafer or slide must be scanned in a dry state. In addition, the enzymatic reaction must be stopped prior to saturation of the reference spots. For horseradish peroxidase this is approximately 2–5 minutes.

It is also possible to use chemiluminescent substrates for alkaline phosphatase or horesradish peroxidase (HRP), or fluoroescence substrates for HRP or alkaline phosphatase. Examples include the dioxetane substrates for alkaline phosphatase available from Perkin Elmer or Attophos HRP substrate from JBL Scientific (San Luis Obispo, Calif.).

The following examples are offered by way of illustration, and not by way of limitation.

Unless otherwise stated, chemicals as used in the examples may be obtained from Aldrich Chemical Company, Milwaukee, Wis. The following abbreviations, with the indicated meanings, are used herein:

ANP=3-(Fmoc-amino)-3-(2-nitrophenyl)propionic acid
NBA=4-(Fmoc-aminomethyl)-3-nitrobenzoic acid
HATU=O-7-azabenzotriazol-1-yl-N,N,N',N'-tetramethyluronium hexafluoro-phosphate
DIEA=diisopropylethylamine MCT=monochlorotriazine
NMM=4-methylmorpholine
NMP=N-methylpyrrolidone
ACT357=ACT357 peptide synthesizer from Advanced ChemTech, Inc., Louisville, Ky.
ACT=Advanced ChemTech, Inc., Louisville, Ky.
NovaBiochem=CalBiochem-NovaBiochem International, San Diego, Calif.
TFA=Trifluoroacetic acid
Tfa=Trifluoroacetyl
iNIP=N-Methylisonipecotic acid
Tfp=Tetrafluorophenyl
DIAEA=2-(Diisopropylamino)ethylamine
MCT=monochlorotriazene
5'-AH-ODN=5'-aminohexyl-tailed oligodeoxynucleotide

EXAMPLES

Example 1

Preparation of Acid Labile Linkers For Use in Cleavable-Tag Sequencing

A. Synthesis of Pentafluorophenyl Esters of Chemically Cleavable Mass Spectroscopy Tags, to Liberate Tags with Carboxyl Amide Termini FIG. 1 shows the reaction scheme.

Step A

TentaGel S AC resin (compound II; available from ACT; 1 eq.) is suspended with DMF in the collection vessel of the ACT357 peptide synthesizer (ACT). Compound I (3 eq.), HATU (3 eq.) and DIEA (7.5 eq.) in DMF are added and the collection vessel shaken for 1 hr. The solvent is removed and the resin washed with NMP (2×), MeOH (2×), and DMF (2×). The coupling of 1 to the resin and the wash steps are repeated, to give compound III.

Step B

The resin (compound III) is mixed with 25% piperidine in DMF and shaken for min. The resin is filtered, then mixed with 25% piperidine in DMF and shaken for 10 min. The solvent is removed, the resin washed with NMP (2×), MeOH (2×), and DMF (2×), and used directly in step C.

Step C

The deprotected resin from step B is suspended in DMF and to it is added an FMOC-protected amino acid, containing amine functionality in its side chain (compound IV, e.g. alpha-N-FMOC-3-(3-pyridyl)-alanine, available from Synthetech, Albany, Oreg.; 3 eq.), HATU (3 eq.), and DIEA (7.5 eq.) in DMF. The vessel is shaken for 1 hr. The solvent is removed and the resin washed with NMP (2×), MeOH (2×), and DMF (2×). The coupling of IV to the resin and the wash steps are repeated, to give compound V.

Step D

The resin (compound V) is treated with piperidine as described in step B to remove the FMOC group. The deprotected resin is then divided equally by the ACT357 from the collection vessel into 16 reaction vessels.

Step E

The 16 aliquots of deprotected resin from step D are suspended in DMF. To each reaction vessel is added the appropriate carboxylic acid $VI_{1-16}$ ($R_{1-16}CO_2H$; 3 eq.), HATU (3 eq.), and DIEA (7.5 eq.) in DMF. The vessels are shaken for 1 hr. The solvent is removed and the aliquots of resin washed with NMP (2×), MeOH (2×), and DMF (2×). The coupling of $VI_{1-16}$ to the aliquots of resin and the wash steps are repeated, to give compounds $VII_{1-16}$.

Step F

The aliquots of resin (compounds $VII_{1-16}$) are washed with $CH_2Cl_2$ (3×). To each of the reaction vessels is added 1% TFA in $CH_2Cl_2$ and the vessels shaken for 30 min. The solvent is filtered from the reaction vessels into individual tubes. The aliquots of resin are washed with $CH_2Cl_2$ (2×) and MeOH (2×) and the filtrates combined into the individual tubes. The individual tubes are evaporated in vacuo, providing compounds $VIII_{1-16}$.

Step G

Each of the free carboxylic acids $VIII_{1-16}$ is dissolved in DMF. To each solution is added pyridine (1.05 eq.), followed by pentafluorophenyl trifluoroacetate (1.1 eq.). The mixtures are stirred for 45 min. at room temperature. The solutions are diluted with EtOAc, washed with 1 M aq. citric acid (3×) and 5% aq. $NaHCO_3$ (3×), dried over $Na_2SO_4$, filtered, and evaporated in vacuo, providing compounds $IX_{1-16}$.

Figure 2:
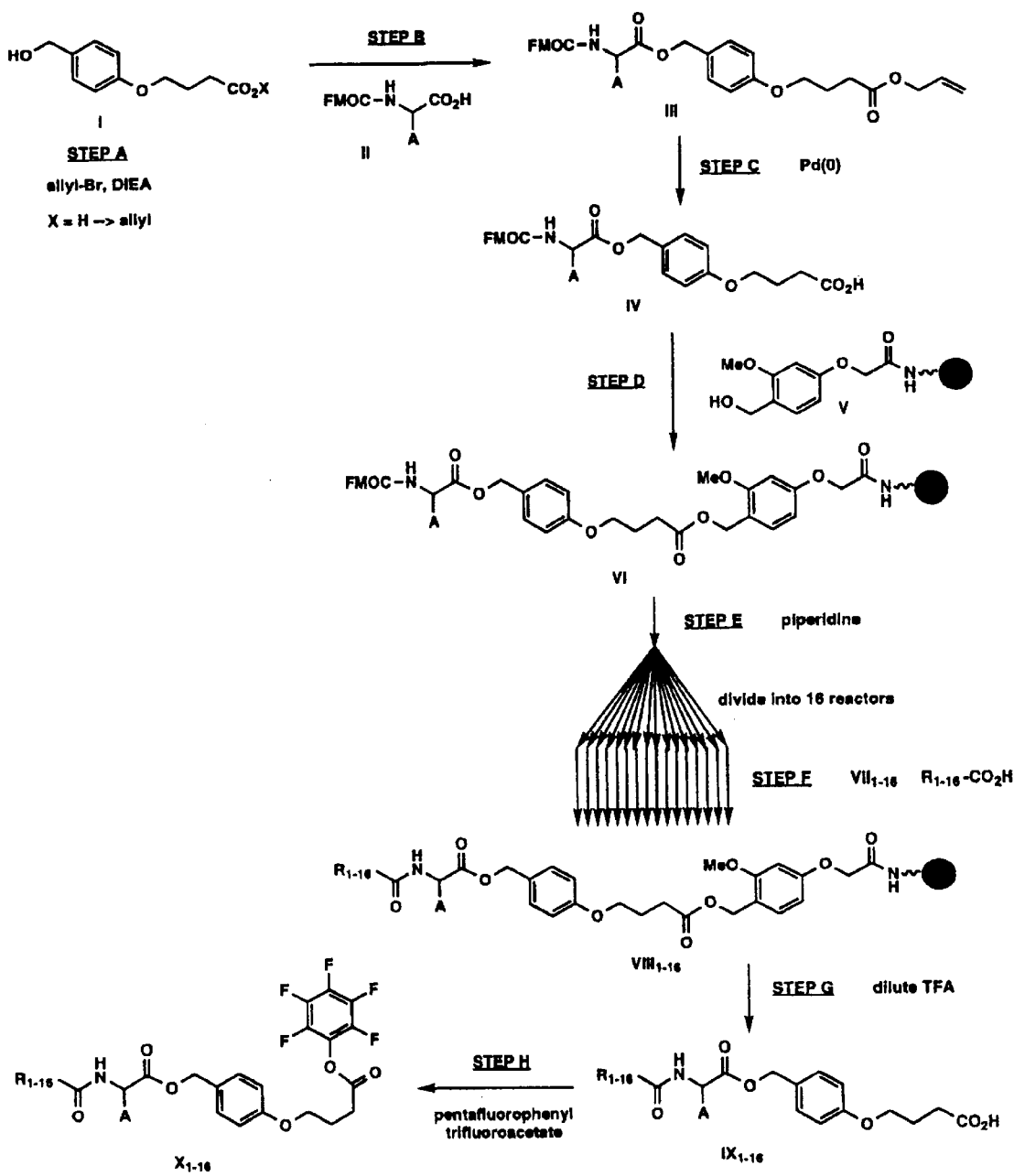
FIG. 2 depicts the flowchart for the synthesis of pentafluorophenyl esters of chemically cleavable mass spectroscopy tags, to liberate tags with carboxyl acid termini.

B. Synthesis of Pentafluorophenyl Esters of Chemically Cleavable Mass Spectroscopy Tags, to Liberate Tags with Carboxyl Acid Termini FIG. 2 shows the reaction scheme.

Step A 4-(Hydroxymethyl)phenoxybutyric acid (compound I; 1 eq.) is combined with DIEA (2.1 eq.) and allyl bromide (2.1 eq.) in $CHCl_3$ and heated to reflux for 2 hr. The mixture is diluted with EtOAc, washed with 1 N HCl (2×), pH 9.5 carbonate buffer (2×), and brine (1×), dried over $Na_2SO_4$, and evaporated in vacuo to give the allyl ester of compound I.

Step B

The allyl ester of compound I from step A (1.75 eq.) is combined in $CH_2Cl_2$ with an FMOC-protected amino acid containing amine functionality in its side chain (compound II, e.g. alpha-N-FMOC-3-(3-pyridyl)-alanine, available from Synthetech, Albany, Oreg.; 1 eq.), N-methylmorpholine (2.5 eq.), and HATU (1.1 eq.), and stirred at room temperature for 4 hr. The mixture is diluted with $CH_2Cl_2$, washed with 1 M aq. citric acid (2×), water (1×), and 5% aq. $NaHCO_3$ (2×), dried over $Na_2SO_4$, and evaporated in vacuo. Compound III is isolated by flash chromatography ($CH_2Cl_2 \rightarrow EtOAc$).

Step C

Compound III is dissolved in $CH_2Cl_2$, $Pd(PPh_3)_4$ (0.07 eq.) and N-methylaniline (2 eq.) are added, and the mixture stirred at room temperature for 4 hr. The mixture is diluted with $CH_2Cl_2$, washed with 1 M aq. citric acid (2×) and water (1×), dried over $Na_2SO_4$, and evaporated in vacuo. Compound IV is isolated by flash chromatography ($CH_2Cl_2 \rightarrow EtOAc+HOAc$).

Step D

TentaGel S AC resin (compound V; 1 eq.) is suspended with DMF in the collection vessel of the ACT357 peptide synthesizer (Advanced ChemTech Inc. (ACT), Louisville, Ky.). Compound IV (3 eq.), HATU (3 eq.) and DIEA (7.5 eq.) in DMF are added and the collection vessel shaken for 1 hr. The solvent is removed and the resin washed with NMP (2×), MeOH (2×), and DMF (2×). The coupling of IV to the resin and the wash steps are repeated, to give compound VI.

Step E

The resin (compound VI) is mixed with 25% piperidine in DMF and shaken for 5 min. The resin is filtered, then mixed with 25% piperidine in DMF and shaken for 10 min. The solvent is removed and the resin washed with NMP (2×), MeOH (2×), and DMF (2×). The deprotected resin is then divided equally by the ACT357 from the collection vessel into 16 reaction vessels.

Step F

The 16 aliquots of deprotected resin from step E are suspended in DMF. To each reaction vessel is added the appropriate carboxylic acid $VII_{1-16}$ ($R_{1-16}CO_2H$; 3 eq.), HATU (3 eq.), and DIEA (7.5 eq.) in DMF. The vessels are shaken for 1 hr. The solvent is removed and the aliquots of resin washed with NMP (2×), MeOH (2×), and DMF (2×). The coupling of $VII_{1-16}$ to the aliquots of resin and the wash steps are repeated, to give compounds $VIII_{1-16}$.

Step G

The aliquots of resin (compounds VIII$_{1-16}$) are washed with CH$_2$Cl$_2$ (3×). To each of the reaction vessels is added 1% TFA in CH$_2$Cl$_2$ and the vessels shaken for 30 min. The solvent is filtered from the reaction vessels into individual tubes. The aliquots of resin are washed with CH$_2$Cl$_2$ (2×) and MeOH (2×) and the filtrates combined into the individual tubes. The individual tubes are evaporated in vacuo, providing compounds IX$_{1-16}$.

Step H. Each of the free carboxylic acids IX$_{1-16}$ is dissolved in DMF. To each solution is added pyridine (1.05 eq.), followed by pentafluorophenyl trifluoroacetate (1.1 eq.). The mixtures are stirred for 45 min. at room temperature. The solutions are diluted with EtOAc, washed with 1 M aq. citric acid (3×) and 5% aq. NaHCO$_3$ (3×), dried over Na$_2$SO$_4$, filtered, and evaporated in vacuo, providing compounds X$_{1-16}$.

Example 2

Demonstration of Photolytic Cleavage of T-L-X

A T-L-X compound as prepared in Example 11 was irradiated with near-UV light for 7 min at room temperature. A Rayonett fluorescence UV lamp (Southern New England Ultraviolet Co., Middletown, Conn.) with an emission peak at 350 nm is used as a source of UV light. The lamp is placed at a 15-cm distance from the Petri dishes with samples. SDS gel electrophoresis shows that >85% of the conjugate is cleaved under these conditions.

Example 3

Preparation of Fluorescent Labeled Primers and Demonstration of Cleavage of Fluorophore Synthesis and Purification of Oligonucleotides The oligonucleotides (ODNs) are prepared on automated DNA synthesizers using the standard phosphoramidite chemistry supplied by the vendor, or the H-phosphonate chemistry (Glenn Research Sterling, Va.). Appropriately blocked dA, dG, dC, and T phosphoramidites are commercially available in these forms, and synthetic nucleosides may readily be converted to the appropriate form. The oligonucleotides are prepared using the standard phosphoramidite supplied by the vendor, or the H-phosphonate chemistry. Oligonucleotides are purified by adaptations of standard methods. Oligonucleotides with 5'-trityl groups are chromatographed on HPLC using a 12 micrometer, 300# Rainin (Emeryville, Calif.) Dynamax C-8 4.2×250 mm reverse phase column using a gradient of 15% to 55% MeCN in 0.1 N Et$_3$NH$^+$OAc$^-$, pH 7.0, over 20 min. When detritylation is performed, the oligonucleotides are further purified by gel exclusion chromatography. Analytical checks for the quality of the oligonucleotides are conducted with a PRP-column (Alltech, Deerfield, Ill.) at alkaline pH and by PAGE.

Preparation of 2,4,6-trichlorotriazine derived oligonucleotides: 10 to 1000 μg of 5'-terminal amine linked oligonucleotide are reacted with an excess recrystallized cyanuric chloride in 10% n-methyl-pyrrolidone in alkaline (pH 8.3 to 8.5 preferably) buffer at 19° C. to 25° C. for 30 to 120 minutes. The final reaction conditions consist of 0.15 M sodium borate at pH 8.3, 2 mg/ml recrystallized cyanuric chloride and 500 ug/ml respective oligonucleotide. The unreacted cyanuric chloride is removed by size exclusion chromatography on a G-50 Sephadex (Pharmacia, Piscataway, N.J.) column.

The activated purified oligonucleotide is then reacted with a 100-fold molar excess of cystamine in 0.15 M sodium borate at pH 8.3 for 1 hour at room temperature. The unreacted cystamine is removed by size exclusion chromatography on a G-50 Sephadex column. The derived ODNs are then reacted with amine-reactive fluorochromes. The derived ODN preparation is divided into 3 portions and each portion is reacted with either (a) 20-fold molar excess of Texas Red sulfonyl chloride (Molecular Probes, Eugene, Oreg.), with (b) 20-fold molar excess of Lissamine sulfonyl chloride (Molecular Probes, Eugene, Oreg.), (c) 20-fold molar excess of fluorescein isothiocyanate. The final reaction conditions consist of 0.15 M sodium borate at pH 8.3 for 1 hour at room temperature. The unreacted fluorochromes are removed by size exclusion chromatography on a G-50 Sephadex column.

To cleave the fluorochrome from the oligonucleotide, the ODNs are adjusted to 1×10$^{-5}$ molar and then dilutions are made (12, 3-fold dilutions) in TE (TE is 0.01 M Tris, pH 7.0, 5 mM EDTA). To 100 μl volumes of ODNs 25 μl of 0.01 M dithiothreitol (DTT) is added. To an identical set of controls no DDT is added. The mixture is incubated for 15 minutes at room temperature. Fluorescence is measured in a black microtiter plate. The solution is removed from the incubation tubes (150 microliters) and placed in a black microtiter plate (Dynatek Laboratories, Chantilly, Va.). The plates are then read directly using a Fluoroskan II fluorometer (Flow Laboratories, McLean, Va.) using an excitation wavelength of 495 nm and monitoring emission at 520 nm for fluorescein, using an excitation wavelength of 591 nm and monitoring emission at 612 nm for Texas Red, and using an excitation wavelength of 570 nm and monitoring emission at 590 nm for lissamine.

| Moles of Fluorochrome | RFU non-cleaved | RFU cleaved | RFU free |
|---|---|---|---|
| 1.0 × 10$^5$M | 6.4 | 1200 | 1345 |
| 3.3 × 10$^6$M | 2.4 | 451 | 456 |
| 1.1 × 10$^6$M | 0.9 | 135 | 130 |
| 3.7 × 10$^7$M | 0.3 | 44 | 48 |
| 1.2 × 10$^7$M | 0.12 | 15.3 | 16.0 |
| 4.1 × 10$^7$M | 0.14 | 4.9 | 5.1 |
| 1.4 × 10$^8$M | 0.13 | 2.5 | 2.8 |
| 4.5 × 10$^9$M | 0.12 | 0.8 | 0.9 |

The data indicate that there is about a 200-fold increase in relative fluorescence when the fluorochrome is cleaved from the ODN.

Example 4

Preparation of Tagged M13 Sequence Primers and Demonstration of Cleavage of Tags Preparation of 2,4,6-trichlorotriazine derived oligonucleotides: 1000 μg of 5'-terminal amine linked oligonucleotide (5'-hexylamine-TGTAAAACGACGGCCAGT-3") (Seq. ID No. 1) are reacted with an excess recrystallized cyanuric chloride in 10% n-methyl-pyrrolidone alkaline (pH 8.3 to 8.5 preferably) buffer at 19 to 25- C for 30 to 120 minutes. The final reaction conditions consist of 0.15 M sodium borate at pH 8.3, 2 mg/ml recrystallized cyanuric chloride and 500 ug/ml respective oligonucleotide. The unreacted cyanuric chloride is removed by size exclusion chromatography on a G-50 Sephadex column.

The activated purified oligonucleotide is then reacted with a 100-fold molar excess of cystamine in 0.15 M sodium borate at pH 8.3 for 1 hour at room temperature. The unreacted cystamine is removed by size exclusion chromatography on a G-50 Sephadex column. The derived ODNs are then reacted with a variety of amides.

The derived ODN preparation is divided into 12 portions and each portion is reacted (25 molar excess) with the pentafluorophenyl-esters of either: (1) 4-methoxybenzoic acid, (2) 4-fluorobenzoic acid, (3) toluic acid, (4) benzoic acid, (5) indole-3-acetic acid, (6) 2,6-difluorobenzoic acid, (7) nicotinic acid N-oxide, (8) 2-nitrobenzoic acid, (9) 5-acetylsalicylic acid, (10) 4-ethoxybenzoic acid, (11) cinnamic acid, (12) 3-aminonicotinic acid. The reaction is for 2 hours at 37° C. in 0.2 M NaBorate pH 8.3. The derived ODNs are purified by gel exclusion chromatography on G-50 Sephadex.

To cleave the tag from the oligonucleotide, the ODNs are adjusted to $1 \times 10^{-5}$ molar and then dilutions are made (12, 3-fold dilutions) in TE (TE is 0.01 M Tris, pH 7.0, 5 mM EDTA) with 50% EtOH (V/V). To 100 µl volumes of ODNs 25 µl of 0.01 M dithiothreitol (DTT) is added. To an identical set of controls no DDT is added. Incubation is for 30 minutes at room temperature. NaCl is then added to 0.1 M and 2 volumes of EtOH is added to precipitate the ODNs. The ODNs are removed from solution by centrifugation at 14,000×G at 4° C. for 15 minutes. The supernatants are reserved, dried to completeness. The pellet is then dissolved in 25 µl MeOH. The pellet is then tested by mass spectrometry for the presence of tags.

The mass spectrometer used in this work is an external ion source Fourier-transform mass spectrometer (FTMS). Samples prepared for MALDI analysis are deposited on the tip of a direct probe and inserted into the ion source. When the sample is irradiated with a laser pulse, ions are extracted from the source and passed into a long quadrupole ion guide that focuses and transports them to an FTMS analyzer cell located inside the bore of a superconducting magnet.

The spectra yield the following information. Peaks varying in intensity from 25 to 100 relative intensity units at the following molecular weights: (1) 212.1 amu indicating 4-methoxybenzoic acid derivative, (2) 200.1 indicating 4-fluorobenzoic acid derivative, (3) 196.1 amu indicating toluic acid derivative, (4) 182.1 amu indicating benzoic acid derivative, (5) 235.2 amu indicating indole-3-acetic acid derivative, (6) 218.1 amu indicating 2,6-difluorobenzoic derivative, (7) 199.1 amu indicating nicotinic acid N-oxide derivative, (8) 227.1 amu indicating 2-nitrobenzamide, (9) 179.18 amu indicating 5-acetylsalicylic acid derivative, (10) 226.1 amu indicating 4-ethoxybenzoic acid derivative, (11) 209.1 amu indicating cinnamic acid derivative, (12) 198.1 amu indicating 3-aminonicotinic acid derivative.

The results indicate that the tags are cleaved from the primers and are detectable by mass spectrometry.

Example 5

Figure 3:
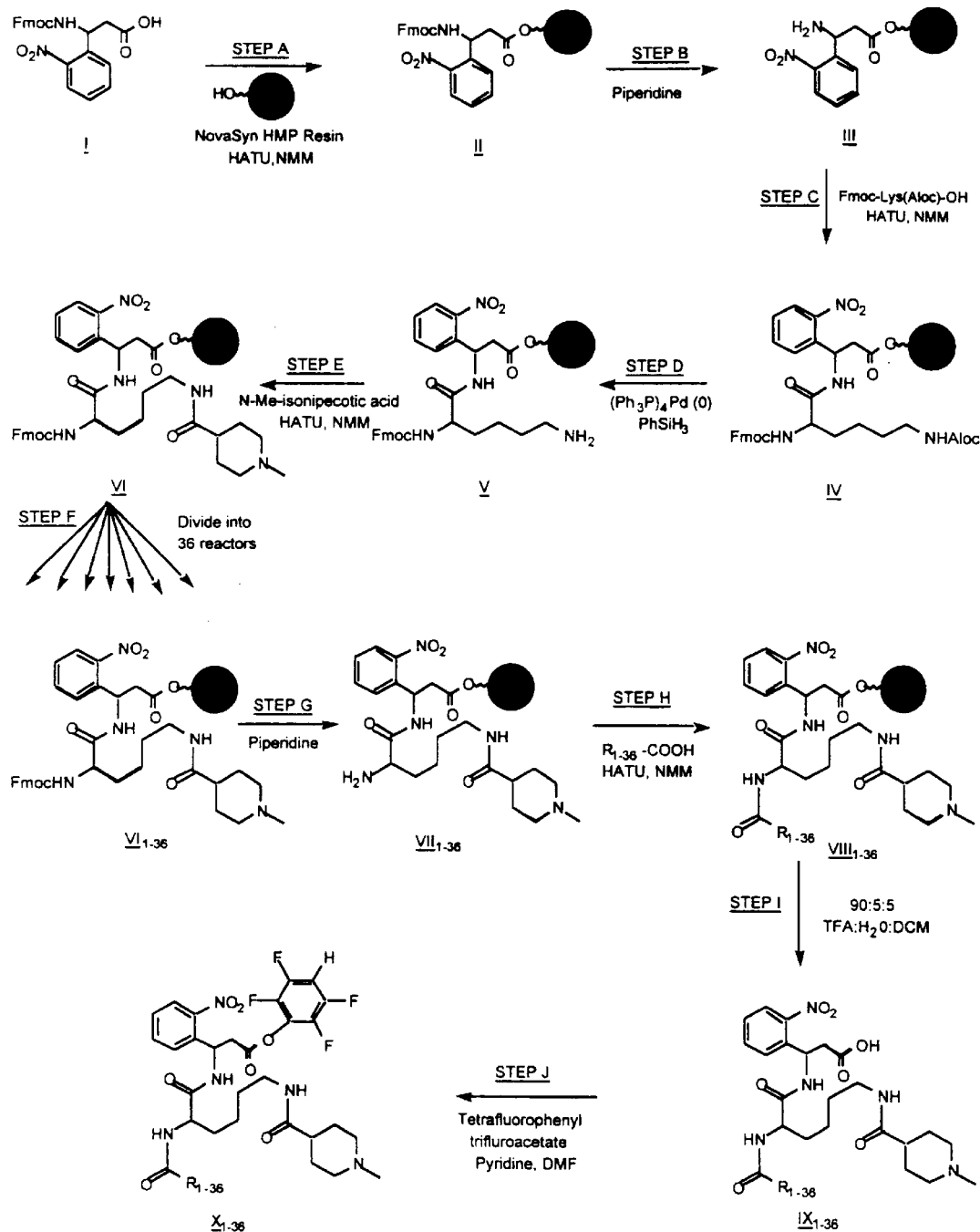
FIGS. 3–6 and 8 depict the flowchart for the synthesis of tetrafluorophenyl esters of a set of 36 photochemically cleavable mass spectroscopy tags.

Preparation of a Set of Compounds of the Formula $R_{1-36}$-Lys($\epsilon$-iNIP)-ANP-Tfp FIG. 3 illustrates the parallel synthesis of a set of 36 T-L-X compounds (X=$L_h$), where $L_h$ is an activated ester (specifically, tetrafluorophenyl ester), $L^2$ is an ortho-nitrobenzylamine group with $L^3$ being a methylene group that links $L_h$ and $L^2$, T has a modular structure wherein the carboxylic acid group of lysine has been joined to the nitrogen atom of the $L^2$ benzylamine group to form an amide bond, and a variable weight component $R_{1-36}$, (where these R groups correspond to $T^2$ as defined herein, and may be introduced via any of the specific carboxylic acids listed herein) is bonded through the α-amino group of the lysine, while a mass spec sensitivity enhancer group (introduced via N-methylisonipecotic acid) is bonded through the ε-amino group of the lysine.

Referring to FIG. 3:

Step A

NovaSyn HMP Resin (available from NovaBiochem; 1 eq.) is suspended with DMF in the collection vessel of the ACT357. Compound I (ANP available from ACT; 3 eq.), HATU (3 eq.) and NMM (7.5 eq.) in DMF are added and the collection vessel shaken for 1 hr. The solvent is removed and the resin washed with NMP (2×), MeOH (2×), and DMF (2×). The coupling of 1 to the resin and the wash steps are repeated, to give compound II.

Step B

The resin (compound II) is mixed with 25% piperidine in DMF and shaken for 5 min. The resin is filtered, then mixed with 25% piperidine in DMF and shaken for 10 min. The solvent is removed, the resin washed with NMP (2×), MeOH (2×), and DMF (2×), and used directly in step C.

Step C

The deprotected resin from step B is suspended in DMF and to it is added an FMOC-protected amino acid, containing a protected amine functionality in its side chain (Fmoc-Lysine(Aloc)-OH, available from PerSeptive Biosystems; 3 eq.), HATU (3 eq.), and NMM (7.5 eq.) in DMF. The vessel is shaken for 1 hr. The solvent is removed and the resin washed with NMP (2×), MeOH (2×), and DMF (2×). The coupling of Fmoc-Lys(Aloc)-OH to the resin and the wash steps are repeated, to give compound IV.

Step D

The resin (compound IV) is washed with $CH_2Cl_2$ (2×), and then suspended in a solution of $(PPh_3)_4Pd$ (0) (0.3 eq.) and $PhSiH_3$ (10 eq.) in $CH_2Cl_2$. The mixture is shaken for 1 hr. The solvent is removed and the resin is washed with $CH_2Cl_2$ (2×). The palladium step is repeated. The solvent is removed and the resin is washed with $CH_2Cl_2$ (2×), N,N-diisopropylethylammonium diethyldithiocarbamate in DMF (2×), DMF (2×) to give compound V.

Step E

The deprotected resin from step D is coupled with N-methylisonipecotic acid as described in step C to give compound VI.

Step F

The Fmoc protected resin VI is divided equally by the ACT357 from the collection vessel into 36 reaction vessels to give compounds $VI_{1-36}$.

Step G

The resin (compounds $VI_{1-36}$) is treated with piperidine as described in step B to remove the FMOC group.

Step H

The 36 aliquots of deprotected resin from step GJ are suspended in DMF. To each reaction vessel is added the appropriate carboxylic acid ($R_{1-36}CO_2H$; 3 eq.), HATU (3 eq.), and NMM (7.5 eq.) in DMF. The vessels are shaken for 1 hr. The solvent is removed and the aliquots of resin washed with NMP (2×), MeOH (2×), and DMF (2×). The coupling of $R_{1-36}CO_2H$ to the aliquots of resin and the wash steps are repeated, to give compounds $VIII_{1-36}$.

Step I. The aliquots of resin (compounds $VIII_{1-36}$) are washed with $CH_2Cl_2$ (3×). To each of the reaction vessels is added 90:5:5 TFA:H20:$CH_2Cl_2$ and the vessels shaken for 120 min. The solvent is filtered from the reaction vessels into individual tubes. The aliquots of resin are washed with $CH_2Cl_2$ (2×) and MeOH (2×) and the filtrates combined into the individual tubes. The individual tubes are evaporated in vacuo, providing compounds $IX_{1-36}$.

Step J

Each of the free carboxylic acids $IX_{1-36}$ is dissolved in DMF. To each solution is added pyridine (1.05 eq.), followed by tetrafluorophenyl trifluoroacetate (1.1 eq.). The mixtures are stirred for 45 min. at room temperature. The solutions are diluted with EtOAc, washed with 5% aq. $NaHCO_3$ (3×), dried over $Na_2SO_4$, filtered, and evaporated in vacuo, providing compounds $X_{1-36}$.

Example 6

Preparation of a Set of Compounds of the Formula $R_{1-36}$-Lys(F-iNIP)-NBA-Tfp

Figure 4:
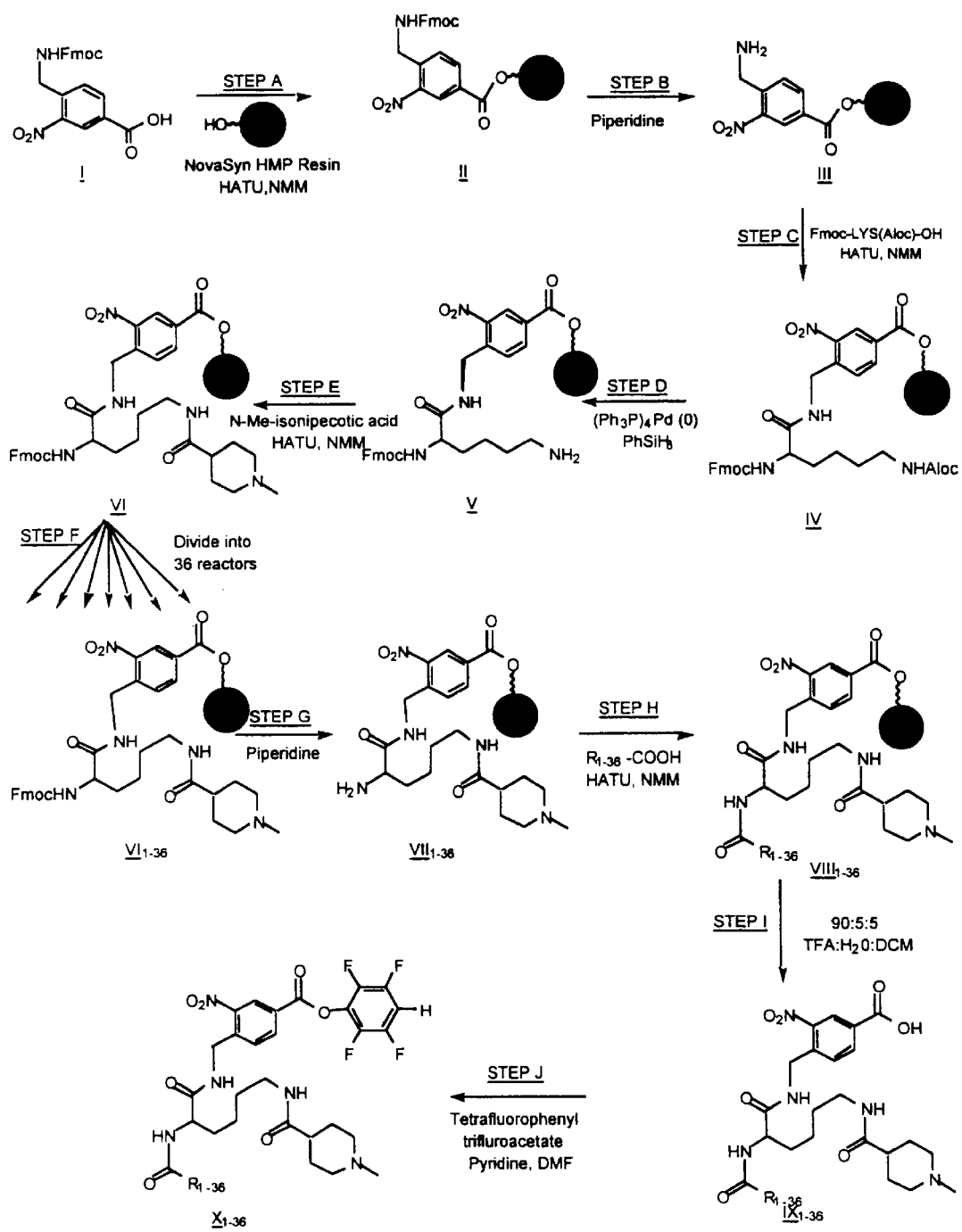

FIG. 4 illustrates the parallel synthesis of a set of 36 T-L-X compounds (X=$L_h$), where $L_h$ is an activated ester (specifically, tetrafluorophenyl ester), $L^2$ is an ortho-nitrobenzylamine group with $L^3$ being a direct bond between $L_h$ and $L^2$, where $L_h$ is joined directly to the aromatic ring of the $L^2$ group, T has a modular structure wherein the carboxylic acid group of lysine has been joined to the nitrogen atom of the $L^2$ benzylamine group to form an amide bond, and a variable weight component $R_{1-36}$, (where these R groups correspond to $T^2$ as defined herein, and may be introduced via any of the specific carboxylic acids listed herein) is bonded through the α-amino group of the lysine, while a mass spec enhancer group (introduced via N-methylisonipecotic acid) is bonded through the ε-amino group of the lysine.

Referring to FIG. 4
Step A

NovaSyn HMP Resin is coupled with compound I (NBA prepared according to the procedure of Brown et al., Molecular Diversity, 1, 4 (1995)) according to the procedure described in step A of Example 5, to give compound II.

Steps B–J

The resin (compound II) is treated as described in steps B–J of Example 5 to give compounds $X_{1-36}$.

Example 7

Figure 5:
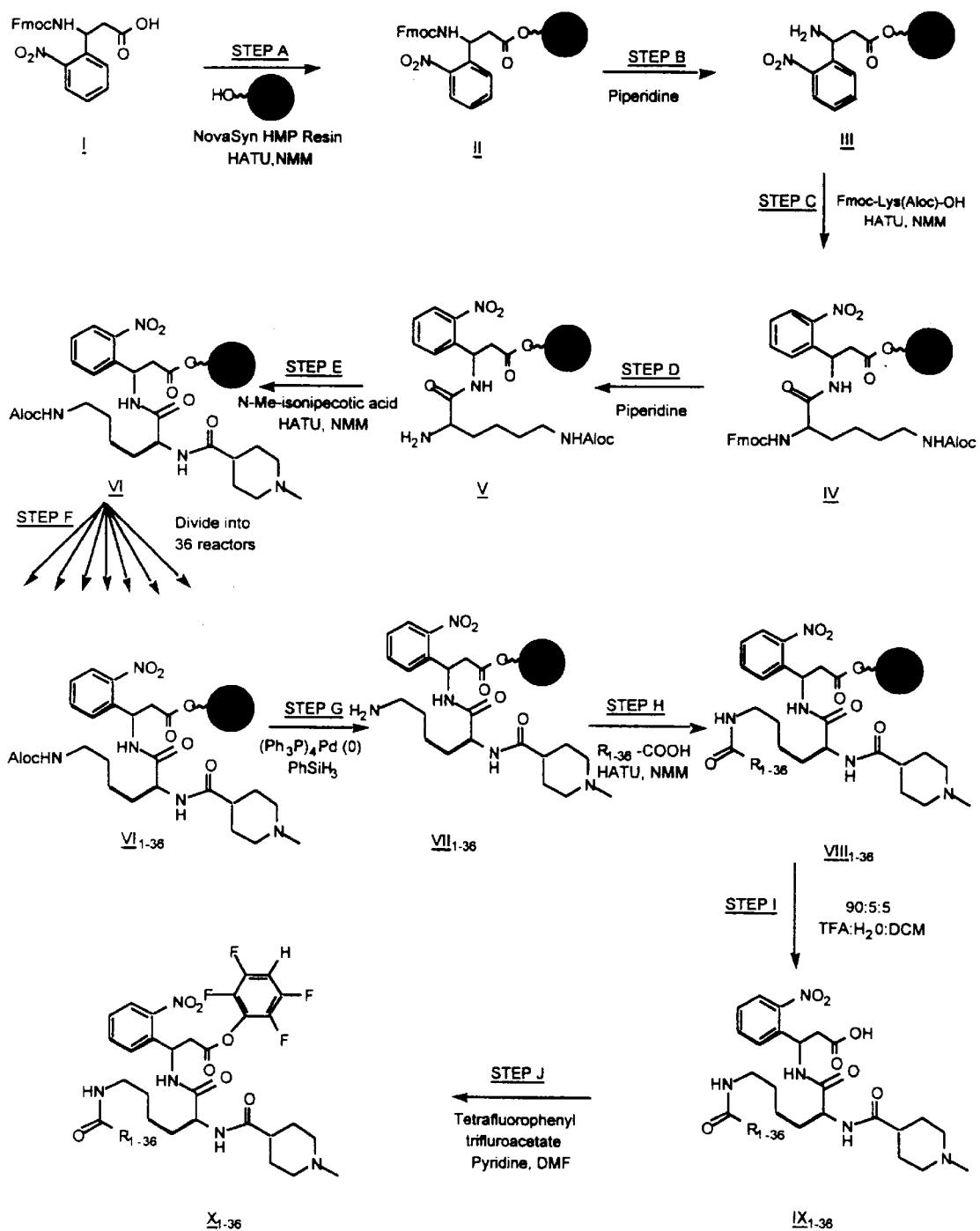

Preparation of a Set of Compounds of the Formula iNIP-Lys (ε-$R_{1-36}$)-ANP-Tfp FIG. 5 illustrates the parallel synthesis of a set of 36 T-L-X compounds (X=$L_h$), where $L_h$ is an activated ester (specifically, tetrafluorophenyl ester), $L^2$ is an ortho-nitrobenzylamine group with $L^3$ being a methylene group that links Lb and $L^2$, T has a modular structure wherein the carboxylic acid group of lysine has been joined to the nitrogen atom of the $L^2$ benzylamine group to form an amide bond, and a variable weight component $R_{1-36}$, (where these R groups correspond to $T^2$ as defined herein, and may be introduced via any of the specific carboxylic acids listed herein) is bonded through the ε-amino group of the lysine, while a mass spec sensitivity enhancer group (introduced via N-methylisonipecotic acid) is bonded through the α-amino group of the lysine.

Referring to FIG. 5:
Steps A–C
Same as in Example 5.

Step D

The resin (compound IV) is treated with piperidine as described in step B of Example 5 to remove the FMOC group.

Step E

The deprotected α-amine on the resin in step D is coupled with N-methylisonipecotic acid as described in step C of Example 5 to give compound V.

Step F

Same as in Example 5.

Step G

The resin (compounds $VI_{1-36}$) are treated with palladium as described in step D of Example 5 to remove the Aloc group.

Steps H–J

The compounds $X_{1-36}$ are prepared in the same manner as in Example 5.

Example 8

Figure 6:
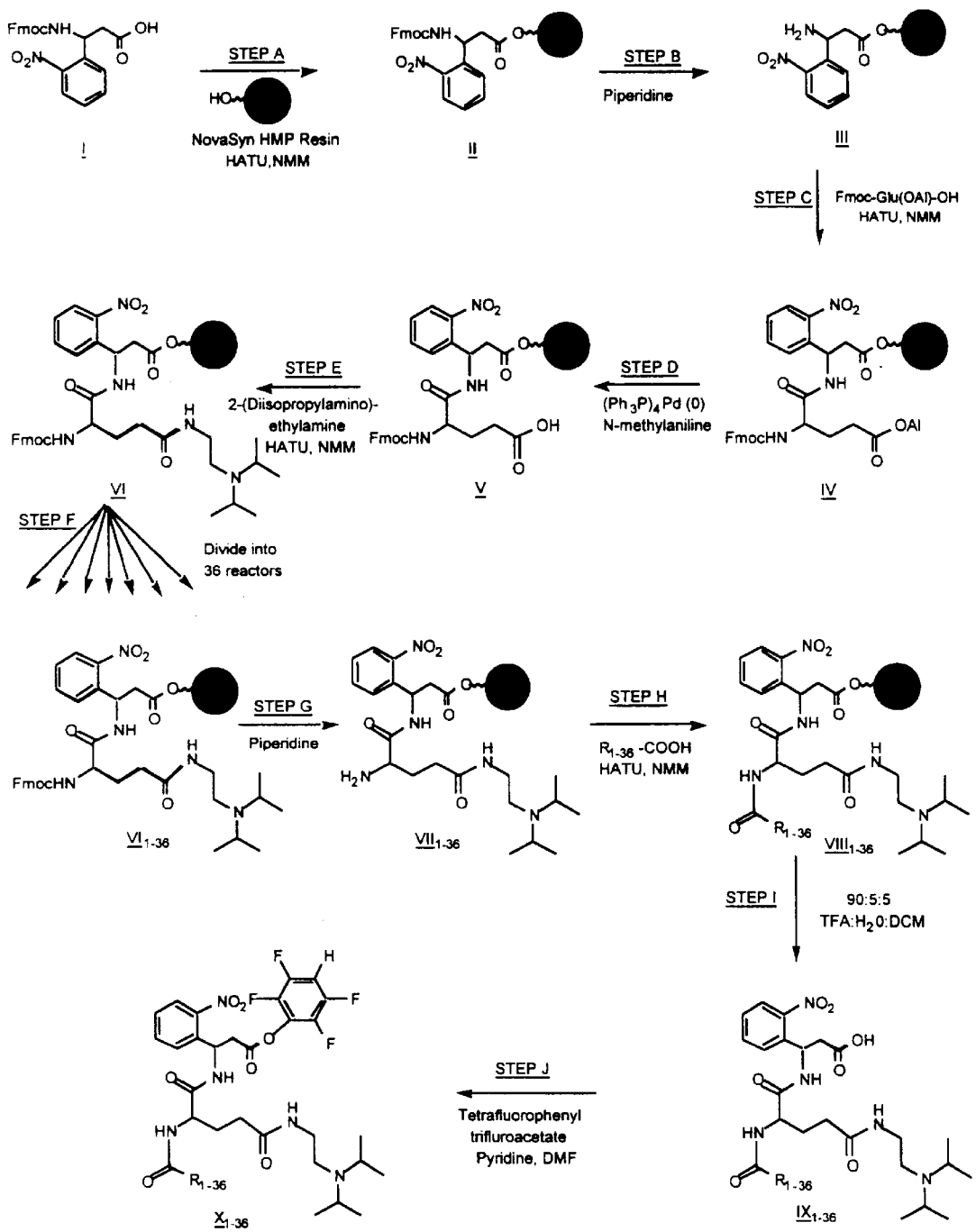

Preparation of a Set of Compounds of the Formula $R_{1-36}$-GLU(γ-DIAEA)-ANP-Tfp FIG. 6 illustrates the parallel synthesis of a set of 36 T-L-X compounds (X=$L_h$), where $L_h$ is an activated ester (specifically, tetrafluorophenyl ester), $L^2$ is an ortho-nitrobenzylamine group with $L^3$ being a methylene group that links $L_h$ and $L^2$, T has a modular structure wherein the α-carboxylic acid group of glutamatic acid has been joined to the nitrogen atom of the $L^2$ benzylamine group to form an amide bond, and a variable weight component $R_{1-36}$, (where these R groups correspond to $T^2$ as defined herein, and may be introduced via any of the specific carboxylic acids listed herein) is bonded through the aα-amino group of the glutamic acid, while a mass spec sensitivity enhancer group (introduced via 2-(diisopropylamino)ethylamine) is bonded through the γ-carboxylic acid of the glutamic acid.

Referring to FIG. 6:
Steps A–B
Same as in Example 5.

Step C

The deprotected resin (compound III) is coupled to Fmoc-Glu-(OAl)-OH using the coupling method described in step C of Example 5 to give compound IV.

Step D

The allyl ester on the resin (compound IV) is washed with $CH_2Cl_2$ (2×) and mixed with a solution of $(PPh_3)_4Pd$ (0) (0.3 eq.) and N-methylaniline (3 eq.) in $CH_2Cl_2$. The mixture is shaken for 1 hr. The solvent is removed and the resin is washed with $CH_2Cl_2$ (2×). The palladium step is repeated. The solvent is removed and the resin is washed with $CH_2Cl_2$ (2×), N,N-diisopropylethylammonium diethyldithiocarbamate in DMF (2×), DMF (2×) to give compound V.

Step E

The deprotected resin from step D is suspended in DMF and activated by mixing HATU (3 eq.), and NMM (7.5 eq.). The vessels are shaken for 15 minutes. The solvent is removed and the resin washed with NMP (1×). The resin is mixed with 2-(diisopropylamino)ethylamine (3 eq.) and NMM (7.5 eq.). The vessels are shaken for 1 hour. The coupling of 2-(diisopropylamino)ethylamine to the resin and the wash steps are repeated, to give compound VI.

Steps F–J
Same as in Example 5.

Example 9

Figure 7:
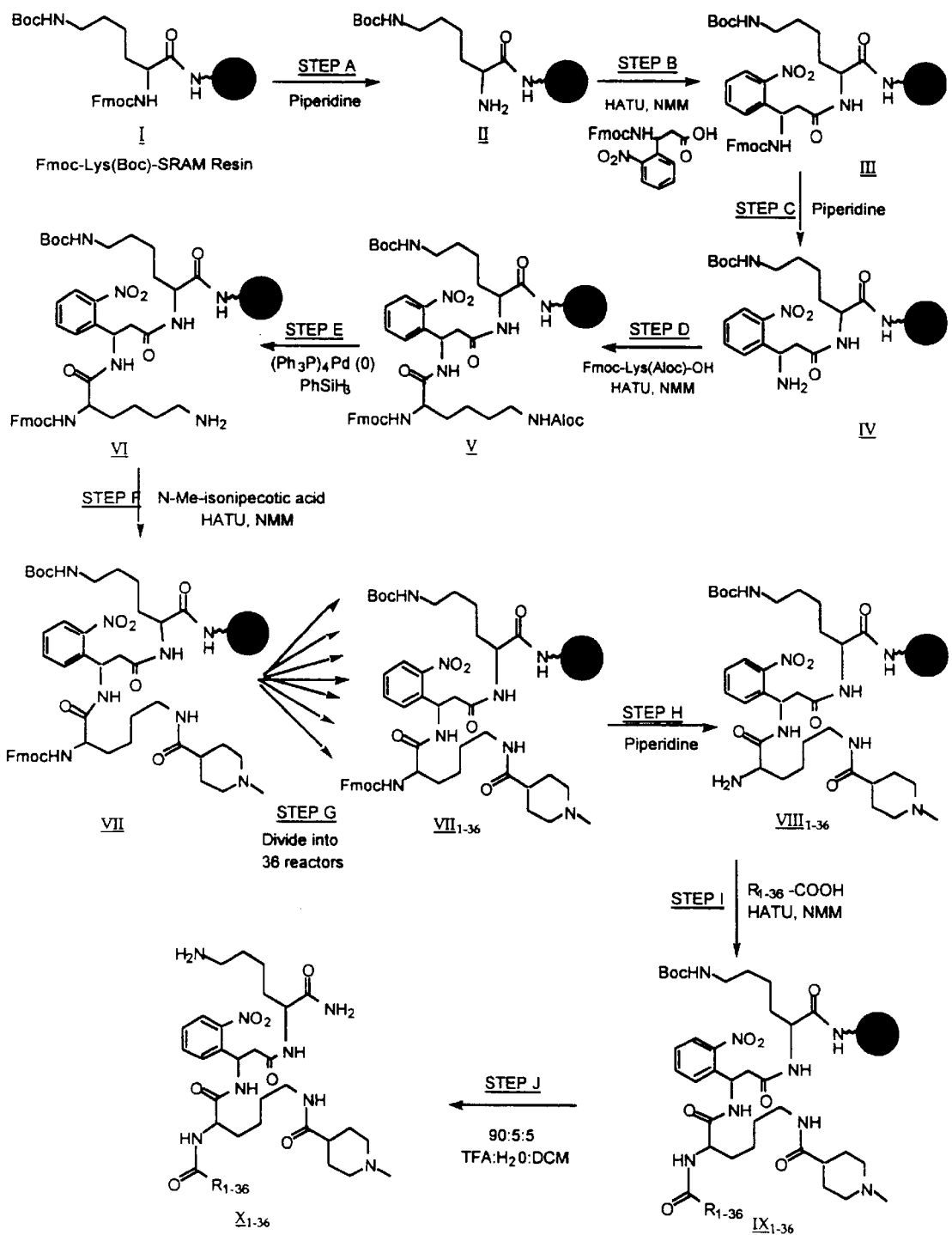
FIG. 7 depicts the flowchart for the synthesis of a set of 36 amine-terminated photochemically cleavable mass spectroscopy tags.

Preparation of a Set of Compounds of the Formula $R_{1-36}$-Lys(ε-iNIP)-ANP-Lys(ε-$NH_2$)-$NH_2$ FIG. 7 illustrates the parallel synthesis of a set of 36 T-L-X compounds (X=$L_h$), where $L_h$ is an amine (specifically, the ε-amino group of a lysine-derived moiety), $L^2$ is an ortho-nitrobenzylamine group with $L^3$ being a carboxamido-substituted alkyleneaminoacylalkylene group that links $L_h$ and $L^2$, T has a modular structure wherein the carboxylic acid group of lysine has been joined to the nitrogen atom of the $L^2$ benzylamine group to form an amide bond, and a variable weight component $R_{1-36}$, (where these R groups correspond to $T^2$ as defined herein, and may be introduced via any of the specific carboxylic acids listed herein) is bonded through the α-amino group of the lysine, while a mass spec sensitivity enhancer group (introduced via N-methylisonipecotic acid) is bonded through the ε-amino group of the lysine.

Referring to FIG. 7:
Step A

Fmoc-Lys(Boc)-SRAM Resin (available from ACT; compound I) is mixed with 25% piperidine in DMF and shaken for 5 min. The resin is filtered, then mixed with 25% piperidine in DMF and shaken for 10 min. The solvent is removed, the resin washed with NMP (2×), MeOH (2×), and DMF (2×), and used directly in step B.
Step B The resin (compound II), ANP (available from ACT; 3 eq.), HATU (3 eq.) and NMM (7.5 eq.) in DMF are added and the collection vessel shaken for 1 hr. The solvent is removed and the resin washed with NMP (2×), MeOH (2×), and DMF (2×). The coupling of 1 to the resin and the wash steps are repeated, to give compound III.
Steps C–J The resin (compound III) is treated as in steps B–I in Example 5 to give compounds $X_{1-36}$.

Example 10

Figure 8:
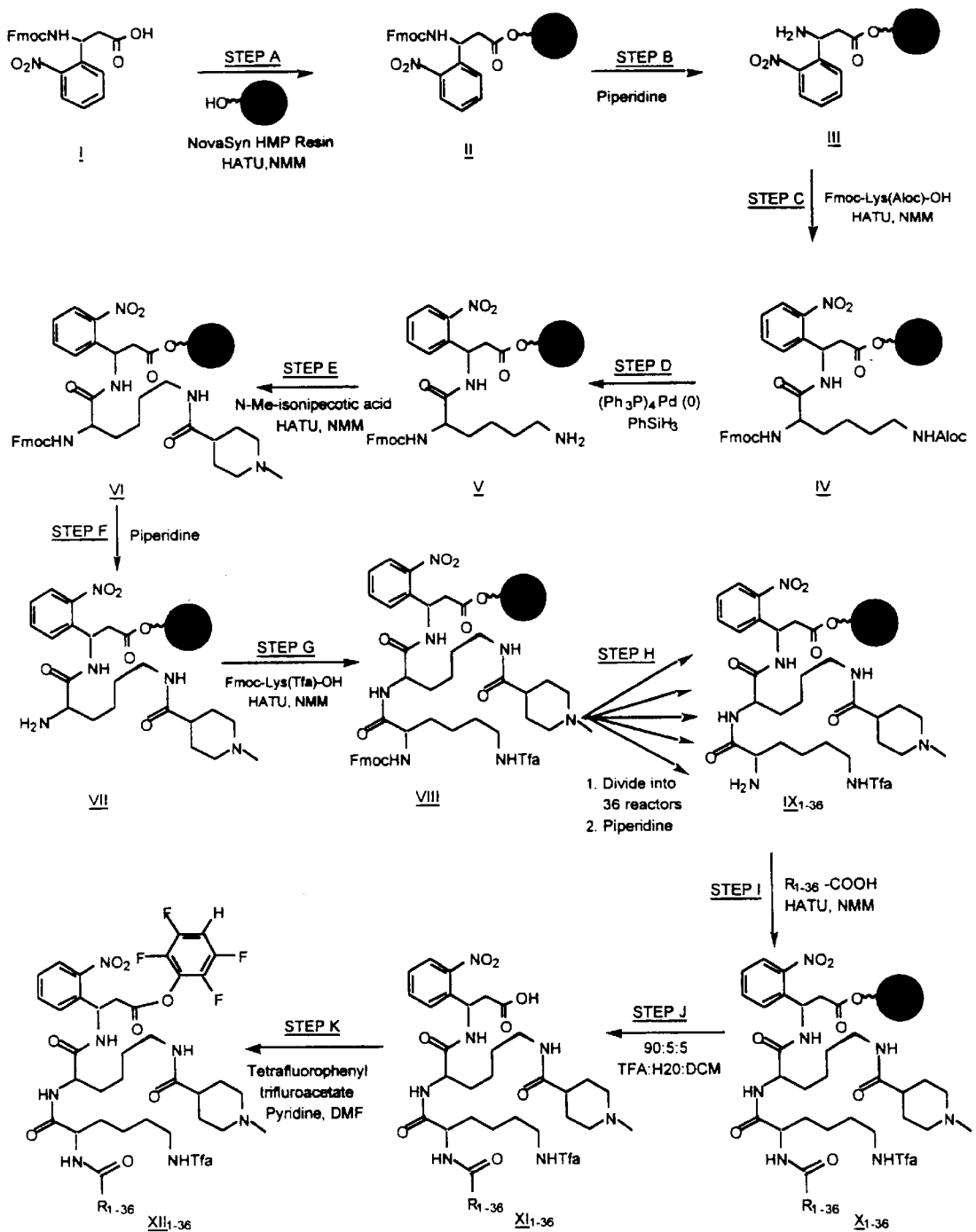

Preparation of a Set of Compounds of the Formula
$R_{1-36}$-Lys(ε-Tfa)-Lys(ε-iINP)-ANP-Tfp FIG. 8 illustrates the parallel synthesis of a set of 36 T-L-X compounds (X=$L_h$), where $L_h$ is an activated ester (specifically, tetrafluorophenyl ester), $L^2$ is an ortho-nitrobenzylamine group with $L^3$ being a methylene group that links $L_h$ and $L^2$, T has a modular structure wherein the carboxylic acid group of a firsi lysine has been joined to the nitrogen atom of the $L^2$ benzylamine group to form an amide bond, a mass spec sensitivity enhancer group (introduced via N-methylisonipecotic acid) is bonded through the ε-amino group of the first lysine, a second lysine molecle has been joined to the first lysine through the α-amino group of the first lysine, a molecular weight adjuster group (having a trifluoroacetyl structure) is bonded through the ε-amino group of the second lysine, and a variable weight component $R_{1-36}$, (where these R groups correspond to $T^2$ as defined herein, and may be introduced via any of the specific carboxylic acids listed herein) is bonded through the α-amino group of the second lysine.

Referring to FIG. 8:
Steps A–E

These steps are identical to steps A–E in Example 5.
Step F

The resin (compound VI) is treated with piperidine as described in step B in Example 5 to remove the FMOC group.
Step G The deprotected resin (compound VII) is coupled to Fmoc-Lys(Tfa)-OH using the coupling method described in step C of Example 5 to give compound VIII.
Steps H–K The resin (compound VIII) is treated as in steps F–J in Example 5 to give compounds $XI_{1-36}$.

Example 11

Figure 9:
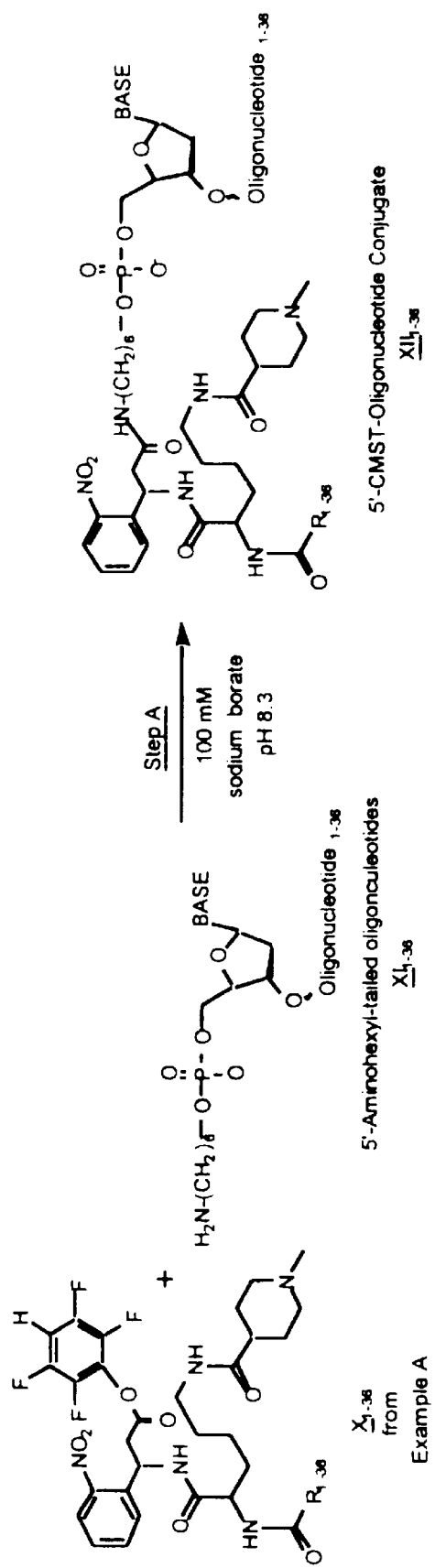
FIG. 9 depicts the synthesis of 36 photochemically cleavable mass spectroscopy tagged oligonucleotides made from the corresponding set of 36 tetrafluorophenyl esters of photochemically cleavable mass spectroscopy tag acids.

Preparation of a Set of Compounds of the Formula
$R_{1-36}$-Lys(ε-iNIP)-ANP-5'-AH-ODN FIG. 9 illustrates the parallel synthesis of a set of 36 T-L-X compounds (X=MOI, where MOI is a nucleic acid fragment, ODN) derived from the esters of Example 5 (the same procedure could be used with other T-L-X compounds wherein X is an activated ester). The MOI is conjugated to T-L through the 5' end of the MOI, via a phosphodiester-alkyleneamine group.

Referring to FIG. 9:
Step A

Compounds $XII_{1-36}$ are prepared according to a modified biotinylation procedure in Van Ness et al., Nucleic Acids Res., 19, 3345 (1991). To a solution of one of the 5'-aminohexyl oligonucleotides (compounds $XI_{1-36}$, 1 mg) in 200 mM sodium borate (pH 8.3, 250 mL) is added one of the Tetrafluorophenyl esters (compounds $X_{1-36}$ from Example 5, 100-fold molar excess in 250 mL of NMP). The reaction is incubated overnight at ambient temperature. The unreacted and hydrolyzed tetrafluorophenyl esters are removed from the compounds $XII_{1-36}$ by Sephadex G-50 chromatography.

Example 12

Figure 10:
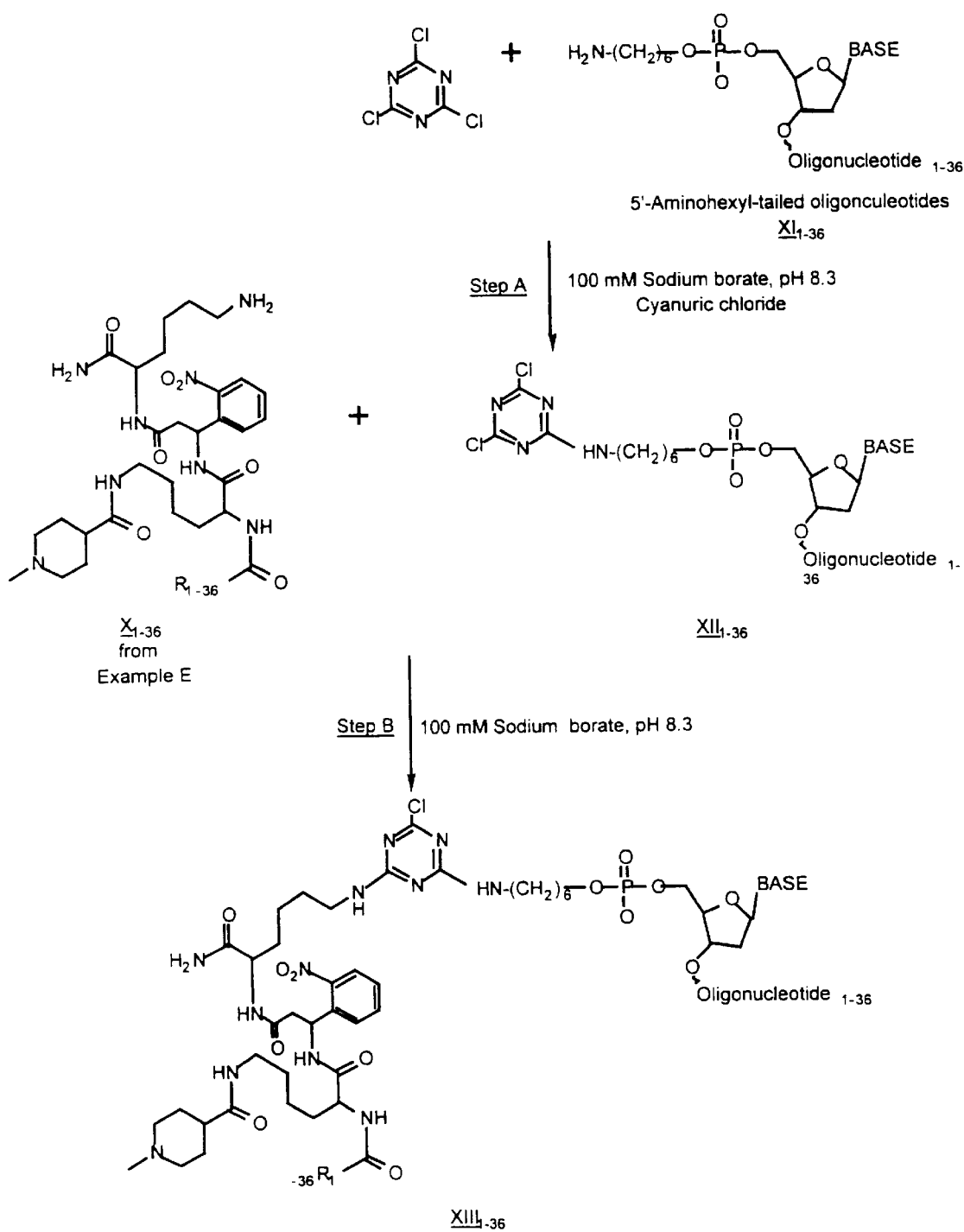
FIG. 10 depicts the synthesis of 36 photochemically cleavable mass spectroscopy tagged oligonucleotides made from the corresponding set of 36 amine-terminated photochemically cleavable mass spectroscopy tags.

Preparation of a Set of Compounds if the Formula
$R_{1-36}$-Lys(ε-iNIP)-ANP-Lys(ε-(MCT-5,-AH-ODN))-$NH_2$ FIG. 10 illustrates the parallel synthesis of a set of 36 T-L-X compounds (X=MOI, where MOI is a nucleic acid fragment, ODN) derived from the amines of Example 9 (the same procedure could be used with other T-L-X compounds wherein X is an amine). The MOI is conjugated to T-L through the 5' end of the MOI, via a phosphodiester—alkyleneamine group.

Referring to FIG. 10:
Step A

The 5'-[6-(4,6-dichloro-1,3,5-triazin-2-ylamino)hexyl] oligonucleotides $XII_{1-36}$ are prepared as described in Van Ness et al., Nucleic Acids Res., 19, 3345 (1991).
Step B To a solution of one of the 5'-[6-(4,6-dichloro-1,3,5-triazin-2-ylamino)hexyl]oligonucleotides (compounds $XII_{1-36}$) at a concentration of 1 mg/ml in 100 mM sodium borate (pH 8.3) was added a 100-fold molar excess of a primary amine selected from $R_{1-36}$-Lys(e-iNIP)-ANP-Lys(e-$NH_2$)—$NH_2$ (compounds $X_{1-36}$ from Example 11). The solution is mixed overnight at ambient temperature. The unreacted amine is removed by ultrafiltration through a 3000 MW cutoff membrane (Amicon, Beverly, Mass.) using $H_2O$ as the wash solution (3×). The compounds $XIII_{1-36}$ are isolated by reduction of the volume to 100 mL.

Example 13

Demonstration of the Simultaneous Detection of Multiple Tags by Mass Spectrometry This example provides a description of the ability to simultaneously detect multiple compounds (tags) by mass spectrometry. In this particular example, 31 compounds are mixed with a matrix, deposited and dried on to a solid support and then desorbed with a laser. The resultant ions are then introduced in a mass spectrometer.

The following compounds (purchased from Aldrich, Milwaukee, Wis.) are mixed together on an equal molar basis to a final concentration of 0.002 M (on a per compound) basis: benzamide (121.14), nicotinamide (122.13), pyrazinamide (123.12), 3-amino-4-pyrazolecarboxylic acid (127.10), 2-thiophenecarboxamide (127.17), 4-aminobenzamide (135.15), tolumide (135.17), 6-methylnicotinamide (136.15), 3-aminonicotinamide (137.14), nicotinamide N-oxide (138.12), 3-hydropicolinamide (138.13), 4-fluorobenzamide (139.13), cinnamamide (147.18), 4-methoxybenzamide (151.17), 2,6-difluorbenzamide (157.12), 4-amino-5-imidazole-carboxyamide (162.58), 3,4-pyridine-dicarboxyamide (165.16), 4-ethoxybenzamide (165.19), 2,3-pyrazinedicarboxamide (166.14), 2-nitrobenzamide (166.14), 3-fluoro-4-methoxybenzoic acid (170.4), indole-3-acetamide (174.2), 5-acetylsalicylamide (179.18), 3,5-dimethoxybenzamide (181.19), 1-naphthaleneacetamide (185.23), 8-chloro-3,5-diamino-2-pyrazinecarboxyamide (187.59), 4-trifluoromethyl-benzamide (189.00), 5-amino-5-phenyl-4-pyrazole-carboxamide (202.22), 1-methyl-2-benzyl-malonamate (207.33), 4-amino-2,3,5,6-tetrafluorobenzamide (208.11), 2,3-napthlenedicarboxylic acid (212.22). The compounds are placed in DMSO at the concentration described above. One µl of the material is then mixed with alpha-cyano-4-hydroxy cinnamic acid matrix (after a 1:10,000 dilution) and deposited on to a solid stainless steel support.

Figure 11:
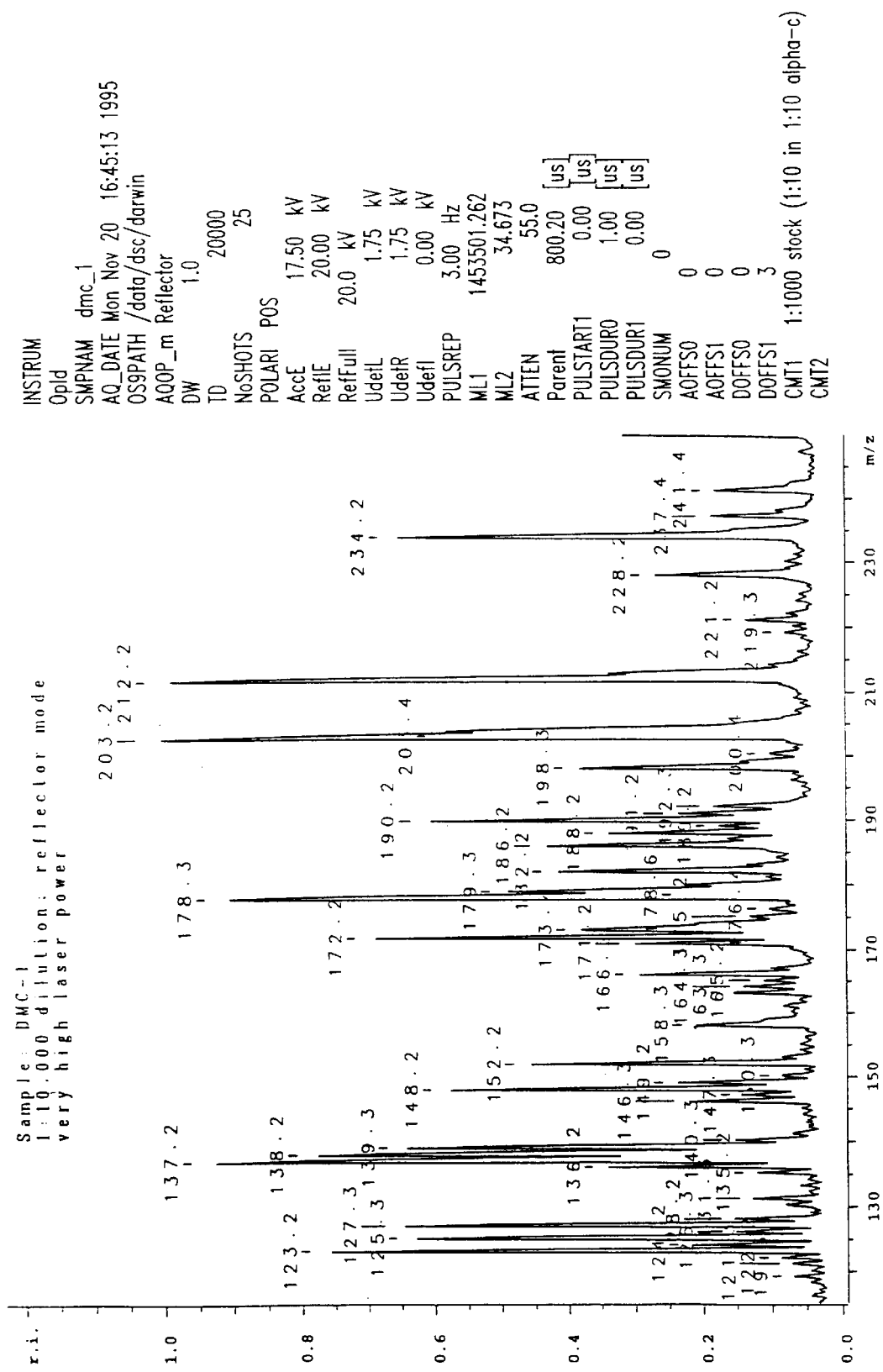
FIG. 11 illustrates the simultaneous detection of multiple tags by mass spectrometry.

The material is then desorbed by a laser using the Protein TOF Mass Spectrometer (Bruker, Manning Park, Mass.) and the resulting ions are measured in both the linear and reflectron modes of operation. The following m/z values are observed (FIG. 11):

| | |
|---|---|
| 121.1→ | benzamide (121.14) |
| 122.1→ | nicotinamide (122.13) |
| 123.1→ | pyrazinamide (123.12) |
| 124.1 | |
| 125.2 | |
| 127.3→ | 3-amino-4-pyrazolecarboxylic acid (127.10) |
| 127.2→ | 2-thiophenecarboxamide (127.17) |
| 135.1→ | 4-aminobenzamide (135.15) |
| 135.1→ | tolumide (135.17) |
| 136.2→ | 6-methylnicotinamide (136.15) |
| 137.1→ | 3-aminonicotinamide (137.14) |
| 138,2→ | nicotinamide N-oxide (138.12) |
| 138.2→ | 3-hydropicolinamide (138.13) |
| 139.2→ | 4-fluorobenzamide (139.13) |
| 140.2 | |
| 147.3→ | cinnamamide (147.18) |
| 148.2 | |
| 149.2 | 4-methoxybenzamide (151.17) |
| 152.2 | 2,6-difluorbenzamide (157.12) |
| 158.3 | 4-amino-5-imidazole-carboxyamide (162.58) |
| 163.3 | |
| 165.2→ | 3,4-pyridine-dicarboxyamide (165.16) |
| 165.2→ | 4-ethoxybenzamide (165.19) |
| 166.2→ | 2,3-pyrazinedicarboxamide (166.14) |
| 166.2→ | 2-nitrobenzamide (166.14) |
| | 3-fluoro-4-methoxybenzoic acid (170.4) |
| 171.1 | |
| 172.2 | |
| 173.4 | indole-3-acetamide (174.2) |
| 178.3 | |
| 179.3→ | 5-acetylsalicylamide (179.18) |
| 181.2→ | 3,5-dimethoxybenzamide (181.19) |
| 182.2→ | 1-naphthaleneacetamide (185.23) |
| 186.2 | 8-chloro-3,5-diamino-2-pyrazinecarboxyamide (187.59) |
| 188.2 | |
| 189.2→ | 4-trifluoromethyl-benzamide (189.00) |
| 190.2 | |
| 191.2 | |
| 192.3 | 5-amino-5-phenyl-4-pyrazole-carboxamide (202.22) |
| 203.2 | |
| 203.4 | 1-methyl-2-benzyl-malonamate (207.33) |
| | 4-amino-2,3,5,6-tetrafluorobenzamide (208.11) |
| 212.2→ | 2,3-napthlenedicarboxylic acid (212.22). |
| 219.3 | |
| 221.2 | |
| 228.2 | |
| 234.2 | |
| 237.4 | |
| 241.4 | |

The data indicate that 22 of 31 compounds appeared in the spectrum with the anticipated mass, 9 of 31 compounds appeared in the spectrum with a n+H mass (1 atomic mass unit, amu) over the anticipated mass. The latter phenomenon is probably due to the protonation of an amine within the compounds. Therefore 31 of 31 compounds are detected by MALDI Mass Spectroscopy. More importantly, the example demonstrates that multiple tags can be detected simultaneously by a spectroscopic method.

The alpha-cyano matrix alone (FIG. 11) gave peaks at 146.2, 164.1, 172.1, 173.1, 189.1, 190.1, 191.1, 192.1, 212.1, 224.1, 228.0, 234.3. Other identified masses in the spectrum are due to contaminants in the purchased compounds as no effort was made to further purify the compounds.

Example 14

Assay of Gene Expression Using Multiple Probes

Sodium borate buffers (SBB) were freshly prepared from boric acid and sodium hydroxide. APB buffer is 0.18 M NaCl, 0.05 M Tris pH 7.6, 5 mM EDTA, and 0.5% Tween 20R. TMNZ buffer is 0.05 M Tris pH 9.5, 1 mM MgCl2, 0.5 mM ZnCl2. FW (filter wash) is 0.09 M NaCl, 50 mM Tris pH 7.6, 25 mM EDTA. SDS/FW is FW with 0.1% sodium dodecyl sulfate (SDS). Lysis and hybridization solution is 3 M guanidinium thiocyante, 2% N-lauroylsarcosine (sarcosyl), 50 mM Tris pH 7.6 and 25 mM EDTA. CAP buffer is 0.1 M sodium citrate and 0.2 M sodium phosphate, pH 6.5. HRP (horseradish peroxidase) substrate solution is 0.1 M sodium citrate pH 6.5, 0.2 M sodium phosphate, 2.87 mM 4-methoxy-1-naphthol, 0.093 mM 3-methyl-2-benzothiazolinone hydrazone hydrochloride and 4 mM hydrogen peroxide. AP (alkaline phosphatase) substrate solution is 1 mM 5-bromo-4-chlorindoyl-3-phosphate, 1 mM nitroblue tetrazolium, and 0.01% Tween 20 in TMNZ. The fluorescent substrate for alkaline phosphatase is 0.5 mM 4-methyl-umbelliferone phosphate, 0.05 M Tris pH 9.5, 1 mM MgCl2, 0.5 mM ZnCl2. Poly(ethyleneimine) was purchased from Polysciences (Warrington, Pa.). Burnished or unpolished nylon beads were purchased from The Hoover Group (Sault St. Marie, Mich.). Triethyloxonium tetrafluoroborate, succinic anhydride and 1-methyl-2-pyrrolidinone were purchased from Aldrich Chemical (Milwaukee, Wis.). Tween 20R and NHS-LC-Biotin were purchased from Pierce (Rockford, Ill.). Guanidine thiocyanate (GuSCN) was purchased from Kodak (Rochester, N.Y.). Cyanuric chloride was from Aldrich Chemical Co. (Milwaukee, Wis.) and was recrystallized from toluene.

A. ODN Synthesis

ODNs complementary (5'-CCTTAGGACAGTCTTCTTCACGC) to conserved or hypervariable regions of the 16S ribosomal RNA (rRNA) of Porphyromonas gingivalis (Pg), were synthesized on either an ABI 380B or a MilliGen 7500 automated DNA synthesizer using the standard cyanoethyl-N,N-diisopropylamino-phosphoramidite (CED-phosphoramidite) chemistry. Amine tails were incorporated onto the 5'-end using the commercially available N-monomethoxytritylaminoihex-6-yloxy-CED-phosphoramidite. ODNs with 5'-monomethoxytritryl groups were chromatographed by HPLC using a Hamilton PRP-1 (7.0×305 mm) reversed-phase column employing a gradient of 5% to 45% CH3CN in 0.1 M Et3NH+OAc-, pH 7.5, over 20 min. After detritylation with 80% acetic acid, the ODN s were precipitated by addition of 3 M sodium acetate and 1-butanol. Analytical checks for the quality of the ODNs were done by ion-exchange HPLC using a Toso-Haas DEAE-NPR column and by denaturing polyacrylamide gel electrophoresis (PAGE).

B. Preparation of the Polymer-coated Nylon Bead

Unpolished nylon beads (25,000, 3/32 inch diameter) in anhydrous 1-methyl-2-pyrrolidinone (1800 mL) were stirred for 5 min. at ambient temperature. Triethyloxonium tetrafluoroborate (200 mL, 1 M in dichloromethane) was added and then stirred for 30 min. at ambient temperature. The liquid was decanted and the beads were washed quickly with 1-methyl-2-pyrrolidinone (4×500 mL). The beads were then stirred for 12–24 hr a 3% (w/v) solution (1 L) of 70,000 MW poly(ethyleneimine) in 1-methyl-2-pyrrolidinone (prepared from a 30% aqueous solution of poly(ethyleneimine)). After decanting the poly(ethyleneimine) solution the beads were washed with 1-methyl-2-pyrrolidinone (2×1 L), SDS/FW (2×1 L), $H_2O$ (10×2 L), and finally with 95% ethanol (1×500 mL). The beads were dried under high vacuum for 4 to 5 h. The amine content of the beads was determined by reaction with picrylsulfonic acid.

C. Preparation of 5'-[6-(4.6-Dichloro-1,3,5-triazin-2-ylamino)-hexyl]-ODNs

To a solution of 5'-aminohexyl ODN (1 mL, 10 mg/mL) in freshly prepared 0.1 M SBB (pH 8.3, 3.2 mL) and H2O (1.8 mL) was added an acetonitrile solution of recrystallized cyanuric chloride (1 mL, 50 mg/mL). The solution was mixed for 30–120 minutes at ambient temperature. The unreacted cyanuric chloride was removed by ultrafiltration through a 3000 MW cutoff membrane (Amicon, Beverly, Mass.) using freshly prepared 0.1 M SBB n(pH 9.3, 4×10 mL) as the wash solution. After the final wash the volume was reduced to 1 mL. The 5'-[6-(4,6-dichloro-1,3,5-triazin-2-ylamino)hexyl]-ODNs are stable for 1 week at 4° C. in 0.1 M SBB (pH 8.3) with no detectable decomposition.

D. Attachment of ODNs to Nylon Beads

PEI-coated nylon beads (500 beads), described above, were placed in an equal volume of freshly prepared 0.1 M SBB (pH 9.3) and vigorously agitated for 30 min. to rehydrate the beads. The borate solution was decanted and the beads were washed once with 0.1 MSBB (pH 8.3) then vocered with an equal volume of fresh 0.1 M SBB. The borate solution of the 5'-[6-(4–6-dichloro-1,3,5-triazin-2-ylamino)hexyl]-ODN (1 mL, 500 mg/mL) was then added to the beads. The mixture was vigorously agitated at ambient temperature for 60 min. The solution was decanted and the beads were then washed with 0.1 M SBB (pH 8.3, 2×500 mL). The beads were treated in three times the volume of the beads with succinic anhydride (10 mg/mL) in 9:1 1-methyl-2-pyrrolidinone: 1.0 M SBB (pH 8.3). The reaction mixture was stirred for 1 h at ambient temperature. The beads were then washed with 1-methyl-2-pyrrolidinone (3×250 mL), dH2O (2×1 L), SDS/FW (5×250 mL), and then with dH2O (4×1 L). The beads were stored in 25 mM EDTA.

E. Design and Labeling the Probes

In this part of the example 5 probes are designed that will permit the differential mRNA expression in stimulated versus unstimulated Jurkat human T-cell lymphoma (JRT 3.5).

100 µg of each of the 5'-terminal amine-linked oligonucleotides described above are reacted with an excess recrystallized cyanuric chloride in 10% n-methyl-pyrrolidone alkaline (pH 8.3 to 8.5 preferably) buffer at 19° C. to 25° C. for 30 to 120 minutes. The final reaction conditions consist of 0.15 M sodium borate at pH 8.3, 2 mg/ml recrystallized cyanuric chloride and 500 ug/ml respective oligonucleotide. The unreacted cyanuric chloride is removed by size exclusion chromatography on a G-50 Sephadex column. The activated purified oligonucleotide is then reacted with a 100-molar excess of cystamine in 0.15 M sodium borate at pH 8.3 for 1 hour at room temperature. The unreacted cystamine is removed by size exclusion chromatography on a G-50 Sephadex column. The derived ODNs are then reacted with amine-reactive fluorochromes. The derived ODN preparation is divided into 3 portions and each portion is reacted with either (a) 20-fold molar excess of Texas Red sulfonyl chloride (Molecular Probes, Eugene, Oreg.), with (b) 20-fold molar excess of Lissamine sulfonyl chloride (Molecular Probes, Eugene, Oreg.), (c) 20-fold molar excess of fluorescein isothiocyanate. The final reaction conditions consist of 0.15 M sodium borate at pH 8.3 for 1 hour at room temperature. The unreacted fluorochromes are removed by size exclusion chromatography on a G-50 Sephadex column. IL-2, IFN-g, GM-CSF, were labelled with Texas Red. c-fos IL-4 and PKC-g were labelled with lissamine and CTLA4/CD28 and GMP kinase were labelled with fluroescein. The IL-2, c-fos and CTLA4 probes were pooled. The IFN-g, IL-4 and GMP kinase probes were pooled and GM-CSF and PKC-g probes were pooled.

F. Solid Support cDNA Synthesis for Gene Expression Assay

```
Oligo DMO 596 5'- ACTACTGATCAGGCGCGCCTTTTTTTTTTTTTTTTTTT -3'
                  spacer    Asc I    (poly dT)20
```

G. Stimulation and RNA Prep

Jurkat line JRT 3.5 is stimulated for 6 hours at a cell density of 1×10e6 cells/ml in serum-free RPMI medium (Life Technologies. Gaithersburg, Md.) in the presence of 10 ng/ml phorbol-12-myristate-13 acetate (Calbiochem, San Diego, Calif.) and 100 ng/ml ionomycin (Calbiochem). Cells are pelleted, washed in 1×PBS (Life Technologies), re-pelleted and lysed in 0.5 ml, per $10^{-6}$ cells, buffer containing 4M guanidine isothiocyanate/1% N-lauryl sarcosine/25 mM sodium citrate pH 7.1 (Fisher Scientific. Pittsburg, Pa.). One-tenth volume 2M sodium acetate (Fisher Scientific) pH 4.2 is added followed by one volume of water saturated phenol (Amresco. Solon, Ohio). After mixing, one-fourth volume chloroform:isoamyl alcohol, (29:1), (Fisher Scientific) is added and the solution is mixed vigorously, then incubated on ice for 10 minutes. The lysate is then spun, the aqueous phase removed and extracted with an equal volume of chloroform:isoamyl alcohol. The aqueous phase is then pooled and the RNA precipitated with 2 volumes of EtOH (Quantum Chemical Corp., Tuscola, Ill.). After centrifugation, the EtOH is decanted and the RNA is air-dried briefly, then resuspended in RNase-free water to a concentration of between 1 and 5 mg/ml.

H. Capture and First Strand Synthesis

One nylon bead bearing the covalently linked oligonucleotide, 5'-ACTACTGATCAGGCGCGCCTTTTT TTTTTTTTTTTTTT-3' (GenSet, La Jolla, Calif.), is added to, 10, ug total cellular RNA, diluted in enough RNase-free water to cover the bead, in a sterile 1.5 ml microfuge tube (Fisher Scientific). The RNA and bead are incubated at 65C for 5 minutes. An equal volume of 2× mRNA hybridization buffer consisting of 50, mM Tris pH 7.5 , 1M NaCl (Fisher Scientific) and 20, ug/ml acetylated-BSA (New England Biolabs, Beverly, Mass.) is added to each tube and the tubes rocked gently for 2 hours at room temperature. The supernatant is removed and the bead is then washed three times in 1× mRNA hybridization buffer. After the final wash is complete, a reverse transcription mix consisting of 1× MMLV-reverse transcriptase buffer, 1, mM dNTP mix, 2, mM DTT (Life Technologies), 20 units Rnasin (Promega. Madison, Wis.)and 10, ug/ml acetylated-BS (New England Biolabs) is added to each tube followed by addition of 600 units MMLV-reverse transcriptase(Life Technologies). This reaction is rocked gently at 42° C. for 2 hours. 1 unit RNase H (Boehringer-Mannheim. Indianapolis, Ind.) is then added and the reaction allowed to continue for another 0.5 hour. The supernatant is again removed and each bead is washed three times in 10 mM Tris pH 8.0, 1 mM EDTA pH 8(Fisher Scientific). Remaining RNA template is removed by boiling the beads in TE with 0.01% SDS (Fisher Scientific).

The nylon solid support was then hybridized with 100 nanograms per ml of the following tagged oligonucleotide probes (5'-GAACTCAAACCTCTGGAGGAAGTG-3', IL-2, 5'-CAGTGCAGAGGCTCGCGAGCTATA-3',IFN-gamma 5'-CTTGACCATGATGGCCAGCCACTA-3', GM-CSF 5'-CATTCCCACGGTCACTGCCATCTC-3', c-fos 5'-GCGACTGTGCTCCGGCAGTTCTAC-3', IL-4 5'-GTGGTTCATCGACGATGCCACGAA-3', PKC-gamma 5'-GAGCTCATGTACCCACCTCCGTAC-3', CTLA4/CD28 5'-ATCTTCGTGCAGCCGCCCTCACTG-3', GMP kinase)

(All oligos are for the human homologs except for GMP kinase which was based on the bovine sequence). Hybridization was in 3 m GuSCN for 8 hours at 37 C. The reaction mixture was gently mixed during the hybridization to promote diffusion of the probe to the solid support. After the 8 hour incubation period, the solid support was washed twice with 3 M GuSCN, 5 times with 0.1× SSC and then placed in 0.01 M dithiothreitol to cleave the fluorochrome from the oligonucleotide,. The mixture is incubated for 15 minutes at room temperature. Fluorescence is measured in a black microtiter plate (Dynatek Laboratories, Chantilly, Va.). The plates are then read directly using a Fluoroskan II fluorometer (Flow Laboratories, McLean, Va.) using an excitation wavelength of 495 nm and monitoring emission at 520 nm for fluorescein, using an excitation wavelength of 591 nm and monitoring emission at 612 nm for Texas Red, and using an excitation wavelength of 570 nm and monitoring emission at 590 nm for lissamine. The results from the probing are as follows:

|  | Unstimulated | Stimulated |
| --- | --- | --- |
| IL-2 | 1.2 rfu | 230 rfu |
| IFN | 0.8 rfu | 120 rfu |
| GM-CSF | 21 rfu | 38 rfu |
| c-fos | 16 rfu | 76 rfu |
| IL-4 | 33 rfu | 12 rfu |
| PKC | 10 rfu | 130 rfu |
| CTLA-4 | ND | ND |
| GMP kinase | 450 rfu | 420 rfu |

Example 15

Detection of a Single Base-Pair Mismatch on a Solid Phase

This example describes the detection of a single-base pair mismatch in an immobilized probe using complementary fluorescently labeled oligonucleotides. The set of probe oligonucleotides consists of one probe which forms perfect base-pairing and one oligonucleotide which contains the mismatch when hybridized. The two oligonucleotides are labeled with different fluorochromes, and after hybridization is allowed to occur at the $T_m$ of the mismatch, the ratio of hybridized fluorochromes is determined.

A "target" oligonucleotide (DMO501: 5'-TTGATTCCCAATTATGCGAAGGAG-3') was immobilized on a set of solid supports. ODN-beads (3/32nd inch diameter) were prepared as previously described (Van Ness et al., Nucl. Acids Res. 19:3345, 1991). The ODN-beads contained 0.01 to 1.2 mg/bead of covalently immobilized ODN. DMO578 is the complement to DMO501 (perfect complement). DMO1969 is the complement to DMO501 with a G→T change at position 11. DMO1971 is the complement to DMO501 with a A→T change at position 12. Each probe oligonucleotide was labeled with either BIODIPY, TAMRA or Texas Red. Hybridization reactions were assembled in 3 M GuSCN, 0.01 M Tris pH 7.6, 5 mM EDTA at 50 ng/ml respective probe. Equal molar ratios of each probe type were used in each hybridization in the presence of 3 solid supports per tube. Hybridizations are performed at 42° C. for 30 minutes with constant agitation. The beads were washed twice with 3 M GuSCN at 42° C. and then with SDS/FW 5 times.

To denature the probe oligonucleotide, the solid supports are placed in 200 μl TE (TE is 0.01 M Tris, pH 7.0, 5 mM EDTA). The mixture is incubated for 10 minutes at 100° C. Fluorescence is measured in a black microtiter plate. The solution is removed from the incubation tubes (200 microliters) and placed in a black microtiter plate (Dynatek Laboratories, Chantilly, Va.). The plates are then read directly using a Fluoroskan II fluorometer (Flow Laboratories, McLean, Va.) using an excitation wavelength of 495 nm and monitoring emission at 520 nm for fluorescein, using an excitation wavelength of 591 nm and monitoring emission at 612 nm for Texas Red, and using an excitation wavelength of 570 nm and monitoring emission at 590 nm for lissamine or TAMRA.

The results are as follows:

TABLE 10

| Probe Mix | Fluorochrome ratio in hybridization mix | Fluorochrome ratio after denaturing |
| --- | --- | --- |
| 578TR/578BD | 1.9/1 | 1.9/1 |
| 578TR/1969BD | 2.0/1 | 25/1 |
| 578TR/1971TA | 0.025/1 | 0.58/1 |
| 578BD/1971TA | 0.014/1 | 0.48/1 |

The results indicate that there is no effect of the fluorochrome on the hybridization as indicated in line 1 that Texas Red (TR) 578 oligonucleotide and 578-BD (BIODIPY) competed evenly for hybridization to the immobilized target since the ratio of labels did not change after hybridization. There is an average of a 20-fold enrichment of perfectly based probes over the mismatched probes in GuSCN allowing certain detection of base-pair mismatches.

Example 16

Figure 15A:
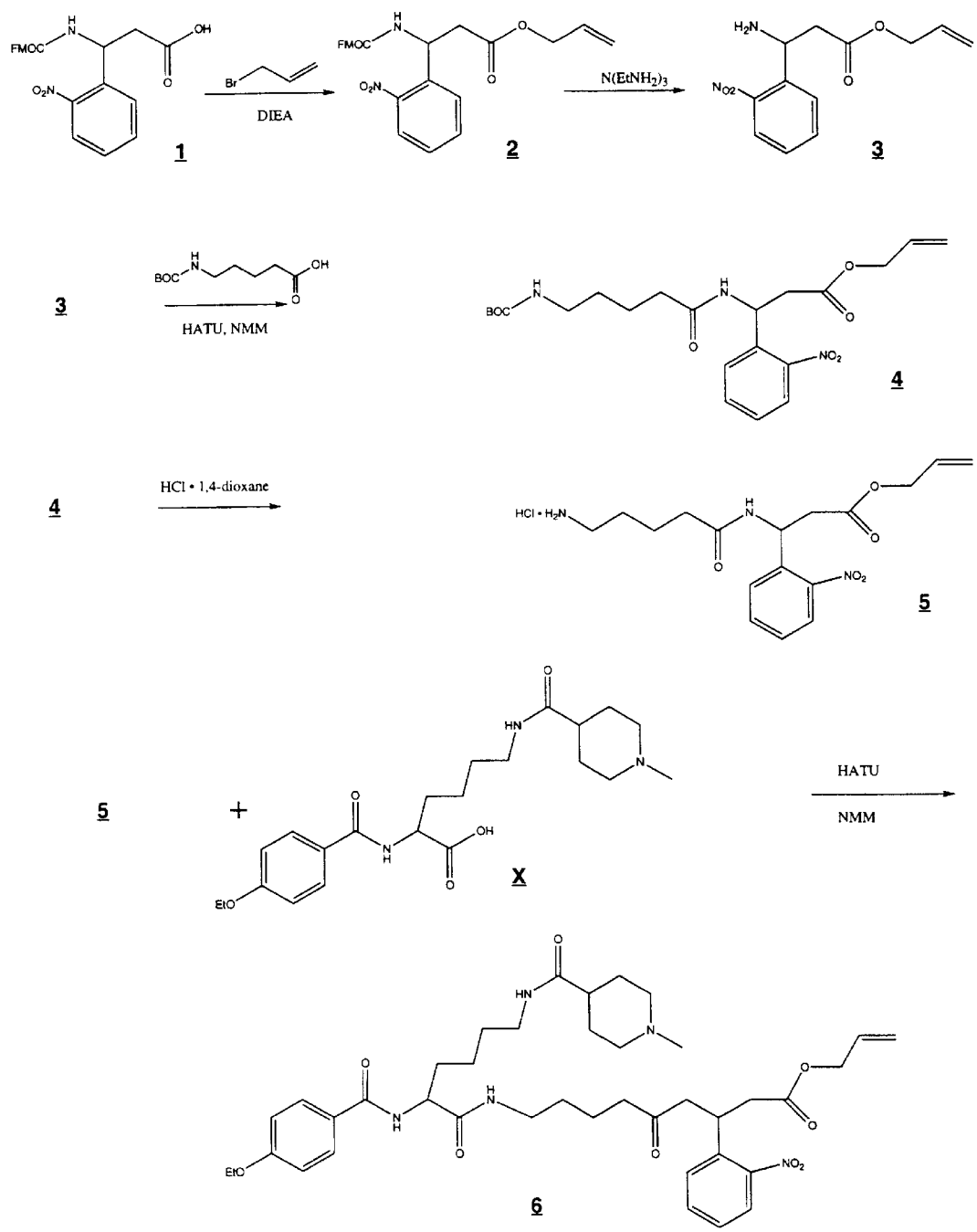
FIGS. 15A and 15B illustrate the preparation of a cleavable tag of the present invention.
Figure 15B:
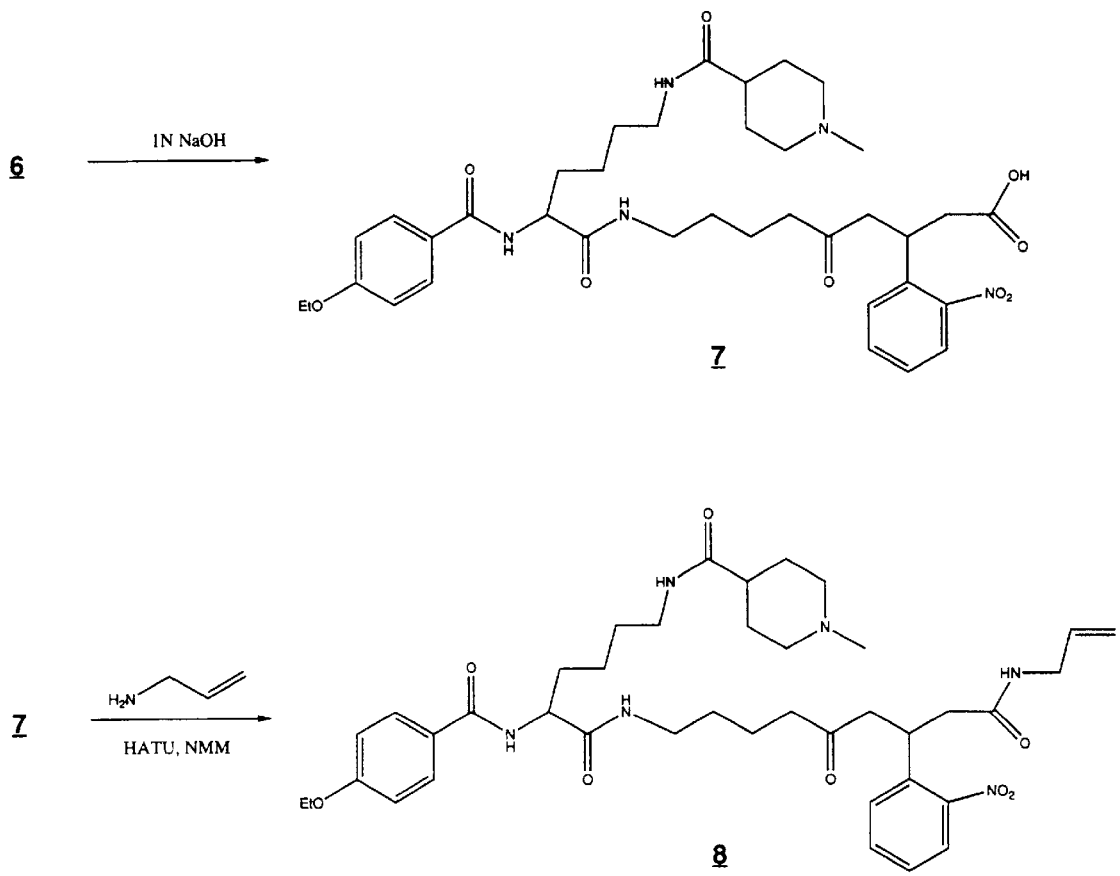

In this Example (16), all reactions were conducted in foil-covered flasks. The sequence of reactions A→F described in this Example is illustrated in FIGS. 15A and 15B. Compound numbers as set forth in this Example refer to the compounds of the same number in FIGS. 15A and 15B.

A. To a solution of ANP linker (compound 1, 11.2 mmol) and diisopropylethylamine (22.4 mmol) in $CHCl_3$ (60 ml) was added allyl bromide (22.4 mmol). The reaction mixture was refluxed for 3 hours, stirred at room temperature for 18 hours, diluted with $CHCl_3$ (200 ml), and washed with 1.0 M HCl (2×150 ml) and $H_2O$ (2×150 ml). The organic extracts were dried ($MgSO_4$) and the solvent evaporated to give compound 2 as a yellow solid.

To a mixture of compound 2 in $CH_2Cl_2$ (70 ml), tris (2-aminoethyl) amine (50 ml) was added and the reaction mixture stirred at room temperature for 18 hours. The reaction was diluted with $CH_2Cl_2$ (150 ml) and washed with pH 6.0 phosphate buffer (2×150 ml). The organic extracts were dried ($MgSO_4$) and the solvent evaporated. The residue was subjected to column chromatography (hexane/EtOAc) to give 1.63 g (58%) of compound 3: $^1H$ NMR (DMSO-$d_6$): δ7.85 (dd, 2H), 7.70 (t, 1H), 7.43 (t, 1H), 5.85 (m, 1H), 5.20 (q, 2H), 4.58 (q, 1H), 4.50 (d, 2H), 2.70 (m, 2H), 2.20 (br s, 2H).

B. To a solution of Boc-5-aminopentanoic acid (1.09 mmol) and NMM (3.27 mmol) in dry DMF (6 ml), was added HATU (1.14 mmol) and the reaction mixture stirred at room temperature for 0.5 hours. A solution of compound 3 (1.20 mmol) in dry DMF (1 ml) was added and the reaction mixture stirred at room temperature for 18 hours. The reaction was diluted with EtOAc (50 ml) and washed with 1.0 M HCl (2×50 ml) and D.I. $H_2O$ (2×50 ml). The organic extracts were dried ($MgSO_4$) and evaporated to dryness. The residue was subjected to column chromatography to give 420 mg (91%) of compound 4: $^1H$ NMR (DMSO-$d_6$): δ8.65 (d, 1H), 7.88 (d, 1H), 7.65 (m, 2H), 7.48 (t, 1H), 6.73 (br s, 1H), 5.85 (m, 1H), 5.55 (m, 1H), 5.23 (q, 2H), 4.55 (d, 2H), 2.80 (m, 2H), 2.05 (t, 2H), 1.33 (s, 9H), 1.20–1.30 (m, 4H).

C. A solution of compound 4 (0.9 mmol) in HCl•1,4-dioxane (20 mmol) was stirred at room temperature for 2 hours. The reaction mixture was concentrated, dissolved in MeOH and toluene, and concentrated again (5×5 ml) to give 398 mg (quantitative) of the compound 5: $^1H$ NMR (DMSO-$d_6$): δ8.75 (d, 1H), 7.88 (d, 1H), 7.65 (m, 2H),7.51 (t, 1H), 7.22 (m, 2H),5.85 (m, 1H), 5.57 (m, 1H), 5.23 (q, 2H), 4.55 (d, 2H), 2.80 (m, 2H), 2.71 (m, 2H), 2.07 (s, 2H), 1.40–1.48 (br s, 4 H).

D. To a solution of compound 21 (0.48 mmol, prepared according to Example 18) and NMM (1.44 mmol) in dry DMF (3 ml), was added HATU (0.50 mmol) and the reaction mixture stirred at room temperature for 0.5 hours. A solution of compound 5 (0.51 mmol) in dry DMF (3 ml) was added and the reaction stirred at room temperature for 18 hours. The reaction mixture was diluted with EtOAc (75 ml) and washed with 5% $Na_2CO_3$ (3×50 ml). The organic extracts were dried ($MgSO_4$) and the solvent evaporated to give 281 mg (78%) of compound 6: $^1H$ NMR (DMSO-$d_6$): δ8.65 (d, 1H), 8.17 (d, 1H), 7.82–7.95 (m, 4H), 7.68 (m, 3H), 7.50 (t, 1H), 6.92 (d, 1H), 5.85 (m, 1H), 5.57 (m, 1H), 5.20 (q, 2H), 4.55 (d, 2H), 4.30 (q, 1H), 4.05 (q, 2H), 2.95 (m, 4H), 2.80 (m, 2H), 2.72 (m, 2H), 2.05 (s, 3H), 2.01 (t, 2H), 1.58–1.77 (m, 3H), 1.50 (m, 4H), 1.30 (q, 3H), 1.17–1.40 (m, 9H).

E. To a mixture of compound 6 (0.36 mmol) in THF (4 ml), was added 1 M NaOH (1 mmol) and the reaction stirred at room temperature for 2 hours. The reaction mixture was acidified to pH 7.0 with 1.0 M HCl (1 ml) and the solvent evaporated to give compound 7 (quantitative): $^1H$ NMR (DMSO-$d_6$): δ8.65 (d, 1H), 8.17 (d, 1H), 7.82–7.95 (m, 4H), 7.68 (m, 3H), 7.50 (t, 1H), 6.92 (d, 1H), 5.52 (m, 1H), 4.30 (q, 1H), 4.05 (q, 2H), 2.95 (m, 4H), 2.80 (m, 2H), 2.72 (m, 2H), 2.05 (s, 3H), 2.01 (t, 2H), 1.58–1.77 (m, 3H), 1.50 (m, 4H), 1.30 (q, 3H), 1.17–1.40 (m, 9H).

F. To a solution of compound 7 (0.04 mmol) and NMM (0.12 mmol) in dry DMF (0.4 ml), was added HATU (0.044 mmol) and the reaction mixture stirred at room temperature for 0.5 hours. Allylamine (0.12 mmol) was added and the reaction mixture stirred at room temperature for 5 hours. The reaction mixture was diluted with EtOAc (15 ml) and washed with 5% $Na_2CO_3$ (3×10 ml). The organic extracts were dried ($MgSO_4$) and the solvent evaporated to yield 15 mg (49%) of compound 8: $^1H$ NMR (DMSO-$d_6$): δ8.49 (d, 1H), 8.17 (d, 1H), 7.82–7.95 (m, 4H), 7.68 (m, 3H), 7.50 (t, 1H), 6.92 (d, 1H), 5.72 (m, 1H), 5.50 (m, 1H), 5.03 (q, 2H), 4.37 (d, 2H), 4.30 (q, 1H), 4.05 (q, 2H), 2.95 (m, 4H), 2.80 (m, 2H), 2.72 (m, 2H), 2.05 (s, 3H), 2.01 (t, 2H), 1.58–1.77 (m, 311), 1.50 (m, 4H), 1.30 (q, 311), 1.17–1.40 (m, 9H).

Example 17

Figure 16A:
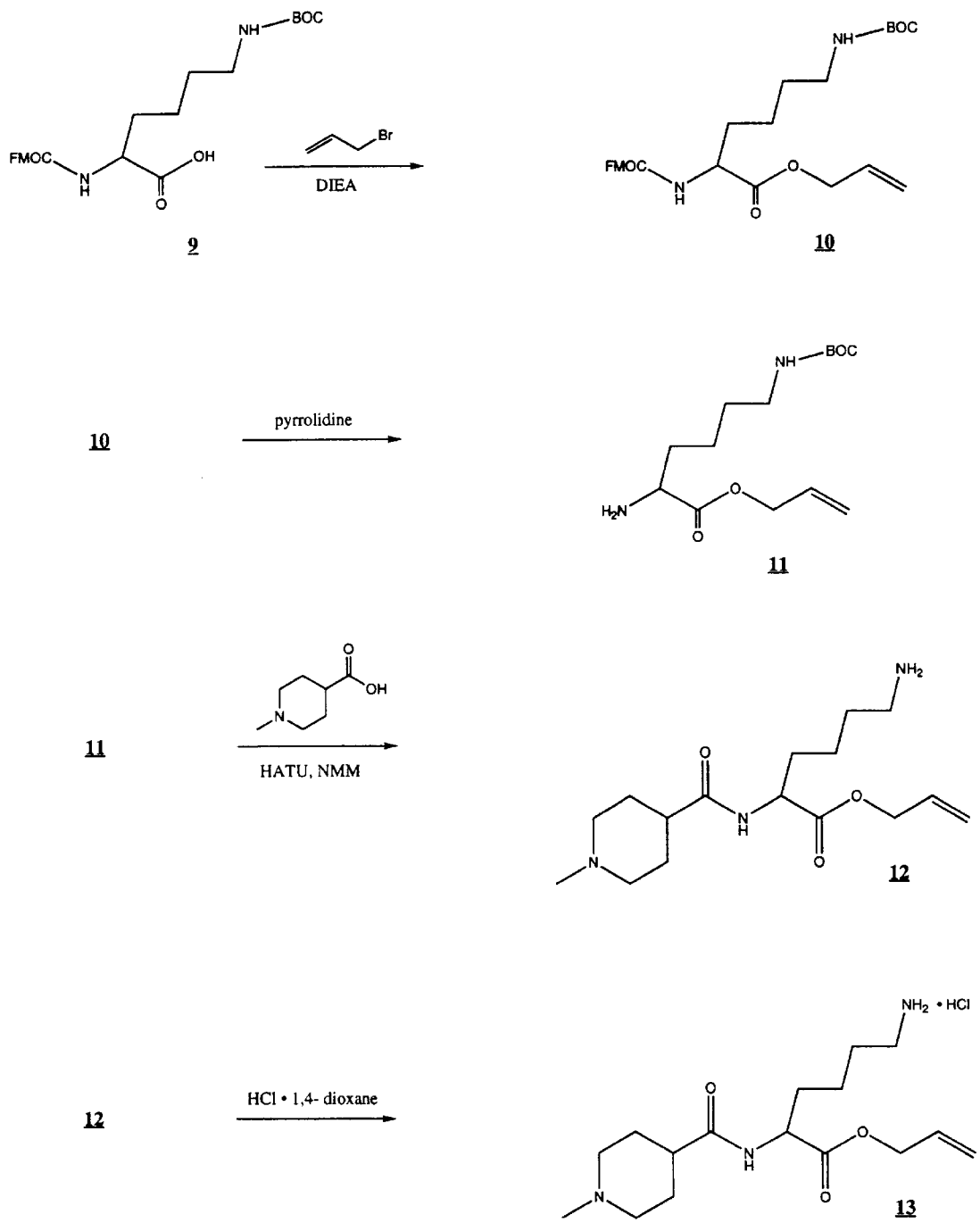
FIGS. 16A and 16B illustrate the preparation of a cleavable tag of the present invention.
Figure 16B:
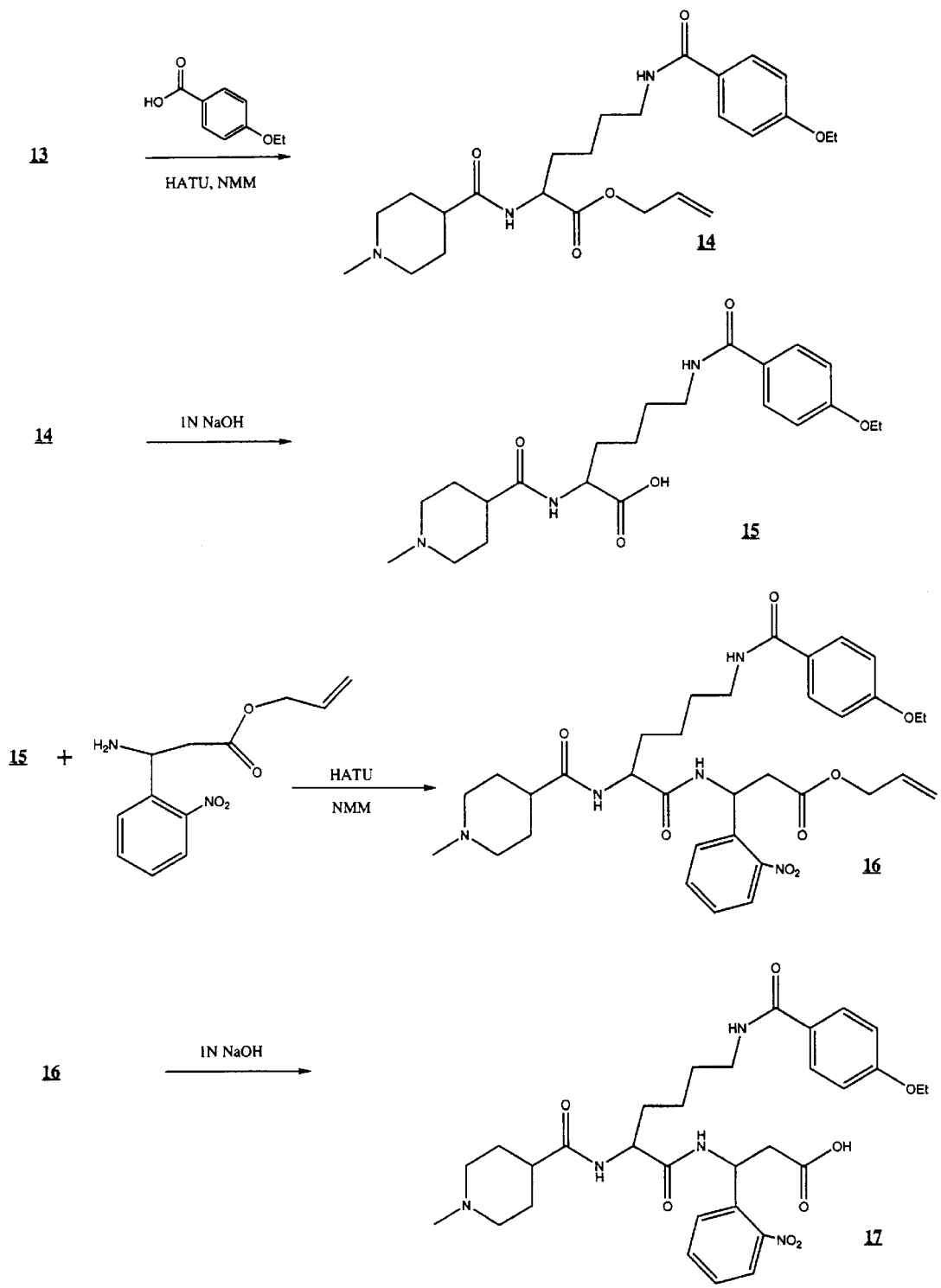

The sequence of reactions A→G as described in this Example 17 is illustrated in FIGS. 16A and 16B. Compound numbers as set forth in this Example refer to the compounds of the same number in FIGS. 16A and 16B.

A. To a solution of Fmoc-Lys(Boc)-OH (compound 9, 33.8 mmol) in $CHCl_3$ (200 ml), was added diisopropylethylamine (67.5 mmol) and allyl bromide (67.5 mmol). The reaction mixture was refluxed for 6 hours, stirred at room temperature for 16 hours, diluted with $CHCl_3$, washed with 1.0 M HCl (2×150 ml), saturated $NaHCO_3$ (1×150 ml) and D.I. $H_2O$ (2×150 ml). The organic extracts were dried ($MgSO_4$) and the solvent evaporated to yield compound 10.

To a solution of compound 10 in $CHCl_3$ (90 ml), was added pyrrolidine (10 eq.) and the reaction was stirred at room temperature for 2.5 hours. The reaction mixture was diluted with $CHCl_3$ (150 ml) and washed with saturated $NaHCO_3$ (3×250 ml). The organic extracts were dried ($MgSO_4$) and the solvent evaporated. The residue was subjected to column chromatography (EtOAc/MeOH) to give 6.52 g (67%) of compound 11: $^1H$ NMR ($CDCl_3$): δ5.90 (m, 1H), 5.27 (m, 2H), 4.60 (d, 2H), 3.48 (t, 1H), 3.10 (d, 2H), 1.40–1.78 (m, 9H),1.40 (s, 9H).

B. To a solution of N-methylisonipecotic acid (1.60 mmol) and N-methyl morpholine (4.80 mmol) in dry DMF (5 ml), was added HATU (1.67 mmol). After 0.5 hours, a solution of compound 11 (1.75 mmol) in dry DMF (2 ml) was added and the reaction mixture stirred at room temperature for 18 hours. The reaction mixture was diluted with $CH_2CL_2$ (60 ml) and washed with saturated $Na_2CO_3$ (3×40 ml). The organic extracts were dried ($MgSO_4$) and the solvent evaporated. The residue was subjected to column chromatography ($CH_2Cl_2$/MeOH/triethylamine) to give 580 mg (88%) of compound 12: $^1H$ NMR (DMSO): δ8.12 (d, 1H), 6.77 (t, 1H), 5.90 (m, 1H), 5.27 (m, 2H), 4.53 (d, 2H), 4.18 (m, 1H),2.62–2.90 (m, 5H), 2.13 (s, 3H),1.85 (m, 2H), 1.57 (m, 5H),1.35 (s, 9H), 1.00 (t, 2H).

C. A mixture of compound 12 (1.39 mmol) in HCl•1,4-dioxane (20 mmol) was stirred at room temperature for 4 hours. The reaction mixture was concentrated, dissolved in MeOH, coevaporated with toluene (5×5 ml) to give 527 mg (quantitative) of compound 13: $^1H$ NMR (DMSO-$d_6$): δ8.12 (d, 1H), 6.77 (t, 1H), 5.90 (m, 1H), 5.27 (m, 2H), 4.53 (d, 2H), 4.18 (m, 1H), 2.65–3.00 (m, 8H), 2.23 (s, 3H),1.85 (m, 2H), 1.57 (m, 5H), 1.00 (t, 2H).

D. To a solution of 4-ethoxybenzoic acid (1 eq.) in dry DMF, is added NMM (3 eq.) and HATU (1.05 eq.). After 0.5 hours, a solution of compound 13 in dry DMF is added. After the completion of the reaction and basic workup, the compound 14 is isolated and purified.

E. To a solution of compound 14 in THF, is added 1N NaOH and the reaction mixture stirred at room temperature. After the completion of the reaction and acidification, the compound 15 is isolated.

F. To a solution of compound 15 (1 eq.) in dry DMF, is added NMM (3 eq.) and HATU (1.05 eq.). After 0.5 hours, a solution of compound 21 (ANP—allyl ester, prepared according to Example 18) in dry DMF is added. After the completion of the reaction and basic workup, the title compound 16 is isolated and purified.

G. To a solution of compound 16 in THF, is added 1N NaOH and the reaction mixture stirred at room temperature. After the completion of the reaction and acidification, the compound 17 is isolated.

Example 18

Figure 17:
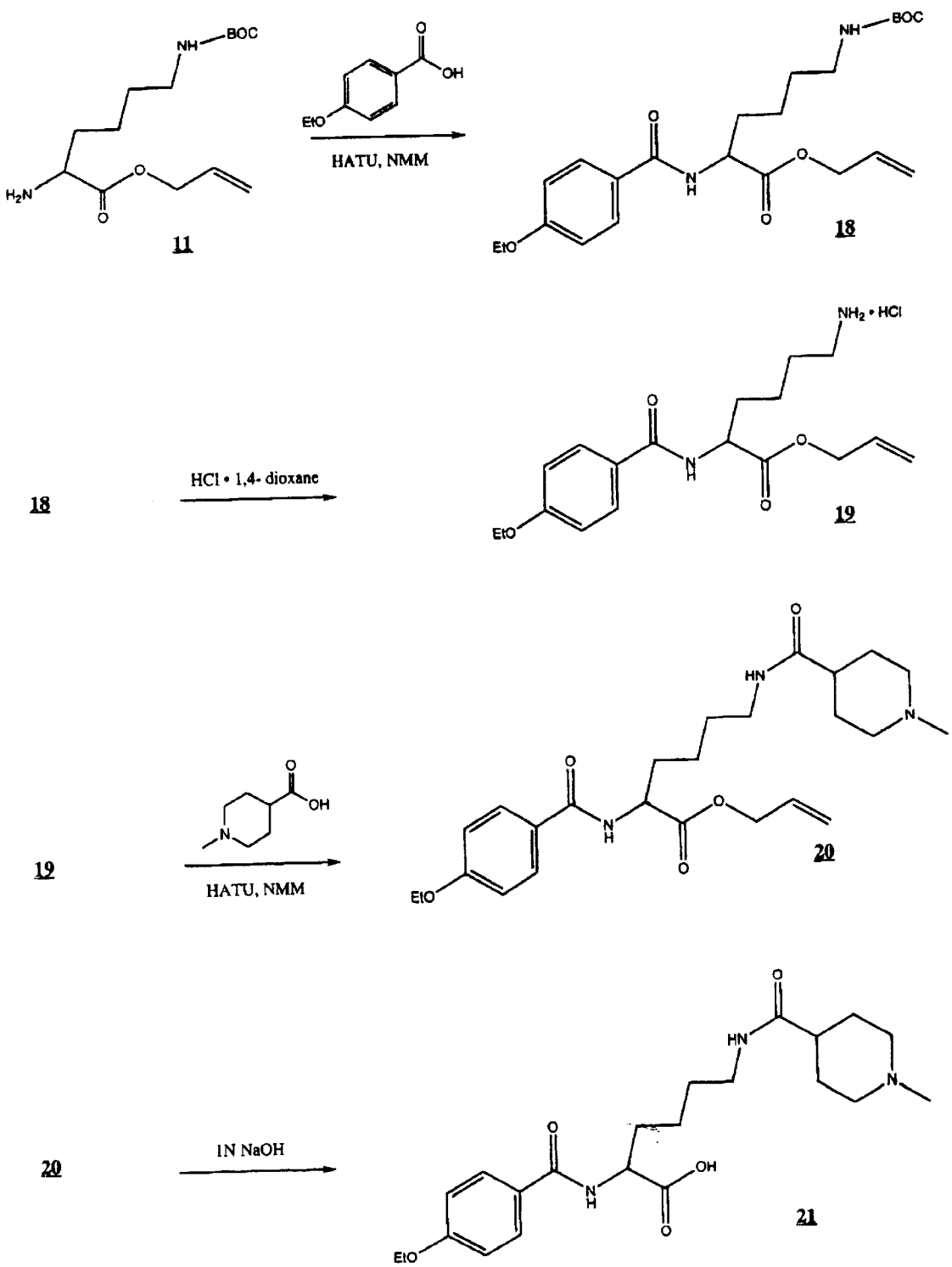
FIG. 17 illustrates the preparation of an intermediate compound useful in the preparation of a cleavable tag of the invention.

The sequence of reaction A through D as described in this Example 18 is illustrated in FIG. 16. Compound numbers as set forth in this Example, as well as Examples 16 and 17, refer to the compounds of the same number in FIG. 17.

A. To a solution of 4-ethoxybenzoic acid (7.82 mmol) and N-methyl morpholine (20.4 mmol) in $CH_2Cl_2$ (10 ml), was added HATU (7.14 mmol). After 0.25 hours, a solution of compound 11 (6.8 mmol) in $CH_2Cl_2$ (6 ml) was added and the reaction mixture stirred at room temperature for 18 hours. The reaction was diluted with $CH_2Cl_2$ (150 ml) and washed with 1.0 M HCl (3×50 ml) and saturated NaHCO$_3$ (3×50 ml). The organic extracts were dried (MgSO$_4$) and the solvent evaporated. The residue was subjected to column chromatography (CH$_2$Cl$_2$/MeOH) to give 2.42 g (82%) of compound 18: $^1$H NMR (CDCl$_3$): δ7.78 (d, 2H), 6.91 (d, 2H), 6.88 (d, 1H), 5.83–5.98 (m, 1H), 5.21–5.38 (m, 2H), 4.80 (q, 1H), 4.66 (d, 2H), 4.06 (q, 2H), 3.11 (q, 2H), 1.90–2.04 (m, 1H), 1.68–1.87 (m, 1H), 1.39 (t, 3H), 1.34 (s, 9H), 1.32–1.58 (m, 4H).

B. A mixture of compound 18 (5.5 mmol) in HCl•1,4-dioxane (14.3 mmol) was stirred at room temperature for 1 hour. The reaction mixture was concentrated, dissolved in MeOH, azeotroped with toluene, and concentrated again (5× ml) to give a quantitative yield of compound 19.

C. To a solution of N-methylisonipecotic acid (6.21 mmol) in dry DMF (15 mL), was added NMM (21.6 mmol) and HATU (5.67 mmol). After 0.5 hours, a solution of compound 19 (5.4 mmol) in dry DMF (10 ml) was added and the reaction stirred at room temperature for 18 hours. The reaction mixture was brought to pH 12 with 1N NaOH (20 ml) and extracted with CHCl$_3$ (2×200 ml). The organic extracts were dried (MgSO$_4$) and the solvent evaporated to give 2.2 g (89%) of compound 20: $^1$H NMR (DMSO-d$_6$): δ8.52 (d 1H), 7.84 (d, 2H), 7.72 (t, 1H), 6.95 (d, 2H), 5.80–5.95 (m, 1H), 5.18–5.31 (dd, 2H), 4.58 (d, 2H), 4.37 (q, 1H), 4.08 (q, 2H), 3.01 (d, 2H), 2.08 (s, 3H), 1.95 (m, 1H), 1.63–1.82 (m, 4H), 1.51 (m, 4H), 1.32 (t, 3H), 1.22–1.41 (m, 6H).

D. To a solution of compound 20 (4.4 mmol) in THF (10 ml), is added 1N NaOH (4.4 mmol) and the reaction mixture stirred at room temperature for 1 hour. The reaction was concentrated, dissolved in THF/toluene (2×5 ml), concentrated, dissolved in CH$_2$Cl$_2$/toluene (1×5 ml) and concentrated again to give a quantitative yield of compound 21: $^1$H NMR (DMSO-d$_6$): δ7.76 (d, 2H), 6.96 (d, 2H), 4.04 (q, 2H), 3.97 (d, 1H), 2.97 (d, 2H), 2.64 (d, 2H), 2.08 (s, 3H), 1.95 (m, 1H), 1.58–1.79 (m, 4H), 1.44 (m, 6H), 1.30 (t, 3H), 1.11–1.35 (m, 4H).

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for detecting the binding of a first member to a second member of a ligand pair, comprising:
    (a) combining a set of first tagged members with a biological sample which may contain one or more second members, under conditions, and for a time sufficient to permit binding of a first member to a second member, wherein said tag is correlative with a particular first member and detectable by non-fluorescent spectrometry or potentiometry;
    (b) separating bound first and second members from unbound members;
    (c) cleaving said tag from said tagged first member; and
    (d) detecting said tag by non-fluorescent spectrometry or potentiometry, and therefrom detecting the binding of said first member to said second member.

2. The method according to claim 1 wherein said first members are bound to a solid support.

3. The method according to claim 2, further comprising, subsequent to the step of separating bound first and second members, washing unbound members from said solid support.

4. The method according to claim 1 wherein the detection of the tag is by mass spectrometry, infrared spectrometry, ultraviolet spectrometry, or, potentiostatic amperometry.

5. The method according to claim 1 wherein greater than 4 tagged first members are combined and wherein each tag is unique for a selected nucleic acid fragment.

6. The method according to claim 1 wherein said bound first and second members are separated from unbound members by a method selected from the group consisting of gel electrophoresis, capillary electrophoresis, micro-channel electrophoresis, HPLC, size exclusion chromatography and filtration.

7. The method according to claim 1 wherein said tagged first members are cleaved by a method selected from the group consisting of oxidation, reduction, acid-labile, base labile, enzymatic, electrochemical, heat and photolabile methods.

8. The method according to claim 4 wherein said tag is detected by time-of-flight mass spectrometry, quadrupole mass spectrometry, magnetic sector mass spectrometry and electric sector mass spectrometry.

9. The method according to claim 4 wherein said tag is detected by potentiostatic amperometry utilizing detectors selected from the group consisting of coulometric detectors and amperometric detectors.

10. The method according to claim 1 wherein steps b, c and d are performed in a continuous manner.

11. The method according to claim 1 wherein steps b, c and d are preformed in a continuous manner on a single device.

12. The method according to claim 11 wherein steps b, c and d are automated.

13. The method according to claim 1 wherein said first member is a nucleic acid molecule.

14. The method according to claim 1 wherein said second member is a nucleic acid molecule.

15. The method according to claims 13 or 14 wherein said nucleic acid molecule is generated by primer extension.

16. The method according to claims 13 or 14 wherein said nucleic acid molecule is generated from non-3'-tagged oligonucleotide primers.

17. The method according to claims 13 or 14 wherein said nucleic acid molecule is generated from tagged dideoxynucleotide terminators.

18. The method according to claims 13 or 14 wherein said first member is a protein, hormone or organic molecule.

19. The method according to claim 18 wherein said protein is selected from the group consisting of antibodies and receptors.

20. A method for analyzing the pattern of gene expression from a selected biological sample, comprising:
    (a) exposing nucleic acids from a biological sample;
    (b) combining said exposed nucleic acids with one or more selected tagged nucleic acid probes, under conditions and for a time sufficient for said probes to hybridize to said nucleic acids, wherein said tag is correlative with a particular nucleic acid probe and detectable by non-fluorescent spectrometry or potentiomery;
    (c) separating hybridized probes from unhybridized probes;
    (d) cleaving said tag from said tagged fragment; and
    (e) detecting said tag by nonfluorescent spectrometry or potentiometry, and therefrom determining the pattern of gene expression of said biological sample.

21. The method according to claim 20 wherein said biological sample is selected from the group consisting of mammalian cells, bacteria and yeast.

22. The method according to claim 21 wherein said mammalian cells contain viruses.

23. The method according to claim 20 wherein said exposed nucleic acids is bound to a solid support.

24. The method according to claim 23 wherein said solid support is a polymer.

25. The method according to claim 23, further comprising, subsequent to the step of separating, washing the solid support.

26. The method according to claim 20 wherein said hybridized probes are separated from unhybridized probes by a method selected from the group consisting of gel electrophoresis, capillary electrophoresis, micro-channel electrophoresis, HPLC, filtration and polyacrylamide gel electrophoresis.

27. The method according to claim 20 wherein said tagged probes are cleaved by a method selected from the group consisting of oxidation, reduction, acid-labile, base labile, enzymatic, electrochemical, heat and photolabile methods.

28. The method according to claim 20 wherein said tag is detected by a method selected from the group consisting of time-of-flight mass spectrometry, quadrupole mass spectrometry, magnetic sector mass spectrometry and electric sector mass spectrometry.

29. The method according to claim 20 wherein said tag is detected by potentiostatic amperometry utilizing detectors selected from the group consisting of coulometric detectors and amperometric detectors.

30. The method according to claim 20 wherein steps c, d and e are performed in a continuous manner.

31. The method according to claim 20 wherein steps c, d and e are performed in a continuous manner on a single device.

32. The method according to claim 31 wherein said device is automated.

33. A compound of the formula:

wherein $T^{ms}$ is an organic group detectable by mass spectrometry, comprising carbon, at least one of hydrogen and fluoride, and optional atoms selected from oxygen, nitrogen, sulfur, phosphorus and iodine; L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid, the compound having a mass of at least 250 daltons; and -L-X has the formula:

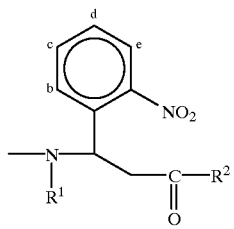

wherein one or more of positions b, c, d or e is substituted with hydrogen, alkyl, alkoxy, fluoride, chloride, hydroxyl, carboxylate or amide; $R^1$ is hydrogen or hydrocarbyl, and $R^2$ comprises a molecule of interest (MOI) other than a nucleic acid fragment.

34. A compound of the formula:

wherein $T^{ms}$ is an organic group detectable by mass spectrometry, comprising carbon, at least one of hydrogen and fluoride, and optional atoms selected from oxygen, nitrogen, sulfur, phosphorus and iodine, and has the formula:

wherein $T^2$ is an organic moiety formed from carbon and one or more of hydrogen, fluoride, iodide, oxygen, nitrogen, sulfur and phosphorus, having a mass of 15 to 500 daltons; $T^3$ is an organic moiety formed from carbon and one or more of hydrogen, fluoride, iodide, oxygen, nitrogen, sulfur and phosphorus, having a mass of 50 to 1000 daltons; J is a direct bond or a functional group selected from amide, ester, amine, sulfide, ether, thioester, disulfide, thioether, urea, thiourea, carbamate, thiocarbamate, Schiff base, reduced Schiff base, imine, oxime, hydrazone, phosphate, phosphonate, phosphoramide, phosphonamide, sulfonate, sulfonamide or carbon-carbon bond; and n is an integer ranging from 1 to 50, and when n is greater than 1, each $T^3$ and J is independently selected;

L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid; and X comprises a molecules of interest (MOI) other than a nucleic acid fragment, and the compound has a mass of at least 250 daltons.

35. A compound according to claim 34 wherein $T^2$ is selected from hydrocarbyl, hydrocarbyl-O-hydrocarbylene, hydrocarbyl-S-hydrocarbylene, hydrocarbyl-NH-hydrocarbylene, hydrocarbyl-amide-hydrocarbylene, N-(hydrocarbyl)hydrocarbylene, N,N-di(hydrocarbyl)hydrocarbylene, hydrocarbylacyl-hydrocarbylene, heterocyclylhydrocarbyl wherein the heteroatom(s) are selected from oxygen, nitrogen, sulfur and phosphorus, substituted heterocyclylhydrocarbyl wherein the heteroatom(s) are selected from oxygen, nitrogen, sulfur and phosphorus and the substituents are selected from hydrocarbyl, hydrocarbyl-O-hydrocarbylene, hydrocarbyl-NH-hydrocarbylene, hydrocarbyl-S-hydrocarbylene, N-(hydrocarbyl)hydrocarbylene, N,N-di(hydrocarbyl)hydrocarbylene and hydrocarbylacyl-hydrocarbylene, as well as derivatives of any of the foregoing wherein one or more hydrogens is replaced with an equal number of fluorides.

36. A compound according to claim 43 wherein $T^3$ has the formula -G($R^2$)-, G is $C_{1-6}$ alkylene having a single $R^2$ substituent, and $R^2$ is selected from alkyl, alkenyl, alkynyl, cycloalkyl, aryl-fused cycloalkyl, cycloalkenyl, aryl, aralkyl, aryl-substituted alkenyl or alkynyl, cycloalkyl-substituted alkyl, cycloalkenyl-substituted cycloalkyl, biaryl, alkoxy, alkenoxy, alkynoxy, aralkoxy, aryl-substituted alkenoxy or alkynoxy, alkylamino, alkenylamino or alkynylamino, aryl-substituted alkylamino, aryl-substituted alkenylamino or alkynylamino, aryloxy, arylamino, N-alkylurea-substituted alkyl, N-arylurea-substituted alkyl, alkylcarbonylamino-substituted alkyl, aminocarbonyl-substituted alkyl, heterocyclyl, heterocyclyl-substituted alkyl, heterocyclyl-substituted amino, carboxyalkyl substituted aralkyl, oxocarbocyclyl-fused aryl and heterocyclylalkyl; cycloalkenyl, aryl-substituted alkyl and, aralkyl, hydroxy-substituted alkyl, alkoxy-substituted alkyl, aralkoxy-substituted alkyl, alkoxy-substituted alkyl, aralkoxy-substituted alkyl, amino-substituted alkyl, (aryl-substituted alkyloxycarbonylamino)-substituted alkyl, thiol-substituted alkyl, alkylsulfonyl-substituted alkyl, (hydroxy-substituted alkylthio)-substituted alkyl, thioalkoxy-substituted alkyl, hydrocarbylacylamino-substituted alkyl, heterocyclylacylamino-substituted alkyl, hydrocarbyl-substituted-heterocyclylacylamino-substituted alkyl, alkylsulfonylamino-substituted alkyl, arylsulfonylamino-substituted alkyl, morpholino-alkyl, thiomorpholino-alkyl, morpholino carbonyl-substituted alkyl, thiomorpholinocarbonyl-substituted alkyl, [N-(alkyl, alkenyl or alkynyl)- or N,N-[dialkyl, dialkenyl, dialkynyl or (alkyl, alkenyl)-amino]carbonyl-substituted alkyl, heterocyclylaminocarbonyl, heterocylylalkyleneaminocarbonyl, heterocyclylaminocarbonyl-substituted alkyl, heterocylylalkyleneaminocarbonyl-substituted alkyl, N,N-[dialkyl]alkyleneaminocarbonyl, N,N-[dialkyl]alkyleneaminocarbonyl-substituted alkyl, alkyl-substituted heterocyclylcarbonyl, alkyl-substituted heterocyclylcarbonyl-alkyl, carboxyl-substituted alkyl, dialkylamino-substituted acylaminoalkyl and amino acid side chains selected from arginine, asparagine, glutamine, S-methyl cysteine, methionine and corresponding sulfoxide and sulfone derivatives thereof, glycjne, leucine, isoleucine, allo-isoleucine, tert-leucine, norleucine, phenylalanine, tyrosine, tryptophan, proline, alanine, omithine, histidine, glutamine, valine, threonine, serine, aspartic acid, beta-cyanoalanine, and allothreonine; alynyl and heterocyclylcarbonyl, aminocarbonyl, amido, mono- or dialkylaminocarbonyl, mono- or diarylaminocarbonyl, alkylarylaminocarbonyl, diarylaminocarbonyl, mono- or diacylaminocarbonyl, aromatic or aliphatic acyl, alkyl optionally substituted by substituents selected from amino, carboxy, hydroxy, mercapto, mono- or dialkylamino, mono- or diarylamino, alkylarylamino, diarylamino, mono- or diacylamino, alkoxy, alkenoxy, aryloxy, thioalkoxy, thioalkenoxy, thioalkynoxy, thioaryloxy and heterocyclyl.

37. A compound of the formula:

$T^{ms}$-L-X wherein $T^{ms}$ is an organic group detectable by mass spectrometry, comprising carbon, at least one of hydrogen and fluoride, and optional atoms selected from oxygen, nitrogen, sulfur, phosphorus and iodine; L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid; X comprises a molecule of interest (MOI) other than a nucleic acid fragment, the compound having a mass of at least 250 daltons; the compound also having the formula:

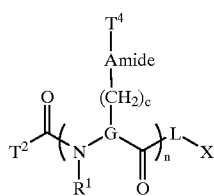

wherein

G is $(CH_2)_{1-6}$ wherein a hydrogen on one and only one of the CH$_2$ groups is replaced with-$(CH_2)_c$-Amide-$T^4$;

$T^2$ and $T^4$ are organic moieties of the formula $C_{1-25}N_{0-9}O_{0-9}H_\alpha F_\beta$ wherein the sum of $\alpha$ and $\beta$ is sufficient to satisfy the otherwise unsatisfied valencies of the C, N, and O atoms;

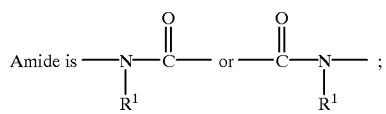

$R^1$ is hydrogen or $C_{1-10}$ alkyl;

c is an integer ranging from 0 to 4; and n is an integer ranging from 1 to 50 such that when n is greater than 1, then G, c, Amide, $R^1$ and $T^4$ are independently selected.

38. A compound of the formula:

$T^{ms}$-L-X wherein $T^{ms}$ is an organic group detectable by mass spectrometry, comprising carbon, at least one of hydrogen and fluoride, and optional atoms selected from oxygen, nitrogen, sulfur, phosphorus and iodine; L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid; X comprises a molecule of interest (MOI) other than a nucleic acid fragment, the compound having a mass of at least 250 daltons, the compound also having the formula:

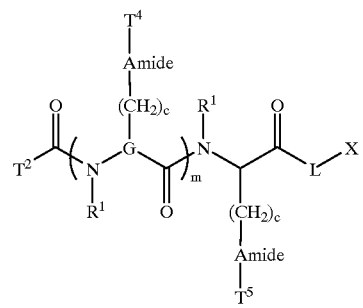

wherein

G is $(CH_2)_{1-6}$ wherein a hydrogen on one and only one of the CH$_2$ groups is replaced with-$(CH_2)_c$-Amide-$T^4$;

$T^2$ and $T^4$ are organic moieties of the formula $C^{1-25}N_{0-9}O_{0-9}H_\alpha F_\beta$ wherein the sum of $\alpha$ and $\beta$ is sufficient to satisfy the otherwise unsatisfied valencies of the C, N, and O atoms;

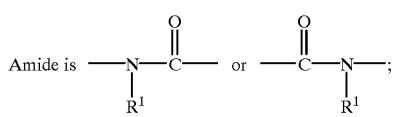

$R^1$ is hydrogen or $C_{1-10}$ alkyl c is an integer ranging from 0 to 4; and $T^5$ is an organic moiety of the formula $C_{1-25}N_{0-9}O_{0-9}H_\alpha F_\beta$ wherein the sum of $\alpha$ and $\beta$ is sufficient to satisfy the otherwise unsatisfied valencies of the C, N, and O atoms; and $T^5$ includes a tertiary or quaternary amine or an organic acid; and m is an integer ranging from 0–49 where when m is greater than 1, then G, c, Amide, $R^1$ and $T^4$ are independently selected.

39. A compound of the formula:

T$^{ms}$-L-X wherein T$^{ms}$ is an organic group detectable by mass spectrometry, comprising carbon, at least one of hydrogen and fluoride, and optional atoms selected from oxygen, nitrogen, sulfur, phosphorus and iodine; L is an organic group which allows a T$^{ms}$-containing moiety to be cleaved from the remainder of the compound, wherein the T$^{ms}$-containing moiety comprises a functional group which supports a single ionized charge state when the compound is subjected to mass spectrometry and is selected from tertiary amine, quaternary amine and organic acid; X comprises a molecule of interest (MOI) other than a nucleic acid fragment, the compound having a mass of at least 250 daltons; the compound also having the formula:

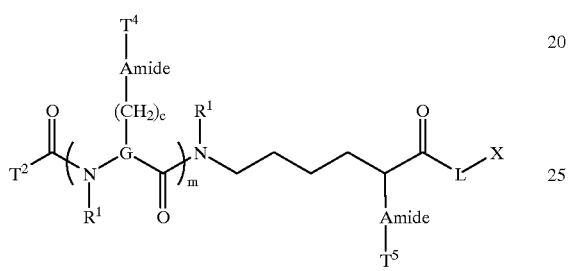

wherein

G is $(CH_2)_{1-6}$ wherein a hydrogen on one and only one of the $CH_2$ groups is replaced with-$(CH_2)_c$-Amide-T$^4$;

T$^2$ and T$^4$ are organic moieties of the formula $C_{1-25}N_{0-9}O_{0-9}H_\alpha F_\beta$ wherein the sum of $\alpha$ and $\beta$ is sufficient to satisfy the otherwise unsatisfied valencies of the C, N, and O atoms;

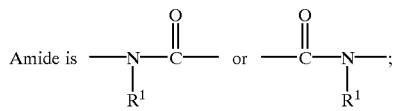

R$^1$ is hydrogen or $C_{1-10}$ alkyl;

c is an integer ranging from 0 to 4; and

T$^5$ is an organic moiety of the formula $C_{1-25}N_{0-9}O_{0-9}H_\alpha F_\beta$ wherein the sum of $\alpha$ and $\beta$ is sufficient to satisfy the otherwise unsatisfied valencies of the C, N, and O atoms; and T$^5$ includes a tertiary or quaternary amine or an organic acid; and m is an integer ranging from 0–49 where when m is greater than 1, then G, c, Amide, R$^1$ and T$^4$ are independently selected.

40. A compound according to any one of claims 38 or 39 wherein -Amide-T$^5$ is selected from:

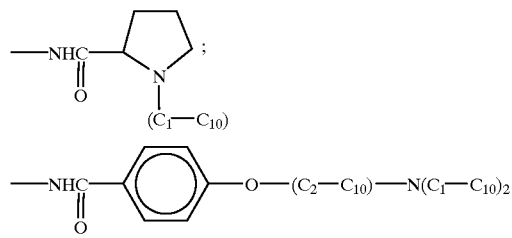

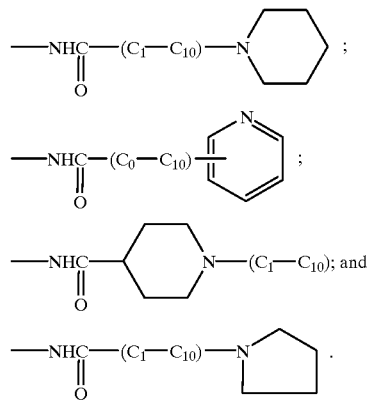

41. A compound according to any of claims 38 or 39 wherein -Amide-T$^5$ is selected from:

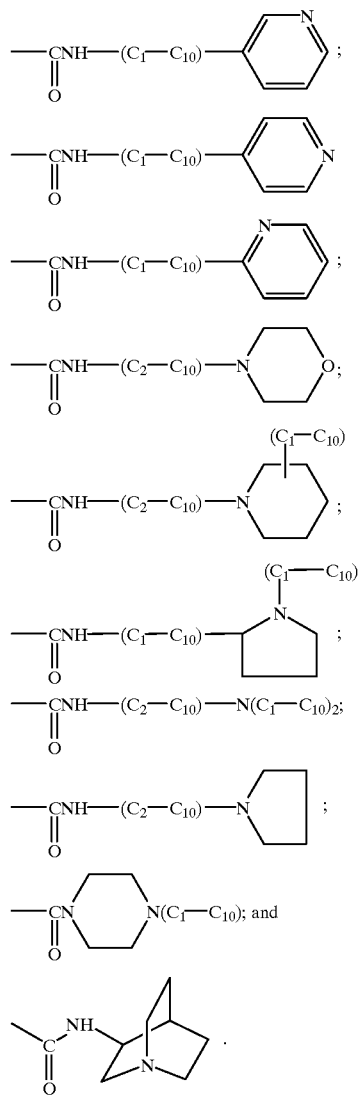

42. A compound according to claim 34 wherein T$^2$ has the structure which results when one of the following organic acids is condensed with an amine group to form T$^2$-C(=O)—N(R$^1$)—: Formic acid, Acetic acid, Propiolic acid, Propionic acid, Fluoroacetic acid, 2-Butynoic acid, Cyclopropanecarboxylic acid, Butyric acid, Methoxyacetic acid, Difluoroacetic acid, 4-Pentynoic acid, Cyclobutanecarboxylic acid, 3,3-Dimethylacrylic acid, Valeric acid, N,N-Dimethylglycine, N-Formyl-Gly-OH, Ethoxyacetic acid, (Methylthio)acetic acid, Pyrrole-2-carboxylic acid, 3-Furoic acid, Isoxazole-5-carboxylic acid, trans-3-Hexenoic acid, Trifluoroacetic acid, Hexanoic acid, Ac-Gly-OH, 2-Hydroxy-2-methylbutyric acid, Benzoic acid, Nicotinic acid, 2-Pyrazinecarboxylic acid, 1-Methyl-2-pyrrolecarboxylic acid, 2-Cyclopentene-1-acetic acid, Cyclopentylacetic acid, (S)-(−)-2-Pyrrolidone-5-carboxylic acid, N-Methyl-L-proline, Heptanoic acid, Ac-b-Ala-OH, 2-Ethyl-2-hydroxybutyric acid, 2-(2-Methoxyethoxy)acetic acid, p-Toluic acid, 6-Methylnicotinic acid, 5-Methyl-2-pyrazinecarboxylic acid, 2,5-Dimethylpyrrole-3-carboxylic acid, 4-Fluorobenzoic acid, 3,5-Dimethylisoxazole-4-carboxylic acid, 3-Cyclopentylpropionic acid, Octanoic acid, N,N-Dimethylsuccinamic acid, Phenylpropiolic acid, Cinnamic acid, 4-Ethylbenzoic acid, p-Anisic acid, 1,2,5-Trimethylpyrrole-3-carboxylic acid, 3-Fluoro-4-methylbenzoic acid, Ac-DL-Propargylglycine, 3-(Trifluoromethyl)butyric acid, 1-Piperidinepropionic acid, N-Acetylproline, 3,5-Difluorobenzoic acid, Ac-L-Val-OH, Indole-2-carboxylic acid, 2-Benzofurancarboxylic acid, Benzotriazole-5-carboxylic acid, 4-n-Propylbenzoic acid, 3-Dimethylaminobenzoic acid, 4-Ethoxybenzoic acid, 4-(Methylthio)benzoic acid, N-(2-Furoyl)glycine, 2-(Methylthio)nicotinic acid, 3-Fluoro-4-methoxybenzoic acid, Tfa-Gly-OH, 2-Napthoic acid, Quinaldic acid, Ac-L-Ile-OH, 3-Methylindene-2-carboxylic acid, 2-Quinoxalinecarboxylic acid, 1-Methylindole-2-carboxylic acid, 2,3,6-Trifluorobenzoic acid, N-Formyl-L-Met-OH, 2-[2-(2-Methoxyethoxy)ethoxy]acetic acid, 4-n-Butylbenzoic acid, N-Benzoylglycine, 5-Fluoroindole-2-carboxylic acid, 4-n-Propoxybenzoic acid, 4-Acetyl-3,5-dimethyl-2-pyrrolecarboxylic acid, 3,5-Dimethoxybenzoic acid, 2,6-Dimethoxynicotinic acid, Cyclohexanepentanoic acid, 2-Naphthylacetic acid, 4-(1H-Pyrrol-1-yl)benzoic acid, Indole-3-propionic acid, m-Trifluoromethylbenzoic acid, 5-Methoxyindole-2-carboxylic acid, 4-Pentylbenzoic acid, Bz-b-Ala-OH, 4-Diethylaminobenzoic acid, 4-n-Butoxybenzoic acid, 3-Methyl-5-CF3-isoxazole-4-carboxylic acid, (3,4-Dimethoxyphenyl)acetic acid, 4-Biphenylcarboxylic acid, Pivaloyl-Pro-OH, Octanoyl-Gly-OH, (2-Naphthoxy)acetic acid, Indole-3-butyric acid, 4-(Trifluoromethyl)phenylacetic acid, 5-Methoxyindole-3-acetic acid, 4-(Trifluoromethoxy)benzoic acid, Ac-L,-Phe-OH, 4-Pentyloxybenzoic acid, Z-Gly-OH, 4-Carboxy-N-(fur-2-ylmethyl)pyrrolidin-2-one, 3,4-Diethoxybenzoic acid, 2,4-Dimethyl-5-CO₂Et-pyrrole-3-carboxylic acid, N-(2-Fluorophenyl)succinamic acid, 3,4,5-Trimethoxybenzoic acid, N-Phenylanthranilic acid, 3-Phenoxybenzoic acid, Nonanoyl-Gly-OH, 2-Phenoxypyridine-3-carboxylic acid, 2,5-Dimethyl-1-phenylpyrrole-3-carboxylic acid, trans-4-(Trifluoromethyl)cinnamic acid, (5-Methyl-2-phenyloxazol-4-yl)acetic acid, 4-(2-Cyclohexenyloxy)benzoic acid, 5-Methoxy-2-methylindole-3-acetic acid, trans-4-Cotininecarboxylic acid, Bz-5-Aminovaleric acid, 4-Hexyloxybenzoic acid, N-(3-Methoxyphenyl)succinamic acid, Z-Sar-OH, 4-(3,4-Dimethoxyphenyl)butyric acid, Ac-o-Fluoro-DL-Phe-OH, N-(4-Fluorophenyl)glutaramic acid, 4'-Ethyl-4-biphenylcarboxylic acid, 1,2,3,4-Tetrahydroacridinecarboxylic acid, 3-Phenoxyphenylacetic acid, N-(2,4-Difluorophenyl)succinamic acid, N-Decanoyl-Gly-OH, (+)-6-Methoxy-a-methyl-2-naphthaleneacetic acid, 3-(Trifluoromethoxy)cinnamic acid, N-Formyl-DL-Trp-OH, (R)-(+)-a-Methoxy-a-(trifluoromethyl) phenylacetic acid, Bz-DL-Leu-OH, 4-(Trifluoromethoxy) phenoxyacetic acid, 4-Heptyloxybenzoic acid, 2,3,4-Trimethoxycinnamic acid, 2,6-Dimethoxybenzoyl-Gly-OH, 3-(3,4,5-Trimethoxyphenyl)propionic acid, 2,3,4,5,6-Pentafluorophenoxyacetic acid, N-(2,4-Difluorophenyl) glutaramic acid, N-Undecanoyl-Gly-OH, 2-(4-Fluorobenzoyl)benzoic acid, 5-Trifluoromethoxyindole-2-carboxylic acid, N-(2,4-Difluorophenyl)diglycolamic acid, Ac-L-Trp-OH, Tfa-L-Phenylglycine-OH, 3-Iodobenzoic acid, 3-(4-n-Pentylbenzoyl)propionic acid, 2-Phenyl-4-quinolinecarboxylic acid, 4-Octyloxybenzoic acid, Bz-L-Met-OH, 3,4,5-Triethoxybenzoic acid, N-Lauroyl-Gly-OH, 3,5-Bis(trifluoromethyl)benzoic acid, Ac-5-Methyl-DL-Trp-OH, 2-Iodophenylacetic acid, 3-Iodo-4-methylbenzoic acid, 3-(4-n-Hexylbenzoyl)propionic acid, N-Hexanoyl-1-Phe-OH, 4-Nonyloxybenzoic acid, 4'-(Trifluoromethyl)-2-biphenylcarboxylic acid, Bz-L-Phe-OH, N-Tridecanoyl-Gly-OH, 3,5-Bis(trifluoromethyl)phenylacetic acid, 3-(4-n-Heptylbenzoyl)propionic acid, N-Hepytanoyl-L-Phe-OH, 4-Decyloxybenzoic acid, N-(α,α,α-trifluoro-m-tolyl) anthranilic acid, Niflumic acid, 4-(2-Hydroxyhexafluoroisopropyl)benzoic acid, N-Myristoyl-Gly-OH, 3-(4-n-Octylbenzoyl)propionic acid, N-Octanoyl-L-Phe-OH, 4-Undecyloxybenzoic acid, 3-(3,4,5-Trimethoxyphenyl)propionyl-Gly-OH, 8-Iodonaphthoic acid, N-Pentadecanoyl-Gly-OH, 4-Dodecyloxybenzoic acid, N-Palmitoyl-Gly-OH, and N-Stearoyl-Gly-OH.

43. A compound according to claim 33 wherein T$^{ms}$ has a mass of from to 10,000 daltons and a molecular formula of $C_{1-500}N_{0-100}O_{0-100}S_{0-10}P_{0-10}H_\alpha F_\beta I_\delta$ wherein the sum of α, β and δ is sufficient to satisfy the otherwise unsatisfied valencies of the C, N and O atoms.

44. A compound according to claim 33 wherein T$^{ms}$ and L are bonded together through a functional group selected from amide, ester, ether, amine, sulfide, thioester, disulfide, thioether, urea, thiourea, carbamate, thiocarbamate, Schiff base, reduced Schiff base, imine, oxime, hydrazone, phosphate, phosphonate, phosphoramide, phosphonamide, sulfonate, sulfonamide or carbon—carbon bond.

45. A compound according to claim 44 wherein the functional group is selected from amide, ester, amine, urea and carbamate.

46. A compound according to claims 34, 37, 38 or 39 wherein L is slected from L$^{hv}$, L$^{acid}$, L$^{base}$, L$^{[O]}$, L$^{[R]}$, L$^{enz}$, L$^{elc}$, L$^A$ and L$^{ss}$, where actinic radiation, acid, base, oxidation, reduction, enzyme, electrochemical, thermal and thiol exchange, respectively, cause the T$^{ms}$-containing moiety to be cleaved from the remainder of the molecule.

47. A compound according to claim 46 wherein L$^{hv}$ has the formula L$^1$-L$^2$-L$^3$, wherein L$^2$ is a molecular fragment that absorbs actinic radiation to promote the cleavage of T$^{ms}$ from X, and L$^1$ and L$^3$ are independently a direct bond or an organic moiety, where L$^1$ separates L$^2$ from T$^{ms}$ and L$^3$ separates L$^2$ from X, and neither L$^1$ nor L$^3$ undergo bond cleavage when L$^2$ absorbs the actinic radiation.

48. A compound according to claim 47 wherein -L$^2$-L$^3$ has the formula:

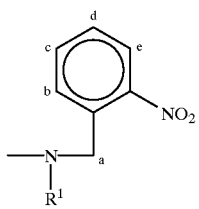

with one carbon atom at positions a, b, c, d or e being substituted with -L$^3$-X and optionally one or more of positions b, c, d or e being substituted with alkyl, alkoxy, fluoride, chloride, hydroxyl, carboxylate or amide; and R$^1$ is hydrogen or hydrocarbyl.

49. A compound according to claim 48 wherein X comprises a molecule of interest (MOI) selected from protein, peptide, oligosaccharide, antibody, antigen, drugs and synthetic organic molecules.

50. A compound according to claim 47 wherein $L^3$ is selected from a direct bond, a hydrocarbylene, -O-hydrocarbylene, and hydrocarbylene-(O-hydrocarbylene)$_n$-H, and n is an integer ranging from 1 to 10.

51. A compound according to claim 33 wherein X comprises a molecule of interest (MOI) selected from protein, peptide, oligosaccharide, antibody, antigen, drugs and synthetic organic molecules.

52. A compound according to claim 34 wherein X comprises a molecule of interest (MOI) selected from protein, peptide, oligosaccharide, antibody, antigen, drugs and synthetic organic molecules.

53. A compound according to claim 37 wherein X comprises a molecule of interest (MOI) selected from protein, peptide, oligosaccharide, antibody, antigen, drugs and synthetic organic molecules.

54. A compound according to claim 38 wherein X comprises a molecule of interest (MOI) selected from protein, peptide, oligosaccharide, antibody, antigen, drugs and synthetic organic molecules.

55. A compound according to claim 39 wherein X comprises a molecule of interest (MOI) selected from protein, peptide, oligosaccharide, antibody, antigen, drugs and synthetic organic molecules.

56. The method of claim 1 wherein the tagged first member is a compound having a mass of at least 250 daltons of the formula:

$$T_{ms}\text{-L-X}$$

wherein, $T^{ms}$ is an organic group detectable by mass spectrometry, comprising carbon, at least one of hydrogen and fluoride, and optional atoms selected from oxygen, nitrogen, sulfur, phosphorus and iodine;

L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid; and X comprises a molecule of interest.

57. The method of claim 1 wherein the tagged first member is a compound having a mass of at least 250 daltons of the formula:

$$T^{ms}\text{-L-X}$$

wherein $T^{ms}$ is an organic group detectable by mass spectrometry, comprising carbon, at least one of hydrogen and fluoride, and optional atoms selected from oxygen, nitrogen, sulfur, phosphorus and iodine; L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid; and -L-X has the formula:

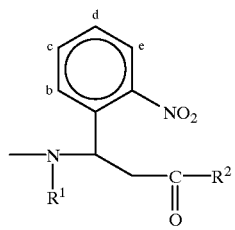

wherein one or more of positions b, c, d or e is substituted with hydrogen, alkyl, alkoxy, fluoride, chloride, hydroxyl, carboxylate or amide; $R^1$ is hydrogen or hydrocarbyl; and $R^2$ comprises a molecule of interest (MOI).

58. The method of claim 1 wherein the tagged first member is a compound having a mass of at least 250 daltons of the formula:

$$T^{ms}\text{-L-X}$$

wherein $T^{ms}$ is an organic group detectable by mass spectrometry, comprising carbon, at least one of hydrogen and fluoride, and optional atoms selected from oxygen, nitrogen, sulfur, phosphorus and iodine, and has the formula:

$$T^2\text{-}(J\text{-}T^3\text{-})_n\text{-}$$

wherein $T^2$ is an organic moiety formed from carbon and one or more of hydrogen, fluoride, iodide, oxygen, nitrogen, sulfur and phosphorus, having a mass of 15 to 500 daltons; $T^3$ is an organic moiety formed from carbon and one or more of hydrogen, fluoride, iodide, oxygen, nitrogen, sulfur and phosphorus, having a mass of 50 to 1000 daltons; J is a direct bond or a functional group selected from amide, ester, amine, sulfide, ether, thioester, disulfide, thioether, urea, thiourea, carbamate, thiocarbamate, Schiff base, reduced Schiff base, imine, oxime, hydrazone, phosphate, phosphonate, phosphoramide, phosphonamide, sulfonate, sulfonamide or carbon-carbon bond; and n is an integer ranging from 1 to 50, and when n is greater than 1, each $T^3$ and J is independently selected; and L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid; and X is a molecule of interest (MOI).

59. The method of claim 1 wherein the tagged first member is a compound having a mass of at least 250 daltons of the formula:

$$T^{ms}\text{-L-X}$$

wherein $T^{ms}$ is an organic group detectable by mass spectrometry, comprising carbon, at least one of hydrogen and fluoride, and optional atoms selected from oxygen, nitrogen, sulfur, phosphorus and iodine; L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid; X is molecule of interest (MOI); the compound also having the formula:

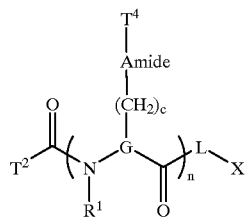

wherein

G is $(CH_2)_{1-6}$ wherein a hydrogen on one and only one of the $CH_2$ groups is replaced with $-(CH_2)_c$-Amide-$T^4$;

$T^2$ and $T^4$ are organic moieties of the formula $C_{1-25}N_{0-9}O_{0-9}H_\alpha F_\beta$ wherein the sum of $\alpha$ and $\beta$ is sufficient to satisfy the otherwise unsatisfied valencies of the C, N, and O atoms;

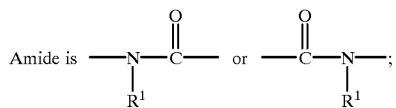

$R^1$ is hydrogen or $C_{1-10}$ alkyl;

c is an integer ranging from 0 to 4; and n is an integer ranging from 1 to 50 such that when n is greater than 1, then G, c, Amide, $R^1$ and $T^4$ are independently selected.

60. The method of claim 1 wherein the tagged first member is a compound having a mass of at least 250 daltons of the formula:

$T^{ms}$-L-X wherein $T^{ms}$ is an organic group detectable by mass spectrometry, comprising carbon, at least one of hydrogen and fluoride, and optional atoms selected from oxygen, nitrogen, sulfur, phosphorus and iodine; L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid; X is a molecule of interest (MOI), the compound also having the formula:

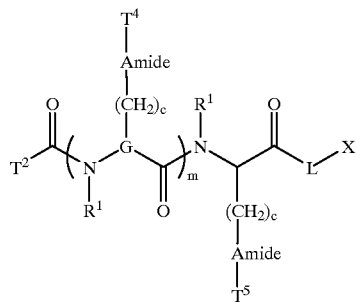

wherein

G is $(CH_2)_{1-6}$ wherein a hydrogen on one and only one of the $CH_2$ groups is replaced with $-(CH_2)_c$-Amide-$T^4$;

$T^2$ and $T^4$ are organic moieties of the formula $C_{1-25}N_{0-9}O_{0-9}H_\alpha F_\beta$ wherein the sum of $\alpha$ and $\beta$ is sufficient to satisfy the otherwise unsatisfied valencies of the C, N, and O atoms;

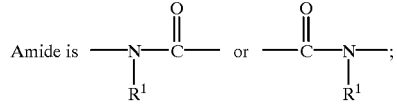

$R^1$ is hydrogen or $C_{1-10}$ alkyl;

c is an integer ranging from 0 to 4; and $T^5$ is an organic moiety of the formula $C_{1-25}N_{0-9}O_{0-9}H_\alpha F_\beta$ wherein the sum of $\alpha$ and $\beta$ is sufficient to satisfy the otherwise unsatisfied valencies of the C, N, and O atoms; and $T^5$ includes a tertiary or quaternary amine or an organic acid; and m is an integer ranging from 0–49 where when m is greater than 1, then G, c, Amide, $R^1$ and $T^4$ are independently selected.

61. The method of claim 1 wherein the tagged first member is a compound having a mass of at least 250 daltons of the formula:

$T^{ms}$-L-X wherein $T^{ms}$ is an organic group detectable by mass spectrometry, comprising carbon, at least one of hydrogen and fluoride, and optional atoms selected from oxygen, nitrogen, sulfur, phosphorus and iodine; L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid; X is a molecule of interest (MOI); the compound also having the formula:

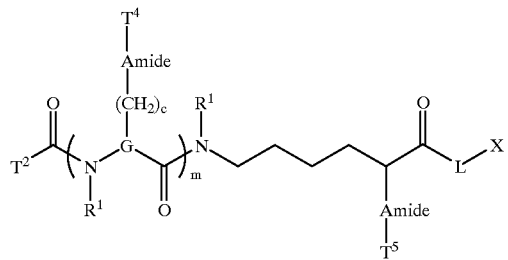

wherein

G is $(CH_2)_{1-6}$ wherein a hydrogen on one and only one of the $CH_2$ groups is replaced with $-(CH_2)_c$-Amide-$T^4$;

$T^2$ and $T^4$ are organic moieties of the formula $C_{1-25}N_{0-9}O_{0-9}H_\alpha F_\beta$ wherein the sum of $\alpha$ and $\beta$ is sufficient to satisfy the otherwise unsatisfied valencies of the C, N, and O atoms;

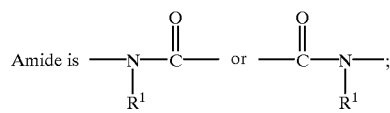

$R^1$ is hydrogen or $C_{1-10}$ alkyl;

c is an integer ranging from 0 to 4; and $T^5$ is an organic moiety of the formula $C_{1-25}N_{0-9}O_{0-9}H_\alpha F_\beta$ wherein the sum of $\alpha$ and $\beta$ is sufficient to satisfy the otherwise unsatisfied valencies of the C, N, and O atoms; and $T^5$ includes a tertiary or quaternary amine or an organic acid; and m is an integer ranging from 0–49 where when m is greater than 1, then G, c, Amide, $R^1$ and $T^4$ are independently selected.

62. The method of claim 20 wherein the tagged nucleic acid probe is a compound having a mass of at least 250 daltons of the formula:

$T^{ms}$-L-X wherein,
$T^{ms}$ is an organic group detectable by mass spectrometry, comprising carbon, at least one of hydrogen and fluoride, and optional atoms selected from oxygen, nitrogen, sulfur, phosphorus and iodine;
L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid; and
X comprises a nucleic acid probe.

63. The method of claim 20 wherein the tagged nucleic acid probe is a compound having a mass of at least 250 daltons of the formula:

$T^{ms}$-L-X wherein $T^{ms}$ is an organic group detectable by mass spectrometry, comprising carbon, at least one of hydrogen and fluoride, and optional atoms selected from oxygen, nitrogen, sulfur, phosphorus and iodine; L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid; and -L-X has the formula:

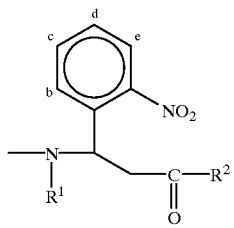

wherein one or more of positions b, c, d or e is substituted with hydrogen, alkyl, alkoxy, fluoride, chloride, hydroxyl, carboxylate or amide; $R^1$ is hydrogen or hydrocarbyl; and $R^2$ comprises a nucleic acid probe.

64. The method of claim 20 wherein the tagged nucleic acid probe is a compound having a mass of at least 250 daltons of the formula:

$T^{ms}$-L-X wherein $T^{ms}$ is an organic group detectable by mass spectrometry, comprising carbon, at least one of hydrogen and fluoride, and optional atoms selected from oxygen, nitrogen, sulfur, phosphorus and iodine, and has the formula:

$T^2$-(J-$T^3$-)$_n$- wherein
$T^2$ is an organic moiety formed from carbon and one or more of hydrogen, fluoride, iodide, oxygen, nitrogen, sulfur and phosphorus, having a mass of 15 to 500 daltons, $T^3$ is an organic moiety formed from carbon and one or more of hydrogen, fluoride, iodide, oxygen, nitrogen, sulfur and phosphorus, having a mass of 50 to 1000 daltons; J is a direct bond or a functional group selected from amide, ester, amine, sulfide, ether, thioester, disulfide, thioether, urea, thiourea, carbamate, thiocarbamate, Schiff base, reduced Schiff base, imine, oxime, hydrazone, phosphate, phosphonate, phosphoramide, phosphonamide, sulfonate, sulfonamide or carbon-carbon bond; and n is an integer ranging from 1 to 50, and when n is greater than 1, each $T^3$ and J is independently selected;
L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid; and
X comprises a nucleic acid probe.

65. The method of claim 20 wherein the tagged nucleic acid probe is a compound having a mass of at least 250 daltons of the formula:

$T^{ms}$-L-X wherein $T^{ms}$ is an organic group detectable by mass spectrometry, comprising carbon, at least one of hydrogen and fluoride, and optional atoms selected from oxygen, nitrogen, sulfur, phosphorus and iodine; L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid; X comprises a nucleic acid probe; the compound also having the formula:

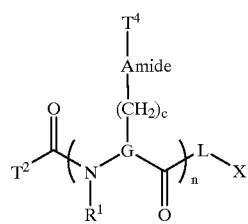

wherein
G is $(CH_2)_{1-6}$ wherein a hydrogen on one and only one of the $CH_2$ groups is replaced with-$(CH_2)_c$-Amide-$T^4$;
$T^2$ and $T^4$ are organic moieties of the formula $C_{1-25}N_{0-9}O_{0-9}H_\alpha F_\beta$ wherein the sum of α and β is sufficient to satisfy the otherwise unsatisfied valencies of the C, N, and O atoms;

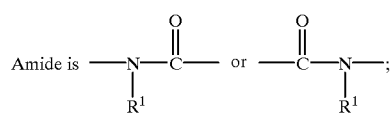

$R^1$ is hydrogen or $C_{1-10}$ alkyl;
c is an integer ranging from 0 to 4; and n is an integer ranging from 1 to 50 such that when n is greater than 1, then G, c, Amide, $R^1$ and $T^4$ are independently selected.

66. The method of claim 20 wherein the tagged nucleic acid probe is a compound having a mass of at least 250 daltons of the formula:

$T^{ms}$-L-X wherein $T^{ms}$ is an organic group detectable by mass spectrometry, comprising carbon, at least one of hydrogen and fluoride, and optional atoms selected from oxygen, nitrogen, sulfur, phosphorus and iodine; L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid; X comprises a nucleic acid probe, the compound also having the formula:

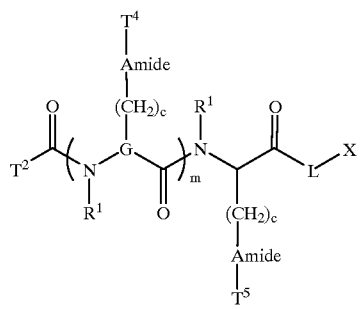

wherein
G is $(CH_2)_{1-6}$ wherein a hydrogen on one and only one of the $CH_2$ groups is replaced with-$(CH_2)_c$-Amide-$T^4$;
$T^2$ and $T^4$ are organic moieties of the formula $C_{1-25}N_{0-9}O_{0-9}H_\alpha F_\beta$ wherein the sum of $\alpha$ and $\beta$ is sufficient to satisfy the otherwise unsatisfied valencies of the C, N, and O atoms;

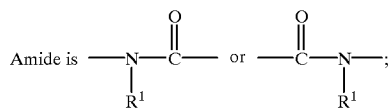

$R^1$ is hydrogen or $C_{1-10}$ alkyl;
c is an integer ranging from 0 to 4; and
$T^5$ is an organic moiety of the formula $C_{1-25}N_{0-9}O_{0-9}H_\alpha F_\beta$ wherein the sum of ax and D is sufficient to satisfy the otherwise unsatisfied valencies of the C, N, and O atoms; and $T^5$ includes a tertiary or quaternary amine or an organic acid; and m is an integer ranging from 0–49 where when m is greater than 1, then G, c, Amide, $R^1$ and $T^4$ are independently selected.

67. The method of claim 20 wherein the tagged nucleic acid probe is a compound having a mass of at least 250 daltons of the formula:

$T^{ms}$-L-X wherein $T^{ms}$ is an organic group detectable by mass spectrometry, comprising carbon, at least one of hydrogen and fluoride, and optional atoms selected from oxygen, nitrogen, sulfur, phosphorus and iodine; L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid; X comprises a nucleic acid probe; the compound also having the formula:

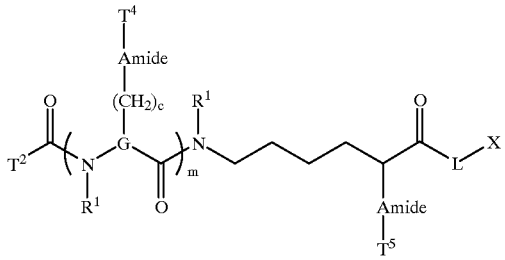

wherein
G is $(CH_2)_{1-6}$ wherein a hydrogen on one and only one of the $CH_2$ groups is replaced with-$(CH_2)_c$-Amide-$T^4$;
$T^2$ and $T^4$ are organic moieties of the formula $C_{1-25}N_{0-9}O_{0-9}H_\alpha F_\beta$ wherein the sum of $\alpha$ and $\beta$ is sufficient to satisfy the otherwise unsatisfied valencies of the C, N, and O atoms;

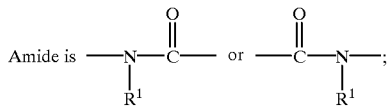

$R^1$ is hydrogen or $C_{1-10}$ alkyl;
c is an integer ranging from 0 to 4; and
$T^5$ is an organic moiety of the formula $C_{1-25}N_{0-9}O_{0-9}H_\alpha F_\beta$ wherein the sum of $\alpha$ and $\beta$ is sufficient to satisfy the otherwise unsatisfied valencies of the C, N, and O atoms; and $T^5$ includes a tertiary or quaternary amine or an organic acid; and m is an integer ranging from 0–49 where when m is greater than 1, then G, c, Amide, $R^1$ and $T^4$ are independently selected.

68. A composition comprising a pair of compounds of the formula:

$T^{ms}$-L-MOI wherein,
$T^{ms}$ is an organic group detectable by mass spectrometry, comprising carbon, at least one of hydrogen and fluoride, and optional atoms selected from oxygen, nitrogen, sulfur, phosphorus and iodine;
L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid;
MOI is a nucleic acid fragment wherein L is conjugated to MOI at other than the 3' end of the MOI; and
the compounds of the pair have non-identical $T^{ms}$ groups, and have identical sequences except at one base position where the bases are non-identical.

69. A composition comprising a pair of compounds of the formula:

$T^{ms}$-L-MOI wherein, $T^{ms}$ is an organic group detectable by mass spectrometry, comprising carbon, at least one of hydrogen and fluoride, and optional atoms selected from oxygen, nitrogen, sulfur, phosphorus and iodine;

L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid;

MOI is a nucleic acid fragment wherein L is conjugated to MOI at other than the 3' end of the MOI; and the compounds of the pair have non-identical $T^{ms}$ groups, and have identical sequences except at two base position where the bases are non-identical.

70. A composition according to claim any of claims 68 or 69, comprising a plurality of the pairs.

71. A composition according to any of claims 68 or 69, comprising a plurality of the pairs, and an equal plurality of non-identical nucleic acids immobilized on a solid support, wherein each member of the plurality of nucleic acids has a base sequence that is exactly complementary to one member of each of the pairs.

72. The method according to claim 1 wherein said first and second members are nucleic acid molecules and differ by at least a single base-pair mismatch.

\* \* \* \* \*

UNITED STATES PATENT AND TRADEMARK OFFICE
CERTIFICATE OF CORRECTION

PATENT NO. : 6,027,890
DATED : Feb. 22, 2000
INVENTOR(S) : Jeffrey Van Ness, et al.

It is certified that error appears in the above-indentified patent and that said Letters Patent is hereby corrected as shown below:

Claim 20, column 96, line 58, "nonfluorescent" should read --non-fluorescent--.

Claim 36, column 98, line 48, "claim 43 wherein" should read --claim 34 wherein--.

Claim 36, column 99, line 21, "glycjne" should read --glycine--.

Claim 36, column 99, line 23, "omithine" should read --ornithine--.

Claim 37, column 99, line 63, "CH, groups" should read --$CH_2$ groups--.

Claim 38, column 100, line 47, "$C^{1-25}N_{0-9}O_{0-9}H_\alpha F_\beta$" should read --$C_{1-25}N_{0-9}O_{0-9}H_\alpha F_\beta$--.

Claim 42, column 104, line 13, "N-Hexanoyl-1-Phe-OH," should read --N-Hexanoyl-L-Phe-OH,--.

Claim 43, column 104, line 25, "from to 10,000" should read --from 15 to 10,000--.

Claim 56, column 105, line 34, "$T_{ms}$-L-X" should read --$T^{ms}$-L-X--.

Claim 60, column 107, line 67, "sum of (x and P" should read --sum of $\alpha$ and $\beta$--.

Claim 66, column 111, line 52, "sum of ax and D" should read --sum of $\alpha$ and $\beta$--.

Signed and Sealed this

Sixth Day of March, 2001

*Attest:*

NICHOLAS P. GODICI

*Attesting Officer*     *Acting Director of the United States Patent and Trademark Office*